US008753831B2

(12) United States Patent
Kalkum et al.

(10) Patent No.: US 8,753,831 B2
(45) Date of Patent: Jun. 17, 2014

(54) METHODS FOR DETECTION OF BOTULINUM NEUROTOXIN

(75) Inventors: Markus Kalkum, Azusa, CA (US); Karine Bagramyan, North Hollywood, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 13/600,186

(22) Filed: Aug. 30, 2012

(65) Prior Publication Data

US 2013/0065259 A1 Mar. 14, 2013

Related U.S. Application Data

(60) Continuation-in-part of application No. 13/306,769, filed on Nov. 29, 2011, now abandoned, which is a division of application No. 12/134,092, filed on Jun. 5, 2008, now Pat. No. 8,067,192.

(60) Provisional application No. 60/942,199, filed on Jun. 5, 2007.

(51) Int. Cl.
*G01N 21/76* (2006.01)
*G01N 21/64* (2006.01)
*G01N 33/53* (2006.01)

(52) U.S. Cl.
USPC ............. 435/7.94; 435/7.32; 435/4; 435/7.92

(58) Field of Classification Search
CPC ........ G01N 33/53; G01N 71/76; G01N 21/64
USPC ............................................ 435/7.94, 8, 501
See application file for complete search history.

(56) References Cited

U.S. PATENT DOCUMENTS

| | | | |
|---|---|---|---|
| 5,965,699 A * | 10/1999 | Schmidt et al. | 530/326 |
| 6,504,006 B1 * | 1/2003 | Shine et al. | 530/323 |
| 6,506,006 B2 | 1/2003 | Lui et al. | |
| 6,696,304 B1 | 2/2004 | Davies | |
| 6,762,280 B2 | 7/2004 | Schmidt et al. | |
| 6,803,475 B2 * | 10/2004 | Wipf et al. | 556/465 |
| 7,034,107 B2 * | 4/2006 | Schmidt et al. | 530/300 |
| 7,157,553 B2 | 1/2007 | Schmidt et al. | |
| 7,611,856 B2 * | 11/2009 | Schmidt et al. | 435/7.72 |
| 7,670,796 B2 | 3/2010 | Shone et al. | |
| 7,846,722 B2 * | 12/2010 | Williams et al. | 435/325 |
| 7,875,436 B2 * | 1/2011 | Fournie-Zaluski et al. | 435/24 |
| 8,067,192 B2 * | 11/2011 | Kalkum et al. | 435/7.94 |
| 2004/0146963 A1 * | 7/2004 | Schmidt et al. | 435/23 |
| 2005/0042623 A1 * | 2/2005 | Ault-Riche et al. | 435/6 |
| 2005/0287622 A1 | 12/2005 | Schmidt et al. | |
| 2006/0024763 A1 * | 2/2006 | Schmidt et al. | 435/7.5 |
| 2006/0063222 A1 * | 3/2006 | Williams et al. | 435/23 |
| 2007/0020678 A1 * | 1/2007 | Ault-Riche et al. | 435/6 |
| 2008/0213255 A1 | 9/2008 | Atassi | |
| 2009/0176259 A1 * | 7/2009 | Kalkum et al. | 435/7.94 |
| 2009/0208993 A1 * | 8/2009 | Fournie-Zaluski et al. | 435/24 |
| 2012/0122123 A1 * | 5/2012 | Boyer et al. | 435/7.92 |
| 2012/0322081 A1 * | 12/2012 | Kalkum et al. | 435/7.4 |
| 2013/0065259 A1 * | 3/2013 | Kalkum et al. | 435/8 |

OTHER PUBLICATIONS

Aina, O.H. et al. From combinatorial chemistry to cancer-targeting peptides. *Mol Pharm* 4, 631-651 (2007).
Aina, O.H. et al. Identification of novel targeting peptides for human ovarian cancer cells using "one-bead one-compound" combinatorial libraries. *Mol Cancer Ther* 4, 806-813 (2005).
Aoki, K.R. & Guyer, B. Botulinum toxin type A and other botulinum toxin serotypes: a comparative review of biochemical and pharmacological actions. *Eur J Neurol* 8 Suppl 5, 21-29 (2001).
Arnon, S.S. et al. Botulinum toxin as a biological weapon: medical and public health management. *JAMA* 285, 1059-1070 (2001).
Arnon, S.S., Schechter, R., Maslanka, S.E., Jewell, N.P. & Hatheway, C.L. Human botulism immune globulin for the treatment of infant botulism. *N. Engl J Med* 354, 462-471 (2006).
Bagramyan, K., et al., "Ultrasensitive Detection of Botulinum Neurotoxins and Antrax Letal Factor in Biological Simples by ALISSA," Methods Mol. Biol. 739:23-36 (2011).
Bagramyan, K., et al., "Attomolar Detection of Botulinum Toxin Type A in Complex Biological Matrices," PLoS One 3(4):e2041 (2008).

Barr, J.R. et al. Botulinum neurotoxin detection and differentiation by mass spectrometry. *Emerg Infect Dis* 11, 1578-1583 (2005).

Boder, E. T., et al., "Yeast Surface Display for Screening Combinatorial Polypeptide Libraries," Nat. Biotech. 15:553-557 (1997).

Boyer, A.E. et al. From the mouse to the mass spectrometer: detection and differentiation of the endoproteinase activities of botulinum neurotoxins A-G by mass spectrometry. *Anal Chem* 77, 3916-3924 (2005).

Boyer, A. E., et al., "Detection and Quantification of Anthrax Lethal Factor in Serum by Mass Spectrometry," Anal. Chem. 79:8463-8470 (2007).

Brossier, F., et al., "Toxins of *Bacillus anthracis*," Toxicon 39:1747-1755 (2001).

Cai, S. & Singh, B.R. Role of the disulfide cleavage induced molten globule state of type a botulinum neurotoxin in its endopeptidase activity. *Biochemistry* 40, 15327-15333 (2001).

Cai, S., Sarkar, H.K. & Singh, B.R. Enhancement of the endopeptidase activity of botulinum neurotoxin by its associated proteins and dithiothreitol. *Biochemistry* 38, 6903-6910 (1999).

Centers for Disease Control and Prevention: Botulism in the United States, 1899-1996. Handbook for Epidemiologists, Clinicians, and Laboratory Workers, Atlanta, GA. Centers for Disease Control and Prevention (1998).

Chao, H.Y., Wang, Y.C., Tang, S.S. & Liu, H.W. A highly sensitive immuno-polymerase chain reaction assay for *Clostridium botulinum* neurotoxin type A. *Toxicon* 43, 27-34 (2004).

Chen, F., Kuziemko, G.M. & Stevens, R.C. Biophysical characterization of the stability of the 150-kilodalton botulinum toxin, the nontoxic component, and the 900-kilodalton botulinum toxin complex species. *Infect Immun* 66, 2420-2425 (1998).

Crowner, B. E., et al., "Iatrogenic Botulism Due to Therapeutic Botulinum Toxin A Injection in a Pediatric Patient," Clin. Neuropharmacol. 30(5):310-313 (2007).

Ekong, T. A.N., et al., "Immunological Detection of *Clostridium botulinum* Toxin Type A in Therapeutic Preparations," J. Immunol. Methods 180:181-191 (1995).

Ferreira, J.L., Maslanka, S., Johnson, E. & Goodnough, M. Detection of botulinal neurotoxins A, B, E, and F by amplified enzyme-linked immunosorbent assay: collaborative study. *J AOAC Int* 86, 314-331 (2003).

Garcia-Rodriguez, C. et al. Molecular evolution of antibody cross-reactivity for two subtypes of type A botulinum neurotoxin. *Nat Biotechnol* 25, 107-116 (2007).

Gill, D. M., "Bacterial Toxins: a Tableo f Letal Amounts," Microbiol. Rev. 46(1):86-94 (1982).

Gu, S., et al., "Botulinim Neurotoxin is Shielded by NTNHA in an Interlocked Complex," Science 335:977-981 (2012).

Hanna, P. C., et al., "On the Role of Macrophages in Ántrax," Proc. Natl. Acad. Sci. USA 90:10198-10201 (1993).

Henkel, J. S., et al., "Catalytic Properties of Botulinum Neurotoxins Subtypes A3 and A4," Biochem. 48(11):2522-2528 (2009).

Jankovic, J., "Botulinum Toxin in Clinical Practice," J. Neurol. Neurosurg. Psychiatry 75:951-957 (2004).

Johnson, E. A., "Clostridial Toxins as Therapeutic Agents: Benefits of Nature's Most Toxic Proteins," Annu. Rev. Microbial. 53:551-575 (1999).

Juskowiak, G.L. et al. Fluorogenic peptide sequences—transformation of short peptides into fluorophores under ambient photooxidative conditions. *J Am Chem Soc* 126, 550-556 (2004).

Kalb, S.R. et al. The use of Endopep-MS for the detection of botulinum toxins A, B, E, and F in serum and stool samples. *Anal Biochem* 351, 84-92 (2006).

Kalb, S.R., Goodnough, M.C., Malizio, C.J., Pirkle, J.L. & Barr, J.R. Detection of botulinum neurotoxin A in a spiked milk sample with subtype identification through toxin proteomics. *Anal Chem* 77, 6140-6146 (2005).

Kautter, D.A. & Solomon, H.M. Collaborative study of a method for the detection of *Clostridium botulinum* and its toxins in foods. *J Assoc Off Anal Chem* 60, 541-545 (1977).

Koepke, R., et al., "Global Occurrence of Infant Botulism," Pediatrics 122:e73 (2008).

Kurazono, H. et al. Minimal essential domains specifying toxicity of the light chains of tetanus toxin and botulinum neurotoxin type A. *J Biol Chem* 267, 14721-14729 (1992).

Lacy, D.B., Tepp, W., Cohen, A.C., DasGupta, B.R. & Stevens, R.C. Crystal structure of botulinum neurotoxin type A and implications for toxicity. *Nat Struct Biol* 5, 898-902 (1998).

Lalli, G., et al., "The Journey of Tetanus and Botulinum Neurotoxins in Neurons," Trends in Microbiol. 11(9): 431-437 (2003).

Lam, K.S. et al. Synthesis and screening of "one-bead one-compound" combinatorial peptide libraries. *Methods Enzymol* 369, 298-322 (2003).

Liu, W., et al. Botulinum toxin type B micromechanosensor. *Proc Natl Acad Sci USA* 100, 13621-13625 (2003).

Long, S. S., Infant Botulism and Treatment with BIG-IV (BabyBIG®) Pediatr. Infect. Dis. J. 26:261-262 (2007).

Maass, D. R., et al., "Alpaca (*Lama pacos*) as a Convenient Source of Recombinant Camelid Heavy Chain Antibodies (VHHs)," J. Immunol. Methods 324(1-2):13-25 (2007).

Marks, J.D. Deciphering antibody properties that lead to potent botulinum neurotoxin neutralization. *Mov Disord* 19 Suppl 8, S101-108 (2004).

Mason, J.T., Xu, L., Sheng, Z.M. & O'Leary, T.J. A liposome-PCR assay for the ultrasensitive detection of biological toxins. *Nat Biotechnol* 24, 555-557 (2006).

Mason, J.T., Xu, L., Sheng, Z.M., He, J. & O'Leary, T.J. Liposome polymerase chain reaction assay for the sub-attomolar detection of cholera toxin and botulinum neurotoxin type A. *Nature Protocols* 1, 2003-2011 (2006).

Melling, J., Hambleton, P. & Shone, C.C. *Clostridium botulinum* toxins: nature and preparation for clinical use. *Eye* 2 ( Pt 1), 16-23 (1988).

Miyawaki, A. Bringing bioluminescence into the picture. *Nat Methods* 4, 616-617 (2007).

Mukherjee, J., et al., "A Novel Strategy for Development of Recombinant Antitoxin Therapeutics Tested in a Mouse Botulism Model," PLoS One 7(1):e29941, doi:10.1371/journal.pone.0029941.

Partikian, A., et al., "Iatrogenic Botulism in a Child with Spastic Quadriparesis," J. Child Neurol. 22:1235-1237 (2007).

Paulmurugan, R. et al. Combinatorial library screening for developing an improved split-firefly luciferase fragment-assisted complementation system for studying protein-protein interactions. *Anal Chem* 79, 2346-2353 (2007).

Paulmurugan, R. et al. Firefly luciferase enzyme fragment complementation for imaging in cells and living animals. *Anal Chem* 77, 1295-1302 (2005).

Ravichandran, E. et al. An initial assessment of the systemic pharmacokinetics of botulinum toxin. *J Pharmacol Exp Ther* 318,1343-1351 (2006).

Rosse, G.E. et al. Rapid identification of substrates for novel proteases using a combinatorial peptide library. *J Comb Chem* 2, 461-466 (2000).

Sakaguchi, G. *Clostridium botulinum* toxins. *Pharmacol Ther* 19, 165-194 (1982).

Schantz, E.J. & Johnson, E.A. Properties and use of botulinum toxin and other microbial neurotoxins in medicine. *Microbiol Rev* 56, 80-99 (1992).

Schantz, E. J., et al., "Microbiological Methods: Standardized Assay for *Clostridium botulinum* Toxins," J. AOAC 61(1):96-99 (1978).

Schiavo, G. et al. Botulinum neurotoxins serotypes A and E cleave SNAP-25 at distinct COOH-terminal peptide bonds. *FEBS Lett* 335, 99-103 (1993).

Schiavo, G., et al., "Tetanus and Botulinum-B Neurotoxins Block Neurotransmitter Release by Proteolytic Cleavage of Synaptobrevin," Nature 359:832-835 (1992).

Schiavo, G. et al. Identification of the nerve terminal targets of botulinum neurotoxin serotypes A, D, and E. *J Biol Chem* 268, 23784-23787 (1993).

Schiavo, G., Matteoli, M. & Montecucco, C. Neurotoxins affecting neuroexocytosis. *Physiol Rev* 80, 717-766 (2000).

Schmidt, J.J. & Stafford, R.G. Fluorigenic substrates for the protease activities of botulinum neurotoxins, serotypes A, B, and F. *Appl Environ Microbiol* 69, 297-303 (2003).

Sharma, S.K., Ferreira, J.L., Eblen, B.S. & Whiting, R.C. Detection of type A, B, E, and F *Clostridium botulinum* neurotoxins in foods by using an amplified enzyme-linked immunosorbent assay with digoxigenin-labeled antibodies. *Appl Environ Microbiol* 72, 1231-1238 (2006).

Sharma, S.K., Ramzan, M.A. & Singh, B.R. Separation of the components of type A botulinum neurotoxin complex by electrophoresis. *Toxicon* 41, 321-331 (2003).

Simpson, L.L. et al. The role of zinc binding in the biological activity of botulinum toxin. *J Biol Chem* 276, 27034-27041 (2001).

Simpson, L. L., "The Origin, Structure, and Pharmacological Activity of Botulinum Toxin," Pharmacol. Rev. 33(3):155-188 (1981).

Smith, L.D. The occurrence of *Clostridium botulinum* and *Clostridium tetani* in the soil of the United States. *Health Lab Sci* 15, 74-80 (1978).

Sobel, J., et al., "Foodborne Botulism in the United States, 1990-2000," Emerging Infectious Diseases 10(9):1606-1611 (2004).

Sugiyama, H., "*Clostridium botulinum* Neurotoxin," Microbiol. Rev. 44(3):419-448 (1980).

Tremblay, J. M., et al., "Camelid Single Domain Antibodies (VHHs) as Neuronal Cell Intrabody Binding Agents and Inhibitors of *Clostridium botulinum* Neurotoxin (BoNT) Proteases," Toxicon. 56(6):990-998 (2010).

Varnum, S. M., et al., "Enzyme-Amplified Protein Microarray and a Fluidic Renewable Surface Fluorescence Immunoassay for Botulinum Neurotoxin Detection Using High-Affinity Recombinant Antibodies," Anal. Chimica Acta 570:137-143 (2006).

Volknandt, W., "The Synaptic Vesicle and Its Targets," Neuroscience 64(2):277-300 (1995).

Walsh, T.J. et al. Tissue homogenization with sterile reinforced polyethylene bags for quantitative culture of *Candida albicans. J Clin Microbiol* 25, 931-932 (1987).

Wein, L.M. & Liu, Y. Analyzing a bioterror attack on the food supply: the case of botulinum toxin in milk. *Proc Natl Acad Sci U S A* 102, 9984-9989 (2005).

Werner, S. B., et al., "Wound Botulism in California, 1951-1998: Recent Epidemic in Heroin Injectors," Clin. Infect. Dis. 31:1018-1024 (2000).

Witcome, M., et al., "Development of In Vitro Assays for the Detection of Botulinum Toxins in Foods," *FEMS Immunol. Med. Microbiol.* 24:319-323 (1999).

Zhang, L., Lin, W.J., Li, S. & Aoki, K.R. Complete DNA sequences of the botulinum neurotoxin complex of *Clostridium botulinum* type A-Hall (Allergan) strain. *Gene* 315, 21-32 (2003).

\* cited by examiner

*Primary Examiner* — Albert Navarro
*Assistant Examiner* — Ginny Portner
(74) *Attorney, Agent, or Firm* — Perkins Coie LLP

(57) ABSTRACT

Provided herein is a large immuno-sorbent surface area assay (ALISSA) for the rapid and sensitive detection of botulinum neurotoxins (BoNTs) and anthrax toxin. This assay is designed to capture a low number of toxin molecules and to measure their intrinsic protease activity via conversion of a fluorogenic or luminescent substrate. Also provided herein are novel peptides that can be specifically cleaved by BoNT and novel peptides that are resistant to cleavage by BoNT. The combination of these cleavable and control peptides can be used for implementation of an exemplary ALISSA used to specifically detect BoNT enzymatic activity. Furthermore, the ALISSA as described herein may also be used in a column based format for use in a high-throughput system for testing large quantities of samples.

21 Claims, 71 Drawing Sheets

[Graph: RFU vs [BoNT/A complex], mol/L, with x-axis from $10^{-9}$ to $10^{-17}$ and y-axis from 0 to 200k]

B

[Bar graph: RFU with conditions BoNT/A: −/+/−/+ and Horse abs: −/−/+/+]

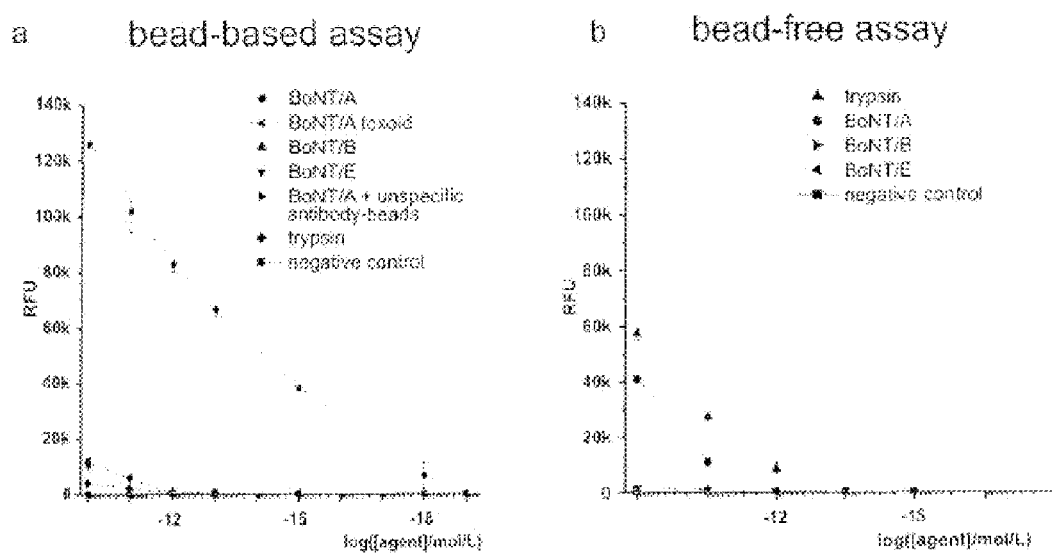
FIGURES 10A and B

FIGURE 11 captured botulinum toxin — bead surface — reporter molecules chemical anchor antibody toxin-reacted reporter molecules give fluorescent signal

A
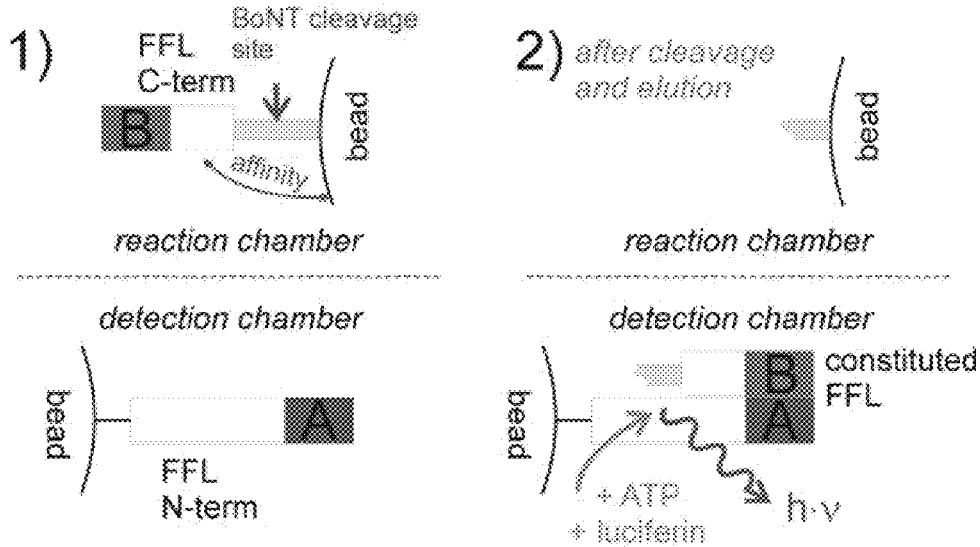
B
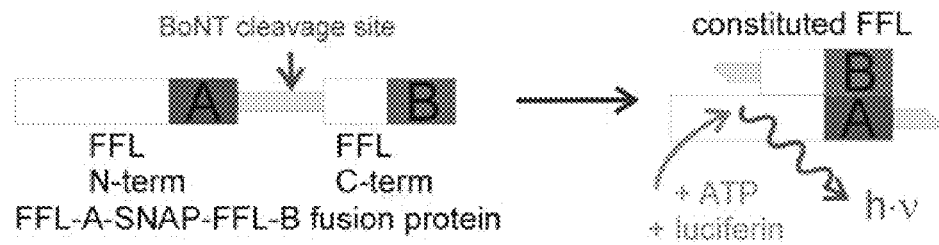
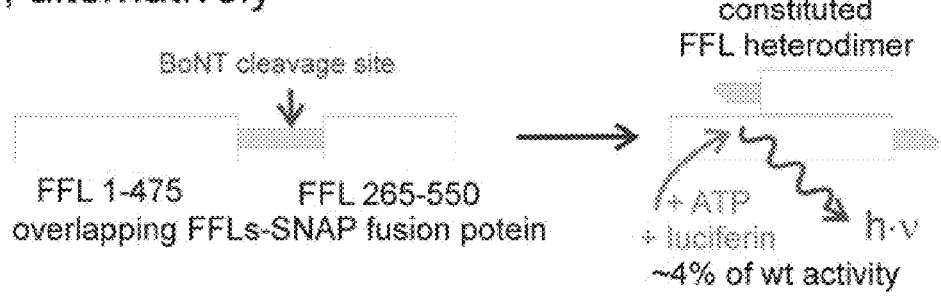
FIGURE 26

Controls

FFLSH + BoNT → incubate

FFLSH → incubate → add Ni-NTA beads, incubate, separate → supernatant, beads

↓ ↓ ↓
add ONE-Glo and measure luminescence
1  2  3

Cleavage Assay

FFLSH + BoNT → incubate → add Ni-NTA beads, incubate, separate → supernatant, beads ↓ ↓
add ONE-Glo and measure luminescence

| Final concentration of calibration peptide (μM) | Volume of 1.0 μM calibration peptide (μL) | Volume of reaction buffer (μL) |
|---|---|---|
| 0.5000 | 500 | 500 |
| 0.2000 | 200 | 800 |
| 0.1000 | 100 | 900 |
| 0.0500 | 50 | 950 |
| 0.0250 | 25 | 975 |
| 0.0125 | 10 | 990 |
| 0.0000 | 0 | 220 |

FIGURE 38

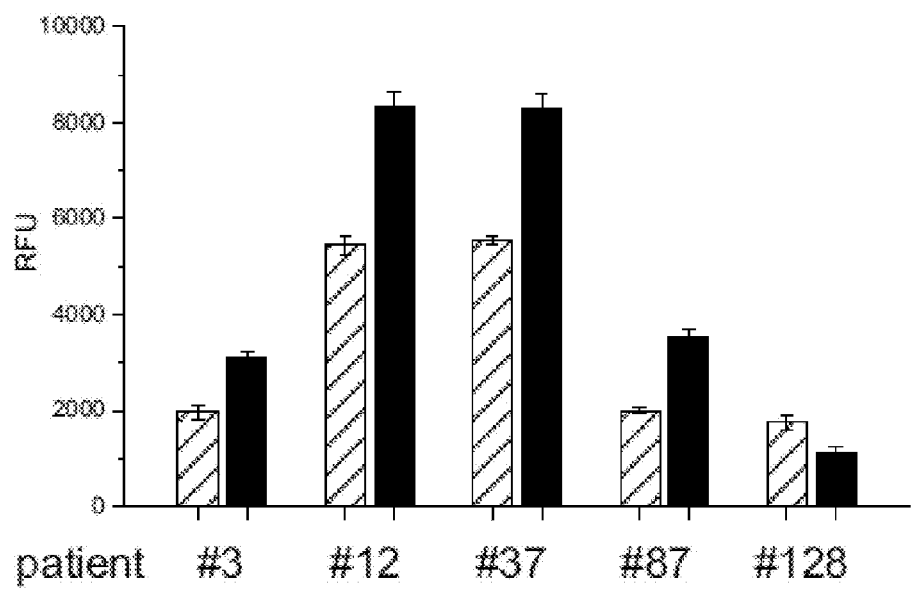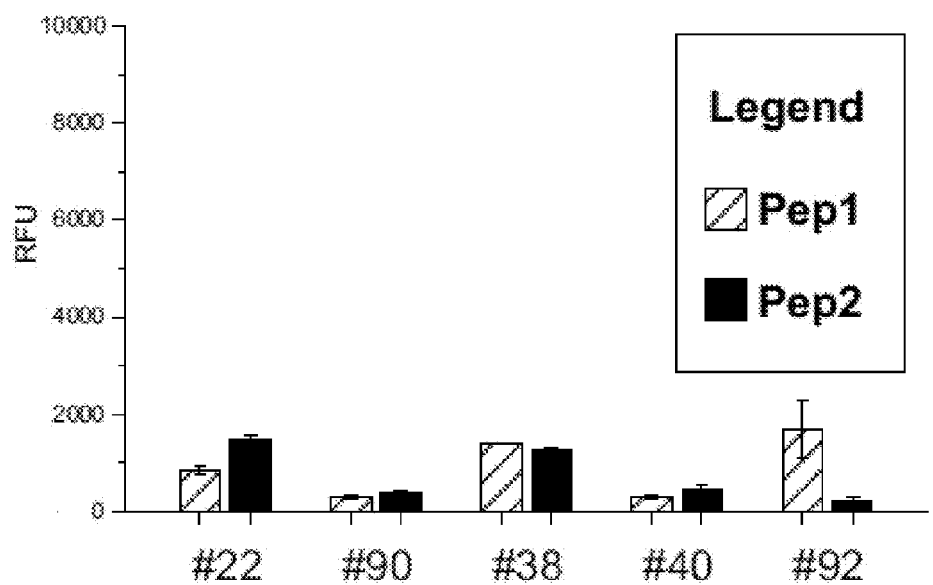
FIGURE 40

FIGURE 41

1. Preparation of antibody-coupled beads
Porous Beads
↓
5A20.4 anti Lca mAb

2. Immunocapturing of BoNT/A complex.

serum from intoxicated mice

3. Enzymatic reaction.

BoNT/A-cleavable  Controls

|                                          | Intravenous (I.V.) injection |        |      | Administration by gavage (I.G.) |       |    |    |
|------------------------------------------|:---:|:---:|:---:|:---:|:---:|:---:|:---:|
|                                          | Group I | | | Group II | Group III | | |
| Amount of BoNT/A complex per mouse:       | 100 pg | 20 pg | 4 pg | 100 pg | 4 µg | | |
| Time of blood withdrawal after intoxication: | | 1h | | 1h  3h  5h  7h | 2h | 5h | 7h |

Intoxicated primary neuronal cells    Non-treated primary neuronal cells
↓
Medium from cells collected and saved
↓
Cells detached by adding 0.5 mL of ice-cold → slides washed twice
5 mM HEPES, pH 7.4                         with 5 mM HEPES, pH 7.4,
and rotated for 30 min at 22°C to induce hypoosmotic stress
↓                                         ↓   ↓
                                         wash I  wash II
Centrifuged at 13,000 x g for 30 min
↓
Lysed with 0.5 mL of ice-cold cell lysis buffer (no EDTA)
(0.025M Tris, 0.15M NaCl, 1% NP-40, 5% glycerol, pH 7.4)
↓
Incubated on ice for 45 minutes
↓
The lysate transferred to a 1.5 mL microcentrifuge tube and
centrifuged at 13,000 x g for 25 minutes to pellet the cell debris
↓   ↓
cell extract   pellet, re-suspended in cell lysis buffer
↓
BoNT/A1 ALISSAs with 5A20.4, anti-LCa mAb

FIGURE 47

A. 20 nM toxin in high K⁺ medium

B. ALISSA with cell intoxication and wash media

High K⁺ buffer:
- 20 nM BoNT/A1
- wash medium

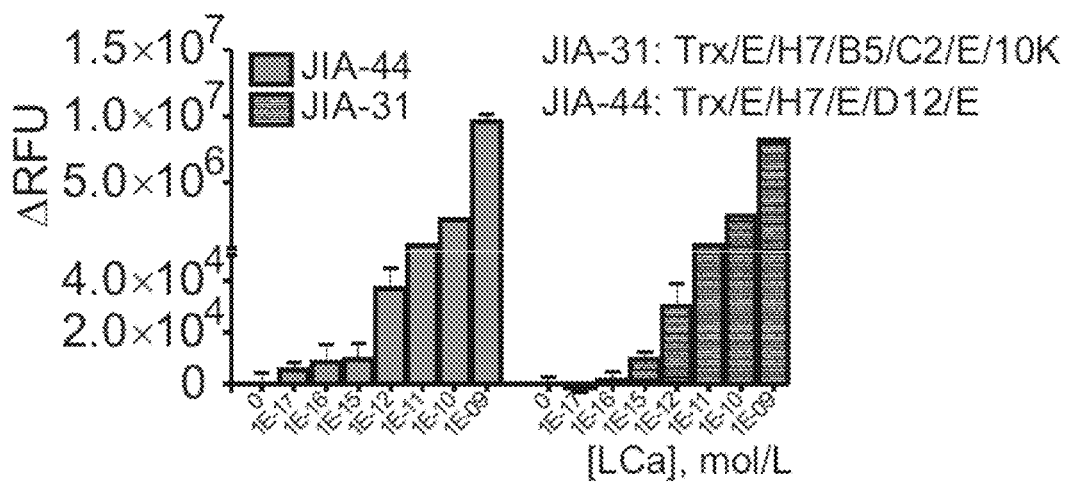
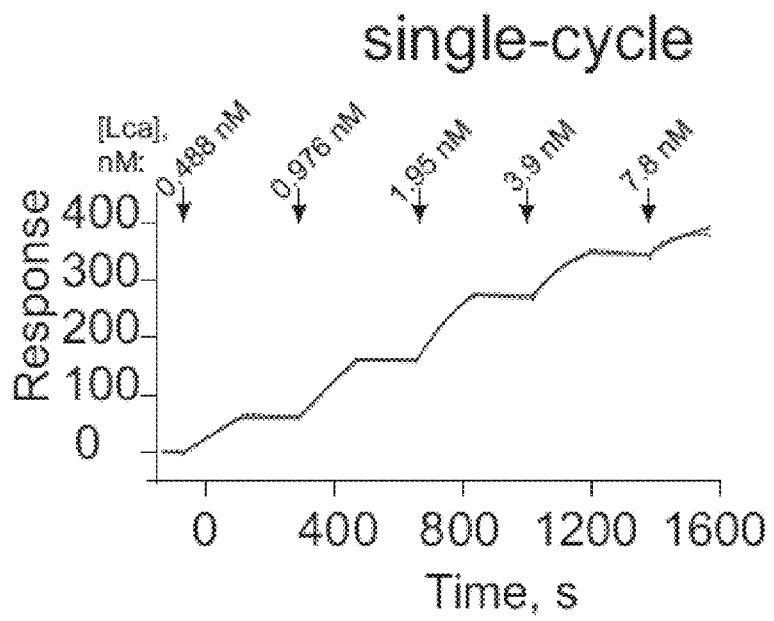
FIGURE 53

A
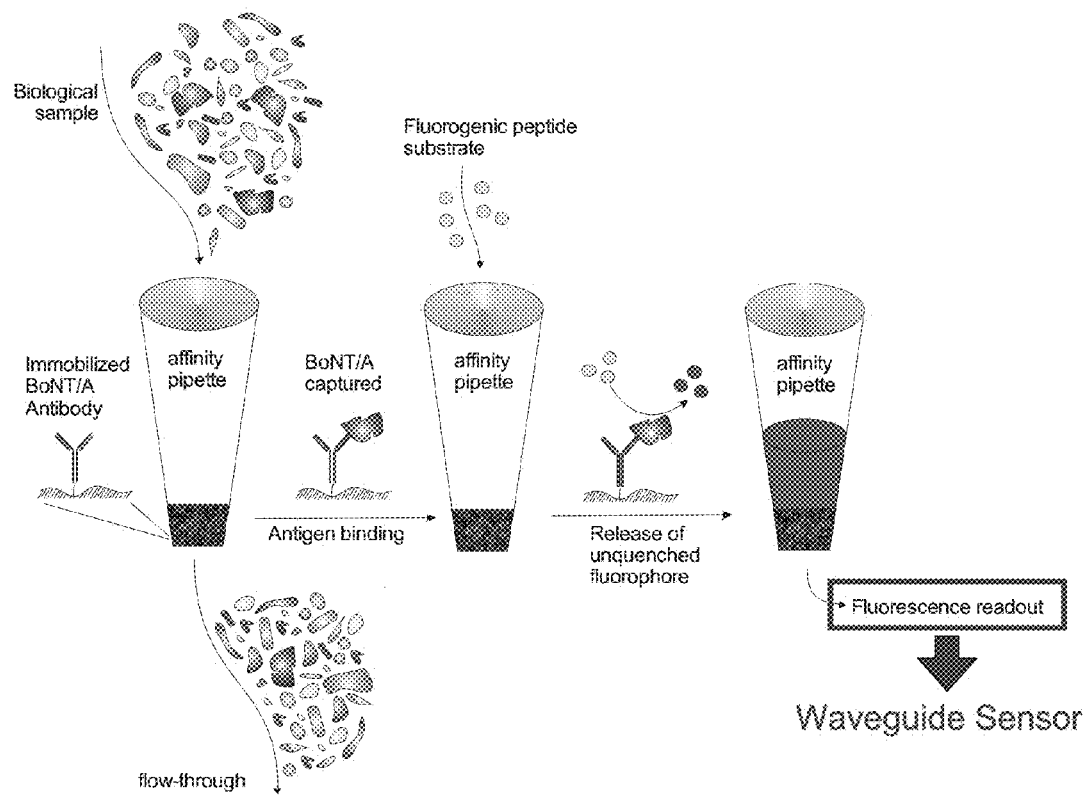
B
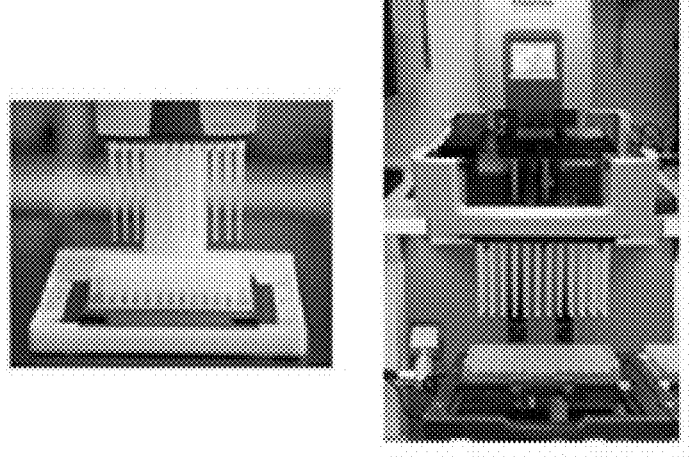
FIGURE 56

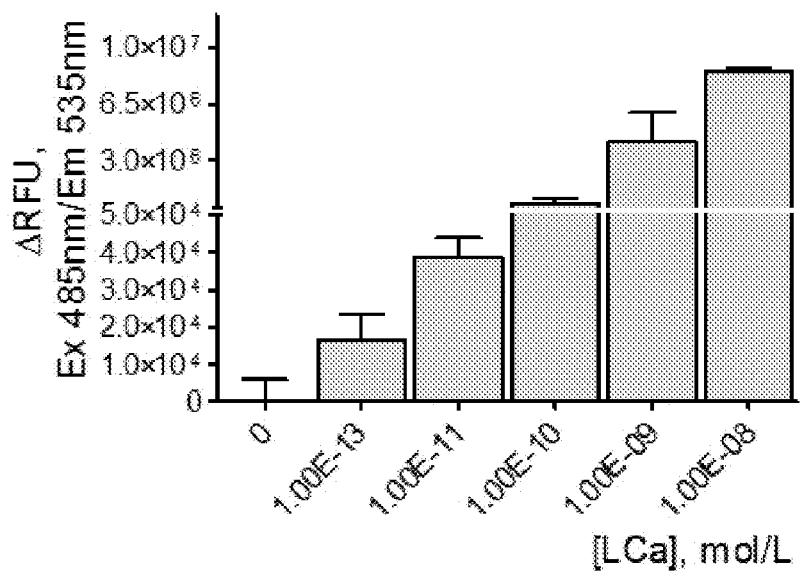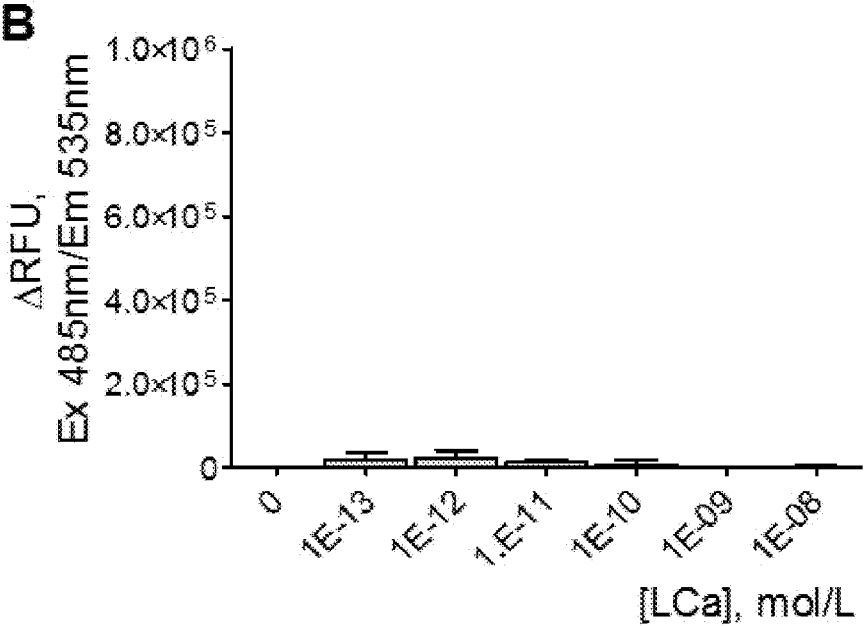
FIGURES 57A and B

FFL[1-478] SNAP25(part) FFL[265-550]-histag (SEQ ID NO: 3)

atggaagacgccaaaaacataaagaaaggcccggcgccattctatcctctagaggatggaaccgctggagagcaact
gcataaggctatgaagagatacgccctggttcctggaacaattgcttttacagatgcacatatcgaggtgaacatcacgta
cgcggaatacttcgaaatgtccgttcggttggcagaagctatgaaacgatatgggctgaatacaaatcacagaatcgtcgt
atgcagtgaaaactctcttcaattctttatgccggtgttgggcgcgttatttatcggagttgcagttgcgcccgcgaacgacattt
ataatgaacgtgaattgctcaacagtatgaacatttcgcagcctaccgtagtgtttgtttccaaaaaggggttgcaaaaaattt
tgaacgtgcaaaaaaaattaccaataatccagaaaattattatcatggattctaaaacggattaccagggatttcagtcgat
gtacacgttcgtcacatctcatctacctcccggttttaatgaatacgattttgtaccagagtcctttgatcgtgacaaaacaattg
cactgataatgaattcctctggatctactgggttacctaagggtgtggcccttccgcatagaactgcctgcgtcagattctcgc
atgccagagatcctattttggcaatcaaatcattccggatactgcgattttaagtgttgttccattccatcacggttttggaatgtt
tactacactcggatatttgatatgtggatttcgagtcgtcttaatgtatagatttgaagaagagctgttttacgatcccttcagga
ttacaaaattcaaagtgcgttgctagtaccaaccctatttcattcttcgccaaaagcactctgattgacaaatacgatttatcta
atttacacgaaattgcttctgggggcgcacctctttcgaaagaagtcggggaagcggttgcaaaacgcttccatcttccagg
gatacgacaaggatatgggctcactgagactacatcagctattctgattacacccgagggggatgataaaccgggcgcg
gtcggtaaagttgttccattttttgaagcgaaggttgtggatctggataccgggaaaacgctgggcgttaatcagagaggcg
aattatgtgtcagaggacctatgattatgtccggttatgtaaacaatccggaagcgaccaacgccttgattgacaaggatgg
atggctacattctggagacatagcttactgggacgaagacgaacacttcttcatagttgaccgcttgaagtctttaattaaata
caaaggatatcaggtggcccccgctgaattggaatcgatattgttacaacaccccaacatcttcgacgcgggcgtggcag
gtcttcccgacgatgacgccggg**AGCAACAAAACCCGTATTGATGAAGCGAACCAGCGTGC
GACCAAAATGCTG**atgtatagatttgaagaagagctgttttacgatcccttcaggattacaaaattcaaagtgcgtt
gctagtaccaaccctatttcattcttcgccaaaagcactctgattgacaaatacgatttatctaatttacacgaaattgcttctg
ggggcgcacctctttcgaaagaagtcggggaagcggttgcaaaacgcttccatcttccagggatacgacaaggatatgg
gctcactgagactacatcagctattctgattacacccgagggggatgataaaccgggcgcggtcggtaaagttgttccatttt
ttgaagcgaaggttgtggatctggataccgggaaaacgctgggcgttaatcagagaggcgaattatgtgtcagaggacct
atgattatgtccggttatgtaaacaatccggaagcgaccaacgccttgattgacaaggatggatggctacattctggagac
atagcttactgggacgaagacgaacacttcttcatagttgaccgcttgaagtctttaattaaatacaaaggatatcaggtggc
ccccgctgaattggaatcgatattgttacaacaccccaacatcttcgacgcgggcgtggcaggtcttcccgacgatgacgc
cggtgaacttcccgccgccgttgttgttttggagcacggaaagacgatgacggaaaaagagatcgtggattacgtcgcca
gtcaagtaacaaccgcgaaaaagttgcgcggaggagttgtgtttgtggacgaagtaccgaaaggtcttaccggaaaact
cgacgcaagaaaaatcagagagatcctcataaaggccaagaagggcggaaagtccgagttg*ctcgagcaccacca
ccaccaccactga*

FIGURE 58

FFL[1-478] SNAP25(part) FFL[265-550]-histag (SEQ ID NO: 4)

MEDAKNIKKGPAPFYPLEDGTAGEQLHKAMKRYALVPGTIAFTDAHIEVNITYAEYFEM
SVRLAEAMKRYGLNTNHRIVVCSENSLQFFMPVLGALFIGVAVAPANDIYNERELLNSM
NISQPTVVFVSKKGLQKILNVQKKLPIIQKIIIMDSKTDYQGFQSMYTFVTSHLPPGFNEY
DFVPESFDRDKTIALIMNSSGSTGLPKGVALPHRTACVRFSHARDPIFGNQIIPDTAILSV
VPFHHGFGMFTTLGYLICGFRVVLMYRFEEELFLRSLQDYKIQSALLVPTLFSFFAKSTL
IDKYDLSNLHEIASGGAPLSKEVGEAVAKRFHLPGIRQGYGLTETTSAILITPEGDDKPG
AVGKVVPFFEAKVVDLDTGKTLGVNQRGELCVRGPMIMSGYVNNPEATNALIDKDGW
LHSGDIAYWDEDEHFFIVDRLKSLIKYKGYQVAPAELESILLQHPNIFDAGVAGLPDDDA
GSNKTRIDEANQRATKMLMYRFEEELFLRSLQDYKIQSALLVPTLFSFFAKSTLIDKYDL
SNLHEIASGGAPLSKEVGEAVAKRFHLPGIRQGYGLTETTSAILITPEGDDKPGAVGKV
VPFFEAKVVDLDTGKTLGVNQRGELCVRGPMIMSGYVNNPEATNALIDKDGWLHSGDI
AYWDEDEHFFIVDRLKSLIKYKGYQVAPAELESILLQHPNIFDAGVAGLPDDDAGELPA
AVVVLEHGKTMTEKEIVDYVASQVTTAKKLRGGVVFVDEVPKGLTGKLDARKIREILIKA
KKGGKSEL*LEHHHHHH**

FIGURE 59

Full Length SNAP-25 (SEQ ID NO: 11)

MAEDADMRNELEEMQRRADQLADESLESTRRMLQLVEESKDAGIRTLVMLDEQGEQL
ERIEEGMDQINKDMKEAEKNLTDLGKFCGLCVCPCNKLKSSDAYKKAWGNNQDGVVA
SQPARVVDEREQMAISGGFIRRVTNDARENEMDENLEQVSGIIGNLRHMALDMGNEID
TQNRQIDRIMEKADSNKTRIDEANQRATKMLGSG

FIGURE 60

"FFL-L1SL2TAH": FFL[1-550]-L1[G_4SG_4]-SNAP25*[171-206]* -L2[G_6]- T[ENLYFQG]-A[K_{8-10}+GLE]-histag[*H6*) (SEQ ID NO:25)

MEDAKNIKKGPAPFYPLEDGTAGEQLHKAMKRYALVPGTIAFTDAHIEVNITYAEYFEM
SVRLAEAMKRYGLNTNHRIVVCSENSLQFFMPVLGALFIGVAVAPANDIYNERELLNSM
NISQPTVVFVSKKGLQKILNVQKKLPIIQKIIIMDSKTDYQGFQSMYTFVTSHLPPGFNEY
DFVPESFDRDKTIALIMNSSGSTGLPKGVALPHRTACVRFSHARDPIFGNQIIPDTAILSV
VPFHHGFGMFTTLGYLICGFRVVLMYRFEEELFLRSLQDYKIQSALLVPTLFSFFAKSTL
IDKYDLSNLHEIASGGAPLSKEVGEAVAKRFHLPGIRQGYGLTETTSAILITPEGDDKPG
AVGKVVPFFEAKVVDLTGKTLGVNQRGELCVRGPMIMSGYVNNPEATNALIDKDGW
LHSGDIAYWDEDEHFFIVDRLKSLIKYKGYQVAPAELESILLQHPNIFDAGVAGLPDDDA
GELPAAVVVLEHGKTMTEKEIVDYVASQVTTAKKLRGGVVFVDEVPKGLTGKLDARKI
REILIKAKKGGKSKL<u>GGGGSGGGG</u>*IDTQNRQIDRIMEKADSNKTRIDEANQRATKMLG
S*<u>GGGGGGG</u>ENLYFQGKKKKKKK(KK)GLE*HHHHHH**\*

FIGURE 61

Full Length Firefly Luciferase "FFL" (SEQ ID NO: 26)

MEDAKNIKKGPAPFYPLEDGTAGEQLHKAMKRYALVPGTIAFTDAHIEVNITYAEYFEM
SVRLAEAMKRYGLNTNHRIVVCSENSLQFFMPVLGALFIGVAVAPANDIYNERELLNSM
NISQPTVVFVSKKGLQKILNVQKKLPIIQKIIIMDSKTDYQGFQSMYTFVTSHLPPGFNEY
DFVPESFDRDKTIALIMNSSGSTGLPKGVALPHRTACVRFSHARDPIFGNQIIPDTAILSV
VPFHHGFGMFTTLGYLICGFRVVLMYRFEEELFLRSLQDYKIQSALLVPTLFSFFAKSTL
IDKYDLSNLHEIASGGAPLSKEVGEAVAKRFHLPGIRQGYGLTETTSAILITPEGDDKPG
AVGKVVPFFEAKVVDLDTGKTLGVNQRGELCVRGPMIMSGYVNNPEATNALIDKDGW
LHSGDIAYWDEDEHFFIVDRLKSLIKYKGYQVAPAELESILLQHPNIFDAGVAGLPDDDA
GELPAAVVVLEHGKTMTEKEIVDYVASQVTTAKKLRGGVVFVDEVPKGLTGKLDARKI
REILIKAKKGGKSKL

FIGURE 62

Octa-lysine Anchor Peptide "Anchor ($K_8$+GLE)" (SEQ ID NO: 30)

K,K,K,K,K,K,K,K,G,L,E

Deca-lysine Anchor Peptide "Anchor ($K_{10}$+GLE)" (SEQ ID NO: 31)

K,K,K,K,K,K,K,K,K,K,G,L,E

Polyhistadine Tag "Histidine Tag ($H_6$)" (SEQ ID NO: 32)

H,H,H,H,H,H

Tobacco Etch Virus Protease Cleavage Site (SEQ ID NO: 33)

ENLYFQG

Serine-Glycine Linker 1 "Linker 1 (G4SG4)" (SEQ ID NO: 34)

G,G,G,G,S,G,G,G,G

Serine-Glycine Linker 2 "Linker 2(G6)" (SEQ ID NO: 35)

METHODS FOR DETECTION OF BOTULINUM NEUROTOXIN

PRIORITY CLAIM

This application is a continuation-in-part of U.S. patent application Ser. No. 13/306,769, filed Nov. 29, 2011; which is a divisional U.S. patent application Ser. No. 12/134,092, filed Jun. 5, 2008, now issued as U.S. Pat. No. 8,067,192; which claims the benefit of U.S. Provisional Patent Application Ser. No. 60/942,199, filed Jun. 5, 2007, all of which are incorporated herein by reference.

GOVERNMENT INTEREST

The present invention was supported by National Institutes of Health grant AI-65359. The government may have certain rights in the present invention.

BACKGROUND

Botulinum neurotoxins (BoNTs) are important medical and cosmetic agents, used to treat dystonias, blepharospasms, hyperhidrosis, and other neurological diseases. However, BoNTs also represent the most toxic substances known and their potential abuse as a threat agent is feared (Arnon 2001; Wein 2005). The detection of Botulinum neurotoxin (BoNT) in complex samples such as foods or clinical specimens represents an analytical challenge. The current "gold standard" in the art for detecting BoNT is the mouse toxicity assay, which can detect as little as 10 pg BoNT (Ferreira 2003). However, BoNT can be lethal to humans in systemic doses as low as 1 to 2 ng/Kg body weight (Arnon 2001). Therefore, there is a need in the art for more sensitive assays for detecting the presence of BoNT in a sample.

BoNTs have gained popularity as cosmetic drugs, and have also been successfully used for the treatment of a variety of neurological and neuromuscular disorders (Schantz 1992; Johnson 1999). Products containing BoNT are approved for the medical treatment of several diseases, i.e. cervical dystonia, torticolis, blepharospasm, hyperhydrosis, strabismus and migraines. Further, the products BOTOX COSMETICS®, VISTABEL®, BOCOUTURE® and AZZALURE® are licensed as an anti-wrinkle treatment. With the ever-increasing medical use of BoNT, its sensitive and specific detection in manufacturing processes as well as clinical research laboratories is of crucial importance. Accordingly, the potency of each batch of BoNT must be determined by the manufacturer before release to ensure the safety and efficacy of the product. This testing is widely performed using the classical mouse LD50 assay, which measures the potency of each batch of the product by determining the dose that will kill 50 percent of the animals. Animal testing for each batch of BoNT is expensive, slow, provides limited throughput, and requires sacrificing animals. Also, because of the lack of a standardized testing procedure, the units of biological activity are often unable to be directly converted into precise doses for human use, and overtreatment with BoNTs can cause iatrogenic forms of botulism (Partikian 2007; Crowner 2007). Thus, there is a need for an alternative method for testing products containing BoNT that is more efficient and cost effective.

Natural BoNT resides within ~300, 500 or 900-kDa protein complexes together with other non-toxic components, the neurotoxin associated proteins (NAPs) (Sakaguchi 1982; Chen 1998; Sharma 2003; Melling 1988; Zhang 2003; Aoki 2001). Several structurally distinct serotypes of BoNT (types A to G) have been discovered. BoNT Type A (BoNT/A) is most prevalent in the Western United States (Smith 1978) and is causatively involved in approximately 60% of the IB cases in California (the rest being mostly attributed to type B) (Arnon 2001). The toxin itself is a 150-kDa zinc-binding metalloprotease that, following expression, is endogenously cleaved into a 100-kDa heavy and a 50-kDa light chain connected by a reducible disulphide bond (Schiavo 2000) and by a belt-like extension of the heavy chain that loops around the light chain (Lacy 1998). The catalytic site is located on the light chain (Kurazono 1992). Reduction of the chain-bridging disulphide bond exposes the catalytic site and enhances its activity (Lacy 1998), also referred to as "activation" of the toxin by some authors and toxin manufacturers (Cai 1999; Cai 2001). The potency of BoNT results from its ability to cleave on or more of the three SNARE proteins involved in fusing acetylcholine-containing synaptic vesicles with terminal motor neurons membrane, triggering muscle contraction (Shiavo 2000).

Detection of low levels of BoNT in a sample using prior art methods is difficult. However, due to the enormous potency of the toxin, which can be lethal for humans in systemic doses of 1 to 2 ng/Kg body weight (Arnon 2001), these low levels can be extremely dangerous. For example, in infant botulism (IB), a condition in which a baby's intestines have become colonized by toxin-secreting *Clostridium botulinum* bacteria, it is possible to detect BoNT in stool samples (Arnon 2006). However, attempts to diagnose IB serologically via detection of BoNT in the blood have been deemed unreliable (Schantz 1992). Nevertheless, the systemic presence of the toxin in IB cannot be disputed, because of its apparent quick distribution throughout the infant's entire body, by which it efficiently shuts down motor neurons distant from the intestinal source. The resulting symptoms can include complete paralysis and respiratory failure.

The definite diagnosis of botulism requires detection of BoNTs in clinical specimens. Most commonly used and relied on is the life mouse assay. This assay can detect as little as 10 pg BoNT (Ferreira 2003). In the life mouse assay, mice are injected intraperitoneally (i.p.) with 0.5 mL/mouse of sample, treated with type A or B antitoxin, and observed for signs of botulism or death, typically over a 48 hour period. Toxicity is expressed by the number of hours until death (Kautter 1977; Sharma 2006). As in many animal experiments, the results of the mouse assay may vary. Four- to five-fold differences in response to a given dose are typical (Sugiyama 1980). Other and generally faster methods for BoNT detection include use of fluorescence resonance energy transfer (FRET) substrates for BoNT (U.S. Pat. No. 6,504,006), various enzyme-linked immunosorbent assays (ELISAs) (Sharma 2006), Enzyme-amplified protein micro arrays with a "fluidic renewable surface fluorescence immunoassay" (Varnum 2006), mass spectrometric assays (Barr 2005; Kalb 2005; Boyer 2005; Kalb 2006), immuno-PCR detection (Chao 2004), and recently, a real-time PCR-based assay that utilizes reporter DNA-filled liposomes which bind to immobilized BoNT/A via gangliosides (Mason 2006a; Mason 2006b). Reported detection limits and sample types for these various methods are summarized in Table 1. Except for the PCR-based assays, most assays are not well suited to provide the desired detection of less than 1 pg/mL BoNT in a complex sample. By approximation, 1 pg/mL corresponds to the lethal concentration under presumed equal distribution throughout the human body.

TABLE 1

Reported performance of existing Botulinum toxin assays

| Test method | Demonstrated for Sample Type | Sensitivity (fg/mL) | Assay Time |
|---|---|---|---|
| Mass spectrometry (Endopep-MS)[22-25] | milk, serum, stool extract | 320,000 | <4 hrs |
| Enzyme-linked immunosorbent assays (ELISA)[19] | liquid and solid foods, serum | 60,000 | 6-8 hrs |
| ELISA-HRP[29] | therapeutic preparations | 9,000 | 4-6 hrs |
| Mouse assay (gold standard)[18] | foods, serum, stool | ~6,000 | typically 48 hrs |
| Enzyme-amplified protein microarray and fluidic renewable surface fluorescence immunoassay[21] | blood, plasma | 1,400 | <10 min. per measurement |
| Immuno-PCR[26] | carbonate buffer | 50 | 4-6 hrs |
| Immuno-PCR with ganglioside-mediated liposome capture[27, 28] | deionized water | 0.02 | 6 hrs |

Anthrax lethal factor (LF) is another zinc metalloprotease that has been successfully been adapted for use in the ALISSA. LF constitutes one of the three components of anthrax toxin that is produced by *Bacillus anthracis*, together with protective antigen (PA) and edema factor (EF) (Brossier 2001). LF specifically cleaves members of the mitogen-activated protein kinase kinase (MAPKK) family, leading to the inhibition of essential signaling pathways. LF alone is not toxic; it requires the presence of PA for its translocation into cells (Brossier 2001). Macrophages are believed to be primarily affected by LF (Hanna 1993). A specific and sensitive assay for the detection of LF is potentially useful for early diagnosis of anthrax infection and is expected to be a useful research tool to advance the understanding of the mechanism of action of anthrax toxin (Boyer 2007).

SUMMARY

Methods are provided for detection of BoNT in complex biological samples with high sensitivity and specificity. In certain of these embodiments, the methods are based on specific affinity enrichment of a target toxin or target enzyme ("target") onto a solid support followed by fluorometric or luminescent readout. In certain of these embodiments, the assays have a sensitivity of at least about 0.5 femtograms target per one mL sample or about 300 target molecules per sample. In certain of these embodiments, the solid support is a bead matrix that contains immobilized, anti-enzyme-specific antibodies and/or anti-toxin-specific antibodies. In other embodiments, binding (also referred to as "capturing") and/or immobilization of the target toxin or enzyme is such that the toxin's or enzyme's activity on its substrate is accelerated. Products and methods may increase enzymatic activity and/or turnover rate when the enzyme is preconjugated to the bead. Such modifications may further allow for enhanced sensitivity and speed of the assay.

In certain embodiments, binding and/or immobilization of the target toxin or enzyme is achieved without resulting in inactivation or reduction of the target activity on its substrate. For example, antibodies may be BoNT-specific antibodies that bind BoNT but do not inactivate BoNT-specific enzymatic activity. In certain embodiments, antibodies may specifically target the catalytic BoNT light chains and bind the BoNT light chain without significantly inhibiting BoNT enzymatic activity. Also, antibodies may be BoNT-specific antibodies that bind BoNT such that the BoNT activity is accelerated.

In certain of these embodiments, the fluorometric readout is based on specific cleavage of a fluorogenic substrate. For example, BoNT-specific cleavage of a fluorogenic BoNT substrate such as the SNAPtide described in U.S. Pat. No. 6,504,006 as well as other coumarin derivatives is useful in certain embodiments. Additional suitable substrates include various soluble NSF attachment protein receptor (SNARE), or one or more fluorogenic toxin or enzyme peptide substrate.

The methods provided herein may be used to detect BoNT type A, B, C, D, E, F, and/or G, or their subtypes. In certain embodiments, methods are provided for detection of BoNT serotypes including subtypes with attomolar sensitivity. The assays include use of a BoNT serotype A assay with a large immuno-sorbent surface area (BoNT/A ALISSA) that has attomolar sensitivity in biological samples such as complex samples, serum and liquid foods.

In other embodiments, luminescent based readout assays are provided for detection of BoNT. The methods include use of bioluminescent BoNT/A and BoNT/B substrates including novel engineered variants of recombinant luciferase proteins. In some embodiments, the bioluminescent substrates include serine-glycine and glycine linkers to optimize the turnover rate for BoNT cleavage of the substrates. In certain embodiments, bioluminescent assays include use of luminescent proteins able to emit light at multiple wavelengths for multiplexed simultaneous detection of one or more serotype.

In certain embodiments, the methods and assays include development and use of novel fluorogenic or bioluminescent substrates for toxin or enzyme detection. Such novel substrates include those having resistance to non-BoNT proteases while remaining cleavable by the target toxin or enzyme. The novel substrates may include fluorogenic synthetic peptides that can be cleaved by the BoNT/A or BoNT/B light chain independent of the BoNT heavy chain. In certain of these embodiments, these fluorogenic substrates can also be used as a toxin-free positive control for the implementation of an assay used to detect BoNT enzymatic activity.

The methods and assays provided are broadly useful and as such may be used to detect a wide variety of toxins and/or other enzymes such as anthrax lethal factor, human chitinases (e.g. CHIT1 or AMCase) and proteases such as fungal protease Pep1 and Pep2 from *Aspergillus fumigatus*, and other toxins exhibiting zinc metalloprotease activity, among other enzyme targets. The assay with a large immuno-sorbent surface area (ALISSA) methods may be expanded for use in detection of any toxin or enzyme including all BoNT serotypes.

The systems, methods and kits provided herein may be used to detect and/or measure toxin or enzyme levels in a variety of samples. In certain embodiments, the methods may be used to measure toxin or enzyme distribution in systemic circulation, in a biological fluid sample, cell, tissue and/or organ of an animal or human. The sensitivity, specificity, speed and simplicity of the methods provided herein are particularly useful for diagnostic, biodefense and pharmacological applications.

In other embodiments, the methods and kits provided herein may be used to evaluate the potency or efficacy of products containing BoNT. For example, the methods and kits may be used to evaluate products that contain, but are not limited to, active ingredients such as onabotulinumtoxinA, rimabotulinumtoxinB, abobotulinumtoxinA and incobotulinumtoxinA to measure the functional activity of the toxin protein. In some embodiments, the method herein can be used to confirm the amount of active ingredient contained in the product, which is useful is a pharmacological production setting, such as a lab or a plant.

The systems and methods provided herein may also be used to detect inhibitors that prevent BoNT cleavage activity. In one embodiment, the methods provided herein can be used as a high-throughput detection system for inhibitors of BoNT enzymatic activity. Such high-throughput detection system is preferably automated for large-scale detection and testing, such as may be used in a diagnostic medical laboratory or in a manufacturing facility.

In addition to the exemplary embodiments described above, further embodiments and aspects will become apparent by reference to the drawings and by study of the following descriptions.

BRIEF DESCRIPTION OF DRAWINGS

FIG. 1(A) shows synthesis of the immuno-affinity matrix for BoNT enrichment. Protein A sepharose beads are coupled to affinity purified anti-BoNT antibodies. The FC domain of the antibodies is cross-linked to the protein A using disuccinimidyl suberate (DSS). Non-cross-linked antibodies are removed through stringent washing. FIG. 1(B): Cleavage of fluorogenic substrate by immuno-affinity enrichment of BoNT/A.

FIG. 2(A) shows immobilized polyclonal rabbit antibody does not significantly inhibit specific proteolytic activity of BoNT/A and FIG. 2(B) shows western blot analysis of BoNT/A using anti-*Clostridium botulinum* A toxoid antibodies. The antibody recognized both heavy (H) and light (L) chain of the toxin.

FIG. 4A-B shows a determination of assay performance. (A) Detection of BoNT/A from two different commercial sources, Metabiologics and the List BioLabs in serum spiked with serially diluted toxin. "Pre-act" indicates toxin pre-activation in 5 mM DTT. (B) Detection of BoNT/A in representative complex samples. The samples were spiked with undiluted human serum, carrot juice, reconstituted non-fat powdered milk, fresh milk and GP-diluent.

FIG. 5A-B shows an evaluation of monoclonal mouse antibodies for ALISSA. FIG. 5A shows an ALISSA with BoNT/A complex-spiked pooled human serum using antibodies to HC (F1-5) and LC (F1-40), protein A agarose beads (Pierce) and #115 peptide (City of Hope). FIG. 5B shows a bead-free reaction of the substrate in presence or absence of the USDA antibodies; 100 pM BoNT/A complex was used where indicated.

FIG. 6A-B shows an evaluation of horse antibodies for ALISSA. FIG. 6A shows a BoNT/A ALISSA in pooled human serum using equine polyclonal anti BoNT/A antibody (CDC, lot #00-0056L, provided by Dr. Steve Arnon at the CDPH), protein A/G agarose beads (Santa Cruz) and SNAPtide (List Biological Laboratories). FIG. 6B shows a bead-free reaction with equal amount of equine antibody and 100 pM BoNT/A complex (Metabiologics).

FIG. 8A-C shows results of BoNT/A substrate cleavage using single or double affinity immunomatrices. Beads bound to F1-40 (BoNT/A LC, mab) (left bar), anti-FITC (goat) (middle bar), or a combination of F1-40 and anti-FITC (right bar), were incubated with BoNT/A specific substrate and supernatant containing BoNT/A complex. Fluorescence of the cleaved substrate was measured after overnight (FIG. 8A) or 48 hour (FIG. 8B) incubation. A similar experiment was performed with no beads (only supernatant containing BoNT/A complex and BoNT/A specific substrate), and fluorescence of the cleaved substrate was measured after 48 hours (FIG. 8C).

FIG. 9 shows a titration assay to determine concentrations of antibody to use for an optimal signal to noise ratio for the double affinity immobilization matrix. The titration experiment was performed using 10 pM BoNT/A complex in 1 mL pooled human serum with 120,000 beads. 0.5 μg of anti-BoNT/A LC antibody was used with increasing concentrations of anti-FITC antibody (0.0-2.5 μg). The ratio of anti-FITC to anti BoNT/A LC ranged from 0-5.

FIG. 10A-D shows a comparison of the specificity, sensitivity and kinetics of bead-based ALISSA (10A) and bead-free assays (10B). FIGS. 10C and 10D illustrate the hydrolysis of SNAPtide by BoNT/A by a linear relationship between the reciprocal substrate concentration and the activity of the enzyme in bead-based ALISSA and bead-free assays, respectively.

FIG. 11 shows a line graph demonstrating the sensitivity of the BoNT ALISSA compared to the "gold standard" mouse bioassay. The BoNT ALISSA is 4-5 orders of magnitude more sensitive than the mouse assay. The numbers shown in boxes represent the mouse $LD_{50}$ calculated per injected 0.5 mL sample. One $LD_{50}$=30 pg BoNT/A complex.

FIG. 12 shows a schematic of one embodiment of a BoNT ALISSA. Antibodies against targets, such as BoNTs or anthrax lethal factor, are conjugated on protein A-coated beads via their Fc regions and then cross-linked. An immobilized toxin protease molecule cleaves fluorogenic reporter molecules and releases unquenched fluorescent products.

FIG. 16 shows the remarkable specificity of novel BoNT cleavable and control peptides. BoNT cleavable peptides (#115; SEQ ID NO: 21 and #116; SEQ ID NO: 22 and control

110, 111, 112, and 113; SEQ ID NOS: 20, 23, 19, and 5, respectively) showed some cleavage upon addition of trypsin (left panel). However, control peptides (#110-113) were not cleaved by BoNT/A complex (middle panel); whereas, BoNT/A cleavable peptides (#115 and #116) were cleaved by BoNT/A complex. Control peptide #112 was not cleaved by either serotype BoNT/A or BoNT/B (right panel). Significantly, BoNT/A cleavable peptide was only cleaved by BoNT/A serotype and not BoNT/B serotype (right panel), which demonstrates that BoNT/A cleavable substrate is highly specific for BoNT/A. Commercial SNAPtide (#521) was cleaved by trypsin and BoNT/A complex (left and middle panels).

Figure 17:
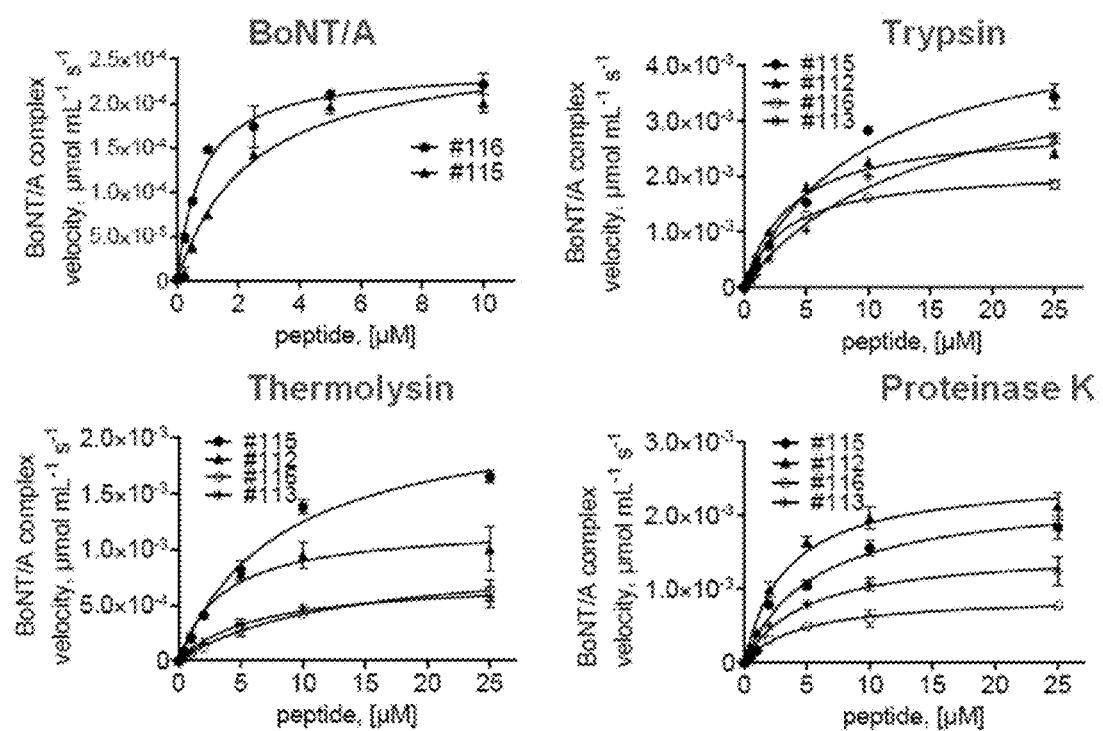

FIG. 17 shows Michaelis-Menten kinetics of BoNT/A cleavable substrates (#115 (SEQ ID NO: 21) and #116 (SEQ ID NO: 22)) and control substrates (#112 (SEQ ID NO: 19) and #113 (SEQ ID NO: 5)) with BoNT/A, trypsin, proteinase K, and thermolysin. Enzymes (10 nM) were incubated for 2 hours with different concentrations of BoNT/A cleavable and control substrates. The velocity of the enzyme reaction is fit as a function of substrate concentration. Peptide cleavage obeys Michaelis-Menten kinetics.

Figure 18:
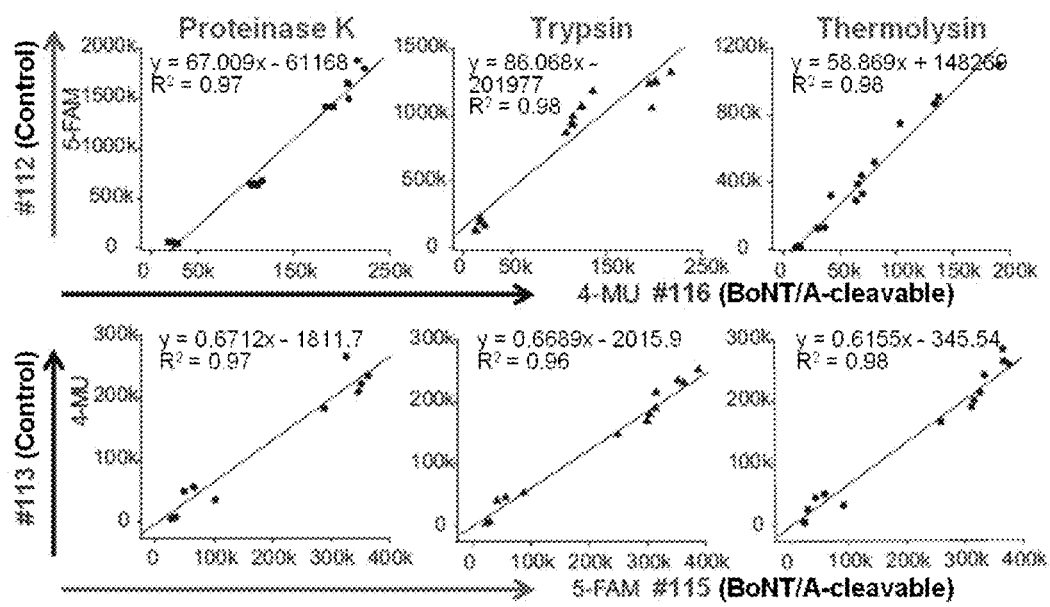

FIG. 18 shows linear relationships between the signal responses of 4-MU and 5-FAM substrates when tested with different enzymes (proteinase K, trypsin, and thermolysin). BoNT/A enzyme concentration tested ranged from 1 pM to 100 pM.

FIG. 19A-D shows cleavage of 5-Fam-(A) or 4-Mu-containing (B) peptides by LC/A subtypes. LC A4 does not cleave BoNT/A-cleavable peptides #115 (A) and #116 (B). Less than 2% of the commercial SNAPtide (#521) was cleaved by LC A4. Peptide solutions (5 µM) were incubated with LCs (20 nM) at 37° C. Western blot analysis of recombinant SNAP25 cleaved (c) by LC A4 compared to its uncleaved (u) form (C). ALISSA performance of 5-Fam-containing BoNT/A-cleavable (#115) and control (#112) peptides in the presence or absence of $Zn^{2+}$-metallo-protease inhibitor, TPEN (100 µM) (D). Rabbit polyclonal to BoNT/A toxoid antibody was used to bind BoNT/A complex from spiked human serum with protein A/G-agarose beads.

Figure 20:
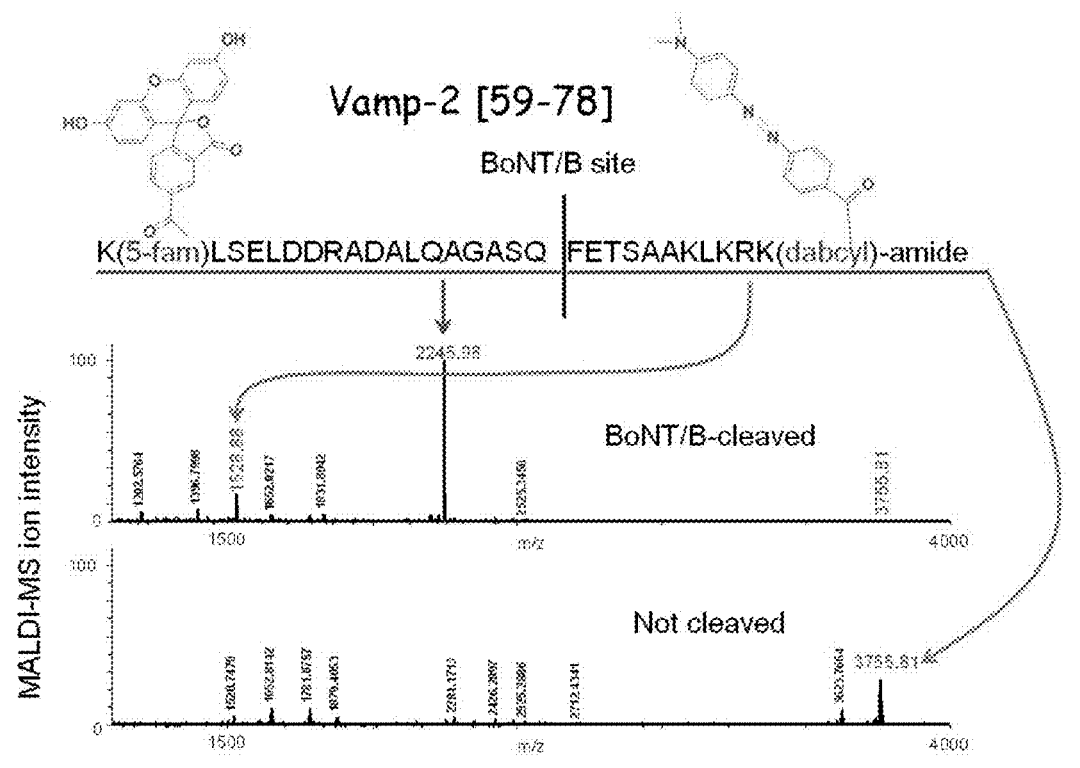

FIG. 20 shows a schematic and matrix-assisted laser desorption/ionization (MALDI) mass spectrum for the novel BoNT/B ALISSA substrate. The BoNT/B specific substrate (SEQ ID NO: 24) contains amino acid residues 59-78 of the VAMP protein that is specifically cleaved by BoNT/B at the expected site of natural VAMP cleavage, between the glutamine and phenylalanine. Both the fluorophore, 5-carboxyfluorexcein (5-FAM), and the quencher, 4-dimethylamino phenyl azo enzoic acid (DABCYL), were placed on the ϵ-amino groups of lysine residues that are part of the natural VAMP sequence, allowing for a non-inhibited enzyme substrate interaction. High specificity cleavage of the substrate by BoNT/B was indicated using MALDI-MS resulting in product at m/z 2245.98 and m/z 1528.88. The uncleaved substrate produced a peak at m/z 3755.81.

Figure 21:
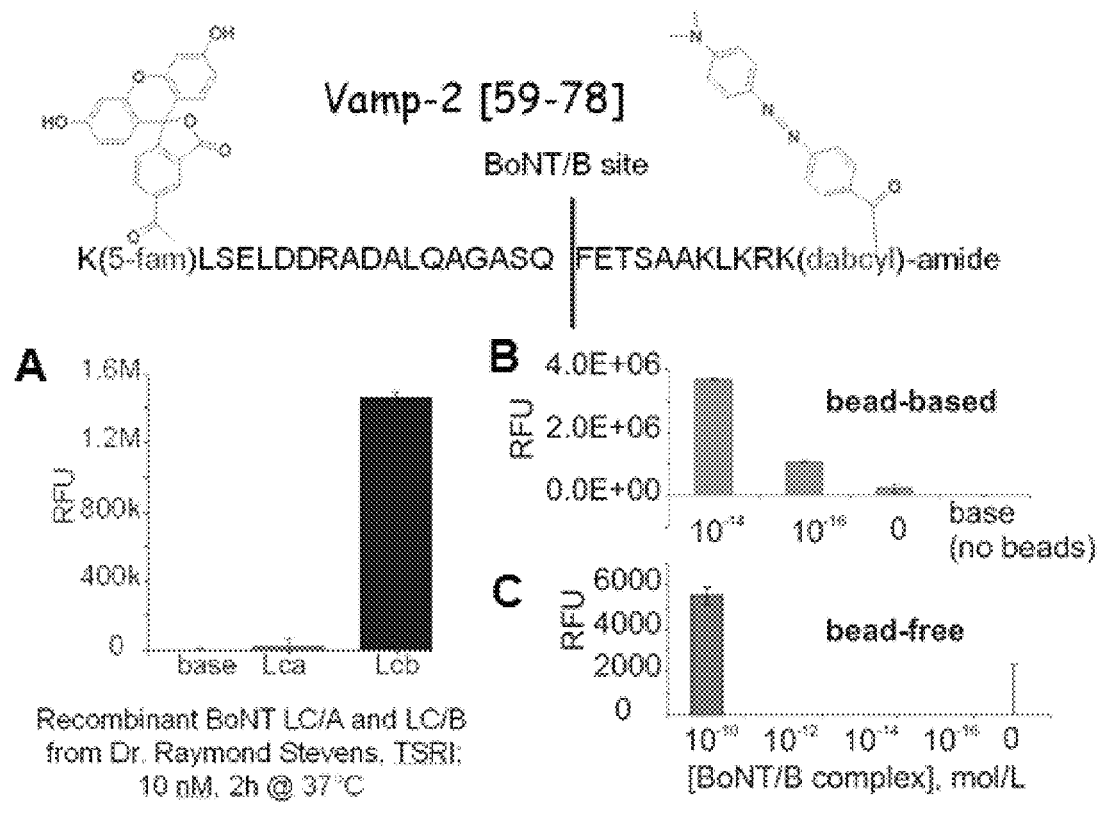

FIG. 21A-C shows the remarkable BoNT/B substrate specificity for the novel substrate for use in BoNT/B ALISSA (SEQ ID NO: 24). The BoNT/B substrate was incubated with either 10 nM recombinant BoNT LC/A or LC/B at 37° C. Specificity of the BoNT/B substrate to BoNT/B LC versus BoNT/A LC was measured fluorometrically (A). The reaction was also performed using BoNT/B complex that was immobilized with anti-BoNT/B antibody in a bead-based assay (B). The bead based assay has a remarkably more sensitive detection limit of BoNT/B substrate cleavage compared with the bead free reaction (C).

Figure 22:
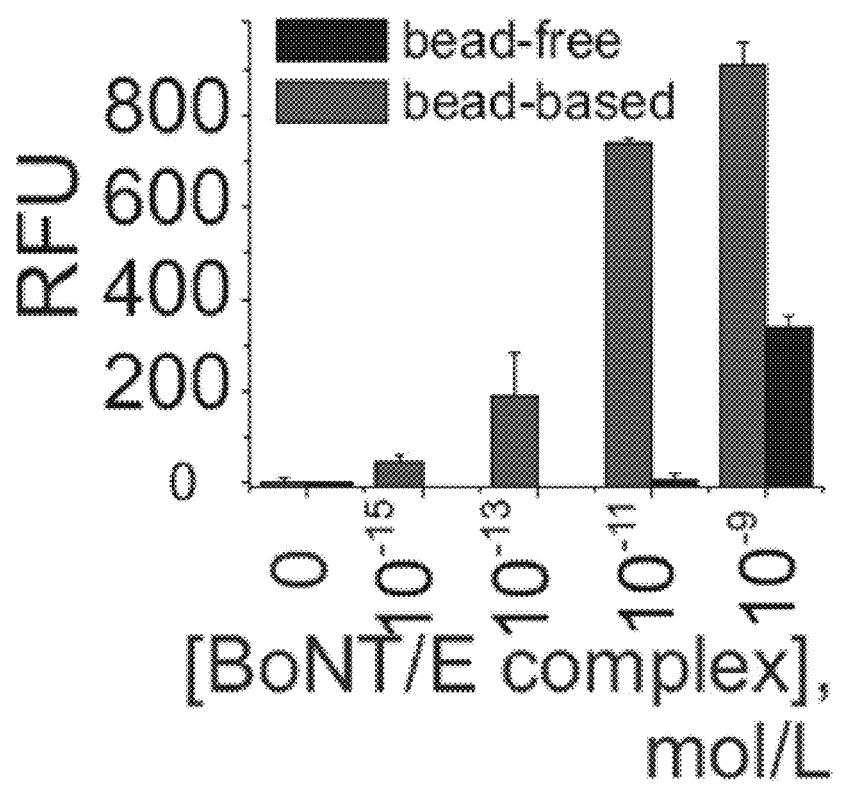

FIG. 22 shows BoNT/E ALISSA with the commercial substrate, SNAP Etide (List Biological Laboratories). The reaction was performed using BoNT/E complex (Metabiologics), immobilized with anti-BoNT/E antibody (Metabiologics) on protein A/G beads (Santa Cruz). The bead-based ALISSA has a limit of detection of ~1 fmol/L BoNT/E complex, whereas the limit of detection for the bead-free reaction is >10 pmol/L.

Figure 23:
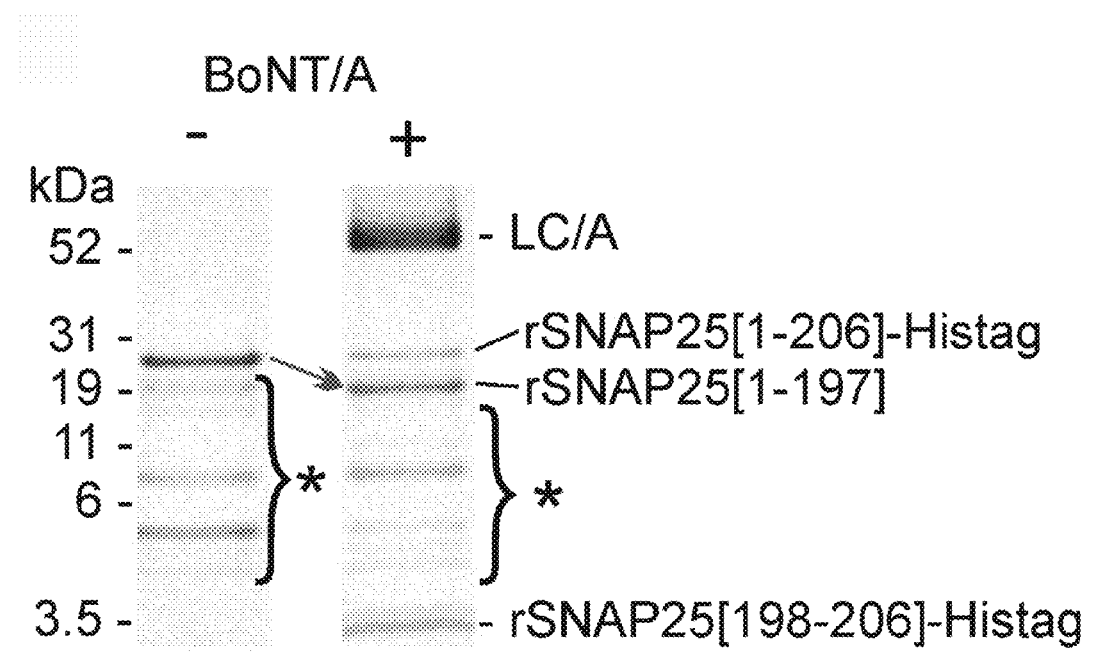

FIG. 23 shows SDS-PAGE analysis of recombinant human SNAP-25 proteolysis reaction in presence of BoNT/A. The gel shift is indicated by the arrow. E. coli protein impurities are denoted by asterisk. The small cleavage product contains the C-terminus of rSNAP25 with the hexahistidine tag and measure about 4 kDa in size, resulting in light-emitting E. coli expressing his-tagged FFL.

Figure 24:
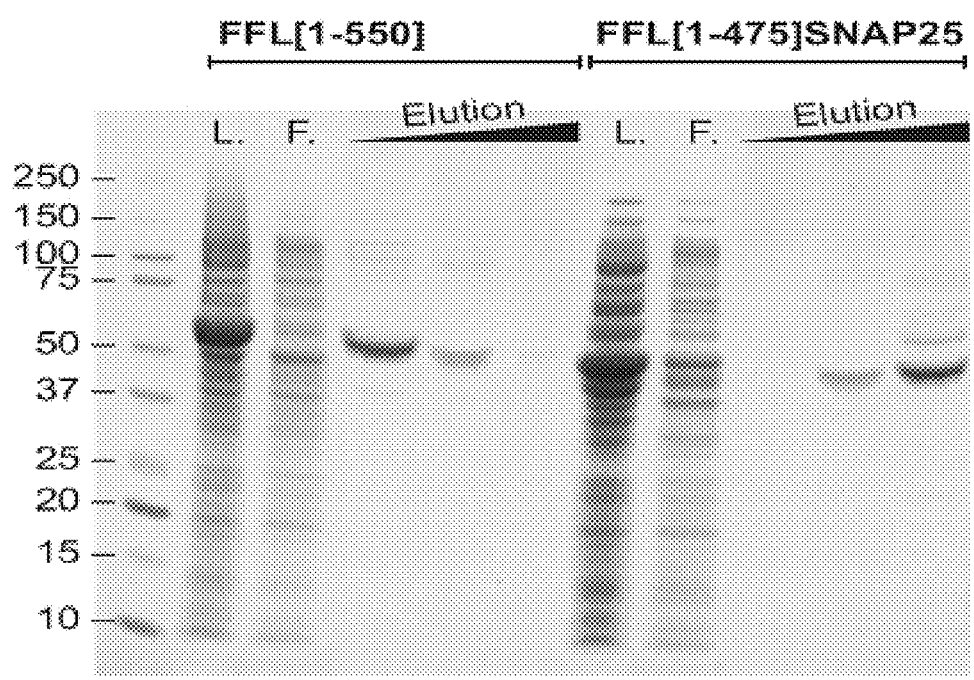

FIG. 24 shows cloning and expression of engineered firefly luciferase (FFL) fusion proteins for the bioluminescent detection of BoNT/A. The SDS gel is an example that demonstrates the progress in the purification of full length FFL[1-550], control, and an N-terminal FFL fragment [1-475] fused to the BoNT/A-cleavable portion of a SNAP25 sequence (residues 187-206).

Figure 25:
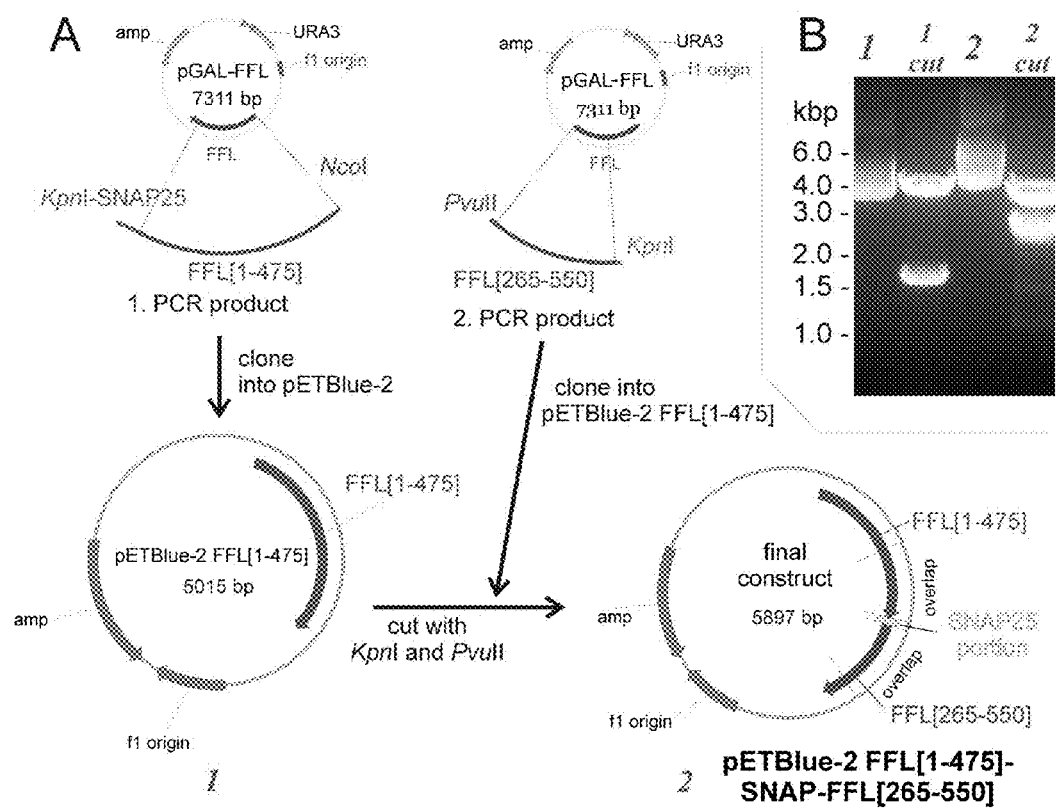

FIG. 25 (A) an exemplary schematic of a synthesis scheme for constructing recombinant overlapping split FFL having a SNAP25-sequence insert (SEQ ID NO: 1). As depicted, two PCR products are generated using a yeast plasmid (pGAL-FFL) as a template and then cloned subsequently into the same pETBlue-2 vector. The BoNT/A cleavage site for SNAP25 (amino acid residues 187 to 206; SEQ ID NO: 6) is embedded into the sequence via synthetic primers (SEQ ID NO: 7 and 8) using a codon-optimized sequence for E. coli. Similar synthesis schemes are employed for constructing split FFL fusion proteins for targeted SNARE sequence of other BoNT serotypes. FIG. 25 (B) shows restriction analysis of the intermediate plasmid depicted in (A) (plasmid "1"; SEQ ID NO: 9) and the final product (plasmid "2"; SEQ ID NO: 10). The identifier "1" is the uncut pETBlue-2 FFL[1-475] vector; "1 cut" is "1" cut with NcoI and KpnI; "2" is the uncut final product pETBlue-2FFL[1-475]-SNAP-FFL[265-550] and "2 cut" is the "2" cleaved with NcoI and PvuII.

FIG. 26A-B shows schematic representations of two strategies for bioluminescent detection system. (A) shows an assay comprising a Dual Chamber system; (B) shows an assay comprising a Single Chamber system. Identifiers "A" and "B" represent non-FFL protein domains having well characterized dimerization properties such as Glutathione S-transferase (GST) and glutathione or IgG FC-region and protein A.

FIG. 27A-B shows the schematic representation of sequence domains of the biolumniogenic BoNT/A substrate and the principle of the bioluminescent assay. FIG. 27A shows FFL-L1SL2TAH that was optimized for rapid BoNT/A cleavage (SEQ ID NO:25): "FFL" represents the full-length firefly luciferase protein containing amino acid residues 1-550; "L1" represents Linker-1, a serine-glycine linker sequence containing four glycines, one serine, and four glycines ($G_4SG_4$); "S" represents a cleavable portion of SNAP25 containing amino acid residues 171-206; "L2" represents Linker-2, a glycine linker sequence containing six glycines; "T" represents an optional positive control, a cleavable sequence containing amino acid residues ENLYFQG recognized by the Tobacco Etch Virus protease; "A" represents a lysine anchor peptide containing eight to ten lysines and one glycine, one leucine, and one glutamic acid ($K_{8-10}$+ GLE); and "H" represents a hexahistidine tag for protein purification ($H_6$). FIG. 27B shows a schematic of the bead-based bioluminescent BoNT detection assay. The lysine-rich anchor sequences are marked with an anchor symbol and are positioned near the bead. BoNT-cleavable sequences (dark grey middle rectangle) are positioned between the anchor and the luciferase components. The luciferase components are located at the end of the substrate, furthest from the bead (dark grey rectangle). When the BoNT-cleavable sequence is cleaved, the cleaved product is released from the bead and the bioluminescent signal can be detected.

FIG. 28A-B shows bioluminogenic BoNT substrates. (A) Recombinant fusion proteins FFL and FFLSH contain full-length luciferase (1-550 residues), Tev cleavage site and polyhistadine ($H_6$) tag. FFLSH contains a BoNT/A cleavable human SNAP25 residues 171-206 (SNAP). (B) BoNT/A cleavage of FFL and FFLSH with and without subsequent addition of $YCl_3$. The concentration of BoNT/A was picomolar; Background=reaction buffer only; s/n=signal to noise.

Figures 29B, 29C:
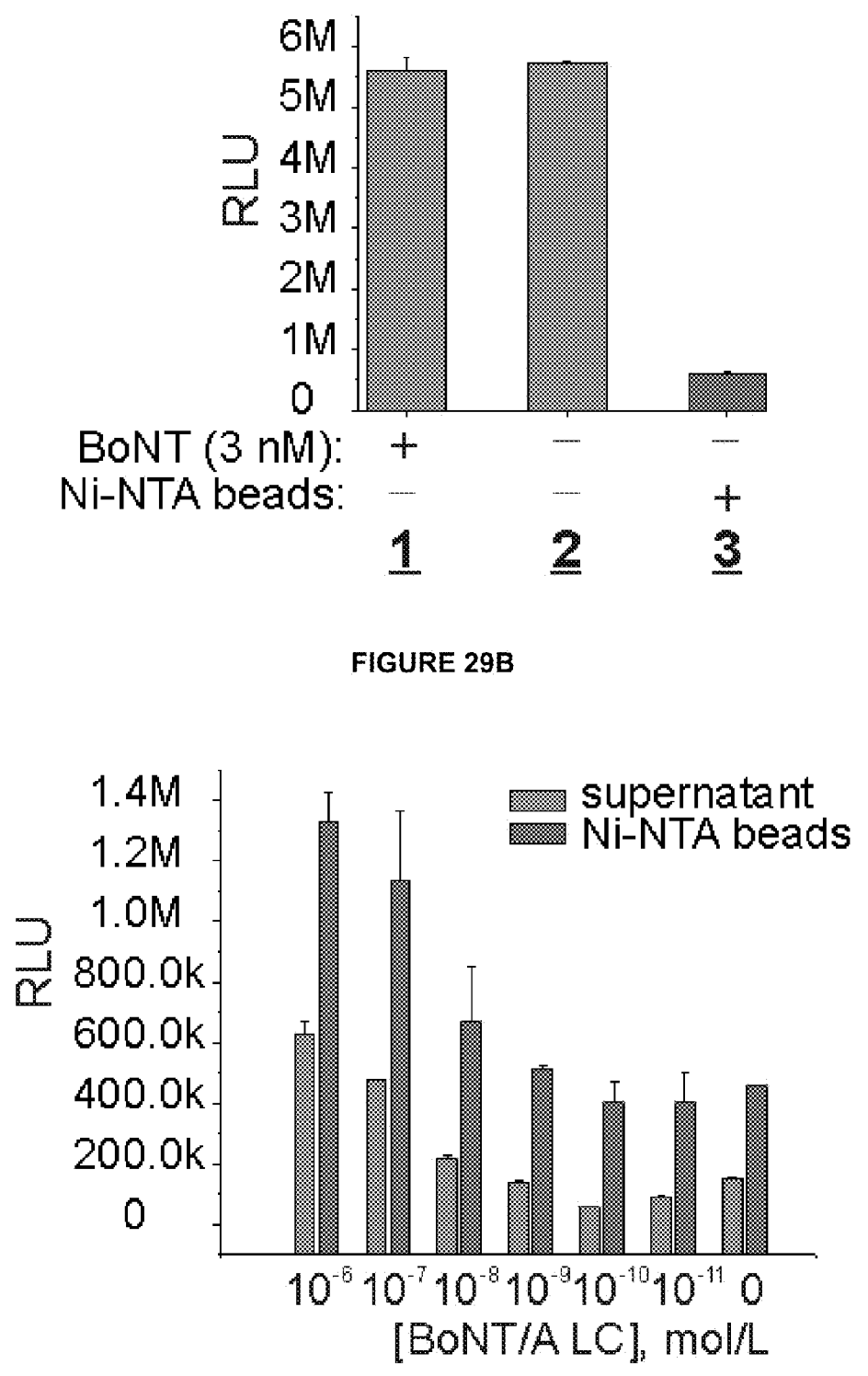

FIG. 29A-C shows the testing of fire fly luciferase protein substrates for BoNT detection. Scheme of the experiments with the hexahistidine-tagged substrate FFL-SNAP25-$His_6$. (FFLSH) (A); results of the control experiments (B); Cleavage assay with a BoNT/A LC dilution series (C). Supernatant only (left bars) and Ni-NTA beads (right bars) were tested. The concentration of FFLSH was 463 nM in all experiments.

FIG. 30(A) shows BoNT-mediated cleavage of the bioluminogenic substrate in solution following binding on Ni-NTA beads. Performance of the sepharose bead-immobilized bioluminogenic substrate in human serum spiked with different BoNT serotypes is shown in FIG. 30(B).

Figure 31:
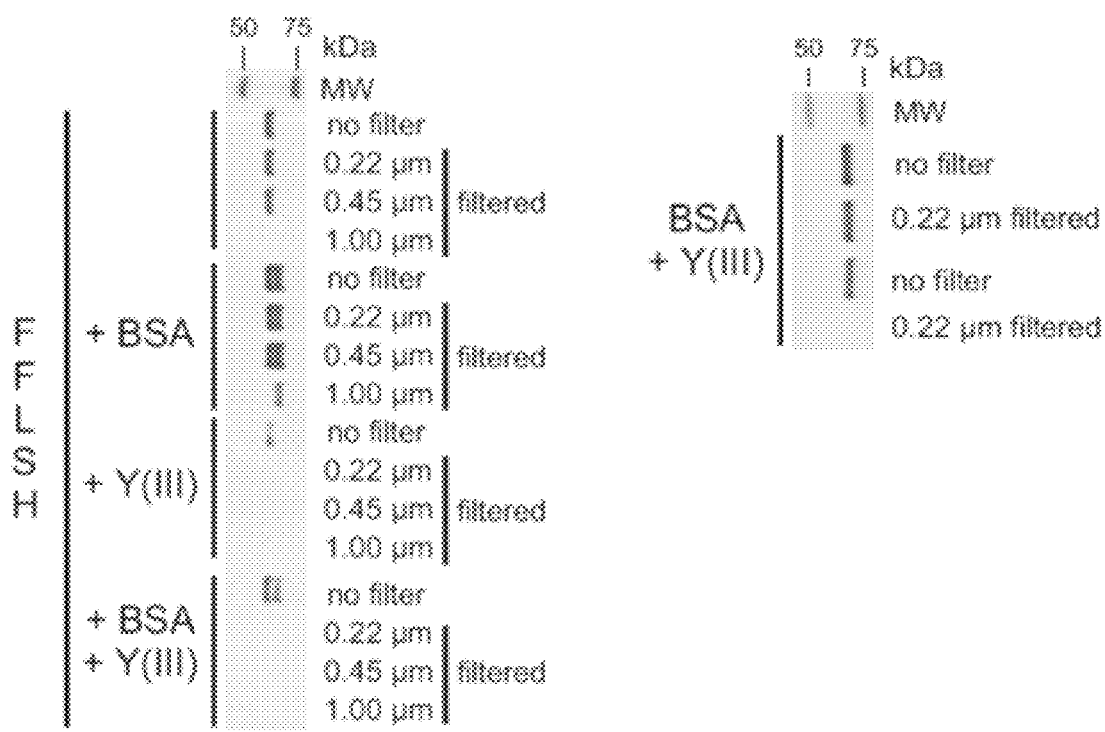

FIG. 31 shows aggregate formation of histidine-tagged luminogenic BoNT substrate FFLSH with yttrium (III) ions. FFLSH and bovine serum albumin (BSA), 1 μg each, were passed through filters of different pore sizes and analyzed by SDS gel electrophoresis (left panel). In the presence of $YCl_3$ (10 mM) FFLSH and FFLSH/BSA mixtures forms micro aggregates that were efficiently removed by filtering. BSA alone does not form aggregates with Y(III) ions (right panel). The 0.22 and 0.45 μm filter contained low protein-binding PDVF membranes, whereas the 1.00 μm filter contained glass fibers. Note that FFLSH but not BSA was already removed by the glass-containing filter in absence of Y(III) ions.

Figure 32:
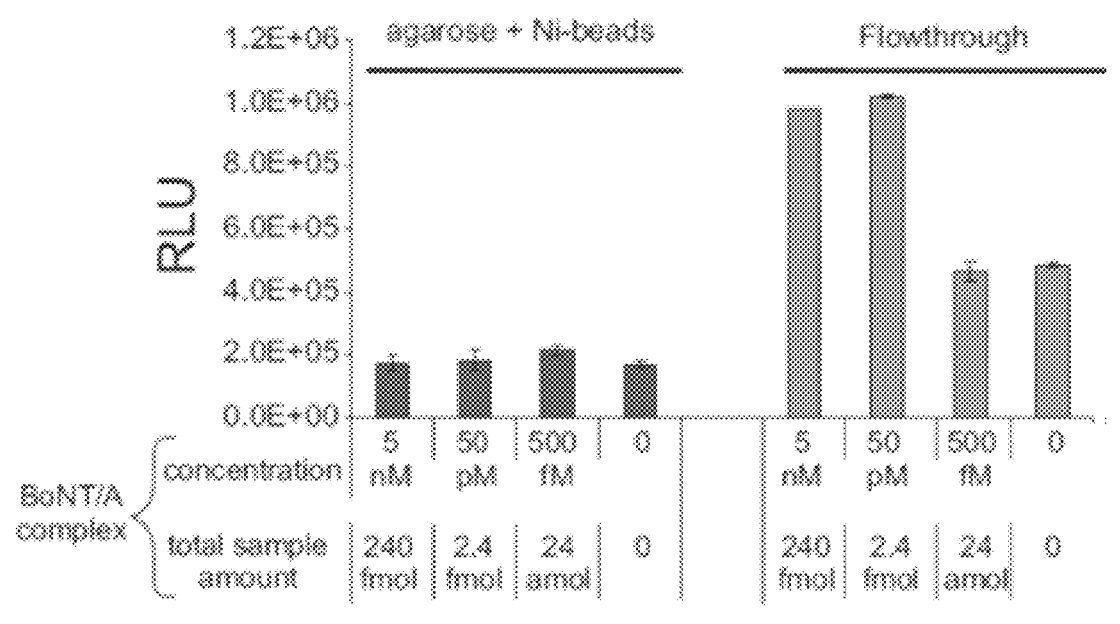

FIG. 32 shows BoNT/A ALISSA with luminogenic substrates. FFLSH (0.1 μg) was treated with ALISSA-bead immobilized BoNT/A complex from BoNT samples of concentrations as indicated. The supernatant was subsequently incubated with Ni-NTA agarose beads. The Ni-NTA beads were collected on spin columns and both beads and flow through were tested for luciferase activity.

Figure 33:
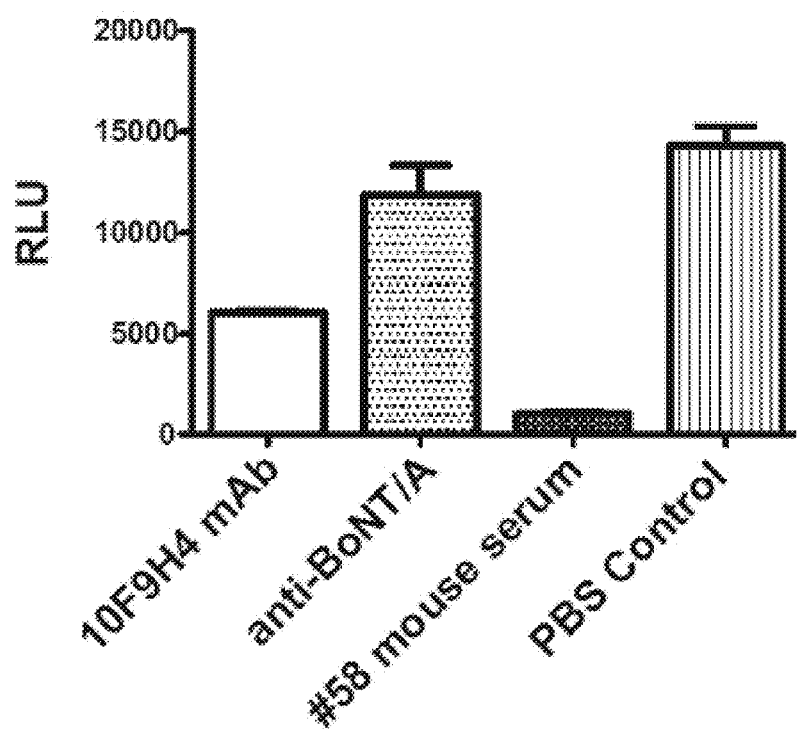

FIG. 33 shows development of the FFL inhibitor domain for BoNT-activatable luminogenic substrates. FFL inhibition assay using equimolar solutions of FFL with ONE-Glo substrate (Promega), in presence of an anti-FFL mAb (10F9H4), anti-BoNT/A IgG (control), serum from an FFL-immunize mouse (#58 mouse serum) and a antibody-free control (PBS).

Figure 34:
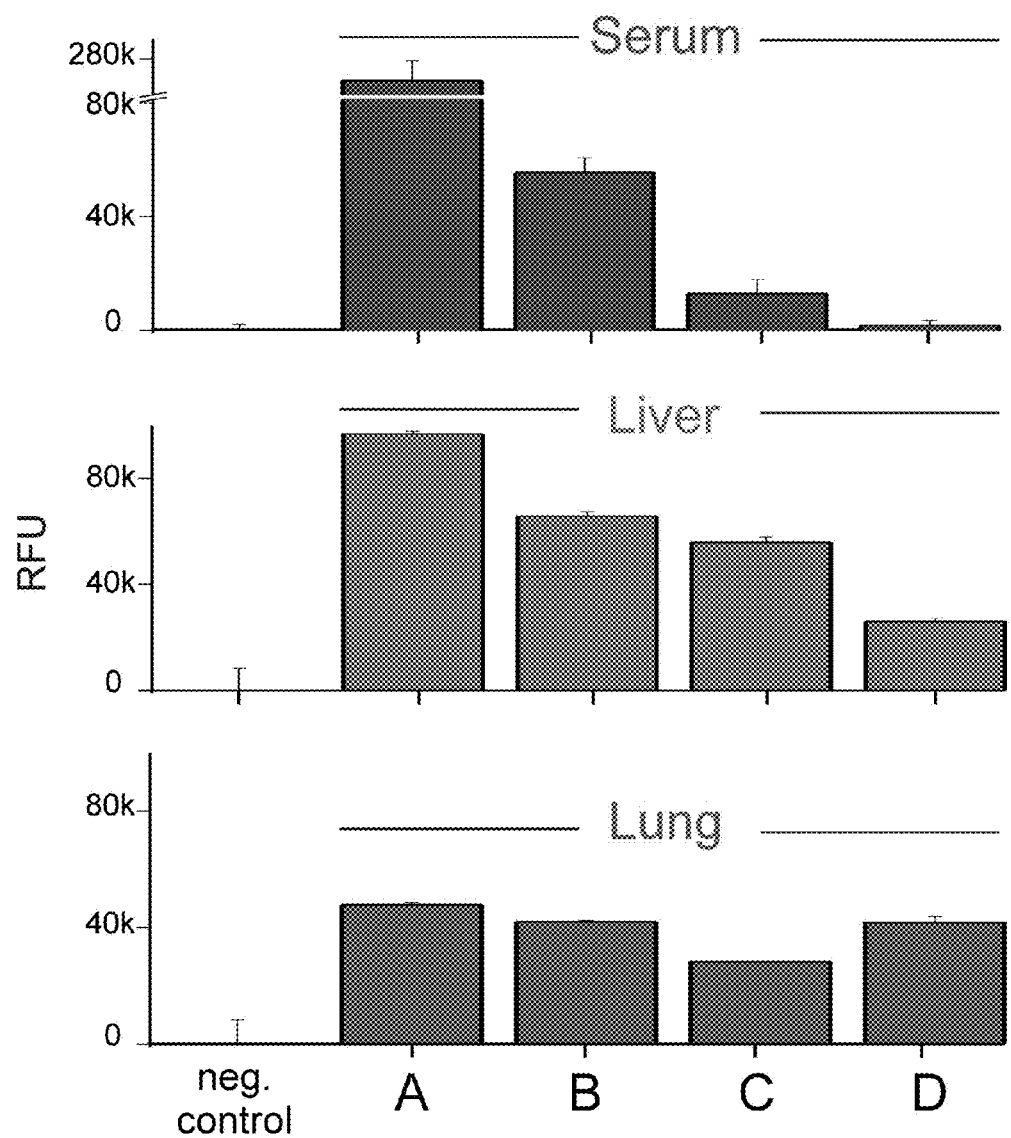

FIG. 34 shows an exemplary BoNT/A ALISSA assay with sera and tissue extracts of intoxicated and non-intoxicated mice. Pairs of mice were i.p. injected with BoNT/A complex in the following amounts: (A) 200 pg; (B) 100 pg; (C) 20 pg; and (D) 0 pg (mock injection). Negative control was reaction buffer only (no serum or organ extracts).

Figure 35:
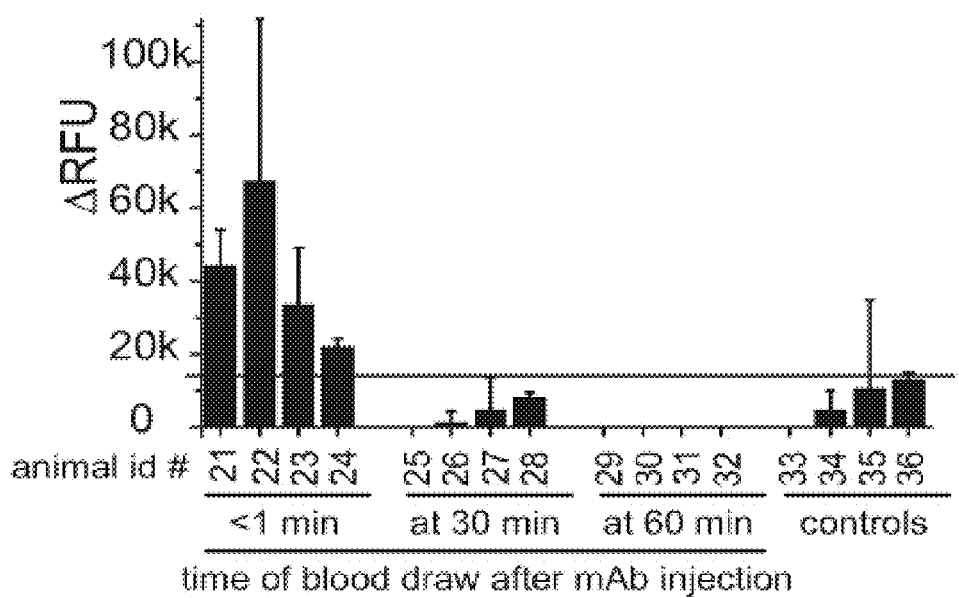

FIG. 35 shows BoNT/A ALISSA detection of BoNT/A in mouse serum in an intoxication/rescue model. Groups of 4 mice were i.v.-injected with 1,000 pg/mouse (143 mouse $LD_{50}$) of BoNT/A complex. 10 min later, mice were injected with a combination of BoNT/A neutralizing mAbs, 2.5 μg F1-2 (anti heavy chain) and 2.5 μg F1-40 (anti light chain), respectively. Blood was drawn at the indicated times after injection of the rescue antibody. 100 μL serum per animal was used for ALISSA detection of BoNT/A. Controls received no BoNT/A. The horizontal bar marks the level of the background signal.

FIG. 36A-D shows ALISSA examples for BoNT/A, E, and anthrax LF. Results of the bead-free reaction (substrate and toxin only) were compared to the bead-based ALISSA (see components) for dilution series of the toxins in serum (a, c, d). ALISSA components were: rabbit polyclonal antibodies to *Clostridium botulinum* A toxoid, protein A/G beads, fluorogenic peptide (SNAPtide), and BoNT/A complex (a); Rabbit polyclonal antibodies against BoNT/E, protein A/G beads, fluorogenic substrate (SNAP Etide), and BoNT/E complex (c); ALISSA with: goat anti-anthrax LF, protein A and G beads and peptide substrate (MAPKKide), and LF (d); Standard curve of the fluorescence signal of unquenched calibration peptide (SNAPtide) in BoNT/A reaction buffer (b).

Figure 37:

FIG. 37 shows the handling of the beaded ALISSA resin in spin columns. The spin column was loaded after the immunoprecipitation step using a Luer-Lock screw adaptor screw cap (a). Multiple sample resins were washed by gravity flow (b).

FIG. 38 shows the dilution table used to generate a standard calibration curve for ALISSA.

Figure 39:
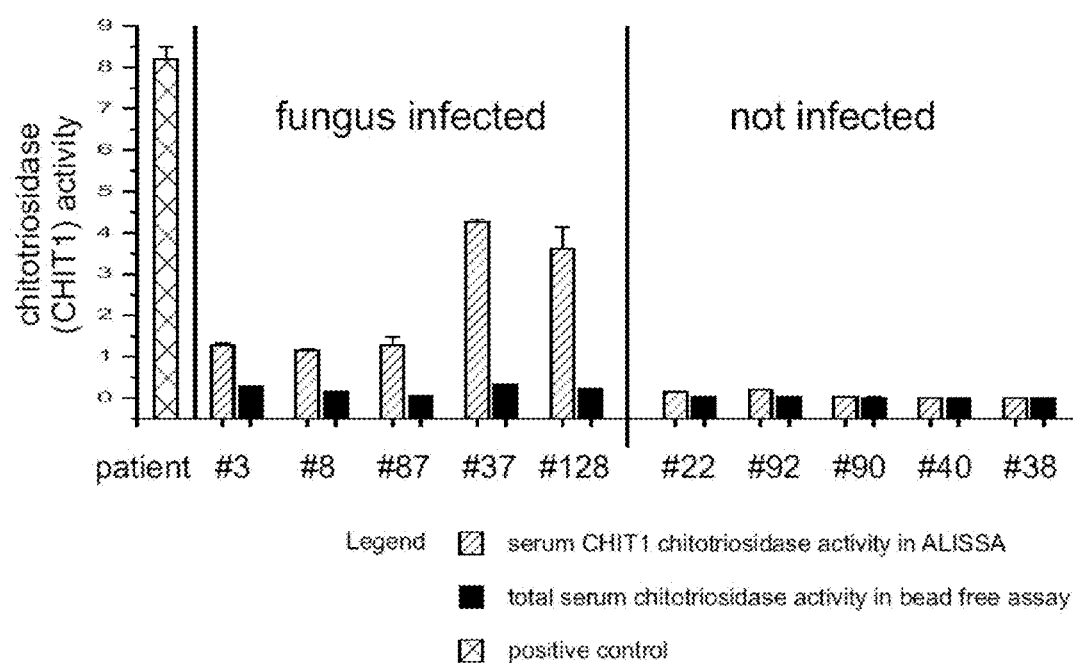

FIG. 39 shows an exemplary ALISSA assay as performed to detect target enzyme chitinase. Sera from 10 patients were tested. The patients are identified as "#3", "#8", "#87", "#37", "#128", "#22", "#92", "#90", "#40", and "#38". Hatched bars correspond to CHIT1 serum ALISSA. Solid bars correspond to serum chitotriosidase activity. Positive control sera are indicated to the far left.

FIG. 40A-B shows an exemplary ALISSA assay as performed to detect target enzyme Pep1 and Pep2 in patients with fungal infection (A) and no fungal infection (B). Patient sera are identified as "#3", "#12", "#37", "#87", "#128", "#22", "#90", "#38", "#40" and "#92". Hatched bars correspond to Pep1 results. Solid bars correspond to Pep2.

Figure 41:
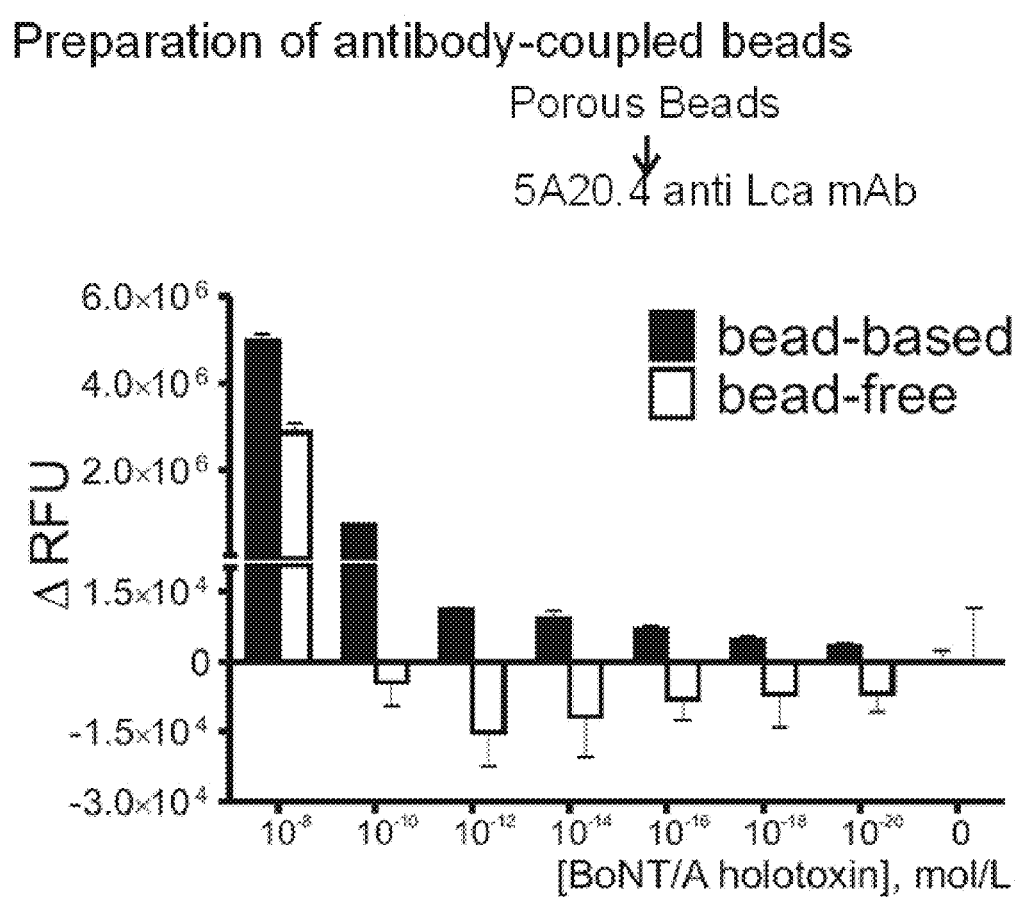

FIG. 41 shows the experimental scheme for the ALISSA detection of BoNT/A in intoxicated mouse sera using a bead-based immunomatrix. The bead-based immunomatrix was prepared using the monoclonal 5A20.4 (anti BoNT/A light chain) antibody (provided by Dr. James Marks, University of California, San Francisco) coupled to porous beads. An experiment was performed using BoNT/A cleavable peptide #115 (SEQ ID NO:21) to test sera with and without anti-body coupled beads (bead-based and bead-free, respectively). The bead-based ALISSA demonstrated superior sensitivity compared with the bead-free experiment.

FIG. 42 shows the steps involved in the ALISSA detection of BoNT/A in intoxicated mouse sera. Step 1 involves preparation of the immunomatrix by coupling the monoclonal 5A20.4 (anti BoNT/A LC) antibody to porous beads. Step 2 involves immunocapturing of the BoNT/A complex present in the serum from intoxicated mice. Step 3 involves the enzymatic reaction used to detect BoNT/A cleavage of fluorescent peptides. BoNT/A cleavable peptide #115 (SEQ ID NO: 21) and control peptide #113 (SEQ ID NO: 5) were tested simultaneously (#115 contains a 5-FAM at the N-terminus and #113 contains a 4-MU at the N-terminus), while cleavable peptide #116 (SEQ ID NO: 22) and control peptide #112 (SEQ ID NO: 19) were tested simultaneously (#116 contains a 4-MU at the N-terminus and #113 contains a 5-FAM at the N-terminus) in the same ALISSAs.

Figure 43:
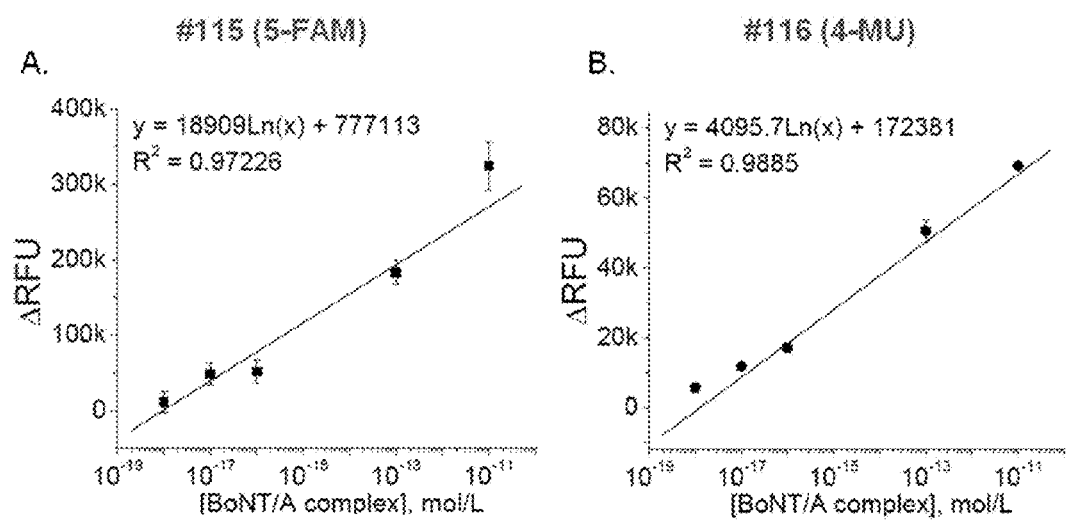

FIG. 43A-B shows the standard curves for the ALISSA with BoNT/A1 complex-spiked pooled mouse serum. Figure A shows the standard curve for the 5-FAM labeled substrate (#115) and Figure B shows the standard curve for the 4-MU labeled substrate (#116).

FIG. 44 shows the experimental scheme for the mouse model of botulism. Mice were either administered BoNT/A complex through intravenous (i.v.) injection or intragastric (i.g.) gavage. Tail blood was drawn at the indicated time and BoNT/A ALISSA was performed using mouse serum. Mice in Group I were administered i.v. injections containing different concentrations of BoNT/A complex (0, 4 pg, 20 pg, and 100 pg BoNT/A complex per mouse); serum was tested for BoNT/A using ALISSA after 1 hour. Mice in Group II were administered i.v. injections containing 100 pg BoNT/A complex per mouse; serum was tested for BoNT/A using ALISSA after 1, 3, 5, and 7 hours. Mice in Group III were administered 4 μg BoNT/A complex through i.g. gavage and serum was tested for BoNT/A using ALISSA after 2, 5, and 7 hours.

Figure 45:
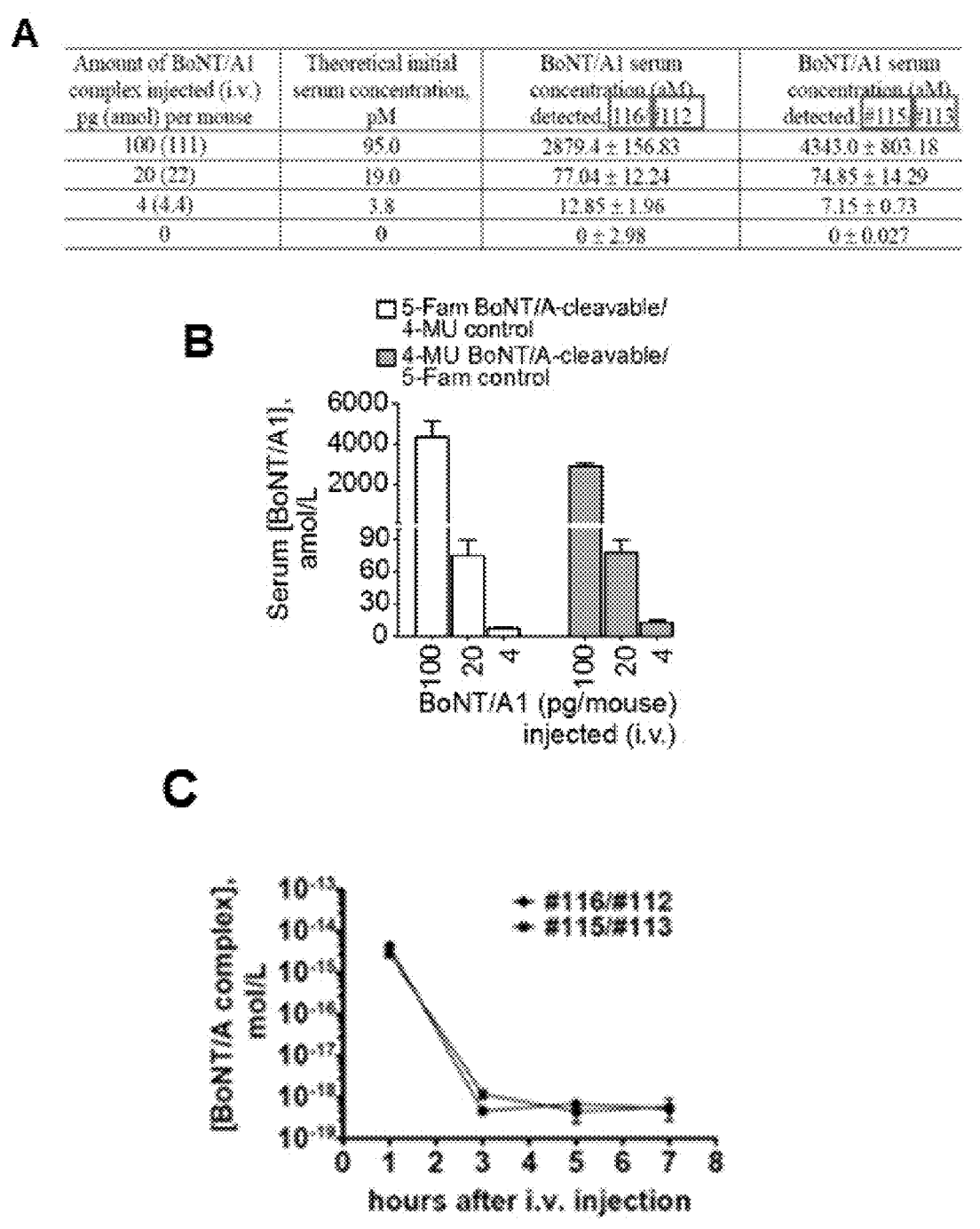

FIG. 45A-C shows quantification of BoNT/A serum of i.v. intoxicated mice (n=4 per group). After 1 hour, the sera from Group I mice were tested using the BoNT/A cleavable substrates (#115 (SEQ ID NO: 21) and #116 (SEQ ID NO: 22) (FIG. 45 A). The concentration of BoNT/A was determined with BoNT/A cleavable substrates, #115 (SEQ ID NO: 21) and #116 (SEQ ID NO: 22), from the ALISSA standard curves generated with BoNT/A complex serially diluted with normal mouse serum. Linear correlation equations were used to convert the fluorescence counts obtained from non-BoNT/A specific cleavable of control substrates, #112 (SEQ ID NO: 19) and #113 (SEQ ID NO: 5). FIG. 45 B shows a bar graph depicting the results from FIG. 45 A. 5-FAM labeled BoNT/A cleavable substrate (#115) combined with 4-MU labeled control peptide (#113) results are shown as the white bar, and 4-MU labeled BoNT/A cleavable substrate (#116) combined with 5-FAM labeled control peptide (#112) results are shown as the grey bar. FIG. 45 C shows a line graph plotting the BoNT/A concentration detected over time (sera was tested at 1, 3, 5, and 7 hours post intoxication. BoNT/A serum concentrations for each time point were calculated by dividing the results of the cleavable peptide by the results of the control peptide.

Figure 46:
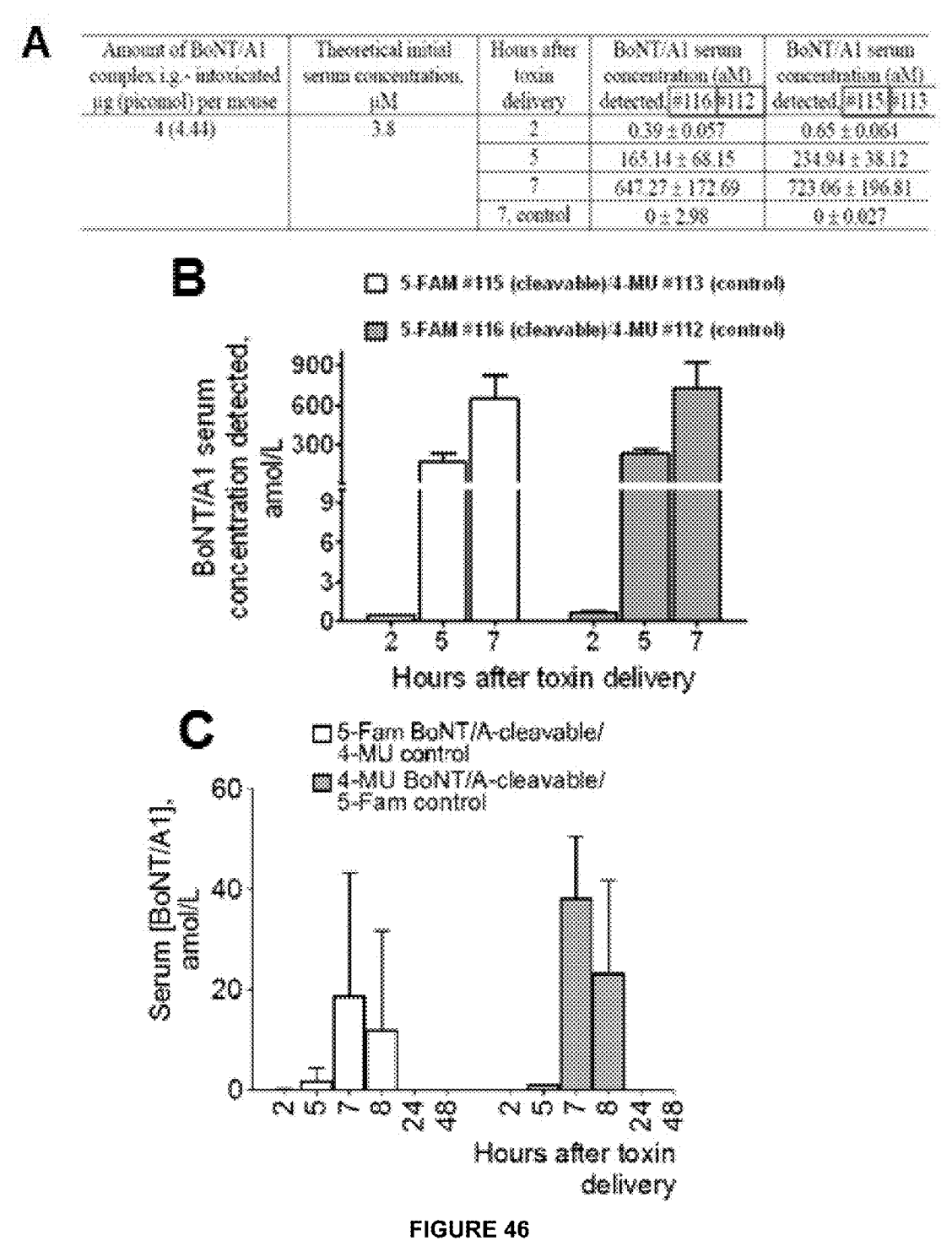

FIG. 46A-C shows the BoNT/A ALISSA results using sera from mice that were administered BoNT/A through i.g. gavage. BoNT/A cleavable substrates, #115 (SEQ ID NO: 21) and #116 (SEQ ID NO: 22), were used to detect the presence of BoNT/A and substrates, #112 (SEQ ID NO: 19) and #113 (SEQ ID NO: 5), were used as negative controls. Mice received 4 μg BoNT/A complex and serum was tested 2, 5, and 7 hours after delivery (FIG. 46 A). The bar graph in FIG. 46 B illustrates that time is required for BoNT/A toxin perfusion into the blood stream. FIG. 46 C shows the results from mice that received 1 μg BoNT/A through i.g. gavage. The tail blood of mice was tested at 2, 5, 7, 8, 24, and 48 hours after toxin delivery.

FIG. 47 shows the experimental protocol for the ALISSA quantification of intraneuronal BoNT/A1.

FIG. 48A-B shows ALISSA standards for BoNT/A quantification. FIG. 48 A shows standards using 20 nM recombinant BoNT light chain (white bar) or BoNT/A1 complex in high potassium ($K^+$) medium. FIG. 48B shows standards for ALISSA with cell intoxication (white bar) and wash media (black bar) in a high $K^+$ buffer. Control values are subtracted from total values.

FIG. 49A-C shows the ALISSA standards and quantification of BoNT/A1 detected in extracts, pellets, supernatants and wash buffers of intoxicated rat primary hippocampus neurons. A standard curve was obtained with the 150-kDa holotoxin spiked into cell lysis buffer (A). Initial experiments detected the presence of toxin in both cell extract and cell pellet (B, black bar and white bar, respectively). Quantification results from ALISSA in extracts (left bar graph), super-natants (middle bar graph), and wash buffer (right bar graph) (C). Different concentrations of BoNT/A1 holotoxin were added to the medium used for cell intoxication (control, no BoNT (white bar); 20 nM BoNT/A1 (black bar); 2 nM BoNT/A1 (grey bar)). At 2 nM BoNT concentration, the cells retained 0.27 fmol BoNT (2,167 active BoNT molecules per cell). The BoNT/A1 concentrations were measured in a final sample volume of 1 mL.

Figure 50:
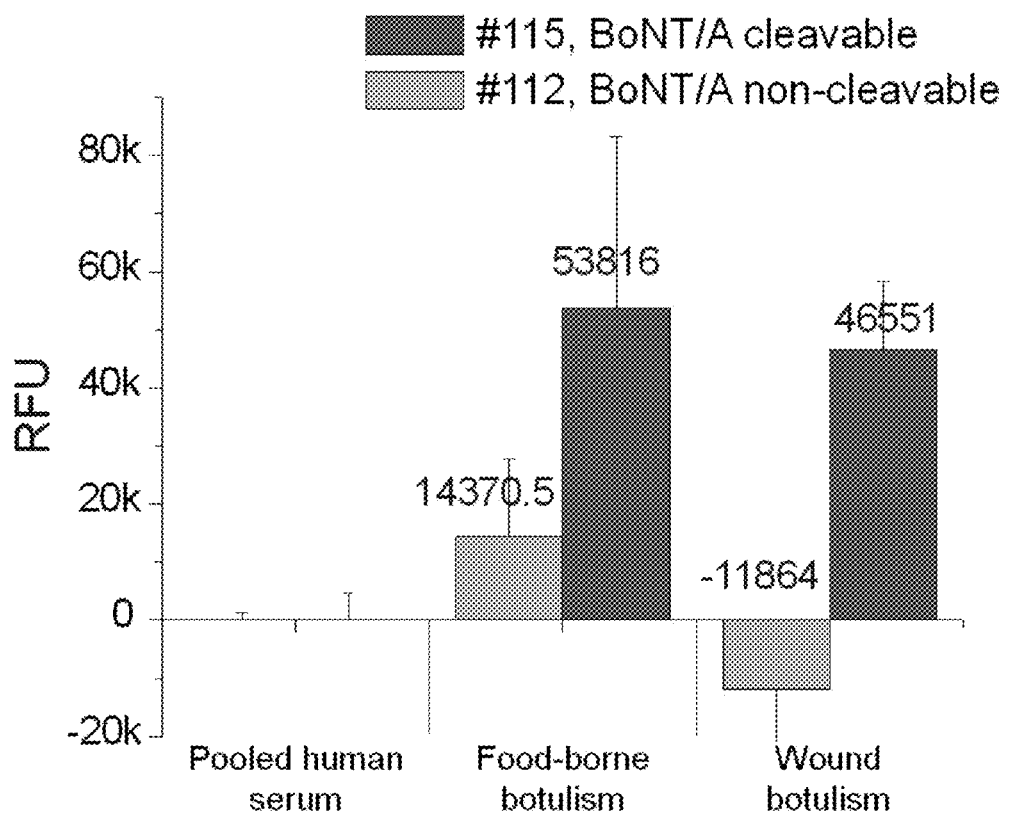

FIG. 50 shows the results from the first BoNT/A ALISSA with sera from adult botulism patients. Sera from uninfected adults (left bar graph), adult patients infected with food-borne botulism (middle bar graph), or adult patients infected with wound botulism (right bar graph) were tested using ALISSA. The BoNT/A cleavable substrate, #115 ((SEQ ID NO: 21), left bar in each pair), and the non-cleavable control peptide, #112 ((SEQ ID NO: 19), right bar in each pair), were tested. Adult sera were provided by the California Department of Public Health.

Figure 51:
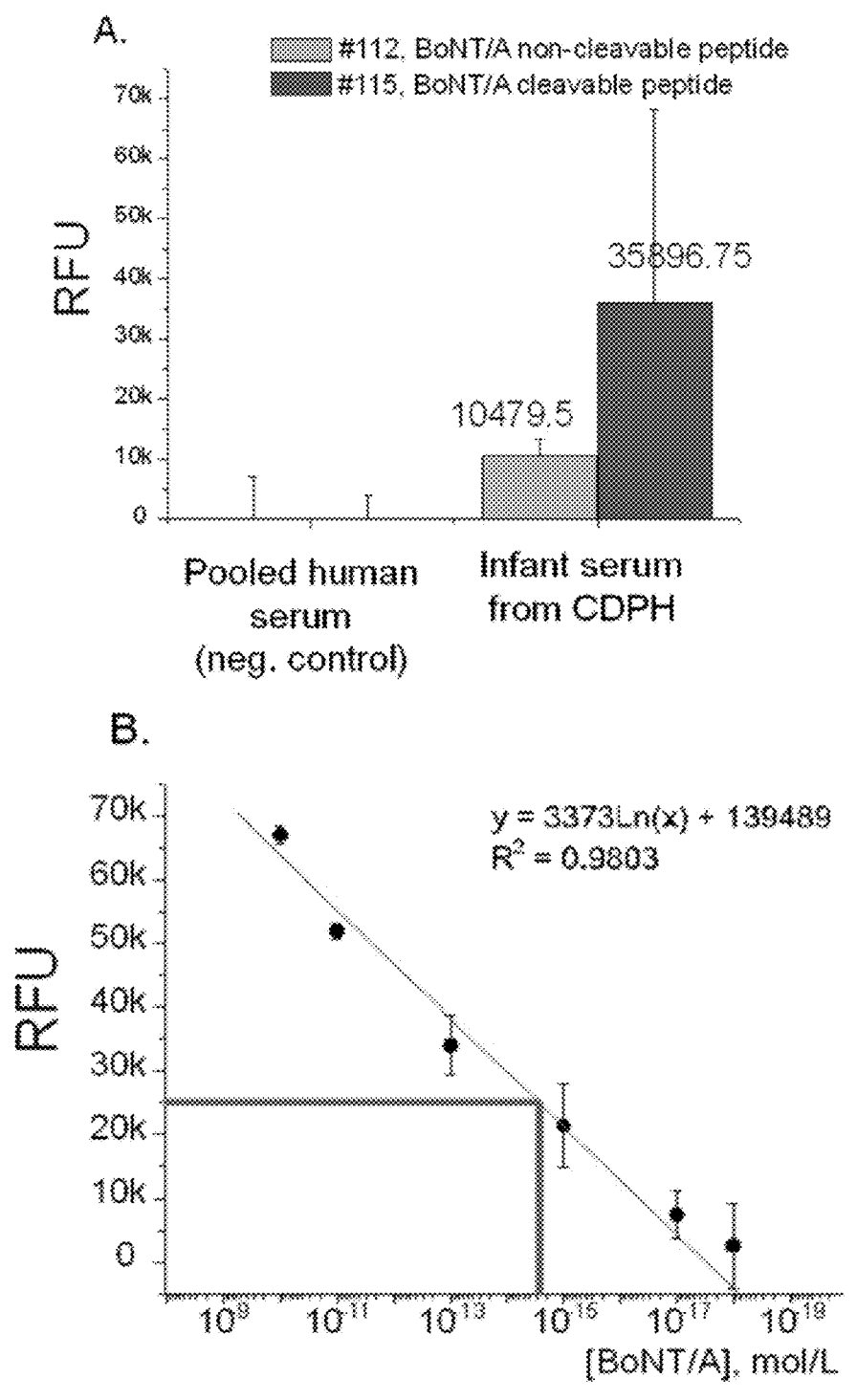

FIG. 51 A-B shows the results from a BoNT/A ALISSA with infant botulism patient serum. Pooled human serum (negative control, left bar graph) and serum from infants infected with botulism (right bar graph) was tested using ALISSA (Figure A). The BoNT/A cleavable substrate, #115 ((SEQ ID NO: 21), left bar in each pair), and the non-cleavable control peptide, #112 (SEQ ID NO: 19), right bar in each pair), were tested in the assay. Infant sera were provided by the California Department of Public Health. Figure B shows the BoNT/A ALISSA standard curve for the assay that allows conversion of RFU into the concentration of BoNT/A holotoxin.

Figure 52A:
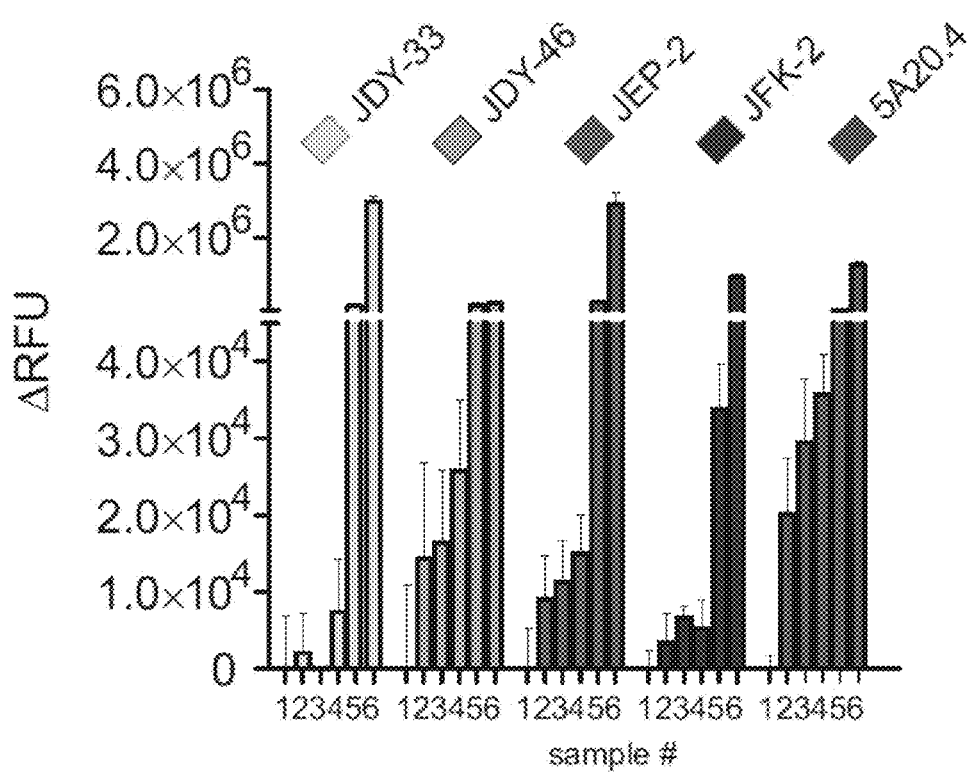
Figure 52B:
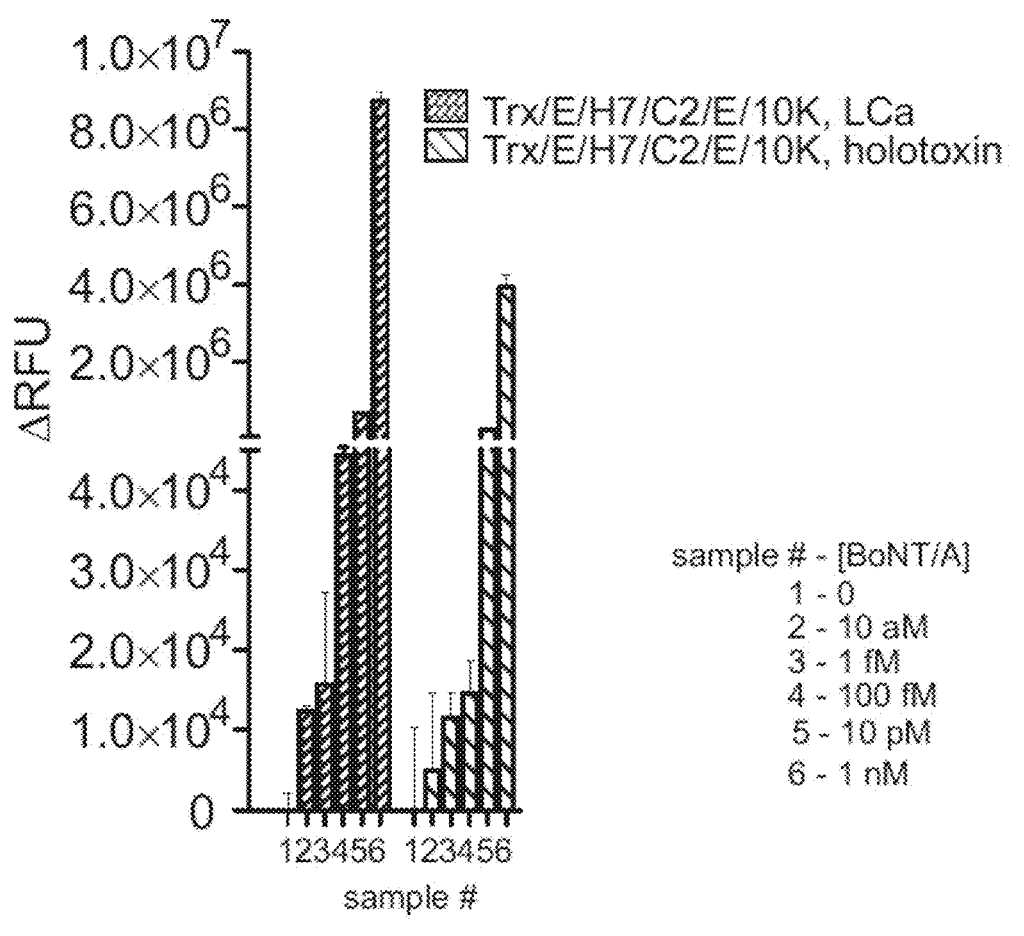

FIG. 52A-B shows screening of anti-BoNT/A camelid antibodies (VHHs) for BoNT ALISSA detection in BoNT-spiked pooled human serum. (A) The VHHs JDY-33, JDY-46, JEP-2, and JFK-2 are directed against BoNT LC. 5A20.4 is a monoclonal humanized anti-BoNT/A LC antibody from Dr James Marks of UCSF. (B) BoNT/A ALISSA with a bivalent heterodimer VHH that consists of a fusion of thioredoxin (Trx), an E-tag (E), the H7 or C2 VHH, and a lysine decamer at their C-terminus (10K).

Figure 53C:
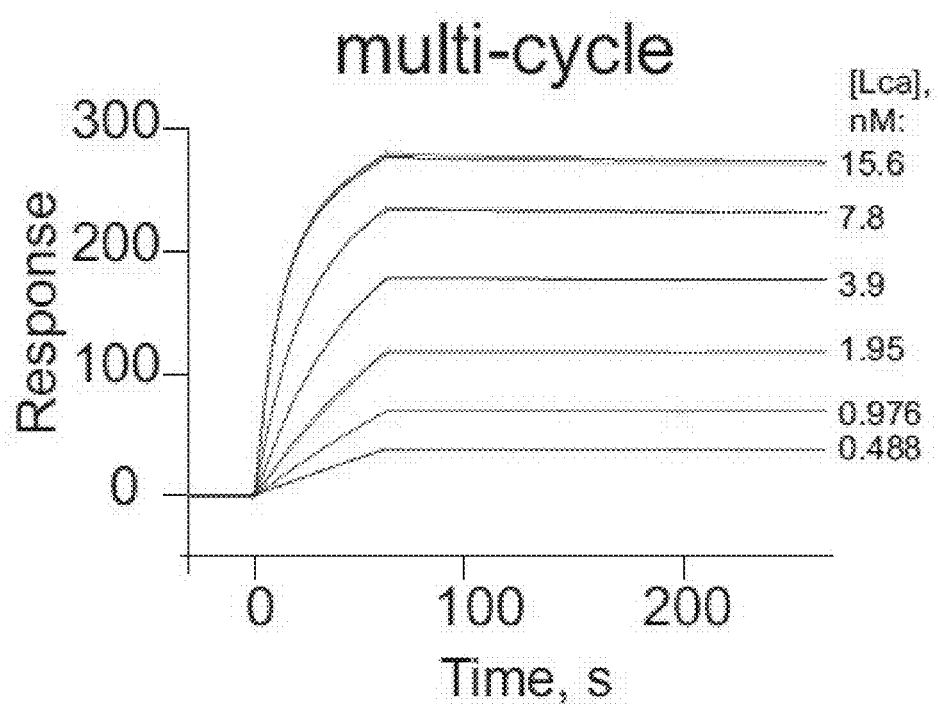

FIG. 53A-C shows BoNT ALISSA with VHH heterodimers and trimers. (A) Comparison of BoNT-specific heterodimer (JIA-44) versus heterotrimer (JIA-31) VHHs in bead-based ALISSA; and (B, C) Surface Plasmon Resonance (SPR) kinetic analysis of the heterodimer in (B) single-cycle and (C) multi-cycle mode. The dissociation constant $K_D$ of the heterodimer VHH JIA-44 was determined to be 64.4 to 65.8 pM.

FIG. 54A-C shows affinity maturation of VHH domains of single chain alpaca antibodies, displayed on S. cerevisiae cells. FACS analysis of (A) H7 mutant and (B) the H7 wild-type (WT). The oval in each upper right quadrant in (A and B) marks the gate used to collect LCa-$FITC^{high}$/C-$Myc^{high}$ cells. (C) Photography of a 96-well microtiter plate with colonies from selected individual yeast cells gated in (A), which are expected to express mutated H7 with a BoNT/A LC binding affinity that is significantly higher than that of the WT. The dark dots in well centers are the living colonies (n=63).

Figure 55:
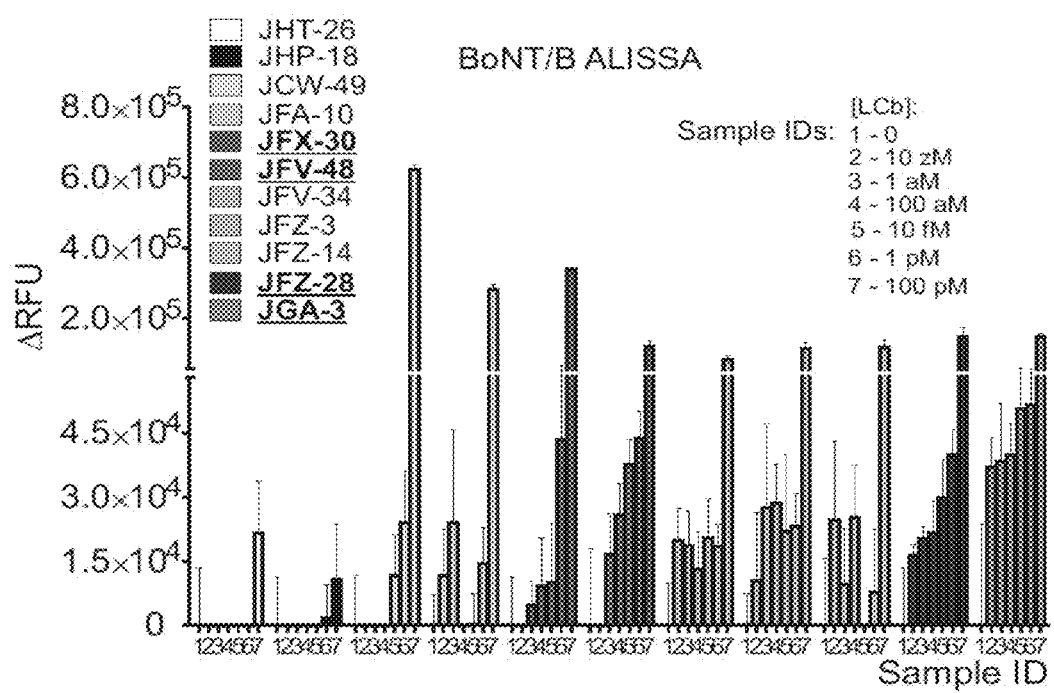
Figure 57C:
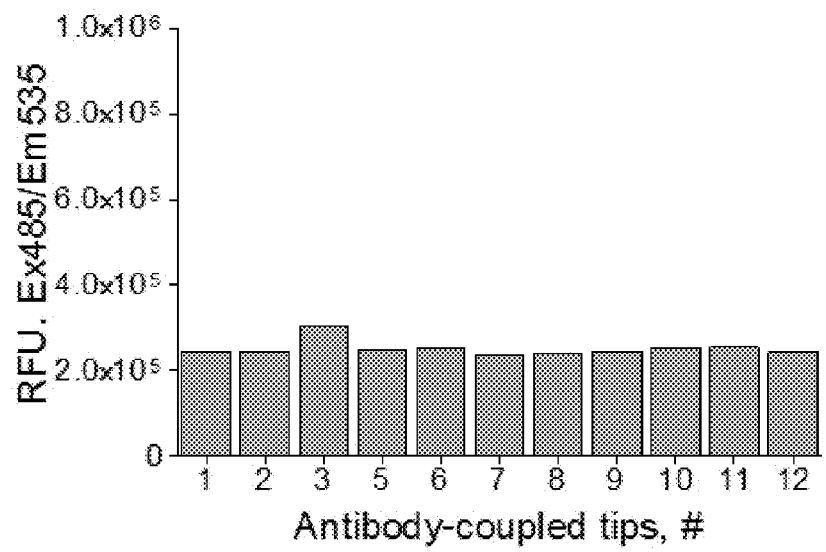
Figure 57D:
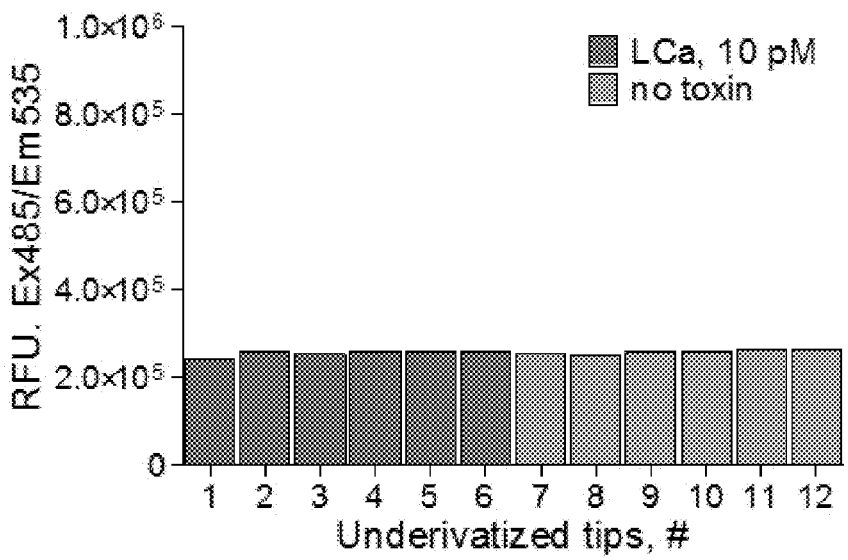
Figure 57E:
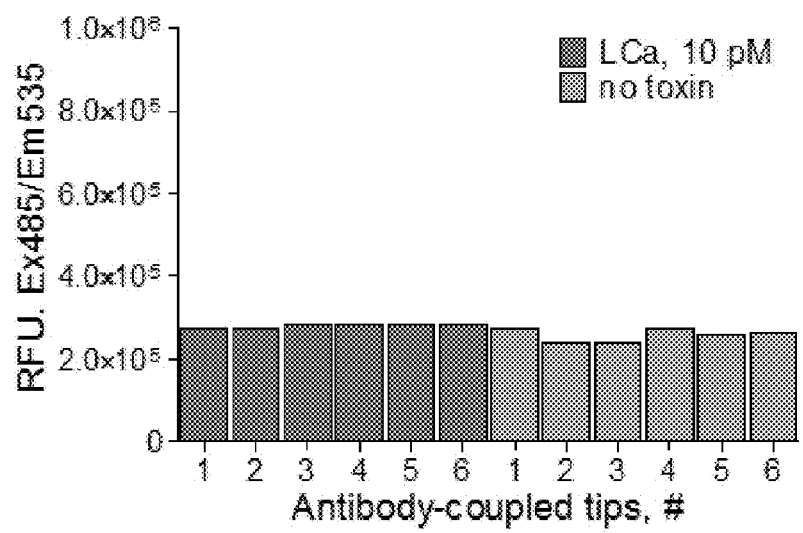
Figure 57F:
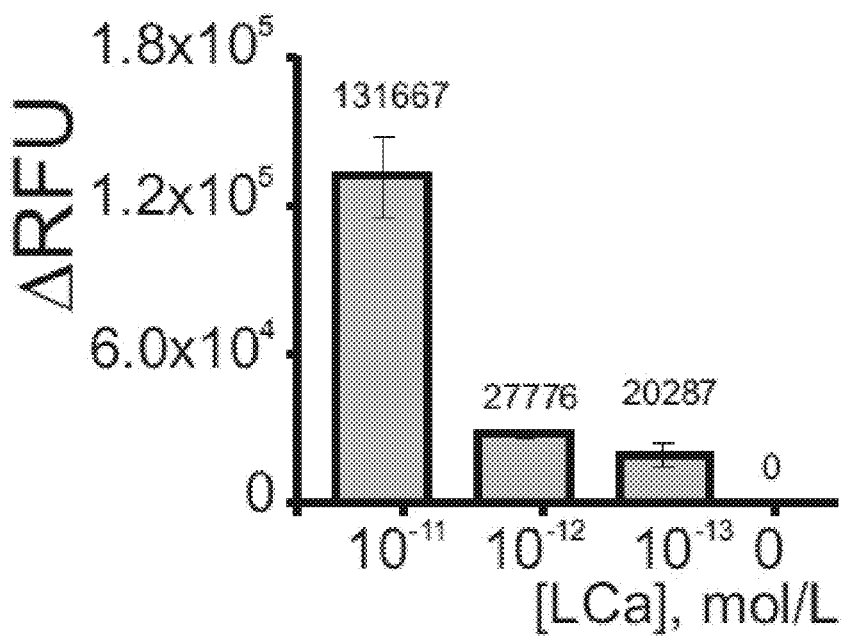

FIG. 55 shows screening of BoNT/B VHHs for best performance in a bead-based BoNT/B ALISSA. The three letter naming scheme (starting with J) was adopted form Dr. Shoemaker who isolated these VHHs.

FIG. 56A-B shows the ALISSA using pipette tips columns containing affinity microcolumns. FIG. 56(A) shows a schematic of the ALISSA using pipette tips containing affinity microcolumns. The biological sample was added to an affinity pipette tip containing the bead-based immunomatrix (immobilized BoNT/A antibody). Flow-through was washed away while BoNT/A was bound by the BoNT/A antibody. BoNT/A specific fluorogenic substrates were added to the affinity pipette tip. Unquenched fluorophore was released upon substrate cleavage. Fluorescence of cleaved substrate was read using a waveguide sensor. FIG. 56B, left panel, shows the affinity pipette tip columns containing microcolumns that can be used in conjunction with an electronic multichannel pipettor. FIG. 56B, right panel, shows the affinity tips fitted onto a Versette automated workstation.

FIG. 57A-F shows BoNT/A ALISSAs using microcolumns. (A) A dilution series was performed using pooled human serum spiked with increasing concentrations of BoNT/A light chain (LCa). Microcolumns were used with an immunomatrix containing BoNT/A specific antibodies (5A20.4). Increasing cleavage of the BoNT/A cleavable substrate is seen with increasing concentrations of BoNT/A, demonstrating that BoNT/A light chains cleave the BoNT/A cleavable substrate. (B) A similar experiment as seen in (A) was performed using affinity microcolumns with an immunomatrix containing antibodies specific to BoNT/B light chains (anti-LCB monoclonal (6B.1)). A dilution series was performed using pooled human serum spiked with increasing concentrations of BoNT/A light chain. Negligible cleavage of the 5-FAM BoNT/A cleavable substrate (#201a) was seen, indicating that BoNT/A does not specifically bind a microcolumn immunomatrix containing BoNT/B antibodies. (C) An ALISSA using microcolumns with an immunomatrix containing the BoNT/A VHH H7 antibody was performed; however, no toxin was added to the microcolumn in this experiment. Each lane represents data from one affinity microcolumn pipette tip. (D) ALISSA with microcolumns was performed using an immunomatrix containing no conjugated antibody. Pooled human serum spiked with 10 pM BoNT/A light chains (dark-grey bars, underivatized tips 1-6) and no toxin (light-grey bars, underivatized tips 7-12) was added to the microcolumn. There was no difference in cleavage of the 5-FAM labelled BoNT/A cleavable substrate (#201a) between those microcolumns treated with BoNT/A and those treated with no BoNT/A. These results indicate that BoNT/A does not bind the immunomatrix non-specifically. Each figure represents the data obtained from one single affinity tip containing a microcolumn. (E) ALISSA with microcolumns was performed using an immunomatrix containing the BoNT/A specific antibody, VHH H7. Microcolumns were either treated with pooled human serum containing 10 pM of BoNT/A or were not treated with BoNT/A. There was no difference in cleavage of 5-FAM labelled BoNT/A control peptide (204a) between the microcolumns treated with BoNT/A and the microcolumns that were not treated with BoNT/A. These results indicate that BoNT/A does not cleave the control peptide. Each figure represents the data obtained from one single affinity tip containing a microcolumn. (F) Results from an automated BoNT/A ALISSA with microcolumns on a Versette liquid handling workstation. The samples were automatically processed on microcolumns loaded with Dr. James Marks' monoclonal antibody 5A20.4. Nine hundred aspirate/dispense cycles were used per sample (in triplicates).

FIG. 58 shows the nucleic acid sequence of FFL1-478SNAP25FFL265-550 (SEQ ID NO:3). In this embodiment of an overlapping split FFL having a SNAP25 sequence insert, nucleic acids encoding amino acids 1 through 478 of FFL is included in the first FFL segment. The corresponding SNAP25 sequences with the BoNT/A cleavage site are indicated in bold and underlined text. The hexahistidine tag is indicated in bold and italic text.

FIG. 59 shows the amino acid sequence of FFL1-478SNAP25FFL265-550 (SEQ ID NO:4). In this embodiment of an overlapping split FFL having a SNAP25 sequence insert, amino acids 1 through 478 of FFL is included in the first FFL segment. The corresponding SNAP25 sequences with the BoNT/A cleavage site are indicated in bold and underlined text. The hexahistidine tag is indicated in bold and italic text.

FIG. 60 shows the complete amino acid sequence of human SNAP25 (SEQ ID NO: 11; Swissprot Accession #P60880). The BoNT/A cleavage and recognition site (SEQ ID NO: 2) is indicated in bold and underlined text.

FIG. 61 shows the complete amino acid sequence of "FFL-L1SL2TAH": FFL[1-550] L1[$G_4SG_4$] SNAP25[171-206] L2[$G_6$] T[ENLYFQG] A[$K_{8-10}$+GLE]-histag (SEQ ID NO:25). The full-length firefly luciferase sequence (amino acid residues 1-550) is indicated in normal text, the glycine/serine linkers are indicated in underlined text, the SNAP25 sequence (amino acid residues 171-206) is indicated in italicized text, the TEV protease cleavage site sequence is indicated in bold text, the lysine-rich anchor sequence is indicated in bolded and underlined text, and the polyhistadine tag is indicated in bolded and italicized text.

FIG. 62 shows the complete amino acid sequence of full length firefly luciferase from *Photinus pyralis* (SEQ ID: NO 26).

FIG. 63 shows the amino acid sequences of peptides Octa-lysine Anchor Peptide "Anchor ($K_8$+GLE)" (SEQ ID NO: 30), Deca-lysine Anchor Peptide "Anchor ($K_{10}$+GLE)" (SEQ ID NO: 31), Polyhistadine Tag "Histidine Tag ($H_6$)" (SEQ ID NO: 32), Tobacco Etch Virus Protease Cleavage Site (SEQ ID NO: 33), Serine-Glycine Linker 1 "Linker 1 ($G_4SG_4$)" (SEQ ID NO: 34), and Serine-Glycine Linker 2 "Linker 2 ($G_6$)" (SEQ ID NO: 35).

DETAILED DESCRIPTION

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

Provided herein is a laboratory method for detecting the activity of a toxin or enzyme that utilizes common lab equipment and commercially available reagents, and is therefore expected to be reproducible by any reasonably well equipped biological laboratory. This method is referred to herein as an Assay with a Large Immuno-sorbent Surface Area (ALISSA). The examples set forth herein provide a detailed protocol for the ALISSA, as well as an analysis of the effect of various experimental parameters on the assay. In certain embodiments, the ALISSA is employed for the detection of botulinum toxin A (BoNT/A). For example, the exemplary experimental results disclosed herein show that the assay can detect less than 0.5 fg of BoNT/A holotoxin in 1 mL serum, milk, or GP-diluent. Based on these results, the ALISSA is at least about 32,000-fold more sensitive than the life mouse assay and about 160,000-fold more sensitive than the Enzyme-linked Immunosorbent Assay (ELISA). In certain embodiments, the turnaround time for the ALISSA is one to two hours, which is significantly faster than the life mouse assay (~48 hours) and faster than ELISA (~3 hours). The exemplary experimental results obtained herein were obtained with BoNT type A (BoNT/A), but could be applied just as easily to other BoNT serotypes or other toxins as well as enzymes.

The ALISSA may be used in combination with or in place of the mouse $LD_{50}$ assay for measuring the potency of products containing BoNT. Owing to its remarkable sensitivity and rapid turnaround time, the ALISSA provides a beneficial value compared with the "gold standard" mouse assay. Additionally, use of the ALISSA may provide a cheaper method of testing BoNT products as it may result in a reduction of the number of samples or subjects required for testing. The methods and kits provided herein may be used to evaluate the potency, stability, and efficacy of products containing BoNT. The methods and kits may also be used to evaluate products that contain, but are not limited to, active ingredients such as onabotulinumtoxinA, rimabotulinumtoxinB, abobotulinumtoxinA and incobotulinumtoxinA to measure the functional activity of the toxin protein. In some aspects, the method herein may be used to confirm the amount of active ingredient contained in the product. The method provided herein may also be used as a high-throughput assay for testing large quantities of samples.

The ALISSA avoids interference with other sample components by using a highly specific affinity matrix and exploiting the natural catalytic activity of the toxin or enzyme ("target") with a target-specific substrate. Both of these steps amplify the signal via localized enrichment of the toxin and enzymatic conversion of multiple substrate molecules per toxin molecule. In certain embodiments, ALISSA comprises two main steps: 1) binding and enrichment of toxin or enzyme on a bead-based enrichment matrix and removal of unspecific binding molecules, and 2) determination of the enzymatic activity of the immobilized toxin or enzyme based on cleavage of a specific fluorogenic or bioluminescent substrate. The enrichment matrix may comprise protein-A, protein-G, or protein A/G conjugated sepharose, agarose, or magnetic beads coupled and cross-linked to anti-toxin, anti-enzyme, or anti-toxin substrate antibodies. For example, the enrichment matrix may comprise protein-A conjugated sepharose beads coupled and cross-linked to anti-BoNT antibodies. Additionally, in other aspects the beads may also be coupled and cross linked to anti-toxin substrate antibodies. The anti-toxin substrate antibodies may bind a portion of the substrate including the fluorophore, the quencher, or amino acids from the SNAP-25 sequence. For example, the enrichment matrix may comprise protein-A/G conjugated agarose beads coupled and cross linked to anti-FITC antibodies that bind the fluorescent 5-FAM label conjugated to the BoNT substrate. In another example, the enrichment matrix comprises protein-A/G conjugated agarose beads coupled and cross liked to anti-DABYCL antibodies that bind the DABYCL conjugated to the BoNT substrate. In yet another example, the enrichment matrix comprises protein-A/G conjugated agarose beads coupled and cross linked to antibodies that bind a portion of the SNAP-25 sequence. Furthermore, the enrichment matrix may comprise a mixture of both anti-toxin antibodies and anti-toxin substrate antibodies. In other aspects the enrichment matrix comprises cyanogen-bromide (CNBr) activated Sepharose beads coupled and cross linked to anchor (lysine rich) sequences fused to a toxin substrate. For example, the enrichment matrix may comprise CNBr-activated Sepharose beads coupled and cross linked to lysine rich sequences fused to a luminescent BoNT substrate. In other aspects, the enrichment matrix may comprise nickel nitrilotriacetic acid (Ni-NTA) beads coupled and cross linked to affinity tags fused to luminogenic BoNT cleavable fusion proteins. The immunosorbent support provided herein can be comprised of either loose beads or one or more fixed columns.

As used herein, the term "target" when used to refer to a toxin or enzyme, is used to refer to any chemical, biochemical or biological species or compound that is known or referred to in the art as a toxin or an enzyme. A target toxin or target enzyme includes those compounds having proteolytic, catalytic or enzymatic activity. A target toxin or target enzyme includes those compounds able to modify a substrate so as to alter or change the substrate's chemical structure or apparent structure or activity. For example, a botulinum neurotoxin type A is a "target" toxin that has proteolytic activity and is able to cleave its specific substrates. For all botulinum serotypes this may include the BoNT complex, holotoxin, and light chains. As another example, a chitinase is a "target" enzyme that has enzymatic activity. In another example, anthrax lethal factor is a "target" enzyme that has enzymatic activity.

As used herein, the term "substrate" is used to refer to any chemical, biochemical or biological species or compound that complexes with, reacts with, is capable of being modified by, or otherwise interacts with a toxin or enzyme having bioactivity. For example, a botulinum type toxin is a protease able to enzymatically cleave specific protein substrates such as synaptic membrane proteins, SNARE proteins or SNAP-25 proteins. As another example, a chitinase substrate interacts with a chitinase enzyme such as endochitinase or exochitinase.

As used herein, the term "fluorogenic substrate", and "fluorophore" may be used interchangeably to describe a substrate that is hydrolyzed by or otherwise reacted with a target toxin upon contact therewith, producing a complex, product or other derivative thereof which liberates fluorescence upon excitation by a suitable light source.

As used herein the term "bioluminescent substrate", "luminescent substrate", and "luminogenic" protein may be used interchangeably to describe a substrate that is activated by or otherwise interacts or reacts with a target toxin upon contact therewith, producing a complex, product, or other derivative thereof which emits light at distinct wavelengths suitable for detection as desired.

As used herein the term "homologous" is used to refer to any nucleic acid or protein sequence that displays at least 90% similarity with an amino acid sequence wherein the resulting protein still retains its desired functional properties.

In accordance with the method of the ALISSA, one or more samples from a source suspected of containing a toxin is obtained and then contacted with a substrate composition comprising a toxin substrate, such as a fluorogenic or luminogenic substrate or a mixture thereof, for a period of time and under conditions sufficient to permit the toxin to react with the toxin substrate to cause a measurable change in a property such as fluorescence or light emission, or the resulting reaction product.

In general, the toxin or enzyme contained in the sample is first bound on an enrichment matrix such as a bead-based immuno-affinity matrix containing immobilized anti-toxin specific antibodies. Immobilization of the antibodies to the matrix can be by a variety of methods, including, for example by covalent crosslinking of the Fc region of the antibody to the beads. Once bound, the toxin or enzyme molecules retain enzymatic function and specificity for its substrate.

The natural substrate of BoNT/A is the 25-kDa synaptosomal-associated protein (SNAP 25), which it cleaves at distinct sites, thereby preventing the release of neurotransmitters (Schiavo 1993a; Schiavo 1993b). In those embodiments wherein BoNT/A is being detected, the enzymatic activity of BoNT/A may be utilized to cleave the fluorogenic substrate SNAPtide, which is a synthetic, commercially available, 13-amino acid peptide that contains the native SNAP-25 cleavage site for BoNT/A (U.S. Pat. No. 6,504,006). In those embodiments wherein a BoNT type other than type A is being detected, the fluorogenic substrate may be any substrate that is specifically cleaved by the BoNT type being detected. For example, if BoNT B, C, D, F or G is the toxin being detected, then the substrate comprises a fragment of vesicle-associated membrane protein (VAMP) containing the respective BoNT cleavage site, and if BoNT C or E is the BoNT toxin, then the toxin substrate comprises a fragment of SNAP-25 containing the respective BoNT cleavage site. In those embodiments where a different class or type of toxin other than a BoNT is being detected, the substrate may be any substrate that is specifically cleaved or catalyzed by the toxin being detected.

One aspect of the ALISSA provides a method for detecting toxin or enzyme which avoids interference with other sample components by use of high toxin-specific affinity matrix and toxin-specific substrates. For example, use of a high affinity BoNT/A enrichment matrix and a BoNT/A-specific substrate reduces or avoids interference by other components present within a sample thus amplifying the signal and increasing the assay's sensitivity. Use of a toxin-specific substrate also exploits the natural proteolytic activity of the toxin. Signal amplification is achieved by localized enrichment of the toxin and through enzymatic conversion of substrate molecules.

In certain embodiments, the capture matrix is designed to stably enrich the toxin while retaining enzymatic activity. The capture matrix may also purify toxin from non-specific components or proteases present within the sample. Use of a beaded protein A matrix to bind anti-toxin antibodies via FC-region allows orientation of the antibody binding domains away from the bead surface and into the surrounding fluid. This augments and provides increased accessibility for toxin molecules. Use of a bead-based assay also allows for wash steps that diminish interference by other proteases. The ALISSA provides a considerably faster and more sensitive method for detecting toxin and its activity. In certain embodiments, the capture matrix is designed to stably enrich the toxin and the toxin substrate while retaining enzymatic activity. In other embodiments the enrichment matrix is a double affinity matrix composed of one antibody directed to the target toxin and another antibody directed to the toxin substrate. This bivalent immobilization matrix results in further enhancement of enzyme catalysis by providing a strong substrate-bead interaction in combination with a strong enzyme-bead interaction. The antibody directed to the toxin substrate may bind the fluorogenic label conjugated to the substrate, the dark quencher conjugated to the substrate, or the amino acid structure of the SNAP-25 peptide.

The ALISSA may also be used with one or more columns for high analytical specificity and detection of toxin or enzyme in complex biological samples. This column-based ALISSA method may be used for specifically binding the target toxin and removing unspecific binding molecules. The column may be packed with a bead-based enrichment matrix that contains bound ligands, which specifically bind the target toxin or enzyme. Briefly, the sample containing the target toxin may be added to the column containing the ligand-bound enrichment matrix. The sample may be introduced to the column via gravity flow or pressure. Additionally, the sample may be incubated with the enrichment matrix to allow the immobilized ligand to bind the target toxin. The sample may then be removed, leaving the target toxin bound to the immobilized ligand on the enrichment matrix within the column while the non-specific molecules may be washed away.

Next, a toxin substrate capable of eliciting a detectable signal may be added to the column containing the target toxins bound to the enrichment matrix. Upon substrate cleavage, the detectable signal may be measured. In some examples, the signal may be detected after elution of the sample containing the detectable signal. In certain examples, the toxin substrate may be either a fluorogenic peptide or a luminogenic peptide. In some embodiments, the column used in the ALISSA is an affinity microcolumn containing an enrichment matrix comprised of an immuno-affinity matrix.

Any variety of one or more commercialized columns may be used for the column-based ALISSA including, but not limited to, gravity-flow columns, spin columns, and pressure columns. In some embodiments, two or more columns may be used for the ALISSA; however, one column is the preferred method of use. Additionally, pipette tip columns containing affinity microcolumns mounted into pipette tips may be used for the column-based ALISSA. In some examples, the pipette tips may be disposable. For example, the affinity microcolumns that may be used in the column-based ALISSA may be dextran glass columns from Intrinsic Bioprobes, Inc. (acquired by Thermo Fischer Scientific) and may contain microcolumns mounted into pipette tips. The affinity microcolumns mounted into pipette tips may be used as described in U.S. Pat. No. 7,087,164 B2. In some examples the microcolumns mounted into pipette tips may be used in conjunction with an inexpensive, robust automated high-throughput method for detecting BoNT in biological samples. For example, a microcolumn robotic pipetting workstation system may be used for the automated microcolumn based BoNT detection system for use as a high-throughput system. The system may be programmed to conduct automated functions such as microcolumn-enrichment of BoNT/A from spiked samples of human serum and microcolumn washes. In other examples, the microcolumns mounted into pipette tips may be used in conjugation with an electronic multichannel pipettor. In certain aspects this exemplary method of detecting BoNT/A may also be used to detect other BoNT serotypes such as B, C, E, and F as well and a wide variety of other toxins or enzymes.

In certain embodiments, antibodies may be conjugated to the enrichment matrix of the affinity microcolumns. For example, the BoNT/A light chain specific monoclonal antibody, 5A20.A, may be conjugated to beads to bind the LC of BoNT/A. However, other affinity reagents may be used for microcolumns such as fusion proteins that contain antigen-binding fragments like scFvs or the binding domains of single chain antibodies. Additionally, recombinant alpaca single chain antibodies (VHH) may be used in the bead-based microcolumn ALISSA for detection of BoNT. To improve the performance of ALISSA, bivalent and multivalent VHHs may be used to bind BoNT. Cyanogen bromide-activated Sepharose beads may be used to coupled VHHs or antibodies to ALISSA beads. In other examples the affinity microcolumns may be optimized to contain VHH proteins generated from affinity maturation of BoNT/A and BoNT/B specific VHH reagents using a yeast display technique. In some aspects, the toxin specific antibodies are immobilized using an immuno-affinity matrix containing protein A/G-coated beads. In other examples, the antibodies may readily be utilized for the ALISSA after direct immobilization via amine groups to Cyanogen-bromide activated Sepharose beads. The ALISSA may improve the diagnosis of botulism and other toxins significantly and may serve to protect humans in biomedical and bio-defense scenarios. The method may also be applied for the routine testing of foods and for forensic investigation.

In certain embodiments, the detailed steps that are necessary for using ALISSA with a bead-based immuno-affinity matrix have been provided. For example, an immunocapture method may be used to bind BoNT toxins including BoNT complexes, holoenzymes, and light chains for use in detecting BoNT. Different antibodies recognizing different epitopes on BoNT may be used to conjugate to the immuno-affinity matrix. For example, antibodies that recognize BoNT/A and BoNT/B (camelid heavy chain antibodies), or BoNT/A light chains (BoNT/A LC) (5A20.4 monoclonal antibody), and BoNT/B LCs (2B24) may be coupled to CNBr-activated Sepharose beads for use in the bead-based ALISSA. These conjugated beads may then be used to bind BoNT complexes, holoenzymes, and/or light chains. BoNT cleavable substrates may then be used to detect BoNT activity as described.

Detection of all BoNT serotypes including subtypes may also achieved utilizing novel fluorogenic or luminogenic substrates. The botulinum neurotoxins cleave a variety of vertebral SNARE (Soluble NSF attachment protein receptor) in vivo and in vitro. While some fluorogenic BoNT substrates based on natural SNARE sequence are known (Schmidt 2003), the possible interference by sterically demanding fluorophore or quencher moieties on the catalytic cleavage reaction of such fluorogenic peptides remains a concern. Novel substrates that achieve higher chemical stability and comparable or superior sensitivity as compared to prior peptides have been provided. Preferably, fluorophore substrates that allow for efficient cleavable fluorophore and quencher combinations are selected for use in the ALISSA assay. Generally, fluorophore and quencher require proximities of about 10 nm or less to allow sufficient FRET-mediated quenching. Closer distances are also preferred to reduce background fluorescence from the quenched substrates. In certain embodiments, use of bioluminescent substrates to allow for luminescent BoNT detection may be desired. Luminescent based assays can reduce or omit the requirement for a light source and provide greater signal-to-noise ratios. Bioluminescent light in particular, can be detected using less complex means such as with miniaturized photomultipliers or microscopic avalanche photodiodes. Furthermore, potential interference from background fluorescence due to inert components of a microfluidic device is alleviated.

Novel fluorogenic substrates for BoNT serotypes such as serotypes A to G are designed through use of peptide libraries having proteinogenic and as well as non-proteinogenic amino acids. Preferably, those substrates having resistance to non-BoNT proteases are selected for use with the ALISSA or other immobilized antibody matrix based assay. More preferably, substrates designed so as to be more specifically and readily cleaved by BoNT are also provided. Thus, the ALISSA may be useful for detecting BoNT of all serotypes and subtypes in one or more biological sample, in vitro or in vivo, using affinity capture of BoNT on microscopic beads coated with antibodies specific to the toxin. The antibody-bound toxin retains its metalloprotease activity. In some aspects, the antibody on the beads is specific to the toxin substrate and binds the toxin substrate on the beads. In some aspects the beads contain a mixture of antibodies directed to the toxin and the toxin substrate. The method includes use of a reporter molecule such as a fluorogenic or bioluminescent substrate that is cleavable by one or more molecules of the bound BoNT. Fluorescence is then detected using a handheld ultraviolet (UV) light, a fluorescence excitation and/or detecting tool, device or any suitable commercially available fluorometer. In some embodiments the ALISSA may also be used to measure the activity of other zinc metalloprotease enzymes.

In certain embodiments, methods are provided for identifying novel fluorogenic and luminogenic substrates that are useful for detecting the presence and/or activity of a toxin or enzyme. Such toxin-specific substrates are useful for detecting, identifying and/or assaying for the presence or activity of a toxin or enzyme in a sample at attomolar levels of sensitivity. For example, it is known that botulinum neurotoxins cleave a variety of SNARE proteins. Sequences of natural SNARE proteins have been used to produce fluorogenic BoNT peptide substrates. Such methods generally entail use of terminal fluorophore and quencher molecule pairing (fluorescence through resonance energy transfer), or FRET moieties. It is difficult, however, to predict the effect that sterically demanding fluorophore or quencher moieties will have on the ability of the toxin to effectively cleave the resulting fluorophore modified substrate molecule. Some embodiments provide novel fluorogenic substrate peptides by employing synthetic peptide libraries to screen for those substrates that readily contain fluorophore and quencher combinations.

Cleavable fluorogenic substrates may be designed and used to detect the presence of BoNT. In some aspects, a cleavable fluorogenic peptide, containing portions of the human SNAP-25 C-terminal sequence with a norleucine corresponding to residue M202, may be used to detect BoNT/A cleavage. For example, the norleucine may be located at the C-terminus of the peptide. A cleavable peptide may be labeled with at least one fluorogenic label conjugated at or near the N-terminus and at least one dark quencher may be conjugated at or near the C-terminus of the substrate. As used herein, the term "near the N-terminus" is used to refer to any position on the substrate that is within 5 amino acids of the N-terminus of the substrate, while the term "near the C-terminus" is used to refer to any position on the substrate that is within 5 amino acids of the C-terminus of the substrate. The fluorogenic label may be conjugated to the substrate via a peptide bond, which enhances the stability of the substrate. Additionally, the substrates may contain arginines of the L-isomeric form. In some embodiments a novel fluorogenic peptide containing the BoNT/B cleavable sequence of vesicle-associated membrane protein (VAMP) may be used to detect BoNT/B cleavage. In other aspects a fluorogenic cleavable peptide BoNT/E peptide may be used to detect the presence of BoNT/E. Additionally, a fluorogenic cleavable and control substrate may be designed and used in the ALISSA to detect all BoNT serotypes, A to G. Internal controls may also be used for an endopeptidase-based BoNT detection assay to determine the specificity of the BoNT ALISSA and the extent of non-specific proteases in a sample. In some aspects the control peptides can be used in combination with the BoNT peptide substrates in the same sample. For example, control peptides labelled with an N-terminal 5-carboxyfluorescein (5-FAM)—can be used with a BoNT cleavable substrate containing a 4-Methylumbelliferone (4-MU) label and visa versa.

In a separate embodiment, methods are provided for the identification of novel luminogenic protein substrates. Using recombinant methodology, genetically engineered variants of recombinant luciferase proteins that become activated by specific BoNT cleavage reactions are provided. Thus, the methods provide luminescent substrates specific for all serotypes and subtypes of botulinum toxin. Luminescence is detected using any suitable commercially available luminometer.

Employed are two general approaches to exploiting bioluminescence for identifying novel bioactive luminogenic substrates. The first includes use of complementation of inactive luciferase fragments to restore active luciferase molecules. The second includes use of specific reactions that release D-luciferin as a substrate for firefly luciferase (FFL from *Photinus pyralis*). Complementation assays for luciferase are described by Paulmurugan et al., "Combinatorial library screening for developing an improved split-firefly luciferase fragment-assisted complementation system for studying protein-protein interactions," *Anal Chem.*, 79:2346-2353 (2007); and Paulmurugan et al., "Firefly luciferase enzyme fragment complementation for imaging in cells and living animals," *Anal. Chem.* 77:1295-1302 (2005). Using described complementation assays, split luciferase constructs are designed for use in detecting the presence of specific enzymatic activity. For example, an inactive N-terminal FFL fragment may be fused to a binding domain of a protein having a known binding affinity for another binding partner. The other protein binding partner may be fused to the C-terminal portion of FFL and to a BoNT/A cleavable SNAP25 sequence, which is further immobilized onto beads. Whereas such constructs are inactive when in their fused, non cleaved state, upon interacting with a target toxin such as BoNT, the proteolytic activity of the toxin cleaves and releases the C-terminal portion of FFL. Upon release and binding of the binding protein domains, the FFL fragments recombine and a detectable luminescent signal is emitted due to restored FFL activity. An example of a protein containing a binding domain with a known binding affinity for another binding partner would be glutathione-S transferase, which has a known binding affinity for a separate glutathione-S transferase molecule.

The luminogenic substrates have the advantage that they can be produced inexpensively and in large quantities from cultures of engineered *E. coli* bacteria. Furthermore, luminogenic substrates reduce the requirements for expensive instrumentation. Simple and very sensitive and even portable luminometers can be used instead of much more expensive fluorometric instrumentation. In certain embodiments, additional fusion proteins with the optimized construct of FFL, linkers, and SNAP-25 may be constructed by adding a green fluorescent protein to its C-terminus and utilizing the N-terminal region to screen the inhibitory sequence through a cloning approach. The inhibitory sequences may encompass both scFvs from the mAbs generated, as well as random peptides and VHHs with randomized CDR3 regions. The luminogenic substrates may be further optimized for better resistance to non-BoNT proteases. The luminogenic substrates may incorporate sufficient sequences of SNAP25 to allow cleavage activation by BoNT/E, A and C. The luminogenic substrates may also include a vesicle associated protein (VAMP) sequence to allow cleavage activation by BoNT/B, C and F. The method may also employ the use of bead immobilization of a fusion protein containing full length firefly luciferase (FFL) protein and a BoNT specific cleavage site on nickel nitrilotriacetic acid (Ni-NTA) beads or Cyanogen bromide-activated Sepharose beads. The fusion protein may be immobilized to the beads via a lysine-rich anchor sequence. When the fusion protein is bound to the beads, the FFL is substantially quenched when compared to the fusion protein in solution. Upon interacting with BoNT, the proteolytic activity releases the FFL from the beads and increases the luminescence in the supernatant. This novel method may be used to detect proteolytic activity of additional proteases when used with a protease specific cleavage site. For example, a cleavage site that can be recognized by the Tobacco Etch Virus (TEV) protease may be used as an optional control. Additionally, glycine and/or serine rich linker sequences may be added to both sides of the SNAP-25 sequence to enhance cleavage by BoNT. Luminogenic substrates for all toxins and enzymes as well as the seven serotypes (A to G) of BoNT may be detected by such specific substrates. In certain embodiments testing for different BoNT serotypes and subtypes in sterile filtrates of clinical isolates of *Clostridium botulinium* may be performed with luminogenic and fluorogenic substrates.

The novel substrates may also be obtained by the usual methods of solid-phase synthesis according to the Merrifield method on an automatic synthesizer such as, for example, the 431A synthesizer from Applied Biosystems. The chemistry used corresponds to Fmoc technology and protection of the side chains allowing cleavage thereof with trifluoroacetic acid, as described by E. Atherton and R. C. Sheppard (1989) in "Solid Phase Peptide Synthesis: a practical approach, IRL Press, Oxford."

The ALISSA technology may also be applicable for use with targets such as enzymes or toxins other than BoNT. For example, anthrax lethal factor (LF) has successfully been adapted for use in the ALISSA. As previously described, anthrax LF is a component of anthrax toxin that exhibits zinc metalloproteinase activity. The ALISSA is capable of quantitatively detecting anthrax LF and reaching femtomolar sensitivities. Thus, ALISSA has the potential to significantly improve the diagnosis of botulism, anthrax infection and potentially other serious infections, and could serve to protect humans in biomedical and biodefense scenarios. Additionally, a specific and sensitive assay for the detection of LF is potentially useful for early diagnosis of anthrax infection and is expected to be a useful research tool to advance the understanding of the mechanism of action of anthrax toxin. Additionally, the ALISSA technology may also be extended to detect human chitinases (e.g. CHIT1 and AMCase) and non-metalloproteases (Pep1 and Pep2 of *Aspergillus fumigatus*).

According to some embodiments, ALISSA may be used to detect systemic BoNT, such as toxin distribution in animal sera and organs. For example, BoNT levels may be measured in serum and organs of BoNT intoxicated mice. In some embodiments, BoNT ALISSAs may be used to measure the systemic content and tissue distribution in sub-lethally BoNT-intoxicated mice. In certain embodiments the pharmacokinetic and serotype-dependent toxin distributions may be determined in organs following parenteral or oral intoxication.

In certain embodiments, the pharmacokinetics of BoNT/A intoxication may be studied using ALISSA. For example, the pharmacokinetic measurements on BoNT intoxication in the mouse model may be used to study the persistence of sub-lethal concentrations of BoNT over extended periods of time. Serum samples from intravenous (i.v.) and intragastric (i.g.) intoxication mice models may be used to study the toxin concentrations during a time course study. This method may be useful due to the widening medical use of BoNT against conditions such as dystonia, depressions, and migraine, and the difficulties associated with such use (Crowner 2007; Jankovic 2004). Furthermore, luminogenic substrates may also be used to detect BoNT during a time course experiment in mice intoxicated with BoNT.

In some embodiments, the BoNT in intoxicated neurons may be quantified using ALISSA. For example, ALISSA may be used to study BoNT/A1-intoxicated rat hippocampal primary neuronal cells. In other examples, ALISSA may be conducted with Neuro2A and M17 cells in vitro as well as with isolated neurons.

According to some embodiments, ALISSA may also be useful for detection of botulism in clinical specimens. For example, ALISSA may be used to detect BoNT in sera from adult patients that have food-borne or wound botulism. In other examples, ALISSA may be used to detect BoNT in sera from infant patients with botulism.

EXAMPLES

Example 1

Materials and Methods

The pure 150 kDa BoNT A toxin (holotoxin) was purchased from two distinct commercial sources: from the List of Biological Laboratories (Campbell, Calif.) and Metabiologics Inc. (Madison, Wis.). The BoNT/A complex, IP and IV mouse assays in 50 mM citrate buffer, pH 5.5 was received from Dr E. Jonson's laboratory, Food Research Institute of the University of Wisconsin-Madison. The intact BoNT/A toxin complex and BoNT/A toxoid were from MetaBiologics. SNAPtide™ (FITC/DABCYL), synthetic peptide containing the native cleavage site for Botulinum toxin type A and SNAPtide°, unquenched calibration peptide for SNAPtide™ (FITC/DABCYL), were purchased from the List of Biological Laboratories. The latter contains the FITC bound to the N-terminal cleaved fragment of SNAPtide; it was used as a calibrant to convert fluorescence intensity units to changes in the molar ratio of peptide cleavage product. All types of BoNT/A toxin were from Hall A, *Clostridium botulinum* producing strain. In one example, the BoNT/A subtype used was A1. Toxin activities for the holotoxin and the complex were $2.1 \times 10^8$ $MLD_{50}$/mg and $3.6 \times 10^7$ $MLD_{50}$/mg, respectively, according to Metabiologics.

In certain embodiments, the fluorogenic peptide is SNAPtide (U.S. Pat. No. 6,504,006) which is a molecular derivative of SNAP25, the natural substrate of BoNT/A. SNAPtide is cleaved by BoNT/A between a fluorophore and a quencher (FRET pair) releasing unquenched fluorophore. The SNAPtide contains a conjugated fluorescein thiocarbamoyl (FITC) quenched by a 4-(dimethylaminoazo) benzene-4-carboxyl (DABCYL)-moiety. The fluorogenic peptide SNAPtide (FITC/DABCYL, product #521) and the unquenched calibration peptide, containing an N-terminally FITC-labeled fragment of SNAPtide (product #528, synthetic, but sequence identical to the BoNT/A cleaved product), were from List Biological Laboratories. In other embodiments, the substrate comprises a SNAPtide peptide wherein the N-terminal fluorescein isothiocyanate was replaced with 5-carboxy fluorescein. Such labeling improves stability of the substrate. In certain embodiments, 4-methylumbelliferone labeling was utilized allowing use of a substrate having blue fluorescence.

Affinity purified Rabbit polyclonal to *Clostridium botulinum* A Toxoid (formaldehyde inactivated Type A Neurotoxin (*C. botulinum*) antibodies were purchased from Abcam (Cambridge, UK). Purified rabbit IgG was from (ICN Biomedical Inc., Aurora, Ohio), Seize® X Protein A Immunoprecipitation Kit was from Pierce (Rockford, Ill.), Trypsin was from Promega, Fetal Bovine Serum was from Invitrogen (Carlsbad, Calif.). Human serum was from Sigma (cat. #H4522) and carrot juice was from Bolthouse Farms (Organics, 100% carrot juice, 1 liter bottle). Other reagents were from Sigma unless indicated. Concentrations of the toxins were determined according to the extinction coefficient (Ahmed et al., 2001) or by Bicinchoninic Acid (BCA, Pierce) Protein Assay, a Micro Assay for dilute protein solutions, with BSA as standard. Both methods gave the same result. The product was exclusively the dichain form of the toxin as judged by the 12% sodium dodecyl sulfate-polyacrylamide gel electrophoresis at room temperature (25° C.) under reducing conditions. Gels were analyzed by Western Blot using Rabbit polyclonal to *Clostridium botulinum* A Toxoid (Abcam). The bands on the gels were visualized by Coomassie Blue or Silver staining or with the SimplyBlue SafeStain kit from Invitrogen (Carlsbad, Calif.).

Example 2

Assay Design

Preparation of the Immunomatrix.

Figure 1:
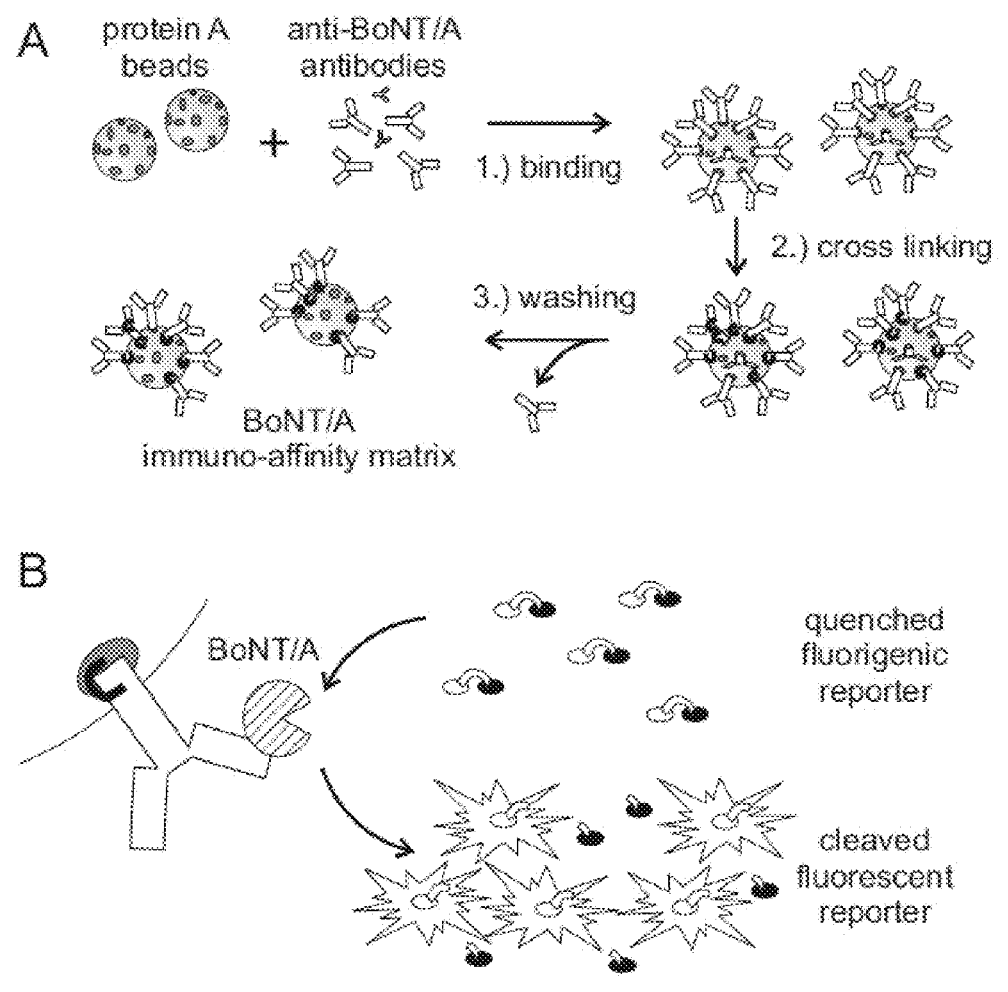
Figure 2:
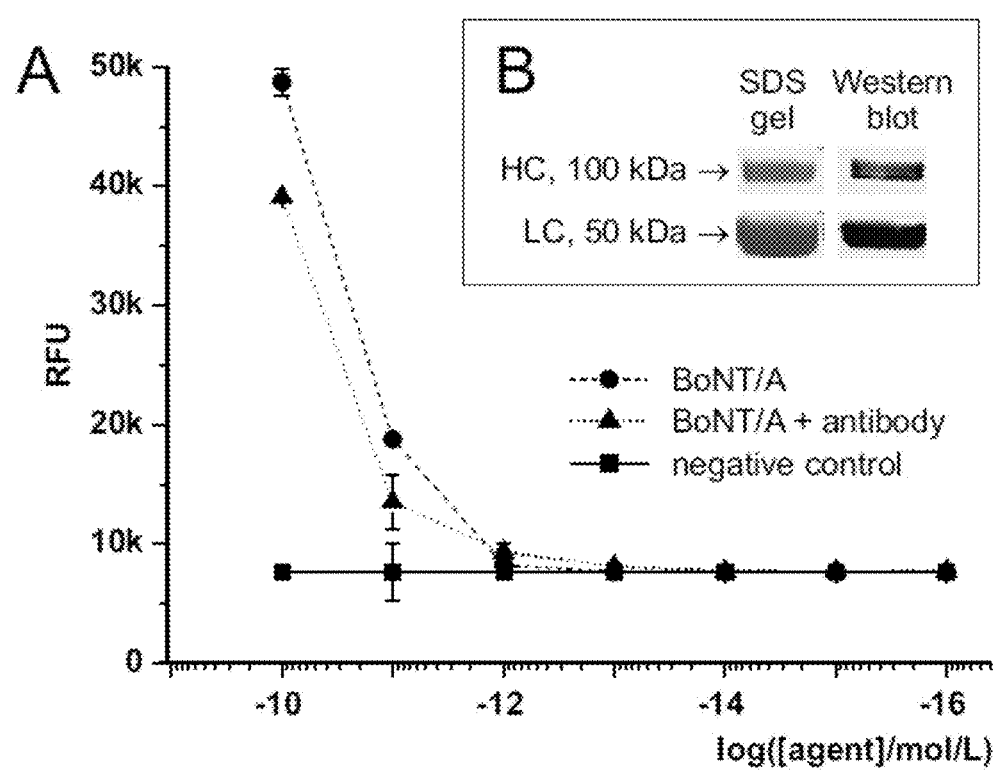

BoNT/A was bound and enriched on a bead-based immuno-affinity matrix and cleansed from unspecific binding molecules. The enrichment matrix consisted of protein-A conjugated sepharose beads coupled and cross-linked to polyclonal anti-BoNT/A antibodies (FIG. 1a). Anti-BoNT/A antibodies were bound and then covalently cross-linked to the bead-immobilized protein A molecules to prevent bleeding off when mixed with sample. The release of antibodies into the sample may otherwise lower the sensitivity of the assay. Capture antibodies were directly and covalently linked to the Protein A support (agarose beads) using the SeizeX Immunoprecipitation Kit (Pierce) as described in the supplier's protocol. Briefly, 125 µg of *Clostridium botulinum* A Toxoid, formaldehyde inactivated Type A neurotoxin (ab 20641) prepared in 0.4 mL of Binding/Wash buffer contained 0.14 M NaCl, 0.008 M sodium phosphate, 0.002 M potassium phosphate and 0.01 M KCl, pH 7.4, were bound and immobilized to a Protein A support using cross-linker Disuccinimidyl suberate (DSS). 25 µL DSS, dissolved in DMSO immediately before use, was added to the spin cup containing the bound antibody support and gently mixed for 30-60 minutes, centrifuged and washed 4 times with 500 µL of ImmunoPure Gentle Elution Buffer (Product No. 21027) with a high-salt, neutral pH elution system to quench the reaction and to remove excess DSS and uncoupled antibody. Alternatively, the beads were centrifuged and washed three times with 500 ul Gentle Elution Buffer and two times with 500 ul Gentle Binding Buffer (Pierce Product No. 21030). The Handee™ Spin Cup Columns with functionalized beads were wrapped with laboratory film to prevent gel from drying and stored at 4° C. until used in experiments. The number of beads varying in sizes between 10-100 µm was estimated microscopically with Reichert Bright-Line Metallized Hemacytometer (Hausser Scientific, USA). The immobilized polyclonal rabbit antibody used herein exhibited binding affinity to the light and heavy chain of BoNT/A, as confirmed by Western blot (FIG. 2b).

BoNT/A Assay with a Large Immuno-Sorbent Surface Area (ALISSA).

The enzymatic activity of the immobilized BoNT/A was determined by cleavage of the specific fluorogenic substrate SNAPtide, a synthetic, commercially available, 13-amino acid peptide that contains the native SNAP-25 cleavage site for BoNT/A (Schmidt 2003; U.S. Pat. No. 6,504,006) (FIG. 1b). BoNT/A holotoxin or its complex, were pre-incubated (where indicated) in 5 mM dithiothreitol (DTT) for 30 minutes at 37° C. in order to reduce and pre-activate the enzyme, immediately following reconstitution in the buffer containing 20 mM HEPES, pH 8.0, 0.05% Tween-20, 0.3 mM $ZnCl_2$, and 1.0 mg/mL BSA to recover of BoNT/A. Pre-activated toxin was used immediately after reconstitution with the buffer. Enzyme was immobilized on the antibodies-bound beads in 1 mL of 3% Carnation non-fat milk in PBS or in a 10% Fetal Bovine Serum (heat inactivated). After the addition of immunomatrix samples were incubated with the food matrix or serum. Suspensions were rotated for indicated times at 8 rpm on a Labquake Shaker/Rotisserie (Barnstead International, Dubuque, Iowa).

The antibody-bound beads with immobilized enzymes were separated by the centrifugation, washed three times with 500 μl PBS buffer, collected and re-suspended in 300 μl of 20 mM HEPES buffer, containing 0.3 mM $ZnCl_2$, 1.25 mM DTT and 0.1% TWEEN-20, pH 8.0. Unbound material was then removed by washing and synthetic peptide was added. Reaction was started by rotating and adding various concentrations of SNAPtide. For assays 4 mM DMSO-stock solution was diluted in 20 mM HEPES, pH 8.0, and a 100 μM stock solution was used. Assays were performed for indicated times in a dark; reaction was stopped by transfer to ice and addition of a 20 mM ethylenediaminetetraacetate (EDTA) (pH 8.0), which was equally effective in blocking the proteolytic activity of both holotoxin and complexed BoNT/A. For work without antibodies-bound beads, the toxin was combined with the same number of beads with no antibodies or with the rabbit IgG-beads.

Conversion of SNAPtide releases the N-terminal fluorophore, fluorescein-thiocarbomoyl (FITC), which is initially quenched by the C-terminal chromophore, 4-((4-(dimethylamino)phenyl)azo)benzoic acid, succinimidyl ester DABCYL, was recorded with Wallac 1420 Multilabel Counter Victor$^{2}$™ spectrophotometer (Perkin Elmer) or with SpectraMax M2 (Molecular Device Corp.) at 485 nm/535 nm as an excitation and emission wavelengths, respectively. The increase in fluorescence intensity is directly proportional to the amount of cleavage that has occurred and thus allows for accurate measurement of botulinum toxin enzymatic activity. Before experiments the beads with cleaved SNAPTide were observed on the glass slides mounted on fluorescent microscope (Olympus BH2-RFCA, Japan). The immobilized polyclonal rabbit antibody used herein did not significantly inhibit the specific proteolytic activity of BoNT/A (FIG. 2*a*).

Example 3

Assay Optimization

The conditions of bead-based assay were optimized to maximize its sensitivity and specificity for one- and ten-attomolar toxin concentrations in 1-mL sample volumes (see FIGS. 3*a-e*)). Therefore, assay sensitivity was repeatedly measured using serial dilutions of BoNT/A in 10% fetal bovine serum (FBS), and the following parameters were evaluated: antibody-protein A cross-linking conditions, post cross-linking bead wash buffers, number of beads, toxin-antibody binding times and temperature, wash buffers for the removal of non-specific antibody binders, SNAPtide concentration, SNAPtide conversion time and the effect of temperature during reaction. For each BoNT/A dilution, the fluorescence intensity was plotted against the variant parameter. Due to the asymptotic nature of the resulting curves, there are no optima for several parameters. However, by analyzing the change in signal gain as a function of a given parameter, efficient values for each parameter which produce the steepest increase in signal gain have readily been achieved, and the assay's performance has become robust and predictable.

During synthesis of the bead-based immunomatrix, use of a neutral wash buffer after binding and cross-linking of the antibody to the protein A beads was found to be critical. When an alternative acidic wash buffer (pH 2.8) was used instead, the antibodies were altered such that they became inactive when exposed to nanomolar concentrations of the toxin, probably through toxin-induced proteolytic cleavage.

The assay performed efficiently and with high sensitivity when using about 100 μL/well SNAPtide in concentrations of about 25 μg/mL (FIG. 3*a*) and 1 uM. A reaction time of one hour for the conversion of the fluorogenic SNAPtide at room temperature (25° C.) was appropriate (FIG. 3*b*). Within limits, the signal-gain of the assay can be enhanced by increasing the number of beads mixed with the sample (FIG. 3*c*) and by extending the enzyme enrichment time as demonstrated in FIG. 3*d*. The most efficient bead concentrations lie between about 100,000 and about 120,000 beads/mL, which correspond to a bead bed volume of approximately 8.7-10.4 μl or approximately 10-12 μl, when left to settle. Further increase of the bead concentration to 500,000/mL raised the signal intensity only by another 28% (FIG. 3*c*). The effect of temperature on the toxin capturing step was also investigated. Sufficient binding required about 3 hrs at about 25° C. incubation for the substrate with the beads, and about one hour when at about 37° C. The measured toxin activity was significantly diminished at about 55° C. (FIG. 3*e*), likely due to toxin deactivation rather then due to decreased antibody binding. An increase in temperature from about 25° C. to about 37° C. during the SNAPtide-conversion reaction improved the signal and reliable readings were obtained for reaction times of about 1 hour.

Pre-activation of the toxin on the beads during the wash step was achieved with 5 mM DTT and produced slightly higher signals when compared to the non-pre-activated toxin (FIG. 4A). However, the subsequent reaction with the fluorogenic reporter had to be performed in 1.25 mM DTT in order to avoid denaturation of the immunoaffinity matrix and because prolonged exposure to the more concentrated reductive agent inactivated the toxin considerably (tested on bead-free toxin).

Stable BoNT-Immobilization Matrix.

Previously, the antibody-coated beads could not be stored for more than two weeks in liquid suspension without experiencing a significant loss of ALISSA sensitivity. Suitable conditions for the extended dry storage of lyophilized ALISSA beads were determine. When freshly reconstituted in liquid buffers, no substantial loss of sensitivity was observed after 3 month of bead storage. Key to the longevity of the bead matrix was the choice of suitable lyophilization conditions. All antibodies were provided by our collaborator, Dr. James D. Marks at the University of California, San Francisco (UCSF).

Suitable Antibodies for BoNT ALISSAs.

Although originally developed with rabbit polyclonal antibodies that recognize both BoNT light chain (LC) and heavy chain (HC), monoclonal antibodies (mAbs) that bind certain BoNT epitopes are also usable in the ALISSA. mAbs enhance specificity, and can positively affect BoNT's metalloprotease activity. The functional and biochemical aspects of antibodies used to develop the ALISSA technology into a reliable product were investigated. More than 37 different monoclonal and polyclonal antibodies have been characterized for their suitability to be used in the ALISSA. The BoNT-binding specificity was investigated and the effect that antibodies exert on the enzymatic activity of antibody-bound BoNT in solution and after surface immobilization was measured. Alongside mAbs provided by the PSWRCE members Dr. Larry Stanker (USDA) and Dr. James Marks (UCSF), a number of murine mAbs that were generated against BoNT LC/A peptides, recombinant (r) LC/A and B, and BoNT toxoid (formaldehyde inactivated complex) were evaluated.

Although both anti-LC and anti-HC mAbs function in the ALISSA, anti-LC antibodies are preferred for most sample matrices that require stringent wash steps. Interestingly, some mAbs enhance the catalytic activity of LC in a bead-free reaction, while others have no catalytic influence or are inhibitory. Certain mAbs bind LC with high affinity, but do not recognize the LC that is present in the BoNT complex. The mAbs that are most suitable for the ALISSA bind LC both when incorporated in the BoNT complex and when free in solution. One polyclonal (old Abcam batch of ab20641) and three mAbs were functional in the BoNT/A ALISSA. One mAb from Larry Stanker at the USDA was usable for the BoNT/B ALISSA, and one polyclonal antibody from Metabiologics provided acceptable results in the BoNT/E ALISSA.

Figure 5:
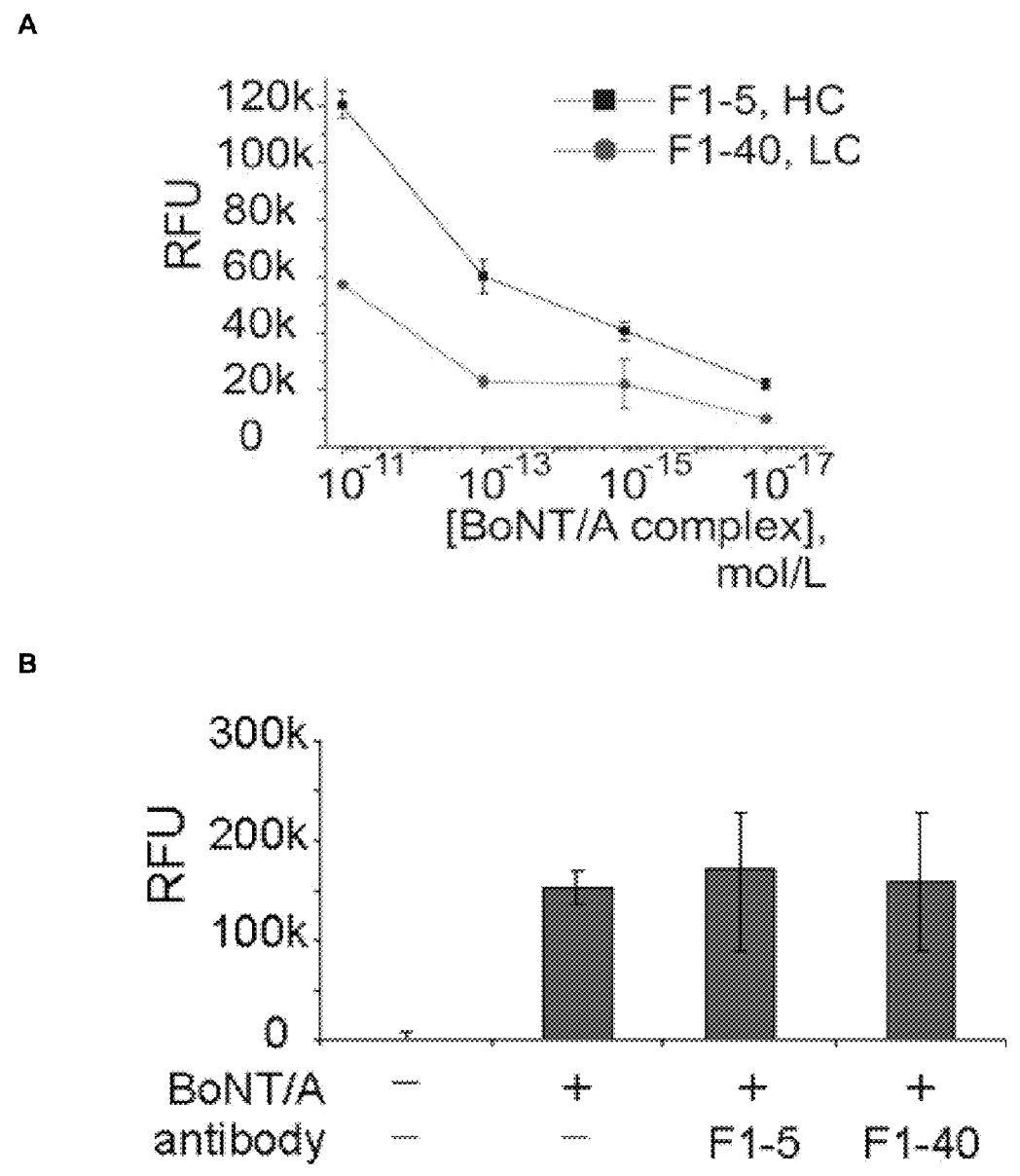

Antibodies reactive to LC or heavy chain (HC) of BoNT/A can be used in the BoNT/A ALISSA (FIGS. 5A and 5B)). The monoclonal mouse antibodies F1-5 against HC, and F1-40 against LC tested, were produced and provided by Dr. Larry Stanker at the USDA. Antibodies that inhibit the catalytic function of BoNT are not suitable for the ALISSA. For example the CDC equine polyclonal antibody used for serotyping did not enhance the sensitivity of the bead-based ALISSA (FIG. 6A) and inhibited BoNT/A's catalytic activity in solution (FIG. 6 B).

In some embodiments, polyclonal, monoclonal antibodies and immobilized single chain Fragment variables (scFvs), derived from mAbs, may be selected such that they bind BoNT light chains (LCs) with nanomolar (or better) affinity and without inhibiting the catalytic activity of BoNT. In certain embodiments, the antibodies bind BoNT LC epitopes in BoNT complex and holotoxin with similar affinity. In other embodiments surface plasmon resonance may be used to measure binding affinities as well as ALISSA assays with immobilized affinity reagents to determine detection limits and linearity for BoNT detection. The pharmacokinetics of these affinity reagents may be tested for the analysis of BoNT from different clinical and medically relevant samples. In certain embodiments the BoNT/A affinity reagents may be used in a research-grade product prototype to be used for the regulatory approval process.

Comparison of Agarose and Magnetic Beads.

Figure 7:
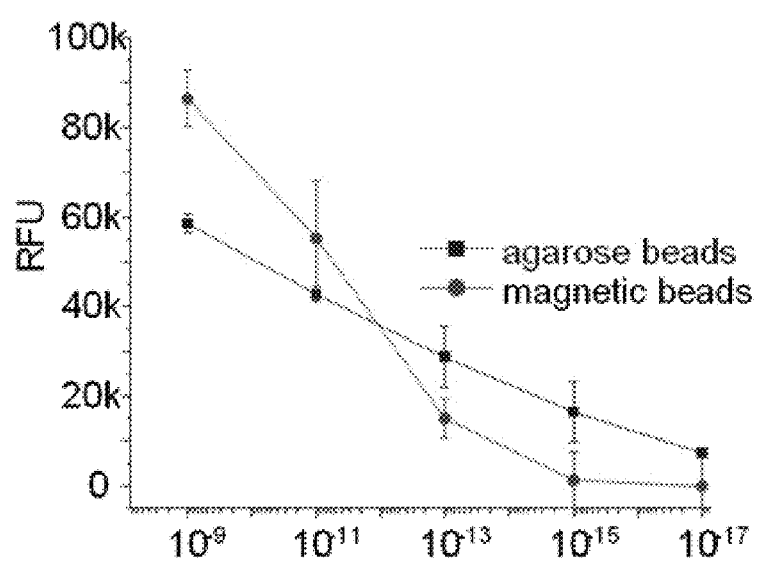
FIG. 7 shows the results of an ALISSA performed using 5 μg of anti-BoNT/A antibody with decreasing concentrations of BoNT/A complex ($10^{-5}$ to $10^{-17}$ mol/L) and approximately 120,000 beads.

A comparison between Protein A coated agarose and magnetic beads was performed to determine the sensitivity of each bead type. Agarose beads (6%) are approximately 10-100 μm in diameter (exclusion limit for proteins ~5,000 kDa); whereas, magnetic Dynabeads, coated with Protein A, are 2.8 μm in diameter and have a smooth surface. ALISSA results demonstrated that the smaller magnetic Dynabeads were more sensitive at higher concentrations of BoNT/A complex ($10^{-9}$ mol/L); whereas, the larger agarose beads were more sensitive at lower concentrations of BoNT/A complex ($10^{-17}$ mol/L) (FIG. 7).

Optimization of ALISSA Immunomatrix Using a Double Affinity Matrix.

The ALISSA method not only immobilizes and thereby concentrates the catalytic subunit of BoNT on the beads, it also substantially accelerates the enzymatic turnover rate of the BoNT-substrate conversion by approximately 18-fold (bead based ALISSA: typical $K_m$=0.2 μM, $V_{max}$=14.5 μM/min/μg; non-bead based assay: typical $K_m$=0.7 μM, $V_{max}$=0.8 μM/min/μg). This enhancement of catalysis is accompanied by a weak interaction between substrate molecules and the bead surface. To further improve enzyme acceleration by strengthening the substrate-bead interaction, the conditions of the ALISSA immunomatrix were optimized to include a double affinity immobilization matrix.

Figure 8:
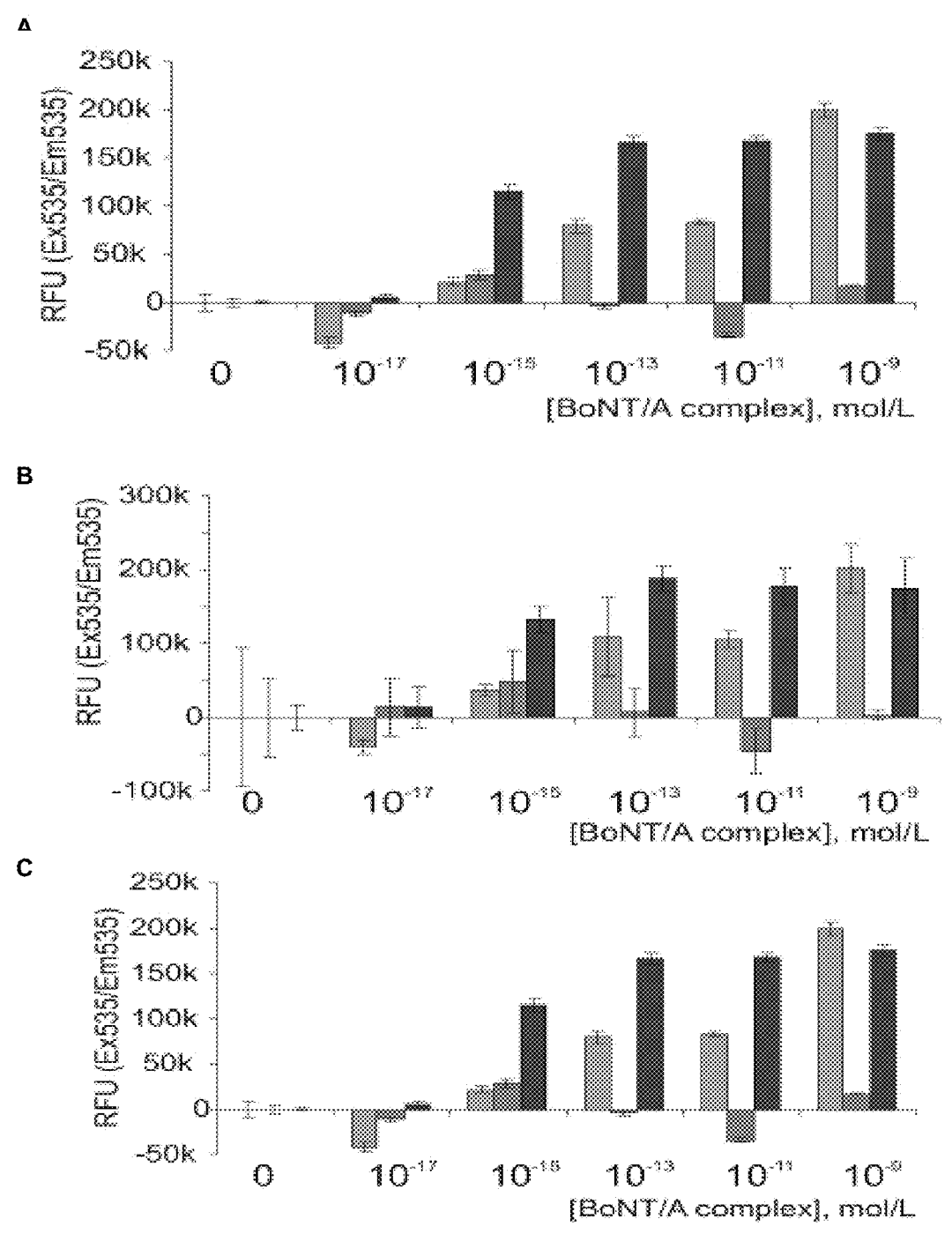

An immobilization matrix was prepared that contained antibodies targeting both BoNT/A (F1-40: monoclonal anti-BoNT/A light chain (LC) antibody) and the BoNT/A cleavable substrate containing an N-terminal 5-carboxyfluorescein group (anti-FITC antibody). Remarkably, when both anti-BoNT and anti-fluorescein antibodies were bound to beads, the ALISSA signal was about two to four-times stronger than when anti-BoNT beads alone were used (FIGS. 8A and B, compare blue bars to orange bars, respectively). The effect was clearly visible throughout a dilution series of BoNT/A in serum (FIGS. 8A and B). However, the effect was not observed when the beads were coated only with the anti-fluorescein antibody (FIGS. 8A and B, green bars). Also, no further enhancement was observed when anti-BoNT and anti-fluorescein antibodies were mounted on separate beads and then mixed before conducting the ALISSA experiment.

Higher fluorescence signals were achieved with the double affinity matrix compared to the single affinity matrices (only anti-BoNT/A LC or anti-FITC) upon overnight (FIG. 8A) and 48 hour incubation (FIG. 8B) (except for the highest BoNT/A concentration point ($10^{-9}$ mol/L) where the signal was comparable between the F1-40/anti-FITC combination and F1-40 alone for both time points). The results were similar when the experiment was performed with supernatant alone (no beads) (FIG. 8C). These results demonstrate that the proximity of a controlled and possibly strong substrate-bead interaction to a strong enzyme-bead interaction can be exploited to enhance the turnover rate of the reaction of an immobilized enzyme.

Figure 9:
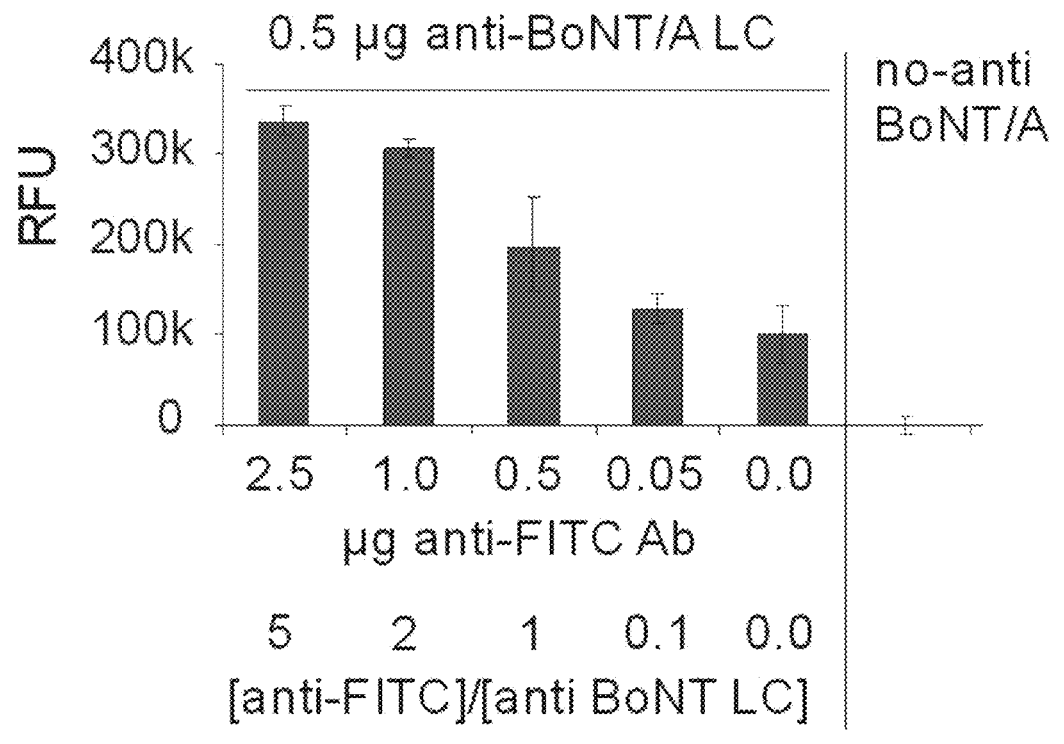

A titration was performed using increasing concentrations of anti-FITC antibody to determine the most effective ratio of anti-BoNT/A LC and anti-FITC to use to provide an optimal signal to noise ratio for the double affinity immobilization matrix. An improved signal to noise ratio was observed with increasing concentrations of anti-FITC antibody (FIG. 9).

Example 4

Assay Performance: Sensitivity

Figure 3A:
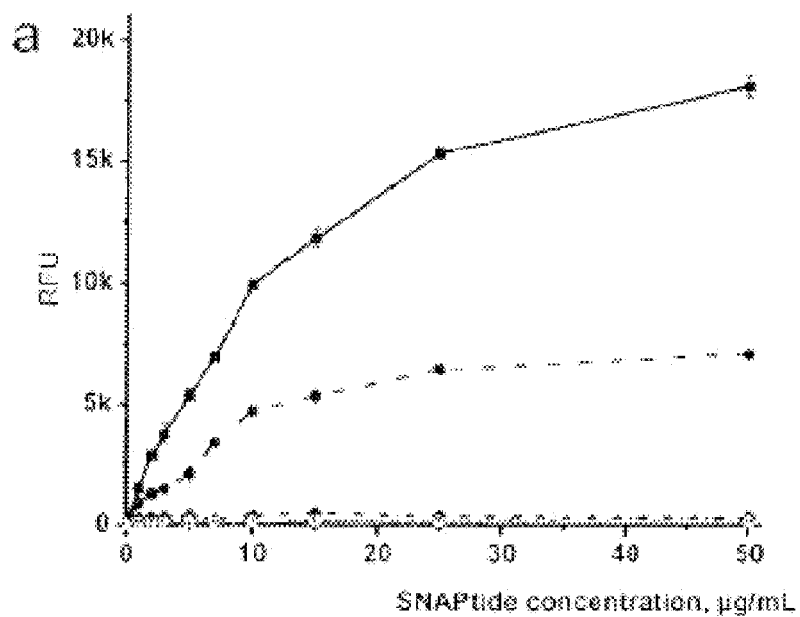
FIG. 3A-E shows an optimization of assay parameters. (A) BoNT/A concentration-dependent cleavage of SNAPtide after one hour reaction time in 1 ml 10% FBS. (B) SNAPtide (25 μg/ml) conversion time-curve by BoNT/A. (C) Effect of the number of beads exposed for 3 hours to 1 ml 10% FBS spiked with BoNT/A. (D) Time course of BoNT/A enrichment on the beads. (E) Effect of temperature on binding of bead-immobilized BoNT/A (from complex) at one hour incubation time.
Figure 3B:
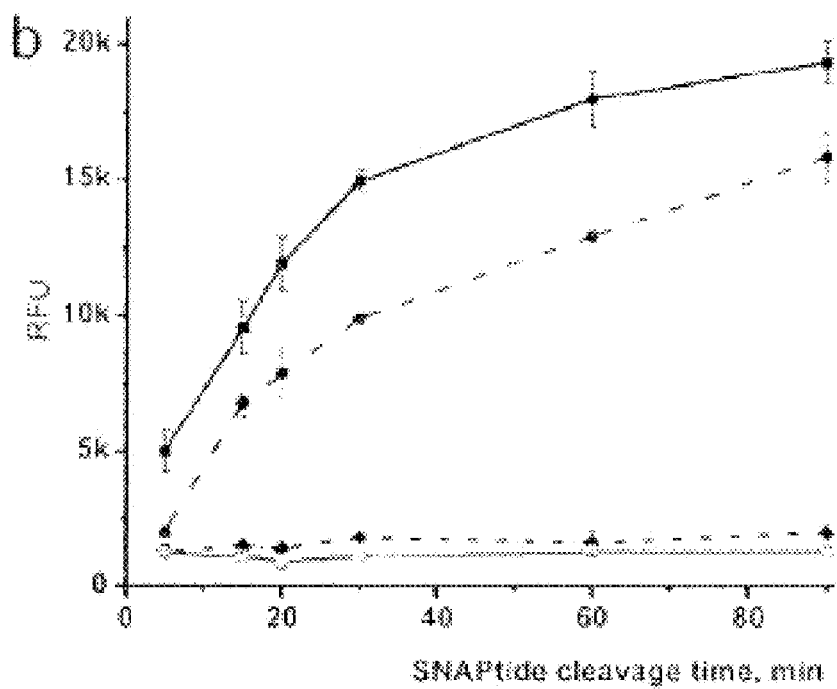
Figure 3C:
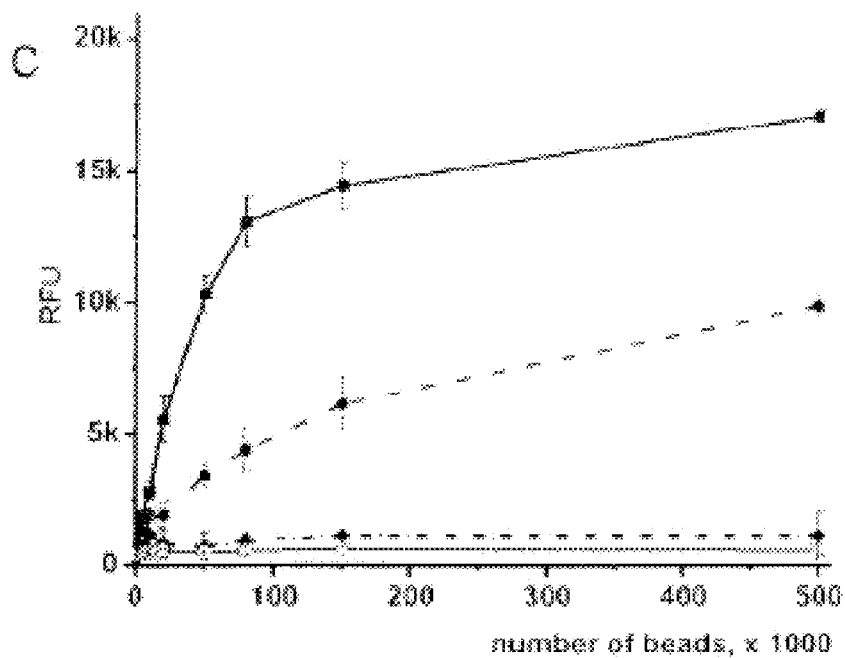
Figure 3D:
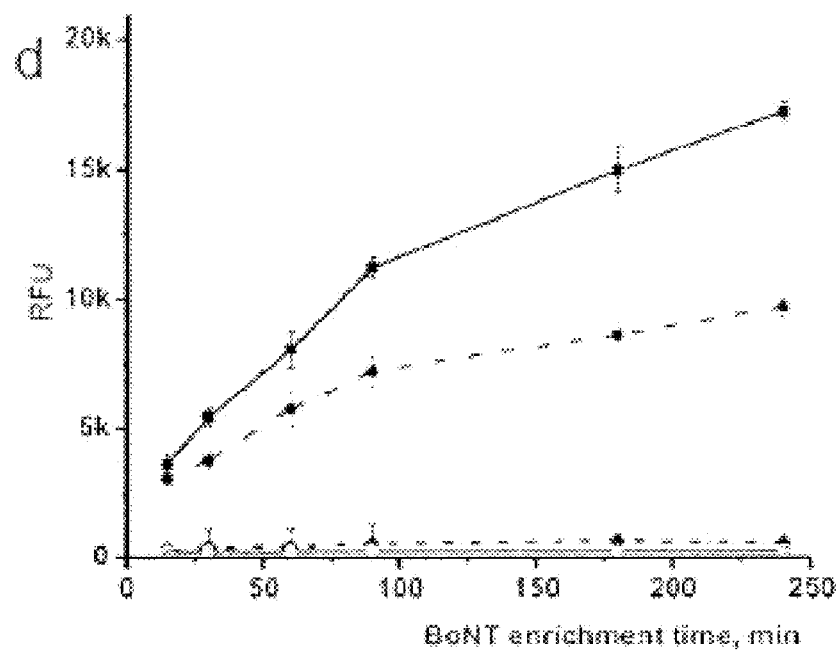
Figure 3E:
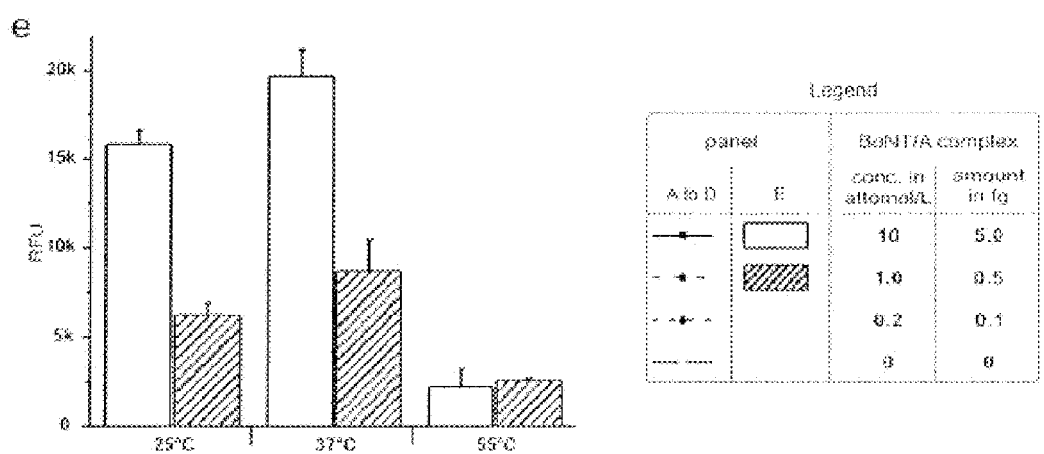
Figure 4:
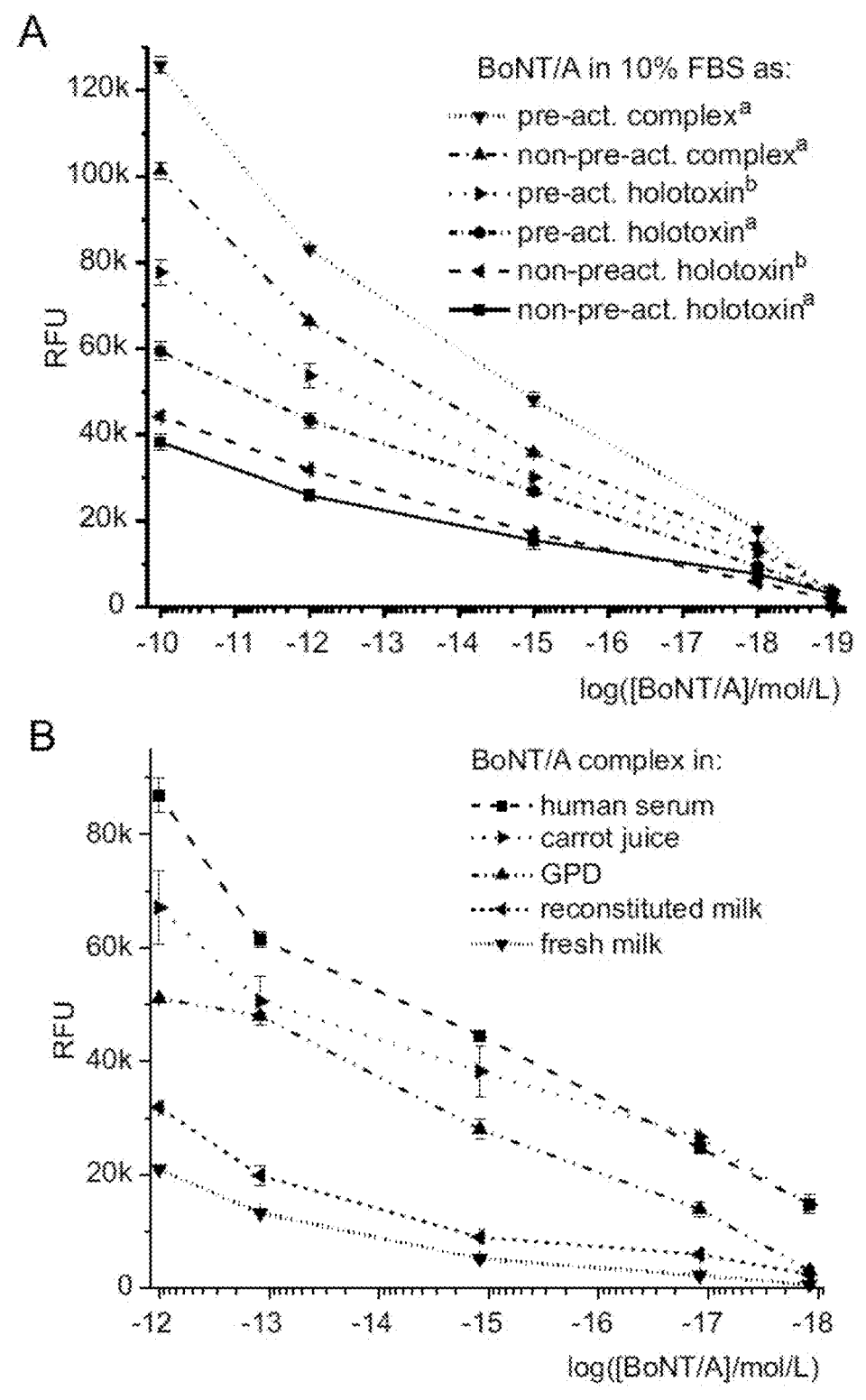

The 150-kDa BoNT/A holotoxin (from two different commercial sources) and the 500-kDa BoNT/A complex were serially diluted and tested by BoNT/A ALISSA in 10% fetal bovine serum (FBS) (FIG. 4A). Significant signals of several thousand relative fluorescence units (RFU) were still observed for concentrations of one attomol/L in 1-mL sample volumes. Signals for toxin complex were always stronger than for identical molar concentrations of holotoxin. The practical detection limit in the diluted serum was extrapolated to be ~0.5 attomol/L, which corresponds to 250 attogram toxin complex in 1 mL sample (FIGS. 3E, 4A). To determine ALISSA use in complex samples, the assay's sensitivity for the toxin complex was also determined in spiked undiluted human serum, carrot juice, reconstituted non-fat powdered milk, fresh milk, and gelatin phosphate (GP) diluent (FIG. 4B). GP diluent is typically used in the life mouse toxicity bioassay. Although somewhat lower than in toxin-spiked samples with 10% FBS, discernable fluorescent intensities above background were still detected for 1 attomol/L toxin complex, with signal intensities of ~14,800, ~14,750, ~3100, ~2500 and ~650 RFU above background in undiluted human serum, 50% carrot juice, GP diluent, non-fat milk and fresh milk, respectively. A fat-solubilizing wash buffer (with HEPES) was required for analyses of fresh milk samples. Overall, the ALISSA signals correlate proportionally with the toxin concentration over several orders magnitude (FIG. 4A-B).

The ALISSA performed with comparable sensitivities in undiluted human serum, 50% carrot juice (adjusted to pH 7.5 with binding buffer), reconstituted powdered milk, fresh milk and GP-diluent. In direct comparison with the mouse assay, the ALISSA was considerably faster and 4-5 orders of magnitude more sensitive.

Example 5

Assay Performance: Specificity and Kinetics

Specificity of the assay and sensitivity and kinetics of the bead-based ALISSA compared to those of the bead-free conversion of the reporter peptide were tested. To test non-specific agents, serum samples were utilized with: 1) beads conjugated to purified nonspecific rabbit IgG; 2) trypsin, because it is also able to cleave SNAPtide, but cannot be enriched on the beads; 3) BoNT type B complex; 4) BoNT type E complex; 5) type A toxoid, which is a non-toxic, antibody-binding formaldehyde inactivated derivative of BoNT/A; and 6) a toxin-free control (FIG. 10a, 10b). The bead-based assay produced low intensity signals with the non-specific agents trypsin, BoNT/A toxoid, BoNT/B and E) and only at the highest tested concentrations of 10-100 pmol/L. The bead-free reaction mixture yielded signals only with trypsin and BoNT/A for concentrations of 1 pmol/L or greater, and these signals were weak. Equimolar trypsin concentrations led to even higher signals than the BoNT/A complex. Toxin type B and E complexes, for which the peptide substrate does not contain specific cleavage sites, produced very weak signals only at the 10 and 100-picomolar concentrations that were even lower than those obtained with the bead-based assay. Interestingly, the bead-based detection of BoNT/A produced significantly higher signals—at any given toxin dilution step—than did the bead-free reaction mixture. For the bead-free reaction mixture discernable signals were only obtained for BoNT/A concentrations greater or equal to 1 pmol/L. In contrast, strong signals were obtained with BoNT/A at concentrations as low as 1 attomol/L when used in the bead-based assay. For the comparison of bead-free versus bead-based assay, toxin concentrations and total toxin amounts were identical in each dilution step.

Figure 10C:
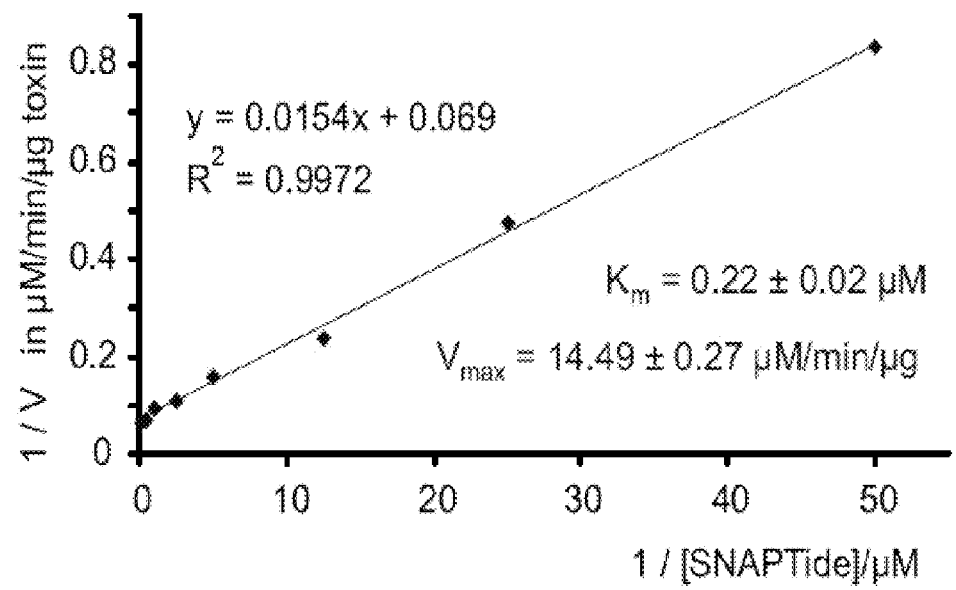
Figure 10D:
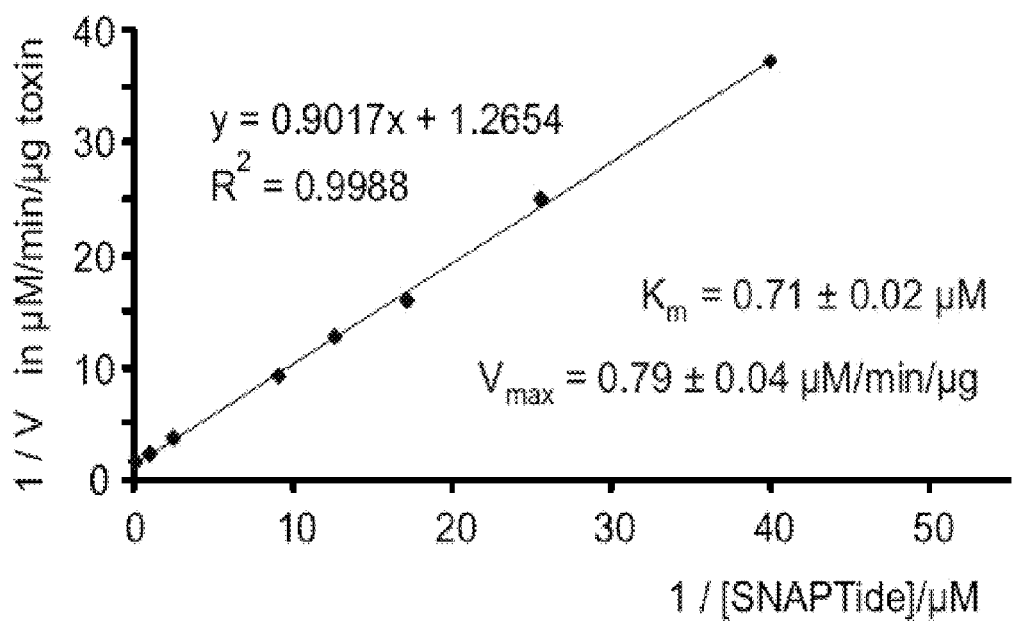

This remarkable enhancement of the substrate cleavage reaction as a response to BoNT/A immobilization prompted a determination of the kinetic parameters of the SNAPtide conversion reaction. For comparative purposes, fixed total BoNT/A complex concentrations of 100 pmol/L were used in 1-mL sample volumes for both the reactions with the free and with the bead-immobilized toxin. At this concentration, BoNT/A is safely detected with either method. Kinetic constants were obtained from plots of initial rates versus eight concentrations of substrate ranging 0.0125 to 5 µM. (Blanch and Clark, 1997; Liu et al., 1999). Initial velocity for reactions was calculated from linear regression analysis as µM of cleaved SNAPTide/min/mg enzyme. The values are the averages of 4 independent determinations±error propagation. The $K_m$ value for the BoNT/A was calculated from the Lineweaver-Burk double reciprocal plot. No-enzyme reference was applied in establishing baseline RFU when there is no enzyme activity. This control contained all components of the BoNT/A reaction mixture except the enzyme, replaced with the equivalent volume of reaction buffer. Background fluorescence was determined by using wells with only SNAPtide. Results are the averages of triplicate determinations The hydrolysis of SNAPtide by BoNT/A obeys Michaelis-Menten kinetics and is characterized by a linear relationship between the reciprocal substrate concentration and the activity of the enzyme (FIGS. 10c, 10d). Michaelis constancies ($K_m$) and maximal conversion rates ($V_{max}$) were calculated from the linear regression of the reciprocal SNAPtide concentration 1/[SNAPtide] versus the reciprocal reaction rate (1/V). The $K_m$ of the immobilized enzyme is 3.2-fold lower than for the free enzyme, suggesting a slightly higher enzyme/substrate affinity. Interestingly, the main effect was found in the rate of catalysis: the immobilized BoNT/A is capable of converting its substrate with an 18-fold increased maximal conversion rate than the free toxin. The corresponding values for $V_{max}$ at 25° C. were 0.79±0.04 µM/min/µg and 14.49±0.27 µM/min/µg for free (non-immobilized) and immobilized enzymes, respectively.

Example 6

Assay Performance

Comparison of BoNT/A ALISSA with the Live Mouse Assay.

Figure 11:
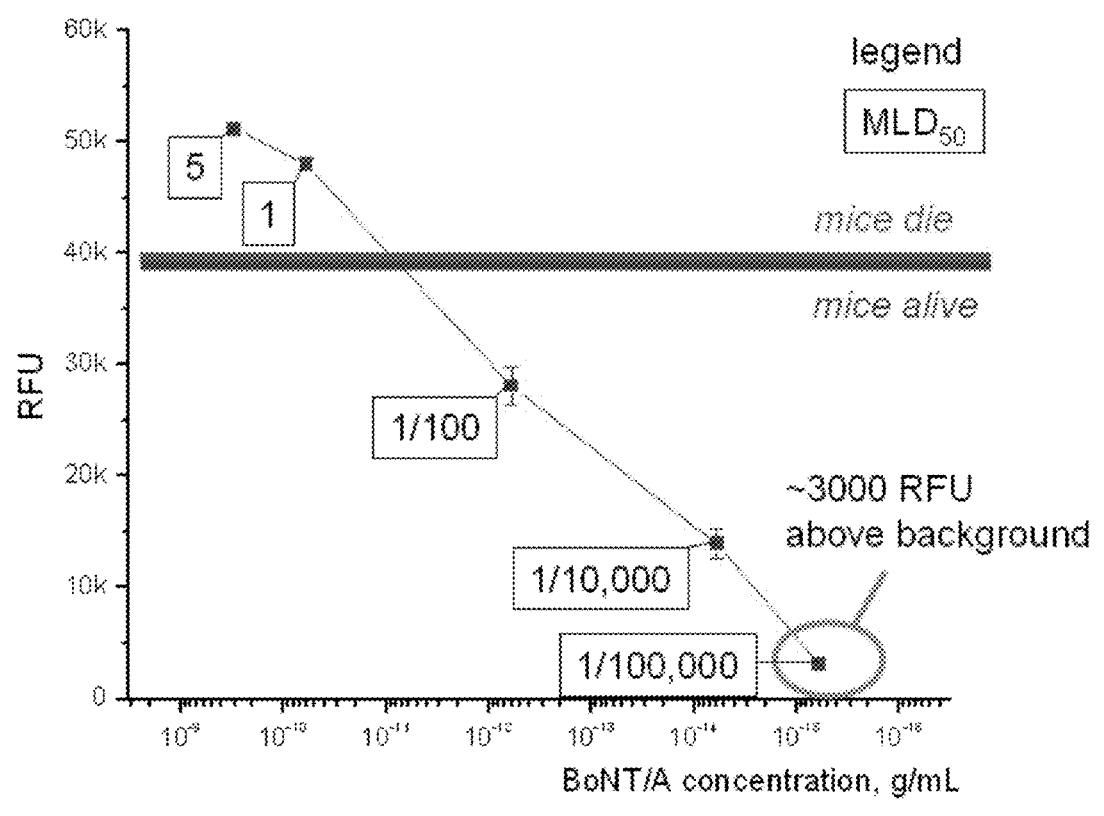

A split aliquot of 100 ng BoNT/A toxin complex was shipped in a refrigerated hazmat container to collaborators at the Infant Botulism Treatment and Prevention Program of the California Department of Public Health (CDPH) in Richmond for use in the diagnostic life mouse bioassay. Identical dilution series of the toxin in GP-diluent were prepared concurrently in pre-prepared and weighed vials at both institutions. The approximate time of the i.p. mouse injections at the two locations coincided by a margin of minutes. Mice weighing 18-22 g each were injected i.p. with 0.5 mL/mouse of sample and watched for signs of botulism or death for the standard 96 hour observation period. The results of BoNT/A ALISSA became available after ~2.5 hours and mice were observed for three days (Table 2, FIG. 11).

The mouse assay was positive for the highest test concentrations of 300 and 60 pg/mL (0.5 mL injected per mouse). Mild symptoms of botulism developed within 96 hours in three of five mice that received one hundreds of the theoretical $LD_{50}$ (0.3 pg). All other animals that received $10^{-4}$ or $10^{-5}$ $LD_{50}$ remained completely disease free and asymptomatic. BoNT/A ALISSA produced clear signals throughout the dilution series. The lowest BoNT/ALISSA fluorescence signal at the lowest test concentration was 0.6 fg/mL ($10^{-5}$ $LD_{50}$), which is still ~3,100 units above background levels.

TABLE 2

Comparison of the mouse bioassay with BoNT/A ALISSA

| [complex] (fg/mL) | $LD_{50}s^a$ | Mouse bioassay result | ALISSA result (RFU) |
|---|---|---|---|
| 300,000.0 | 5 | 5/5 dead in <4 hrs | 51,105 ± 95 |
| 60,000.0 | 1 | 5/5 dead in <21 hrs | 48,009 ± 464 |
| 600.0 | $10^{-2}$ | 3/5 mild symptoms[b] | 28,049 ± 1713 |
| 6.0 | $10^{-4}$ | 5/5 disease free[b] | 13,954 ± 1324 |
| 0.6 | $10^{-5}$ | 5/5 disease free[b] | 3,116 ± 15 |
| 0.0 | 0 | n.d. | 0 ± 8 |

[a] calculated per injected 0.5 mL sample; one $LD_{50}$ = 30pg BoNT/A complex;
[b] all mice alive after 69 hrs;
n.d., not determined The BoNT/A ALISSA avoids interference with other sample components by using a highly BoNT/A-specific affinity matrix and by using a BoNT/A-specific substrate to exploit the natural proteolytic activity of the toxin. Both steps also amplify the signal by 1) localized enrichment of the toxin; and 2) through enzymatic conversion of billions of substrate molecules per toxin molecule. The capture matrix is designed to stably enrich the toxin, while retaining its enzymatic activity and by purifying the toxin from other non-specific proteases contained in the sample. The beaded-protein A matrix binds to the antibodies via the Fc regions, orienting the antigen binding domains away from the bead surface and into the surrounding sample fluid (FIG. 12). This provides higher accessibility to target toxin molecules.

The plateaus observed in the assay's response curves used to optimize substrate concentration and size and volume proportions of the immunosorbent matrix represent saturation effects that indicate when the substrate concentration is no longer rate-limiting. Antibody binding capacity was about 50 ug antibody per one million beads which estimates to an antibody dissociation constant kD at half maximum saturation to be approximately 15 nM. Use of antibodies having higher binding affinity will increase assay sensitivity. High affinity anti-BoNT antibodies have been used as antitoxins to neutralize systemic botulinum toxin in botulism patients (Marks 2004; Garcia-Rodriguez 2007). This mode of "neutralization" however, should not be confused with inactivation of the toxin's enzymatic activity by steric hindrance of the catalytic site resulting from antibody binding. Antibody-mediated "neutralization" of toxin in vivo depends on formation of antibody-antigen complex and hepatic accumulation and clearance (Ravichandran 2006; Simpson 2001).

Figure 13:
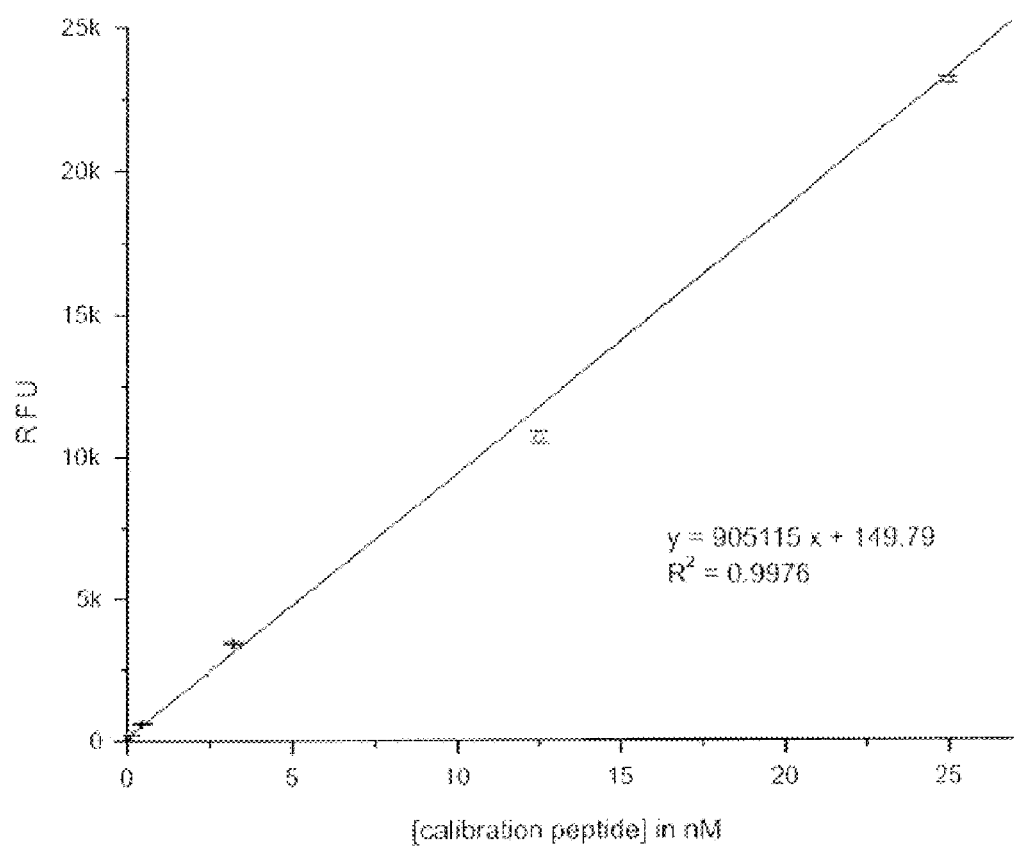
FIG. 13 shows a standard curve of the fluorescence signal of the unquenched calibration peptide, which is structurally identical to the FITC-containing cleavage product resulting from BoNT/A hydrolysis of SNAPtide by BoNT/A; "y" in RFU; "x" in nM; "R" is the correlation coefficient.

Use of a standard curve to measure concentration-dependent intensity of fluorescence signal of un-quenched calibration peptide (FIG. 13) allowed determination of the molar conversion rate for the substrate molecules. A calculated substrate conversion rate of approximately two billion substrate molecules per one immobilized toxin molecule per hour was calculated for the 10 attomolar toxin concentration. The reaction being limited by the rate at which the toxin becomes inactivated. Factors such as chelation of the zinc atom by DTT, denaturation of the toxin by the reducing buffer, or proteolytic degradation of the toxin either through autoproteolysis or by a contaminant protease may also contribute to inactivation of the toxin.

In certain embodiments, optimal temperature is 37° C. coincident with the temperature at which the natural action of the toxin occurs and at which IgG antibody binding may be optimal. Higher temperatures may inactivate the toxin. Preferably, the pH of the sample is approximately neutral (between about 6 and about 8). Assay sensitivity may also be further increased by reducing background fluorescence of uncleaved substrate such as uncleaved SNAPtide.

In certain embodiments, a peptide conjugated FRET pair with a 2,4-dinitrophenyl acceptor and a 4-methyl-7-dimethylamino-coumarin donor may be used as a substrate. These and other FRET pairs having better spectral overlap can allow lower background fluorescence with good kinetic properties.

In certain embodiments, an approximately 18-fold increase in maximum conversion rate $v_{max}$ and a three-fold higher affinity to the substrate (three-fold lower $k_M$) for the immobilized toxin was observed as compared to free toxin in solution (FIGS. 10C and 10D). The average bead surface area in the ALISSA assay is approximately 7.85 cm² per sample (based on a 50 μm average bead diameter) whereas the antigen-binding surface area in a conventional solid-phase or solid-state ELISA with a 96-well flat-bottom microplate measures only about 0.256 cm² per well. Thus, the available reaction surface area in the ALISSA is about 30-fold greater than provided by prior art methods. Such immobilized toxin is also better protected from proteolysis and aggregation. Molecules of unstable BoNT/A light chain are sufficiently separated to diminish any autocatalytic degradation. Use of bead-based assay also allows for more stringent wash procedures thereby diminishing interference by other proteases. This was demonstrated for BoNT/A when compared to equimolar concentrations of trypsin, BoNT/B and BoNT/E. The increased reaction surface area and control of diffusion through more frequent substrate-enzyme interactions also contributes to the improved enzymatic activity.

Example 7

Fluorogenic Substrates

Figure 14:
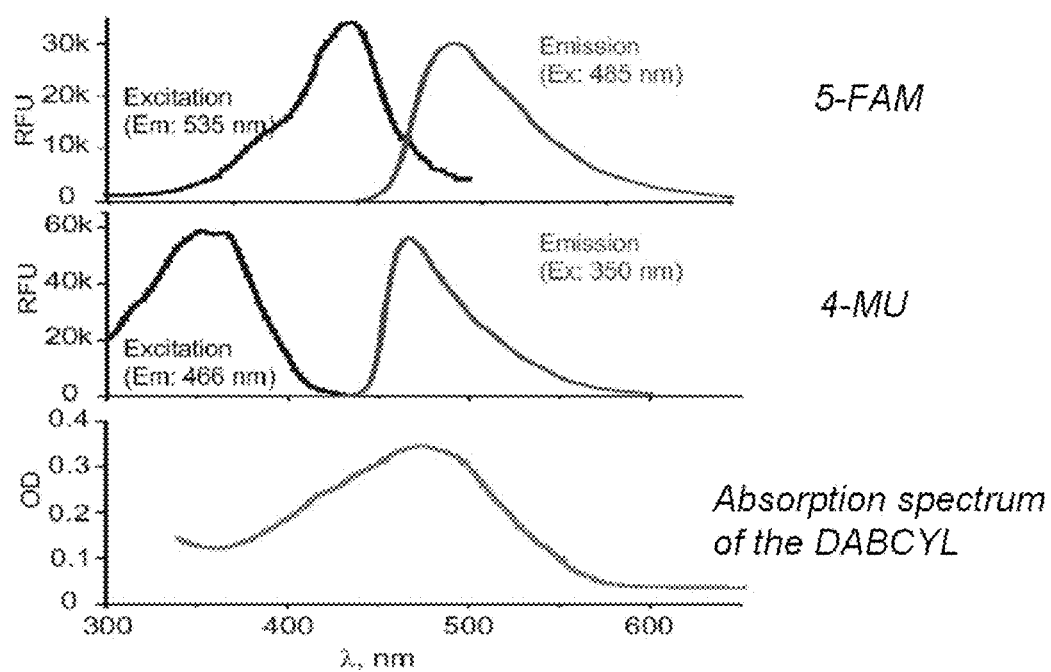
FIG. 14 shows the spectrums of the fluorophores (5-FAM and 4-MU) and quencher (DABCYL) of the BoNT cleavable and control peptides. Upon excitation, the 5-FAM fluorophore (Ex/Em=535 nm/485 nm) and the 4-MU fluorophore (Ex/Em=466 nm/350 nm) will be quenched by DABCYL if the peptide is not cleaved.

Fluorogenic peptides were synthesized using standard Fmoc chemistry methodology well known in the art. Commercial SNAPtide (List Biological Laboratories) contains a fluorescein isothiocyanate (FITC)-labelled N-terminus and a thiourea group that is unstable over time or when in the presence of acids. This can result in undesired background signal. To avoid this, different SNAPtide-like peptides that were N-terminally labelled with either 5-carboxyfluorescein (5-FAM)- or 4-Methylumbelliferone (4-MU) were synthesized. Each fluorophore is conjugated at or near the N-terminus region of the peptide via a peptide bond, which enhances the stability of the substrate. Additionally, the peptides contain a dark quencher, DABCYL, conjugated at or near their C-terminus. Upon excitation, the DABCYL suppressed the fluorescence emission of the 5-FAM and 4-MU labeled peptides when the peptides were not cleaved and the fluorescent label and DABCYL remained close together (FIG. 14). However, when the peptide was cleaved by BoNT/A, the fluorescent label and DABCYL were separated and the fluorescent label emitted light energy upon excitation. Each of the novel peptides contains arginines having an L-isomeric form.

Figure 15:
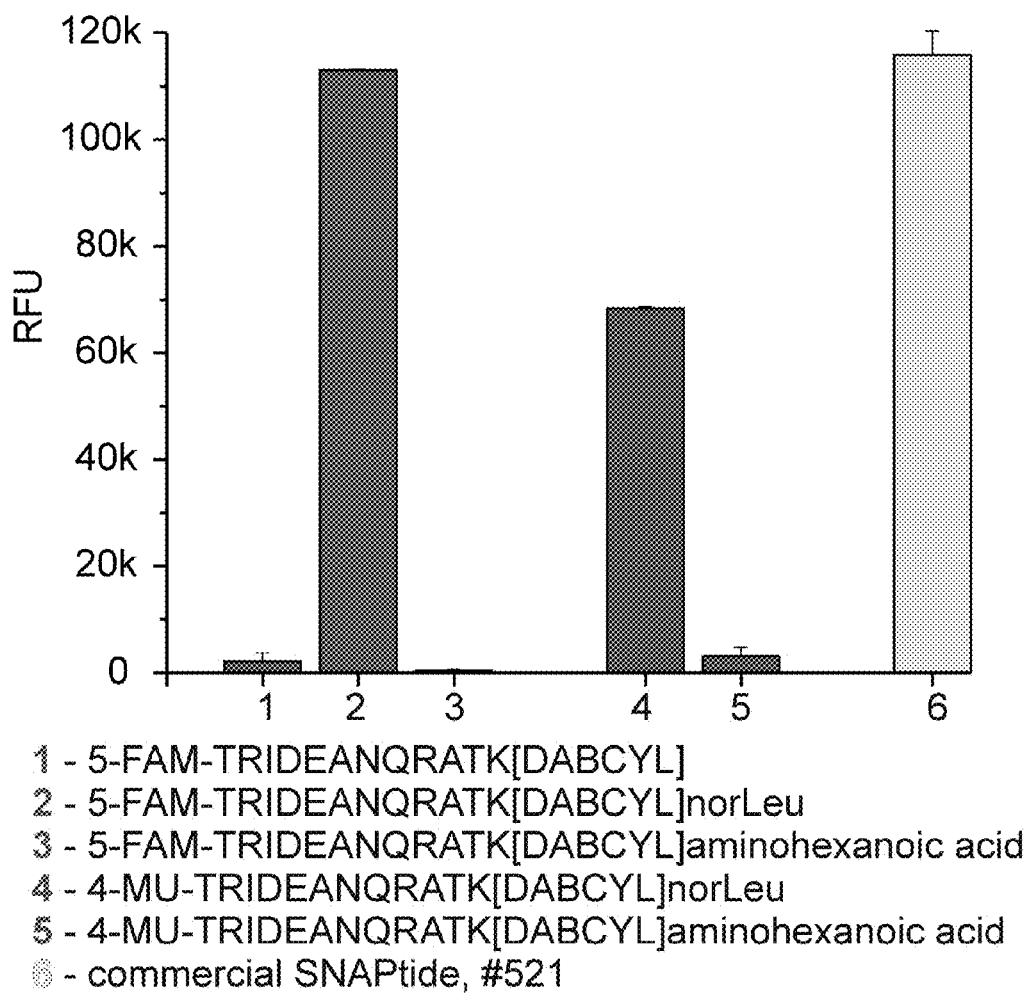
FIG. 15 shows an analysis of alternative fluorogenic BoNT/A substrates as compared with commercial SNAPtide. About 5 μM substrate solutions were incubated with 2 nM BoNT/A complex for 1 hr at 37° C. 1 to 5 indicate COH-made synthetic BoNT/A and their sequences [1-SEQ ID NO:20 (#110); 2-SEQ ID NO: 21 (#115); 3-SEQ ID NO:19 (#112); 4-SEQ ID NO:22 (#116); 5-SEQ ID NO:5 (#113); 6-commercial SNAPtide]; DABCYL is 4-(dimethylaminoazo) benzene-4-carboxylic acid conjugated to the ε-amino group of lysine.

The effect of the substrate's C-terminal amino acid corresponding to M202 in the native human SNAP-25 sequence (SEQ ID NO: 11) was also determined. Commercial SNAPtide replaces the M202 in the native sequence with a Norleucine residue. This Norleucine residue provided efficient cleavage of the substrate as deletion or replacement with 6-aminohexanoic acid greatly diminished the efficiency of the BoNT/A-mediated cleavage reaction (FIG. 15). The Norleucine used is a non-oxidizable surrogate for the methionine residue located at 202. Peptides that contain the Norleucine residue and showed efficient cleavage by BoNT/A are:

(SEQ ID NO: 21)
115: 5-FAM-ThrArgIleAspGluAlaAsnGlnArgAlaThrLys

[DABCYL]-Nle;
and (SEQ ID NO: 22)
116: 4-MU-ThrArgIleAspGluAlaAsnGlnArgAlaThrLys

[DABCYL]-Nle;

wherein Nle is Norleucine (Table 3).

Peptides that do not contain a Norleucine or 6-aminohexanoic acid and are not cleaved by BoNT are:

(SEQ ID NO: 20)
110: 5-FAM-ThrArgIleAspGluAlaAsnGlnArgAlaThrLys

[DABCYL];
and (SEQ ID NO: 23)
111: 4-MU-ThrArgIleAspGluAlaAsnGlnArgAlaThrLys

[DABCYL] (Table 4).

Peptides #112 and #113 that contain 6-aminohexanoic acid in place of the Norleucine residue located at 202 that are not cleaved by BoNT/A as shown in FIG. 14 are:

(SEQ ID NO: 19)
112: 5-FAM-ThrArgIleAspGluAlaAsnGlnArgAlaThrLys

[DABCYL]-Hex;
and (SEQ ID NO: 5)
113: 4-MU-ThrArgIleAspGluAlaAsnGlnArgAlaThrLys

[DABCYL]-Hex;

wherein Hex is 6-aminohexanoic acid (Table 5).

By applying a manual docking approach supported by functional assays, several novel substrates were produced (Table 3 (SEQ ID NO: 21 and 22), Table 6 (SEQ ID NO: 12), Table 7 (SEQ ID NO: 13), and Table 8 (SEQ ID NO: 14)). The chemical structures (identified as "1", "2" and "3") of each exemplary substrate is depicted below its corresponding table listing of amino acid sequence. In the below exemplary embodiments, each of the novel peptide substrates contains 12 amino acid residues.

Additional control peptides that contain 6-aminohexaonic acid that cannot be cleaved by BoNT were produced (Table 4 (SEQ ID NO: 20 and 23), and Table 5 (SEQ ID NO: 19 and 5)). In addition, control peptides having an RA to EL mutation (indicated in bold text) were produced (Table 9; SEQ ID NOS: 15, 17-18). The BoNT/A protease cannot efficiently cleave the control peptides while other proteases are able to cleave these peptides, making them suitable control peptides for use in the ALISSA. The control peptides allow for compensation of the background signal resulting from non-BoNT/A protease activity or non-target protease activity.

TABLE 3

Cleavable Peptides:
115: [5-Fam]TRIDEANQRATK[DABCYL]-Nle (SEQ ID NO: 21)
116: [4-Mu]TRIDEANQRATK[DABCYL]-Nle (SEQ ID NO: 22)

| Number | 1 Letter Code | Amino acid name and modification |
|---|---|---|
| 1 | [5-Fam]T or [4-Mu]T | Threonine with a 5-carboxyfluorescein or 4-Methylumbelliferone conjugated to its α-amino group (as illustrated by SEQ ID NOS: 21 and 22, respectively) |
| 2 | R | Arginine |
| 3 | I | Isoleucine |
| 4 | D | Aspartic acid |
| 5 | E | Glutamic acid |
| 6 | A | Alanine |
| 7 | N | Asparagine |
| 8 | Q | Glutamine |
| 9 | R | Arginine |
| 10 | A | Alanine |
| 11 | T | Threonine |
| 12 | K[DABCYL] | Lysine with DABCYL conjugated to its ε-amino group |
| 13 | Nle | Norleucine with an amide C-terminus |

115 (SEQ ID NO: 21)

116 (SEQ ID NO: 22)

TABLE 4

Control Peptides:
110: [5-Fam]TRIDEANQRATK[DABCYL] (SEQ ID NO: 20)
111: [4-Mu]TRIDEANQRATK[DABCYL] (SEQ ID NO: 23)

| Number | 1 Letter Code | Amino acid name and modification |
|---|---|---|
| 1 | [5-Fam]T or [4-Mu]T | Threonine with a 5-carboxyfluorescein or 4-Methylumbelliferone conjugated to its α-amino group (as illustrated by SEQ ID NOS: 20 and 23, respectively) |
| 2 | R | Arginine |
| 3 | I | Isoleucine |
| 4 | D | Aspartic acid |
| 5 | E | Glutamic acid |
| 6 | A | Alanine |
| 7 | N | Asparagine |
| 8 | Q | Glutamine |
| 9 | R | Arginine |
| 10 | A | Alanine |
| 11 | T | Threonine |
| 12 | K[DABCYL] | Lysine with DABCYL conjugated to its ε-amino group |

110 (SEQ ID NO: 20)

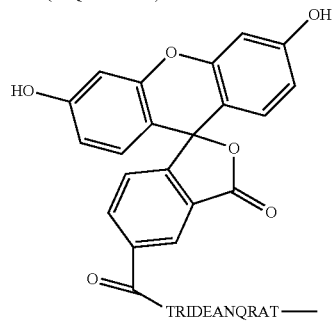

111 (SEQ ID NO: 23)

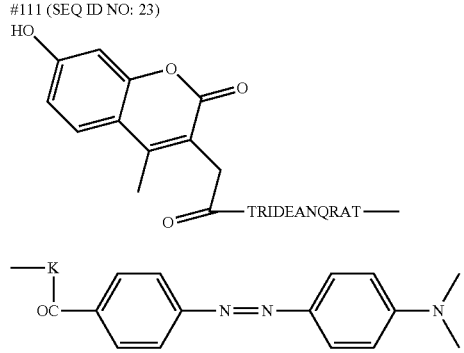

TABLE 5

Control Peptides:
112: [5-Fam]TRIDEANQRATK[DABCYL]-Hex (SEQ ID NO: 19)
113: [4-Mu]TRIDEANQRATK[DABCYL]-Hex (SEQ ID NO: 5)

| Number | 1 Letter Code | Amino acid name and modification |
|---|---|---|
| 1 | [5-Fam]T or [4-Mu]T | Threonine with a 5-carboxyfluorescein or 4-Methylumbelliferone conjugated to its α-amino group (as illustrated by SEQ ID NOS: 19 and 5, respectively) |
| 2 | R | Arginine |
| 3 | I | Isoleucine |
| 4 | D | Aspartic acid |

TABLE 5-continued

Control Peptides:
112: [5-Fam]TRIDEANQRATK[DABCYL]-Hex (SEQ ID NO: 19)
113: [4-Mu]TRIDEANQRATK[DABCYL]-Hex (SEQ ID NO: 5)

| Number | 1 Letter Code | Amino acid name and modification |
|---|---|---|
| 5 | E | Glutamic acid |
| 6 | A | Alanine |
| 7 | N | Asparagine |
| 8 | Q | Glutamine |
| 9 | R | Arginine |
| 10 | A | Alanine |
| 11 | T | Threonine |
| 12 | K[DABCYL] | Lysine with DABCYL conjugated to its ε-amino group |
| 13 | Hex | 6-Amino hexanoic acid |

112 (SEQ ID NO: 19)

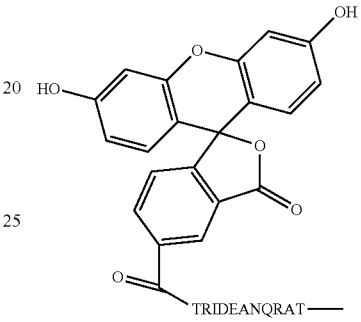

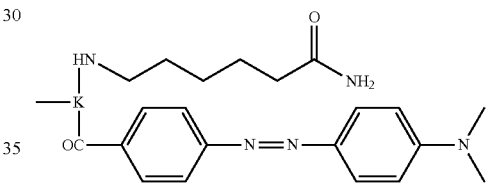

113 (SEQ ID NO: 5)

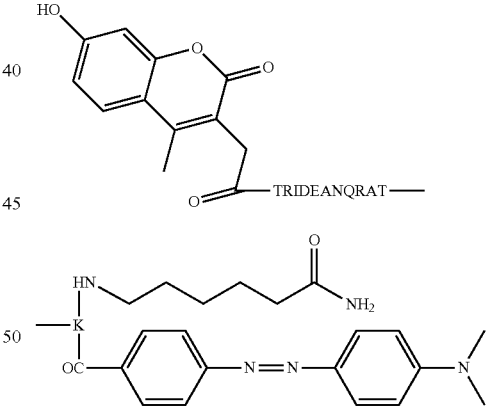

TABLE 6

Cleavable Peptide:
K[5-Fam]IDEANQRATK[DABCYL]Nle-amide (SEQ ID NO: 12)

| Number | 1-letter Code | Amino acid name and modification |
|---|---|---|
| 1 | K[5-Fam] | Lysine with 5-carboxyfluorescein conjugated to its ε-amino group |
| 2 | I | Isoleucine |
| 3 | D | Aspartic acid |
| 4 | E | Glutamic acid |
| 5 | A | Alanine |
| 6 | N | Asparagine |

TABLE 6-continued

Cleavable Peptide:
K[5-Fam]IDEANQRATK[DABCYL]Nle-amide (SEQ ID NO: 12)

| Number | 1-letter Code | Amino acid name and modification |
|---|---|---|
| 7 | Q | Glutamine |
| 8 | R | Arginine |
| 9 | A | Alanine |
| 10 | T | Threonine |
| 11 | K[DABCYL] | Lysine with DABCYL conjugated to its ε-amino group |
| 12 | Nle | Norleucine with an amide C-terminus |

1) K[5-Fam]IDEANQRATK[DABCYL]-norleu-amide

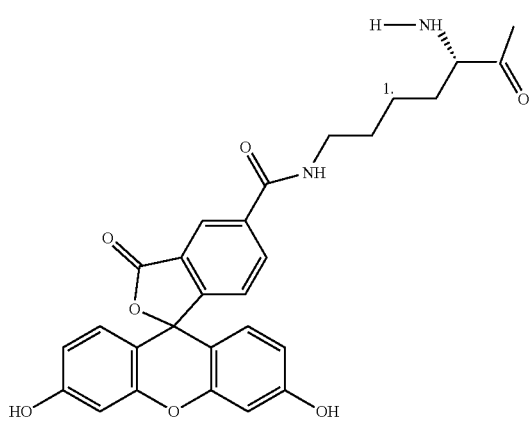

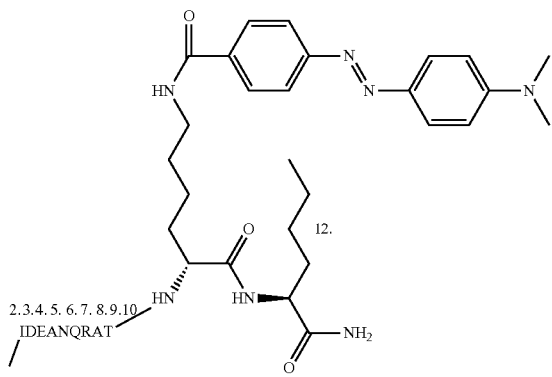

Chemical Formula: $C_{94}H_{127}N_{23}O_{26}$
Exact Mass: 1993.9323
m/z: 1994.9356

TABLE 7

Cleavable Peptide
Fam-K[5-Fam]IDEANQRATK[DABCYL]Nle-amide (SEQ ID NO: 13)

| Number | Code | Amino acid name and modification |
|---|---|---|
| 1 | 5-Fam-K[5-Fam] | Lysine with 5-carboxyfluorescein conjugated to its α and ε-amino groups |
| 2 | I | Isoleucine |
| 3 | D | Aspartic acid |
| 4 | E | Glutamic acid |
| 5 | A | Alanine |

TABLE 7-continued

Cleavable Peptide
Fam-K[5-Fam]IDEANQRATK[DABCYL]Nle-amide (SEQ ID NO: 13)

| Number | Code | Amino acid name and modification |
|---|---|---|
| 6 | N | Asparagine |
| 7 | Q | Glutamine |
| 8 | R | Arginine |
| 9 | A | Alanine |
| 10 | T | Threonine |
| 11 | K[DABCYL] | Lysine with DABCYL conjugated to its ε-amino group |
| 12 | Nle | Norleucine with an amide C-terminus |

2) 5-Fam-K[5-Fam]IDEANQRATK[DABCYL]-norleu-amide

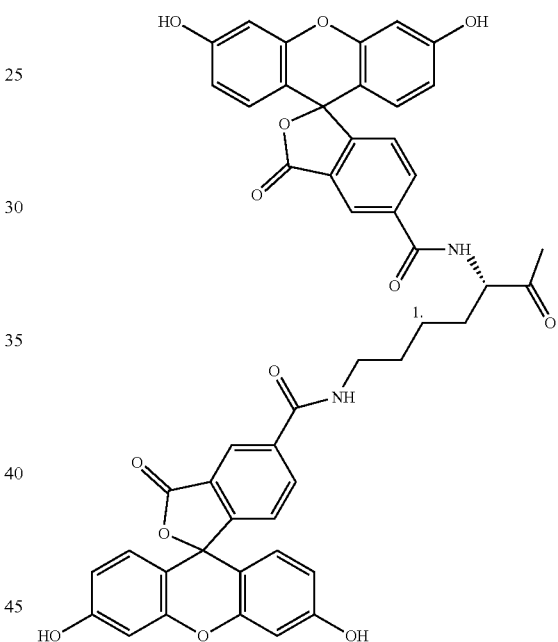

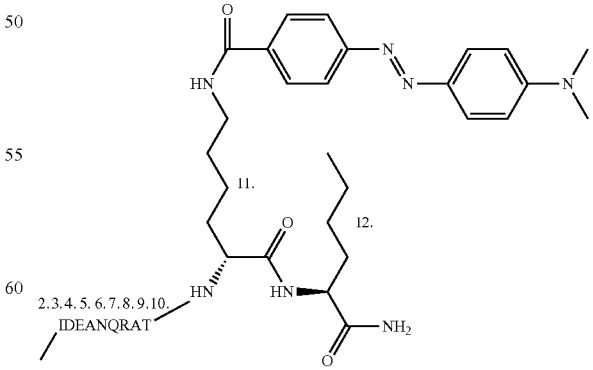

Chemical Formula: $C_{115}H_{137}N_{23}O_{32}$
Exact Mass: 2351.9800
m/z: 2352.9834

TABLE 8

Cleavable Peptide:
Alternative to above 2 substrates: 5-Fam-KIDEANQRATK[DABCYL]Nle-amide
(SEQ ID NO: 14)

| Number | Code | Amino acid name and modification |
|---|---|---|
| 1 | 5-Fam-K | Lysine with a 5-carboxyfluorescein conjugated to its α-amino group |
| 2 | I | Isoleucine |
| 3 | D | Aspartic acid |
| 4 | E | Glutamic acid |
| 5 | A | Alanine |
| 6 | N | Asparagine |
| 7 | Q | Glutamine |
| 8 | R | Arginine |
| 9 | A | Alanine |
| 10 | T | Threonine |
| 11 | K[DABCYL] | Lysine with DABCYL conjugated to its ε-amino group |
| 12 | Nle | Norleucine with an amide C-terminus |

TABLE 9

Control Peptides:
5-Fam-K[5-Fam]IDEANQELTK[DABCYL]Nle-amide (SEQ ID NO: 15);
5-Fam-KIDEANQELTK[DABCYL]Nle-amide (SEQ ID NO: 17); and
K[5-Fam]IDEANQELTK[DABCYL]Nle-amide (SEQ ID NO: 18).

| Number | Code | Amino acid name and modification |
|---|---|---|
| 1 | 5-Fam-K[5-Fam]; 5-Fam-K; or K[5-Fam] | Lysine with a 5-carboxyfluorescein conjugated to either its α or ε-amino group or to both (there are three possibilities as illustrated by SEQ ID NOS: 15, 17 and 18) |
| 2 | I | Isoleucine |
| 3 | D | Aspartic acid |
| 4 | E | Glutamic acid |
| 5 | A | Alanine |
| 6 | N | Asparagine |
| 7 | Q | Glutamine |
| 8 | E | Glutamic acid |
| 9 | L | Leucine |
| 10 | T | Threonine |
| 11 | K[DABCYL] | Lysine with DABCYL conjugated to its ε-amino group |
| 12 | Nle | Norleucine with an amide C-terminus |

These exemplary control peptides cannot be efficiently cleaved by botulinum neurotoxin serotype A, but can be cleaved by other proteases. Hence they can be used in the ALISSA assay as a control for non-specific (non-BoNT/A) protease activity. Below is the structure of one (SEQ ID NO: 18) of the three possible versions of the control peptides found in Table 9.

Control Peptide
K[5-Fam]IDEANQELTK[DABCYL]-norleu-amide
Chemical Formula: $C_{96}H_{128}N_{20}O_{28}$
Exact Mass: 2008.9207
m/z: 2009.9240
Control Peptide
Chemical Formula: $C_{96}H_{128}N_{20}O_{28}$
Exact Mass: 2008.9207
m/z: 2009.9240

By employing the above-described methods, several new substrates were identified for use in the ALISSA assay. The substrates exhibited higher chemical stability and high sensitivity for BoNT detection when used as substrate. These substrates include, but are not limited to:

(SEQ ID NO: 12)
Lys[5-Fam]IleAspGluAlaAsnGlnArgAlaThrLys[DABCYL]Nle;

(SEQ ID NO: 13)
5-Fam-Lys[5-Fam]IleAspGluAlaAsnGlnArgAlaThrLys[DABCYL]Nle;

(SEQ ID NO: 14)
5-Fam-LysIleAspGluAlaAsnGlnArgAlaThrLys[DABCYL]Nle;

(SEQ ID NO: 21)
(5-Fam)-ThrArgIleAspGluAlaAsnGlnArgAlaThrLys[DABCYL]Nle;

(SEQ ID NO: 22)
(4-Mu)-ThrArgIleAspGluAlaAsnGlnArgAlaThrLys[DABCYL]Nle;

(SEQ ID NO: 16)
LysIleAspGluAlaAsnGlnArgAlaThrLysNle;

and (SEQ ID NO: 27)
203: Lys-(4-Mu)-IleAspGluAlaAsnGlnArgAlaThrLys[DABCYL]-Nle, wherein Nle is Norleucine.

Peptides useful as control peptides were also generated by employing the above-described methods. Said control peptides include, but are not limited to:

(SEQ ID NO: 5)
(4-Mu)-ThrArgIleAspGluAlaAsnGlnArgAlaThrLys[DABCYL]Hex;

(SEQ ID NO: 15)
5-Fam-Lys[5-Fam]IleAspGluAlaAsnGlnGluLeuThrLys[DABCYL]Nle;

(SEQ ID NO: 17)
5-Fam-LysIleAspGluAlaAsnGlnGluLeuThrLys[DABCYL]Nle;

(SEQ ID NO: 18)
Lys[5-Fam]IleAspGluAlaAsnGlnGluLeuThrLys[DABCYL]

Nle;

(SEQ ID NO: 19)
(5-Fam)-ThrArgIleAspGluAlaAsnGlnArgAlaThrLys
[DABCYL]Hex;

(SEQ ID NO: 28)
204: Lys[5-Fam]IleAspGluAlaAsnGlnArgAlaThrLys
[DABCYL]Hex;

(SEQ ID NO: 29)
205: Lys[4-MU]IleAspGluAlaAsnGlnArgAlaThrLys
[DABCYL]Hex;

(SEQ ID NO: 20)
(5-Fam)-ThrArgIleAspGluAlaAsnGlnArgAlaThrLys
[DABCYL];
and (SEQ ID NO: 23)
(4-Mu)-ThrArgIleAspGluAlaAsnGlnArgAlaThrLys
[DABCYL], wherein Hex is 6-aminohexanoic acid and Nle is Norleucine.

The following table summarizes the BoNT/A cleavable and control substrates provided herein:

Example 8

Characterization of Fluorogenic BoNT Cleavable Substrates and Control Peptides for BoNT ALISSA Specificity of Novel BoNT Cleavable and Control Peptides.

Other proteases have the ability to cleave the BoNT cleavable peptides; therefore, control peptides were produced for BoNT/A (see Example 7, peptides #110, 111, 112, and 113 (SEQ ID NOS: 20, 23, 19, and 5, respectively). The sequences of the BoNT cleavable peptide and the non-cleavable control peptide are almost identical. They contain the same amino acid residues (Q and R) at the BoNT/A cleavage site, but differ in their last residue, five amino acids from the cleavage site (norleucine replaced with its isomer, aminohexanoic acid). These control substrates cannot be cleaved by BoNTs, but can be cleaved by some non-BoNT-related proteases. Therefore, the control peptides were used in the ALISSA assay as a control for non-specific (BoNT/A) protease activity.

Figure 16:
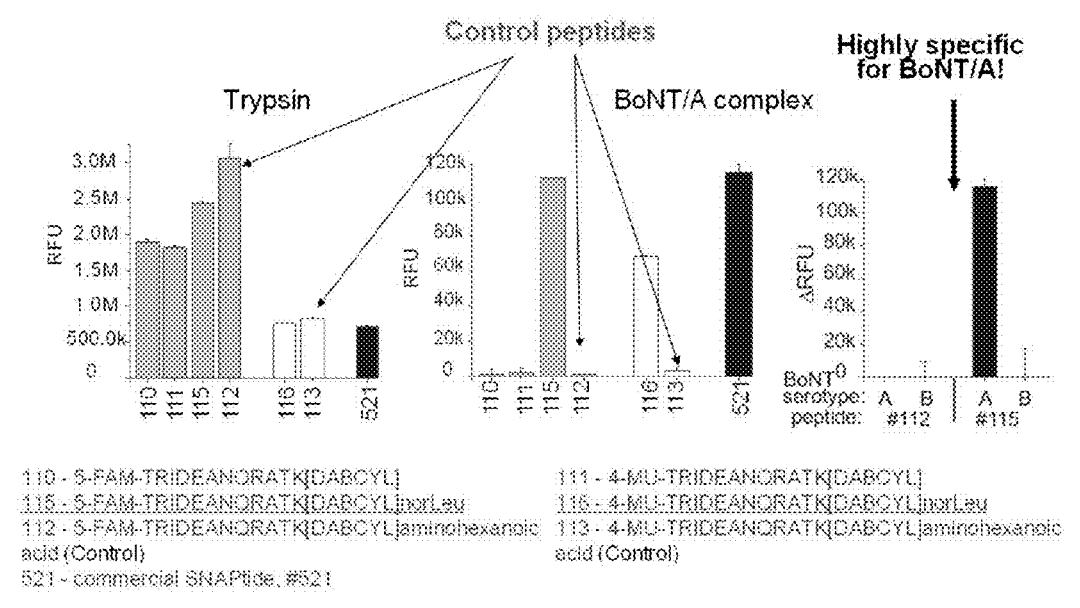

Cleavage specificity of the novel BoNT/A cleavable peptides (#115 (SEQ ID NO: 21) and #116 (SEQ ID NO: 22)) and control peptides (#110 (SEQ ID NO: 20); #111 (SEQ ID NO: 23); #112 (SEQ ID NO: 19); and #113 (SEQ ID NO: 5)) was tested using trypsin, BoNT/A complex, and BoNT/A and B serotypes (FIG. 16). The control peptides were only cleaved by trypsin and not by BoNT/A complex (FIG. 16, left and

TABLE 10

| SEQ ID NO: | Peptide # | Code | BoNT/A Cleavable or Control |
|---|---|---|---|
| 5 | #113 | [4MU]-TRIDEANQRATK[DABCYL]-Hex-CONH$_2$ | control |
| 12 | #201 | K[5-Fam]IDEANQRATK[DABCYL]-Nle-CONH$_2$ | cleavable |
| 13 | | Fam-K[5-Fam]IDEANQRATK[DABCYL]-Nle-CONH$_2$ | cleavable |
| 14 | | 5-Fam-KIDEANQRATK[DABCYL]-Nle-CONH$_2$ | cleavable |
| 15 | | 5-Fam-K[5-Fam]IDEANQELTK[DABCYL]-Nle-CONH$_2$ | control |
| 17 | | 5-Fam-KIDEANQELTK[DABCYL]-Nle-CONH$_2$ | control |
| 18 | | K[5-Fam]IDEANQELTK[DABCYL]-Nle-CONH$_2$ | control |
| 19 | #112 | [5FAM]-TRIDEANQRATK[DABCYL]-Hex-CONH$_2$ | control |
| 20 | #110 | [5FAM]-TRIDEANQRATK[DABCYL]-CONH$_2$ | control |
| 21 | #115 | [5FAM]-TRIDEANQRATK[DABCYL]-Nle-CONH$_2$ | cleavable |
| 22 | #116 | [4MU]-TRIDEANQRATK[DABCYL]-Nle-CONH$_2$ | cleavable |
| 23 | #111 | [4MU]-TRIDEANQRATK[DABCYL]-CONH$_2$ | control |
| 27 | #203 | K[4MU]-IDEANQRATK[DABCYL]-Nle-CONH$_2$ | cleavable |
| 28 | #204 | K[5FAM]-IDEANQRATK[DABCYL]-Hex-CONH$_2$ | control |
| 29 | #205 | K[4MU]-IDEANQRATK[DABCYL]-Hex-CONH$_2$ | control |

CONH$_2$ = amide C-terminus; 5FAM = 5-carboxyfluorescein; 4MU = 4-methylumbelliferone; Hex = 6-aminohexanoic acid; Nle = Norleucine.

middle panels). Moreover, the control peptide, #112, was not cleaved by addition of BoNT/A or BoNT/B serotypes (FIG. 16, right panel). This demonstrates that, together with the BoNT/A cleavable peptide substrates, the control peptides can be used to determine the specificity of the BoNT/A ALISSA and the extent of non-specific proteases in a sample.

Additionally, the BoNT/A cleavable peptide, #115, showed high specificity for BoNT/A as demonstrated in the ALISSA using two different BoNT serotypes. Peptide #115 was only cleaved upon addition of BoNT/A serotype and not BoNT/B serotype (FIG. 16, right panel). This shows the remarkable specificity that BoNT/A cleavable peptides have for only the BoNT/A serotype.

Kinetic Analysis of BoNT Cleavable and Control Peptides.

An investigation of the kinetic properties of BoNT cleavable peptides and control peptides was performed (FIGS. 17-18). As the nature of protease contaminants in a clinical sample is unknown, representative proteases from the families of residue specific serine (trypsin), broad-spectrum serine (proteinase K), and zinc metallo-(thermolysin) proteinases were tested (FIG. 17). BoNT cleavable and control peptides obeyed Michaelis-Menten kinetics when tested with all of the different enzymes tested. Table 11 lists the kinetic affinity (Michaelis-Menten constant $K_M$), the catalytic turnover rates ($k_{cat}$), and the catalytic efficiency ($k_{cat}/K_M$) for both BoNT-cleavable substrates and controls. This comparison of kinetic properties of the peptides in presence of different proteases demonstrates that potential protease sample contaminants cleave the controls with similar efficiency as they cleave the BoNT/A substrates.

TABLE 11

| Enzyme/ Kinetic Parameters | BoNT/A- cleavable | Control | BoNT/A- cleavable | Control |
|---|---|---|---|---|
| BoNT/A | #115 (5-FAM) | #112 (5-FAM) | #116 (4-MU) | #113 (4-MU) |
| $k_{cat}, s^{-1}$ | 47.85 ± 02.44 | — | 49.39 ± 01.52 | — |
| $K_M, \mu M$ | 4.99 ± 0.88 | — | 2.62 ± 0.37 | — |
| $k_{cat}/K_M, \mu M^{-1} s^{-1}$ | 9.59 ± 1.89 | — | 18.85 ± 3.26 | — |
| Trypsin | | | | |
| $k_{cat}, s^{-1}$ | 98.98 ± 9.75 | 58.72 ± 4.17 | 42.78 ± 1.21 | 83.90 ± 8.35 |
| $K_M, \mu M$ | 9.67 ± 2.15 | 3.75 ± 0.79 | 3.40 ± 0.29 | 13.26 ± 2.70 |
| $k_{cat}/K_M, \mu M^{-1} s^{-1}$ | 10.23 ± 1.52 | 15.66 ± 2.14 | 12.58 ± 1.14 | 6.33 ± 2.31 |
| Thermolysin | | | | |
| $k_{cat}, s^{-1}$ | 45.32 ± 3.52 | 24.26 ± 1.72 | 18.93 ± 0.62 | 14.66 ± 0.71 |
| $K_M, \mu M$ | 8.16 ± 1.51 | 3.58 ± 0.76 | 12.66 ± 0.86 | 6.45 ± 0.80 |
| $k_{cat}/K_M, \mu M^{-1} s^{-1}$ | 5.56 ± 0.26 | 6.78 ± 1.89 | 1.5 ± 0.32 | 2.27 ± 0.79 |
| Proteinase K | | | | |
| $k_{cat}, s^{-1}$ | 45.89 ± 4.68 | 50.73 ± 3.28 | 18.11 ± 1.11 | 30.64 ± 2.17 |
| $K_M, \mu M$ | 5.46 ± 1.49 | 3.37 ± 0.67 | 4.48 ± 0.78 | 4.87 ± 0.96 |
| $k_{cat}/K_M, \mu M^{-1} s^{-1}$ | 8.40 ± 0.64 | 15.05 ± 2.89 | 4.04 ± 1.11 | 6.29 ± 2.05 |

A linear relationship between the signal responses of 4-MU and 5-FAM peptides was observed in the presence of different proteases (FIG. 18).

Cleavability of Substrates and Controls with BoNT Subtypes A1 to A5.

Figure 19:
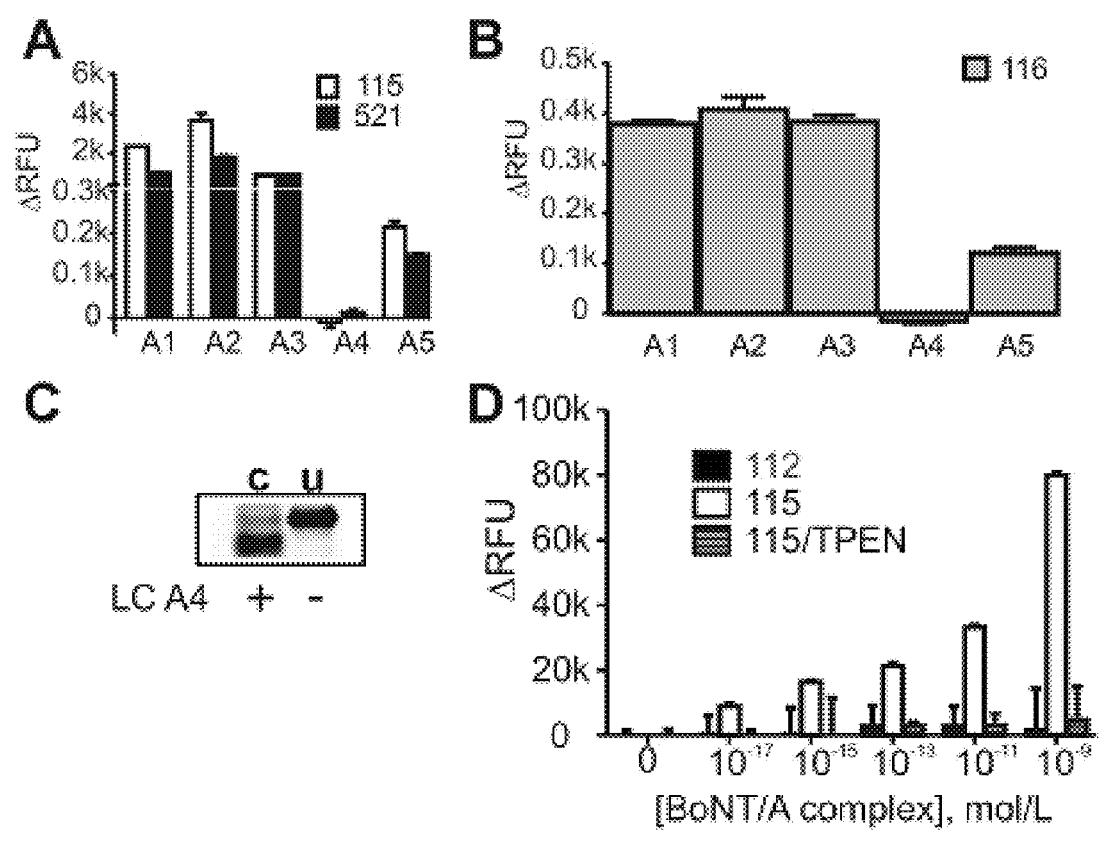

As the BoNT ALISSA was originally developed for BoNT/A subtype A1, the peptide substrates were tested to determine whether they could be cleaved by other BoNT/A subtypes (A2 to A5). The BoNT/A peptide substrates were cleaved by all known BoNT/A subtypes except for A4 (FIG. 19, A and B). None of the control peptides (#112, #113) were cleaved by any of the BoNT/A subtypes (not shown). The experiments were performed with recombinant light chains (LCs) of A2 to A5 kindly provided by Dr. Andreas Rummel, MHH Institute for Toxicology, Hannover, Germany. The A4 subtype does not cleave the BoNT/A-cleavable substrates nor the commercial FITC-containing commercial SNAPtide (#521) from List Biological Laboratories (Campbell, Calif.) (FIG. 19, A and B). However, LC A4 hydrolyzes a SNAP25 protein, BoNT/A natural substrate (FIG. 19, C). The remarkable reduction in cleavage rate of commercial SNAPtide by LC A4 was previously reported by others (Henkel 2009). In our hands LC A4 showed only 1.12% of activity with SNAPtide (#521) compared to LC A1 (FIG. 19, A). In certain embodiments the ALISSA can be used to test other BoNT serotypes as well.

Zinc Metalloprotease Activity of BoNT.

The BoNT ALISSA measures the specific zinc metalloprotease activity of immunoaffinity-enriched BoNT. The BoNT cleavable and control peptides were further tested in the ALISSA with protein A/G agarose beads and rabbit polyclonal to BoNT/A toxoid antibody in spiked pooled human serum. Only the cleavable substrate (#115, white bar) was cleaved upon addition of increasing concentrations of BoNT/A complex, while the control substrate (#112, black bar) showed only little cleavage by BoNT/A (FIG. 19 D). The zinc chelator, N,N,N',N'-Tetrakis (2-pyridylmethyl)ethylenediamine (TPEN), suppressed BoNT metalloprotease activity (#115/TPEN, striped bar). This confirmed that the concentration-dependent increase in fluorescent signal of BoNT cleavable substrate #115 was due to zinc metalloprotease activity of bead-immobilized BoNT. The negligible fluorescent signal generated by cleavage of control substrate #112 indicated the presence of non-specific protease activity in the assay.

Substrate Cleavage by BoNT Light Chains.

The BoNT holotoxin consists of a heavy chain (HC) and a light chain (LC), which perform different functions. The BoNT HC binds the receptor and delivers the LC to its target substrate. The BoNT LC is responsible for the catalytic activity of BoNT by cleaving its specific substrate. Separately, the BoNT HC and LC components are not toxic. Therefore, substrates were identified that can be cleaved by the BoNT/A holotoxin, complex or the non-toxic LCs alone ((SEQ ID NO: 21 and 22), (SEQ ID NO: 12), (SEQ ID NO: 13), and (SEQ ID NO: 14)). Cleavage by the non-toxic LC is a useful feature for the development of toxin free positive controls for the implementation of the ALISSA assay, e.g. in a research or clinical laboratory. In certain embodiments, the ALISSA may be used with BoNT light chains of known subtypes for BoNT A and B.

This set of substrates represents an exemplary complete set of BoNT cleavable substrates and internal controls for an endopeptidase-based BoNT detection assay. No other endopeptidase-based BoNT assay contains BoNT-specific controls and allows discriminating non-BoNT specific protease activity from BoNT-specific activity. Therefore, this assay design represents an important step towards future clinical application of the BoNT ALISSA on clinical specimens.

In some embodiments the control peptides can be used in combination with the BoNT peptide substrates in the same sample. For example, control peptide #112 (5-FAM) can be used in combination with BoNT/A cleavable substrate #116 (4-MU), and control peptide #113 (4-MU) can be used in combination with BoNT/A cleavable substrate #115 (5-FAM).

Example 9

Novel Fluorogenic Substrate for BoNT/B and BoNT/E

A novel fluorogenic substrate for a BoNT/B ALISSA was designed and synthesized at the City of Hope core facility for peptide synthesis. The BoNT/B substrate contains the BoNT/B cleavable sequence of vesicle-associated membrane protein (VAMP) (Table 12, FIG. 20, SEQ ID NO: 24). This substrate was used in an ALISSA to test for BoNT specificity of substrate cleavage using BoNT/A and BoNT/B recombinant light chains (LCs). The BoNT/B LC demonstrated remarkable specificity for the substrate compared with the BoNT/A LC that did not cleave the substrate (FIG. 21A). Additionally, specificity of the BoNT/B substrate to BoNT/B complex was demonstrated in a bead-based ALISSA and a bead free reaction (FIGS. 21B and C, respectively). This substrate is a useful feature for the development of a toxin-free positive control for the implementation of the BoNT/B ALISSA assay because it can be used with the non-toxic BoNT/B LC. In certain embodiments a control peptide is used in the ALISSA for BoNT/B.

TABLE 12

| BoNT/B Cleavable Substrate K[5-Fam]LSELDDRADALQAGASQFETSAAKLKRK[DABCYL]-amide (SEQ ID NO: 24) | | |
|---|---|---|
| Number | Code | Amino acid name and modification |
| 1 | K[5-Fam] | Lysine with a 4-Methylumbelliferone conjugated to its ε-amino group |
| 2 | L | Leucine |
| 3 | S | Serine |
| 4 | E | Glutamic acid |
| 5 | L | Leucine |
| 6 | D | Aspartic acid |
| 7 | D | Aspartic acid |
| 8 | R | Arginine |
| 9 | A | Alanine |
| 10 | D | Aspartic acid |
| 11 | A | Alanine |
| 12 | L | Leucine |
| 13 | Q | Glutamine |
| 14 | A | Alanine |
| 15 | G | Glycine |
| 16 | A | Alanine |
| 17 | S | Serine |
| 18 | Q | Glutamine |
| 19 | F | Phenylalanine |
| 20 | E | Glutamic acid |
| 21 | T | Threonine |
| 22 | S | Serine |
| 23 | A | Alanine |
| 24 | A | Alanine |
| 25 | K | Lysine |
| 26 | L | Leucine |
| 27 | K | Lysine |
| 28 | R | Arginine |

TABLE 12-continued

| BoNT/B Cleavable Substrate K[5-Fam]LSELDDRADALQAGASQFETSAAKLKRK[DABCYL]-amide (SEQ ID NO: 24) | | |
|---|---|---|
| Number | Code | Amino acid name and modification |
| 29 | K[DABCYL] | Lysine with DABCYL conjugated to its ε-amino group |

(SEQ ID NO: 24)

K(5-fam)LSELDDRADALQAGASQFETSAAKLKRK(dabcyl)-amide

The ALISSA has also been expanded to detect BoNT/E, spiked in pooled human serum, using a combination of a commercial substrate (SNAP Etide) and a suitable antibody. The BoNT/E ALISSA reaches femtomolar sensitivity (FIG. 22). The commercial BoNT/E substrate SNAP Etide incorporates ortho-Aminobenzoic acid (o-Abz) as a fluorescence donor and 2,4-dinitrophenyl (Dnp) as an acceptor (quencher). o-Abz has a much lower quantum yield than coumarin or fluorescein derivatives, which is most likely limiting the sensitivity of the newly developed BoNT/E ALISSA. In one embodiment the BoNT/E ALISSA may be improved by modifying the chemistry of the substrate's fluorophore/quencher pair. In certain embodiments a fluorogenic cleavable and control substrate may be designed and used in the ALISSA to detect all BoNT serotypes, A to G.

Example 10

Bioluminescent Substrates

A series of protein engineering experiments were conducted to determine whether extended sequences of recombinant SNAP25 (FIG. 60) can be expressed in bacteria and remain cleavable by BoNT. Experiments were also conducted to determine whether recombinant firefly luciferase (FFL) with C-terminal histidine tags or other modifications remain functional. Functional recombinant SNAP25 (rSNAP25) was expressed using commercial brain cDNA library. Gel-shift experiment demonstrated that rSNAP25 is readily cleaved by BoNT/A (FIG. 23) while having a C-terminal hexahistidine tag. The rSNAP25 was also cleaved at a faster rate as compared to fluorogenic peptide SNAPtide. To generate recombinant FFL, a firefly luciferase yeast plasmid (pGAL-FFL) was obtained from a gene depository and used as a template to construct a pET-vector based on recombinant firefly luciferase expression system. The recombinant FFL had a C-terminal hexahistidine tag and was readily expressed in *E. coli*. When FFL-expressing bacteria were combined with 5-fluoroluciferin, the resulting light signal was strong enough to be visible with the naked eye indicating that the protein was functional. The signal exceeded the maximally permissible luminescence signal strength of a Victor luminometer plate reader.

Fluorogenic peptide library for producing substrates was established using previously described methods (Aina 2007; Juskowiak 2004; Rosse 2000). Synthetic peptide libraries are generated using natural and non-natural or non-proteinogenic amino acids to improve resistance toward non-target proteases. As described further below, a beaded synthesis resin support was used to perform a one-bead-one-compound approach in which each bead contains only one type of peptide in picomolar quantities. The method used was as described previously (Aina 2005; Lam 2003). On-bead conversion of the substrate was performed for several cycles of selection by first incubating the peptide bead library without BoNT in presence of a relevant sample type (e.g. serum or homogenized mouse organs) for extended periods of time. Peptides containing unstable peptides become fluorescent and were removed by particle sorting using a flow cytometer. The beads that remained non-fluorescent were then exposed to BoNT. Beads that became rapidly fluorescent in presence of BoNT were separated with either a micromanipulator (tetrad dissection microscope at COH) or flow cytometer. The library was constructed such that the peptides can be dissociated from the beads readily (e.g. by CNBr cleavage) in order to allow decoding of the sequence of the fluorogenic substrate by mass spectrometry.

Example 11

One-Bead-One-Peptide Libraries

One-bead-one-peptide libraries were generated by Fmoc (fluoren-9-ylmethoxycarbonyl) chemistry. Using a split and mix approach, the synthetic peptides begin with a block of 3 D-amino acids followed by 5 randomized L-amino acids and another block of 3-D-amino acids. Addition of 3 D-amino acids to the N- and C-termini of a peptide increases its stability. Natural proteinogenic, D-amino acids, rare as well as unnatural amino acids (Table 13) are used. The number of beads used is about three times greater than the number of possible permutations to obtain statistically relevant and reproducible results. For example, if 13 different amino acids are used for synthesis of randomized 5-mer peptides, 1.6 billion compounds are obtained and therefore 3.6 billion beads are screened. When testing a suitable linker with an existing substrate, where an undesired amount of the cleaved fluorophore containing peptide remains on the resin beads used to generate the library, the linker will be tested with existing substrate and if desired, the order of fluorophore and quencher can be reversed. Decoding of the novel fluorogenic substrate sequence is then performed by mass spectrometry analysis.

Listed below in Table 13 are commercially available (e.g. Sigma Chemicals), non-natural amino acids that are suitable for use in generating one or more library of fluorogenic peptides.

TABLE 13

| Short name | Full name, synonym |
|---|---|
| (S)-Fmoc-4-chloro-β-Homophe-OH | (S)-3-(Fmoc-amino)-4-(4-chlorophenyl)butyric acidFmoc-4-chloro-L-β-Homophe-OH |
| (R)-Fmoc-4-fluoro-β-Homophe-OH | (R)-3-(Fmoc-amino)-4-(4-fluorophenyl)butyric acid, Fmoc-4-fluoro-D-β-Homophe-OH |
| (S)-Fmoc-3-cyano-β-Homophe-OH | (S)-3-(Fmoc-amino)-4-(3-cyanophenyl)butyric acid, Fmoc-3-cyano-L-β-Homophe-OH |

TABLE 13-continued

| Short name | Full name, synonym |
|---|---|
| (S)-Fmoc-3-methyl-β-Homophe-OH | (S)-3-(Fmoc-amino)-4-(3-methylphenyl)butyric acid, Fmoc-3-methyl-L-β-Homophe-OH |
| (S)-Fmoc-3-trifluoromethyl-β-Homophe-OH | (S)-3-(Fmoc-amino)-4-[3-(trifluoromethyl)phenyl]butyric acid, Fmoc-3-(trifluoromethyl)-L-β-Homophe-OH |
| (S)-Fmoc-2-trifluoromethyl-β-Homophe-OH | (S)-3-(Fmoc-amino)-4-[2-(trifluoromethyl)phenyl]butyric acid, Fmoc-2-(trifluoromethyl)-L-β-Homophe-OH |
| (S)-Fmoc-4,4-diphenyl-β-Homoala-OH | (S)-3-(Fmoc-amino)-4,4-diphenylbutyric acid, Fmoc-4,4-diphenyl-D-β-Homoala-OH |
| (S)-3-(Fmoc-amino)-4-(2-naphthyl)butyric acid | Fmoc-4-(2-naphthyl)-L-β-Homoala-OH, Fmoc-β-2-Homonal-OH |
| (R)-Fmoc-4-(3-pyridyl)-β-Homoala-OH | (R)-3-(Fmoc-amino)-4-(3-pyridyl) butyric acid, Fmoc-4-(3-pyridyl)-D-β-Homoala-OH |
| (S)-3-(Fmoc-amino)-5-phenyl-pentanoic acid | Fmoc-5-phenyl-L-β-norvaline |
| (R)-3-(Fmoc-amino)-5-phenyl-pentanoic acid | Fmoc-5-phenyl-D-β-norvaline |
| (S)-3-(Fmoc-amino)-5-hexenoic acid | Fmoc-4-vinyl-L-β-Homoala-OH |
| (S)-3-(Fmoc-amino)-6-phenyl-5-hexenoic acid | Fmoc-4-styryl-L-β-homoalanine |
| (S)-Fmoc-3,4-difluoro-β-Homophe-OH | (S)-3-(Fmoc-amino)-4-(3,4-difluorophenyl) butyric acid, Fmoc-3,4-difluoro-L-β-Homophe-OH |
| (S)-Fmoc-4-chloro-β-Homophe-OH | (S)-3-(Fmoc-amino)-4-(4-chlorophenyl) butyric acidFmoc-4-chloro-L-β-Homophe-OH |
| Fmoc-4-Abz-OH | 4-(Fmoc-amino)benzoic acid |
| (R)-Fmoc-4-(3-pyridyl)-β-Homoala-OH | (R)-3-(Fmoc-amino)-4-(3-pyridyl)butyric acid, Fmoc-4-(3-pyridyl)-D-β-homoalanine |
| 4-(Fmoc-aminomethyl) benzoic acid | 4-(Fmoc-aminomethyl)benzoic acid |
| Fmoc-homocycloleucine | 1-(Fmoc-amino)cyclohexanecarboxylic acid |
| Fmoc-β-(3-benzothienyl)-D-Ala-OH | Fmoc-3-(3-benzothienyl)-D-alanine |

Use of purified fusion proteins as substrates will allow for further characterization of the novel fusion substrates. Mass spectrometry and gel electrophoresis will be used on the purified proteins to measure the efficiency of the cleavage reaction.

Example 12

Identification of Luminogenic Protein Substrates

Genetically engineered variants of recombinant luciferase protein that become activated by specific cleavage reactions are obtained using the following strategies: 1) complementation of inactive luciferase fragments to restore active luciferase molecules; and 2) specific reactions to release the D-luciferin as a substrate for firefly luciferase (FFL from *Photinus pyralis*).

Split FFL constructs are designed and used to detect presence of a specific proteolytic activity. Mutants of FFL can be used to emit light at distinct wavelength varying from greenish-yellow (~560 nm) to orange and red (605 to 613 nm) which allows multiplex detection of several agents on a single device. Also, the color of the light emitted by *Renilla reniformis* (sea pansy) luciferase (RLuc) can be tuned by the chemical environment in which the light-emitting coelenterazine oxidation is performed (Miyaki et al., "Bringing bioluminescence into the picture," *Nature Methods,* 4:616-617 (2007)).

Using this cloning strategy, a set of rSNAP-25/FFL fusion constructs were generated with pETblue-2 and pET28a expression vectors. Because co-expression of overlapping split FFL domains reconstitutes active FFL, an overlapping FFL fusion construct that is interrupted by an integral SNAP-25 sequence containing the BoNT/A cleavage site (within SNAP-25 residues 187 to 206) was cloned and expressed. The resulting fusion protein encompasses FFL[1-475]SNAP-25 [187-206]FFL[265-550] (brackets denote the amino acid ranges). In addition an overlapping FFL fusion protein encompassing FFL[1-478]SNAP-25[187-206]FFL[265-550] was constructed (SEQ ID NO: 3; FIG. 58) and expressed as product (SEQ ID NO: 4; FIG. 59).

Full length firefly luciferase [1-550] (SEQ ID NO:26, FIG. 62) and a fusion protein containing N-terminal FFL [1-475] followed by a cleavable SNAP sequence [187-206] containing a polyhistidine tag was successfully cloned and expressed in E. coli (FIG. 24). Additionally, a fusion protein containing N-terminal SNAP25[187-206] followed by full length FFL [1]550] was also designed, purified, and tested to determine whether N-terminal SNAP-25 can alter FFL activity. Strong signals were obtained from bacterial expressing the fusion protein SNAP-25[187-206]-FFL[1-550], with signal doubling in intensity when in presence of BoNT/A complex. Overlapping split FFL construct FFL[1-475]-SNAP25[187-206]-FFL[265-550] also produced a clear nearly two-fold signal increase in presence of BoNT/A. Overlapping split FFL construct FFL[1-478]-SNAP25[187-206]-FFL[265-550] (SEQ ID NO: 4) also produced a significant increased signal in presence of BoNT/A. The construct FFL[1-475]-SNAP25[187-206] produced an insignificant signal when in presence or absence of BoNT/A treatment.

FIGS. 25 A and B provide a synthesis schematic and cloning strategy for recombinant overlapping luciferase fragments having an interspaced SNAP25 sequence for BoNT/A detection. For other BoNT serotypes, the corresponding sequences from the appropriate SNARE complex molecule are used.

Example 13

Expandable Bioluminescent Detection System

A dual-strategy approach was employed to create an expandable bioluminescent detection system for the detection of toxin or protease activity. This system was initially developed for detection of BoNT/A as a model, and can readily expandable to detection of all BoNT classes and subtypes as well as other toxins or enzymes having measurable activity. Strategy 1 comprises a dual reaction chamber including 2 vials and two types of beads (FIG. 26A). This strategy uses FFL fusion proteins to recombine and to restore FFL activity similar to previously described methods (Paulmurugan et al., "Combinatorial library screening for developing an improved split-firefly luciferase fragment-assisted complementation system for studying protein-protein interactions," Anal Chem 79:2346-2353 (2007); Paulmurugan et al., "Firefly luciferase enzyme fragment complementation for imaging in cells and living animals," Anal Chem 77:1295-1302 (2005)). The N-terminal region of FFL that is unable to support bioluminescent reactivity (residues 1 to 475 or shorter) was fused to the binding domain of a known protein having a well characterized binding affinity for another binding partner. The other binding partner was fused to the C-terminal portion of FFL (residues 476 to 550) and to a BoNT/A cleavable SNAP25 sequence (FIG. 26 A1). The modified C-terminal FFL fusion was attached to beads via the SNAP25 domain and maintained in a macrofluidic reaction chamber that is capable of interfacing to 1 ml sized sample volumes. Interaction with BoNT/A cleaves the C-terminal FFL fusion, leaving the substrate on the bead surface, to which it has a specific affinity (e.g. by use of a histidine-tag) (FIG. 26 A2). Alternatively, the cleaved substrate can be bound on a specific enrichment column. After sufficient exposure to the sample, the accumulated cleaved substrate was eluted and transferred to a microfluidic reaction chamber where it encountered the immobilized N-terminal FFL domain fusion protein. Combination of the FFL fragments occurs through dimerization of the binding protein domains and bioluminescence is detected in the presence of adenosine triphosphate (ATP) and luciferin. The advantage of the dual chamber is that accumulation of cleaved substrate can be obtained over time for samples that do not require further purification, such as, for example, clear serum samples. Turbid samples may require additional purification such as by immuno-capture of the toxin, for which a single chamber (described below) may be more suitable.

In Strategy 2, a single chamber system is employed wherein a luminogenic FFL derivative is directly exposed to affinity-enriched toxin such as BoNT/A (FIG. 26 B). The luminogenic FFL derivative can either be constructed directly to the fusion protein or with a fusion of overlapping FFL fragments that are spaced by a cleavable SNAP25 sequence. We have found that the overlapping FFL fragments (1-478) and (265-550) recombine to produce up to 4% of the activity of FFL, possibly by formation of a heterodimer.

Example 14

Bioluminogenic Substrate Using a Bioluminescent Bead-Based Detection System

Figure 27:
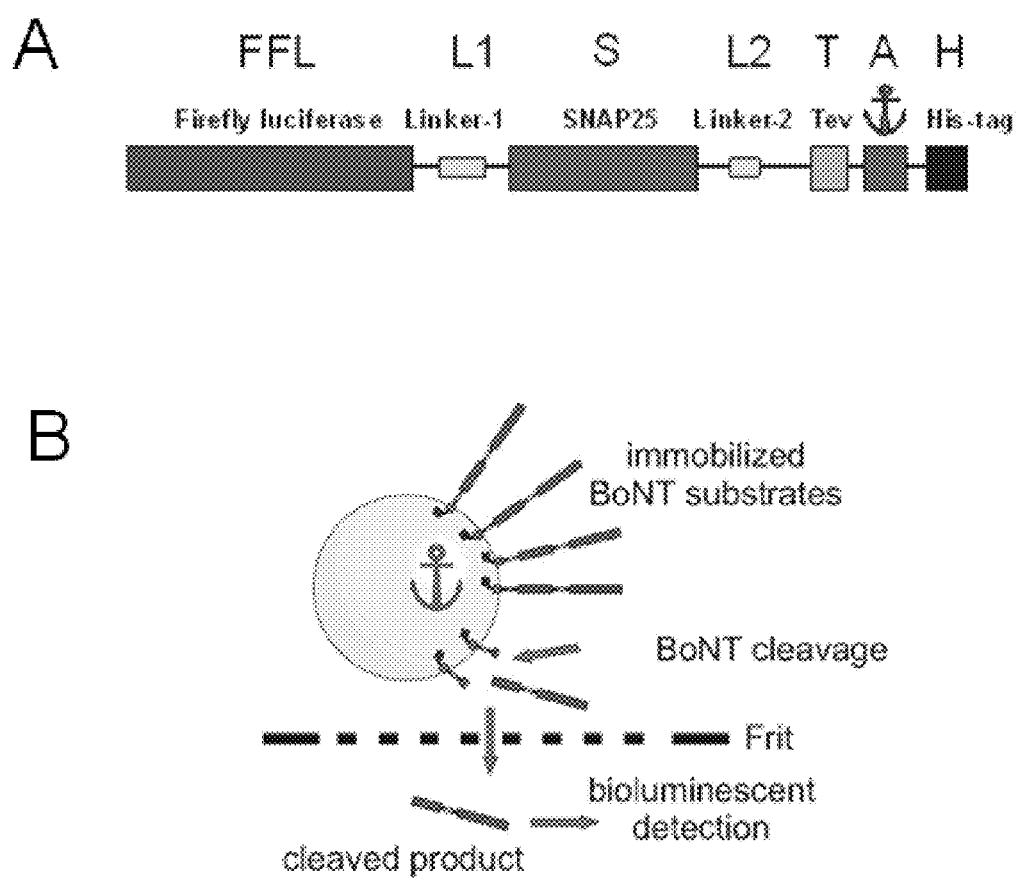

A bioluminogenic BoNT/A peptide, FFL(1-550)SNAP (187-206)-TEVsite-His$_6$, (FFLSH), was developed and optimized to detect BoNT/A activity using a bead-based bioluminescent detection system. The peptide is comprised of a fusion protein containing full-length bioluminogenic firefly luciferase (FFL) (amino acid residues 1-550), a SNAP-25 sequence (amino acid residues 171-206) that can be cleaved by BoNT/A, a positive control cleavage site, and an affinity tag. This fusion peptide was further optimized to contain linker sequences on both sides of the SNAP-25 sequence and a lysine-rich anchor sequence (FFL(1-550)-L1-SNAP(187-206)-L2-TEVsite-A-His$_6$ (FFL-L1SL2TAH (SEQ ID NO: 29) (FIGS. 27 A and 61). These luminogenic peptide can be recombinantly expressed in E. coli and immobilized onto beads (FIG. 27 B).

More specifically, the FFL-L1SL2TAH fusion protein was immobilized onto CNBr activated Sepharose beads via an octa- or deca-lysine anchor peptide (Anchor (K$_8$+GLE): K,K, K,K,K,K,K,K,G,L,E (SEQ ID NO: 30) and Anchor K$_{10}$+ GLE): K,K,K,K,K,K,K,K,K,K,G,L,E (SEQ ID NO:31)) and contains a polyhistidine tag (Histidine Tag (H$_6$): H,H,H,H, H,H (SEQ ID NO: 32)) for protein purification (FIG. 27 A; "A" and "H", respectively; FIG. 63). Additionally, a cleavage site that can be recognized by the Tobacco Etch Virus (TEV) protease (ENLYFQG (SEQ ID NO: 33)) was inserted as a positive control (FIG. 27 A; "T"; FIG. 63); the addition of this cleavage site is optional. To optimize the turnover rate for the BoNT/A catalysed proteolysis, a serine-glycine linker was introduced at the N-terminus of the SNAP25 peptide (Linker 1 (G$_4$SG$_4$): G,G,G,G,S,G,G,G,G (SEQ ID NO: 34)) and a glycine linker was introduced at the C-terminus (Linker 2 (G$_6$): G,G,G,G,G,G (SEQ ID NO: 35)) of the SNAP25 peptide (FIG. 27 A; "L1" and "L2", respectively; FIG. 63). This bioluminogenic FFL fusion protein can also serve as a soluble, non-immobilized substrate, with the inhibitory domain replacing the anchor peptide. The incorporation of glycine rich linkers on both sides of the SNAP-25 sequence (FFL-L1SL2TAH, FIG. 27, SEQ ID NO: 25, FIG. 61) resulted in cleavage of the bioluminogenic FFL fusion protein at a ~30-fold higher rate by BoNT/A light chain (LC) than the same substrate that lacked one or both linkers.

In some embodiments the FFL-L1SL2TAH fusion protein linker regions may contain additional glycine or serine residues. Additionally, the FFL-L1SL2TAH fusion protein may be immobilized onto Cyanogen-bromide (CNBr) activated Sepharose beads or nickel nitrilotriacetic acid (Ni-NTA) beads.

Example 15

Detection of BoNT Using Bioluminescent Fusion Proteins

Testing Fire Fly Luciferase Protein Substrates for BoNT Detection.

As previously described, recombinant luciferase proteins that become activated by specific cleavage reactions mediated by the neurotoxin's metalloprotease activity were genetically engineered. We have successfully managed to clone and express the following BoNT/A substrate-firefly luciferase (FFL) fusion proteins and controls in *E. coli*:

```
                                         (SEQ ID NO: 25)
FFL[1-475]SNAP25[187-203]-His₆,

FFL[1-550]-His tag (full length FFL, control),

SNAP25[187-203][FFL1-550]-His₆

FFL(1-550)SNAP(187-206)-TEVsite-His₆, (FFLSH),
and

FFL(1-550)-L1-SNAP(187-206)-L2-TEVsite-A-His₆(FFL-

L1SL2TAH.
```

Figure 28:
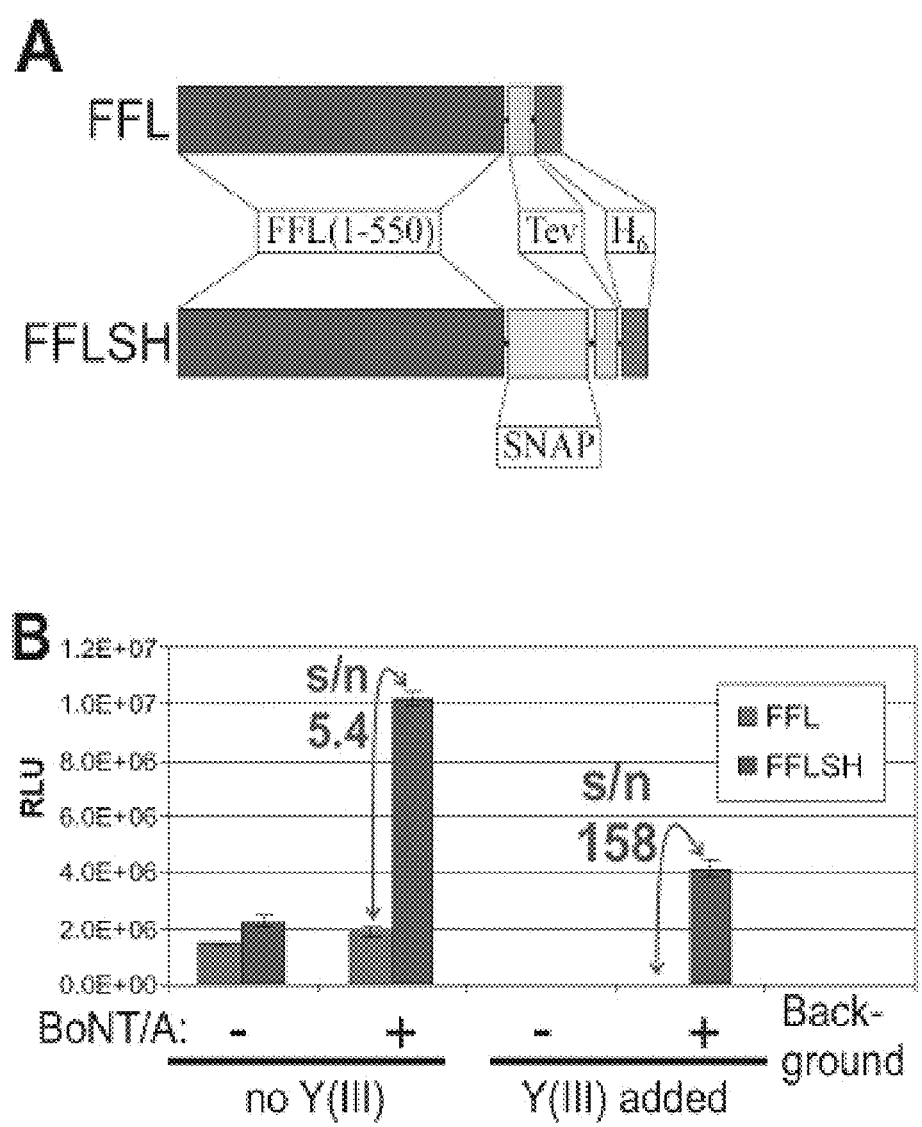
Figure 30:
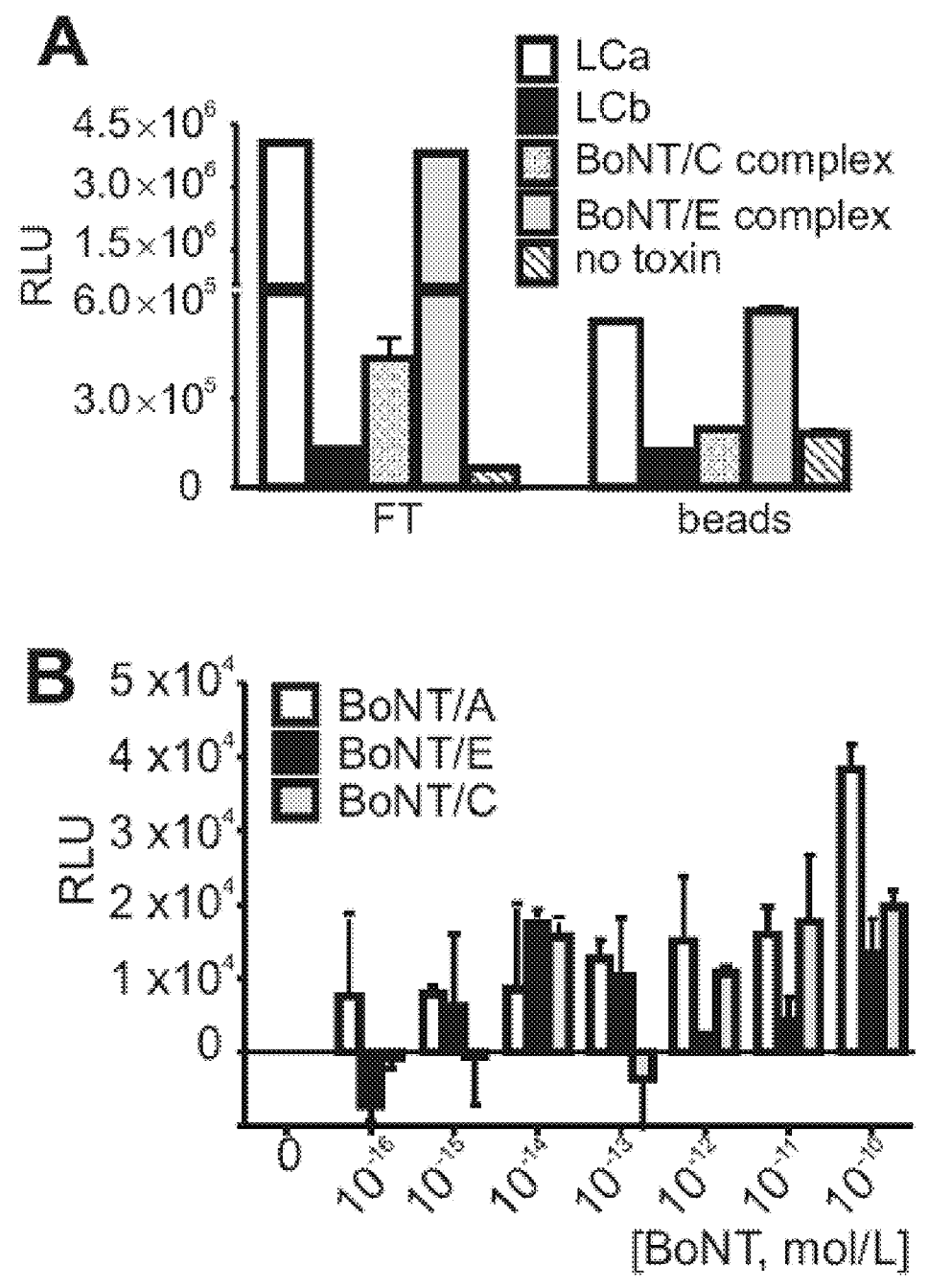

The luminescence signal of the full length recombinant FFL [1-550] reaches 16×10⁶ relative luminescence units (RLU) when combined with ONE-Glo reagent (5'-fluoroluciferin containing, from Promega), whereas the fusion of incomplete N-terminal FFL with the BoNT/A cleavable substrate sequence (FFL[1-475]SNAP25[187-203]-His₆) gave only a residual signal of 25×10³ RLU, which was expected. SNAP25[187-203][FFL1-550]-His₆ produced a signal of approximately 5×10⁶ RLU. It is anticipated that FFL[1-475]SNAP25[187-203]-His₆ can be cleaved by BoNT/A after which it should be able to reconstitute active FFL when combined with the c-terminal portion of FFL (residues 265 to 550), however, the recombinantly expressed c-terminal portion of FFL was unstable. Therefore, FFL(1-550)SNAP(187-206)-TEVsite-His₆ (FFLSH) was expressed and purified. FFLSH contains a BoNT/A cleavable site as well as a TEV-protease cleavable site for control experiments, followed by a hexahistidine tag (His₆) for bead-immobilization (FIG. 28 A). BoNT/A cleavage removes the tag from FFLSH, but not from FFL (control). TEV cleavage removes the tag from both FFL and FFLSH. Prior to BoNT/A-exposure, FFLSH generated the same bioluminescent light signal intensity as FFL (FIG. 28 B). After treatment with BoNT/A, the intensity of the cleaved FFLSH was 5.4-fold higher than that of the non-cleavable FFL control. This signal-to-noise difference was further enhanced by subsequent addition of yttrium (III) salts, which quenched light generation of uncleaved FFLSH and FFL in a H₆ tag-dependent manner. The BoNT/A-cleaved and tag-free form of FFLSH produced 158-fold more light than BoNT-treated FFL that still contained the H₆ tag (FIG. 28 B). The bioluminescence of FFLSH in solution, on nickel nitrilotriacetic acid (Ni-NTA) beads, with and without BoNT/A LC treatment was evaluated (FIG. 29 A). As previously described, when this fusion protein was bound to Ni-NTA beads, the FFL bioluminescence was substantially quenched when compared to FFLSH in solution (FIG. 29 B). BoNT light chain (LC) A cleaves the FFLSH at the SNAP25-cleavage site for BoNT/A, resulting in increased luminescence in the supernatant. The cleavage of FFLSH is dependent on the concentration of LC A (FIG. 29 C). Additionally, as the bioluminogenic substrate is based on the SNAP25 sequence, this substrate can be cleaved by BoNT serotypes A, C, and E, but not B (FIG. 30 A, B).

The mechanism by which Y (III) salt addition quenches the light production of H₆-tagged luciferases was investigated. In presence of the H₆ tag and Y (III) ions, FFL and FFLSH form insoluble microaggregates that do not pass through PVDF-filters with pore-sizes smaller or equal 0.45 μm (FIG. 31). The aggregates are unable to catalyze the bioluminescence reaction. Adsorption onto surfaces is similar to aggregate formation and has been shown to denature luciferase molecules (Hlady 1991).

Furthermore, H₆ and alternative tags were used to remove non-BoNT-cleaved FFLSH from the sample by affinity chromatography. Instead of using Y (III) ions to inhibit uncleaved FFL or FFLSH, uncleaved FFLSH was removed with chromatographic nickel nitrilotriacetic acid (Ni NTA) beads. This method was successfully for an FFLSH-based ALISSA prototype. A bead-bound BoNT/A from spiked human serum samples was reacted with FFLSH. Ni NTA beads were then added and the supernatant was mixed with luciferase reaction buffer (ONE-Glo, Promega) containing ATP, Mg²⁺ and 5-fluoroluciferin. Without any optimization of the FFLSH substrate, as little as 2.4 fmol BoNT/A complex in a 150 μL sample was detected (FIG. 32). However, the extra step of having to remove uncleaved FFLSH by addition of Ni NTA beads is inconvenient and adds extra time to the assay execution. The observed bioluminescent detection signals of BoNT-cleaved FFLSH were virtually free of background noise, which is a substantial advantage over ALISSA with fluorogenic peptides.

Detection of Dual-Step Enzyme Cascades with Bioluminescent Readout for Use in the ALISSA.

As previously described, the original BoNT/A ALISSA uses fluorogenic peptide substrates for the detection of BoNT's enzymatic activity. These peptide substrates are costly in production and contribute to a substantial level of background fluorescence even when they are present in their un-reacted, uncleaved form. Therefore, novel luminogenic substrates that produce a highly specific bioluminescent signal when exposed to BoNT were produced. Such substrates consist of fusion proteins that are recombinantly expressed in *E. coli*, which make their production inexpensive and efficient. The substrates contain a luciferase domain (firefly or *renilla*), a BoNT-cleavable domain, and an inhibitor of the bioluminescent activity of the intact fusion protein. In order to generate the appropriate inhibitor domain, mice were immunized with recombinant firefly luciferase (FFL), splenocytes were selected from immune mice, and then fused to myeloma cells to produce hybridoma cells that express FFL-inhibitory monoclonal antibodies (FIG. 33).

A live-colony screening system for *E. coli* cells that produce FFL was tested and can be used to produce the luminogenic BoNT substrate. Using a digital camera with a long time-exposure (>16 s), FFL-expressing *E. coli* bacteria on agar plates can be detected. This system may be used to screen for fusion proteins that will contain inhibited (inactive) FFL and green fluorescent protein. Colonies that are fluorescent and only produce a bioluminescent signal upon exposure to BoNT will encode plasmid DNA for the desired substrate.

Example 16

Detection of Systemic BoNT

Detection of BoNT in Serum and Organs of Intoxicated Mice Using ALISSA.

Using the ALISSA method described herein, BoNT/A levels were measured in serum and organs of intoxicated mice. The ALISSA was performed on serum, lung and liver of mice that had been intraperitoneally injected with different doses of BoNT/A complex or with a mock injection of buffer only (control mice) (FIG. 34). Organs were homogenized using the Whirl bag method (Walsh et al., "Tissue homogenization with sterile reinforced polyethylene bags for quantitative culture of *Candida albicans*," *J. Clin Microbiol.* 25:931-932 (1987). BoNT/A was detected systemically as shown in FIG. 34. BoNT/A was detected in blood and liver harvested two hours after injection with toxin. BoNT/A levels in the lung remained low. To apply existing and novel BoNT ALISSAs to measure toxin distribution in animal sera and organs. In some embodiments BoNT ALISSAs may be used to measure the systemic content and tissue distribution in sub-lethally BoNT-intoxicated mice. In certain embodiments the pharmacokinetic and serotype-dependent toxin distributions may be determined in organs following parenteral or oral intoxication.

Detection of BoNT in the Blood of Animals in the Course of an Intoxication/Rescue Experiment.

The BoNT/A ALISSA method herein was used to determine the concentration of BoNT/A in the blood of animals in the course of an intoxication/rescue experiment (FIG. 35). Briefly, mice were injected with lethal doses of BoNT/A, followed by injection of a rescue agent containing a mixture of monoclonal antibodies that neutralize BoNT/A. The ALISSA technique was used to directly measure the clearance of BoNT/A from the circulation. While BoNT/A activity was clearly detected 1 min. after injection of the rescue antibodies, most of it was removed from circulation within 30 min. The ALISSA antibody used in this study was the original polyclonal anti-BoNT/A rabbit antibody from abcam that binds to different epitopes than the mAbs used for the rescue experiment.

Example 17

Ultrasensitive Detection of BoNT and Anthrax Lethal Factor in Biological Samples by ALISSA Abstract.

As previously described, both botulinum neurotoxins (BoNTs) and anthrax lethal factor, a component of anthrax toxin, exhibit zinc metalloprotease activity. The assay detailed here is capable of quantitatively detecting these proteins by measuring their enzymatic functions with high sensitivity. The detection method encompasses two steps: (1) specific target capture and enrichment and (2) cleavage of a fluorogenic substrate by the immobilized active target, the extent of which is quantitatively determined by differential fluorometry. Because a critical ingredient for the target enrichment is an immobilization matrix made out of hundreds of thousands of microscopic, antibody-coated beads, this detection method is termed an assay with a large immunosorbent surface area (ALISSA). The binding and reaction surface area in the ALISSA is approximately 30-fold larger than in most microtiter plate-based enzyme-linked immunosorbent assays (ELISAs). ALISSA reaches atto (10-18) to femto (10-15) molar sensitivities for the detection of BoNT serotypes A and E and anthrax lethal factor. In addition, ALISSA provides high specificity in complex biological matrices, such as serum and liquid foods, which may contain various other proteases and hydrolytic enzymes. This methodology can potentially be expanded to many other enzyme targets by selecting appropriate fluorogenic substrates and capture antibodies. Important requirements are that the enzyme remains active after being immobilized by the capture antibody and that the substrate is specifically converted by the immobilized enzyme target at a fast conversion rate. A detailed protocol to conduct ALISSA for the detection and quantification of BoNT serotypes A and E and anthrax lethal factor is described.

Introduction.

Botulinum neurotoxins (BoNTs) are considered the most potent toxins known. By extrapolation from primate studies, the lethal human dose is 1-2 ng/kg body weight when intravenously injected (Gill 1982). Seven BoNT serotypes (A-G) are known to be produced by Gram-positive anaerobic bacteria of the genus *Clostridium* (Arnon 2001). BoNT/A and B (and to some extent E and F) are the main etiological agents of human botulism (Long 2007). Infant, food-borne and wound botulism are its most common forms (Koepke 2008; Werner 2000; Sobel 2004). Natural BoNT is produced as a 900-kDa complex that contains the 150-kDa holotoxin consisting of a 50-kDa light and 100-kDa heavy chain, plus several nontoxic neurotoxin-associated proteins (NAPs) (Simpson 1981; Sakaguchi 1982). Once in the bloodstream, the BoNT holotoxin targets and enters motor neurons, inside which the toxin's light chain zinc metalloprotease subunit hydrolyzes SNARE proteins (Volknandt 1995). BoNT cleaved SNARE proteins no longer mediate the fusion of acetylcholine-containing synaptic vesicles with the terminal motor neuron membrane (Lalli 2003). This efficiently shuts down neurotransmitter release into the neuromuscular junction, leading to flaccid paralysis on the macroscopic scale. Each BoNT serotype cleaves one or more of the three SNARE proteins (SNAP25, VAMP, and syntaxin) at specific peptide bonds (Lalli 2004; Schiavo 1993; Schiavo 1993; Schiavo 2000; Schiavo 1992).

BoNTs have gained popularity as cosmetic drugs in recent years, and have also been successfully used for the treatment of a variety of neurological and neuromuscular disorders (Schantz 1992; Johnson 1999). However, because of the lack of a standardized testing procedure, the units of biological activity are often unable to be directly converted into precise doses for human use, and overtreatment with BoNTs can cause iatrogenic forms of botulism (Partikan 2007; Crowner 2007). BoNT is also a potential biothreat agent because of its extreme potency and lethality, its ease of production and transport, and the need for prolonged intensive care of intoxicated persons (Arnon 2001).

The clinical diagnosis of botulism requires the presence of the toxin be demonstrated in a clinical specimen. The mouse bioassay is most commonly used. For example, it is applied for the analysis of stool and enema samples from suspected cases of infant botulism (CDC 1998; Schantz 1978). Mice are intraperitoneally injected with a sterile filtered sample and observed for signs of botulism. Furthermore, neutralizing antibodies can be used to specify the serotype of the causative BoNT. The mouse bioassay has a detection limit of 10-20 pg of neurotoxin, and typically requires up to 4 days turnaround time (CDC 1998). The assay detailed here can detect BoNT/A and BoNT/E with atto (10-18) and femto (10-15) molar sensitivity, respectively, and requires only a fraction of the time of the mouse bioassay (2.5 h ALISSA for BoNT/A) (Bagyramyan 2008).

Anthrax lethal factor (LF) is another zinc metalloprotease that has been successfully been adapted for use in the ALISSA. LF constitutes one of the three components of anthrax toxin that is produced by *Bacillus anthracis*, together with protective antigen (PA) and edema factor (EF) (Brossier 2001). LF specifically cleaves members of the mitogen-activated protein kinase kinase (MAPKK) family, leading to the inhibition of essential signaling pathways. LF alone is not toxic; it requires the presence of PA for its translocation into cells (Brossier 2001). Macrophages are believed to be primarily affected by LF (Hanna 1993). A specific and sensitive assay for the detection of LF is potentially useful for early diagnosis of anthrax infection and is expected to be a useful research tool to advance the understanding of the mechanism of action of anthrax toxin (Boyer 2007).

Detection Principle.

The method described here is referred to as an assay with a large immuno-sorbent surface area (ALISSA) (Bagramyan 2008). ALISSA measures the specific proteolytic activity of BoNT/A, BoNT/E, or LF after its capture and enrichment on a beaded immunoaffinity matrix that contains target-specific antibodies. Antibodies were chosen such that the enzyme retains its catalytic activity after immobilization. Following the removal of nontoxin-specific sample components through stringent washes, the toxin-specific enzyme activities are determined by measuring the cleavage of specific fluorogenic peptide substrates (Bagramyan 2008). Fluorogenic peptide substrates for BoNTs and LF are commercially available, or can be synthesized by classical solid-phase peptide chemistry (Schmidt 2003). The fluorogenic substrates contain a fluorescence donor and acceptor pair. Fluorescence of the fluorophore is quenched via the Förster resonance energy transfer (FRET) effect when the donor and acceptor are in close proximity to each other (preferably less than 10 nm) (Forster 1948). The toxin's proteolytic activity hydrolyzes a peptide bond that leads to the separation of donor and acceptor, thereby releasing the unquenched fluorescence of the fluorophore (FIG. 1B). In contrast to the classical FRET effect, the acceptors used here are nonfluorescent. Therefore, the difference in the fluorescence of the donor before and after enzymatic cleavage is measured in the ALISSA. The peptide substrates used here contain N-terminal fluorescein labels, such as 5-carboxyfluorescein (5Fam) or fluorescein isothiocyanate (FITC) as donors with 4,4-dimethylamino azobenzene-4¢-carboxylic acid (Dabcyl) as an acceptor near the C-terminus; or alternatively, they contain a donor/acceptor pair of ortho-aminobenzoic acid (o-Abz)/2,4-dinitrophenyl (dnp).

Another critical component of the ALISSA is the beaded immunomatrix. Its immunosorbent surface area is approximately 30-fold larger than the typical microplate well surface of a classical enzyme-linked immunosorbent assay (ELISA), and at least 5 mg of antibody are used for each data point of an ALISSA measurement (Bagramyan 2008). The target-binding light chains of the antibodies are directed away from the bead surface and toward the sample solution by immobilization via their heavy chains, the Fc regions, on protein A/G-coated agarose beads. Bleeding of antibodies into the sample solution would have a detrimental effect on the assay's sensitivity. Therefore, the antibodies are loaded well below the specified loading capacity of the beads and are covalently conjugated with the beads by an irreversible chemical cross-linker.

The ALISSA not only concentrates and preserves enzyme activities of the immobilized toxin, but also has a profound effect on kinetic properties. Enzymatic turnover rates of ALISSA-immobilized enzymes are dramatically increased over those of the reaction of nonimmobilized enzymes, leading to a strong signal amplification effect on the order of billions of cleaved substrate molecules per bound toxin molecule per hour (Bagramyan 2008).

The ALISSA for BoNT/A was originally used to detect BoNT/A in spiked samples of human serum, gelatin phosphate diluent (GPD, used in clinical diagnosis of infant botulism) and liquid foods, such as milk and carrot juice (Bagramyan 2008). ALISSA's high sensitivity (attomolar detection of BoNT/A) is accompanied by high target specificity and robustness. Nontoxin proteases of most sample types do not lead to false-positive ALISSA signals because they are removed in stringent wash steps (FIG. 36A-D).

ALISSA has now been expanded to detect anthrax LF and BoNT serotype E, but the detection of many other targets seems feasible, provided that suitable substrates and antibodies can be obtained. Thus, ALISSA has the potential to significantly improve the diagnosis of botulism, anthrax infection and potentially other serious infections, and could serve to protect humans in biomedical and biodefense scenarios.

Materials

Instruments.

A 100SD Microcentrifuge was used from USA Scientific, USA for centrifugation. For more than five assays a microcentrifuge was used, such as Eppendorf Model 5417R, or a centrifuge that accommodated 15-mL conical tubes (e.g., Beckman Allegra 6R). A Microplate mixer (e.g., Multi-Microplate Genie, Scientific Industries, Inc., USA) and Rotisserie from Labquake (Barnstead International, Dubuque, Iowa) were used for mixing and rotating, respectively. A standard laboratory incubator (37° C.) was used for incubation purposes. A microtiter plate reading spectrofluorometer: e.g., Wallac 1420 Multilabel Counter Victor2 (PerkinElmer) or SpectraMax M2 or better (Molecular Devices, USA) was used to measure fluorescence. The Victor2 spectrofluorometer performed at much higher sensitivity than the SpectraMax M2 instrument. However, the SpectraMax M2 could be manually set to any desired excitation/emission wavelength in the UV/VIS spectrum, which was very helpful for initial assay design. In contrast, the Victor2 required a set of optical filters with fixed transmission wavelengths.

Plastic Ware.

The plastic ware used in the experiments was sterile and protease free, and was preferably autoclaved. The following plastic ware materials were used throughout the experiment: 2 mL microcentrifuge collection tubes; 1.5 mL microcentrifuge sample tubes; 15 mL conical polypropylene tubes (BD, Falcon, USA); 0.5 mL and 2.0 mL Seal-Rite microcentrifuge tubes, amber (USA Scientific); 96-well 300-μL black microplates or 96-well 150-μL black microplates (Whatman or Greiner, USA); luer-lock disposable syringes: 1, 3, and 5 mL (Cole-Parmer, USA); and 5 mL and 1 mL Mobicol columns with 10-μm pore size for lower and upper filters (MoBiTec GmbH, Germany) or screw cap spin columns (Pierce, USA). Spin columns were recycled for reuse by removing the upper filter and washing the column multiple (at least five) times in 70% ethanol and then in ultrapure protease-free water (ten times). The columns were then dried and equipped with a new upper filter (MoBiTec, Germany).

Reagents.

BoNT serotypes A and E from *Clostridium botulinum* in the form of the 900-kDa complex, 150-kDa holotoxin, or 50-kDa light chain were from List Biological Laboratories or Metabiologics, Inc. (Madison, Wis.). In some countries, the possession and laboratory use of BoNTs is regulated by law, and restrictions regarding permissible amounts and shipping exist. The catalytic BoNT light chain and anthrax LF are generally accepted as nontoxic. BoNTs should be handled with extreme caution and aerosol formation must be avoided. The use of a class II or III biological safety cabinet was recommended for experimentation with BoNTs. Recombinant *B. anthracis* anthrax lethal factor was from List Biological Laboratories. Rabbit polyclonal antibody for *C. botulinum* A Toxoid, ab20641 was from Abcam (Cambridge, Mass.) and mouse monoclonal antibody for light chain of BoNT/A was a gift from Dr. Larry Stanker, US Department of Agriculture. Rabbit polyclonal antibody for *C. botulinum* toxin serotypes E was from Metabiologics, Inc. (Madison, Wis.) and goat anti-lethal factor from *B. anthracis* was from List Biological Laboratories.

ALISSA Substrates.

The following substrates were from List Biological Laboratories: SNAPtide peptide substrate (FITC/Dabcyl) for *C. botulinum* neurotoxin type A, or SNAPtide (o-Abz/Dnp) peptide substrate for neurotoxin type A; SNAPtide, unquenched calibration peptides for SNAPtide peptide substrate with FITC/Dabcyl and o-Abz/Dnp; SNAP Etide (o-Abz/Dnp) peptide substrate for *C. botulinum* neurotoxin type E; and the MAPKKide peptide substrate (Dabcyl/FITC) for anthrax lethal factor.

As an alternative to FITC-labeled SNAPtide, it was also possible to obtain custom-synthesized peptides from various sources. A fluorogenic BoNT/A substrate was successfully used containing the following sequence: 5Fam-TRIDEAN-QRATK(DABCYL)X-amide (#115, SEQ ID NO: 21), where 5Fam is at the α-amino group, Dabcyl at the ε-amino group of lysine, and X is norleucine with an amide C-terminus. The 5Fam label was much more stable than the FITC-labeled N-terminus, leading to lower background fluorescence.

Reagents and Buffer Conditions.

The following regents were used during the course of the experiment: deionized water (ultrapure) with 18 MΩ/cm or lower conductivity, protease-free, 0.2 μm filtered, and autoclaved; 4-(2-Hydroxyethyl)-1-piperazineethanesulfonic acid (HEPES acid); acetonitrile, $CH_3CN$ (30%); zinc chloride ($ZnCl_2$); sodium chloride (NaCl); tween-20; dimethyl sulfoxide (DMSO); ethylenediaminetetraacetic acid (EDTA), 20 mM, pH 8.2; disuccinimidyl suberate (DSS), No-Weigh format, M.W. 368.35 g/mol, spacer arm 11.4 Å, 8×2 mg vials (Pierce, USA); pooled human serum (Sigma or Innovative Research, USA); HEPES potassium salt; and immobilized protein A/G Plus, 50% slurry (Pierce, USA) or immobilized protein A/G Plus, 25% slurry (Santa Cruz Biotechnology, Inc., USA).

The following buffers conditions were used: Coupling buffer (10×): 100 mM sodium phosphate, 1.5 M NaCl, pH 7.2; Immunoprecipitation (IP)/wash buffer: 25 mM Tris, 150 mM NaCl, 1 mM EDTA, 1% Nonidet P-40 (NP-40, US Biological, USA), 5% glycerol, pH 7.4; Conditioning buffer (100×): neutral pH buffer (Pierce Crosslink Immunoprecipitation Kit, Pierce, USA); Elution buffer: pH 2.8 (Crosslink Immunoprecipitation Kit, Pierce, USA), or 100 mM glycine HCl buffer, pH 2.8, or from Gentle Ag/Ab Binding and Elution Buffer Kit (Pierce, USA); Reconstitution and reaction buffer for BoNT/A light chain: 20 mM HEPES, pH 8.2, 0.5 mg/mL bovine serum albumin (BSA) or 0.1% Tween-20; Reconstitution buffer for BoNT/A holotoxin: 20 mM HEPES, pH 8.0, 2.5 mM DTT, 0.3 mM $ZnCl_2$, and 1.0 mg/mL BSA; Reaction buffer for BoNT/A holotoxin and complex: 20 mM HEPES, 0.3 mM, $ZnCl_2$, 2.5 mM DTT, and 0.1% Tween-20, pH 8.0; Reconstitution buffer for BoNT/E: 50 mM HEPES, pH 7.8, 0.1% Tween-20; Reaction buffer for BoNT/E: 50 mM HEPES, pH 7.8, 200 mM NaCl, 0.1% Tween-20; and Reconstitution and reaction buffer for anthrax LF: 20 mM HEPES, pH 7.2, 125 μg/mL BSA. The quenched SNAPtides, SNAP Etide, and MAPKKide were prepared as 2.5 mM stock solutions and the unquenched calibration peptides as 1 μM stocks, all in DMSO. Stock solutions of reconstituted fluorogenic substrates were kept at −20° C. in small aliquots. Unnecessary freeze/thaw cycles were avoided. Dry peptide powders were stored in a desiccator in the cold. All fluorogenic substrates were kept in the dark.

Methods

Preparation of the Immunomatrix.

Binding of Antibody to Protein A/G Plus Agarose

The following protocol was adapted from the Pierce Crosslink Immunoprecipitation (IP) protocol (Pierce, Rockford, Ill., USA) with some additional modifications. This protocol was designed to yield enough antibody-coated beads for ten assay reactions (5 μg antibody per reaction and data point). It is recommended that the ALISSA be conducted at least in duplicate (two reactions per sample). The procedure can be proportionally scaled to prepare immunomatrix for up to 20 assay reactions using the same plastic ware and column sizes.

Ten mL of coupling buffer (1×) was prepared for each IP reaction by diluting the coupling buffer (10×) with ultrapure water. The protein A/G plus agarose beads were evenly suspended by gently swirling the bottle. Using a pipettor equipped with a cut pipette tip, 100 μL of the suspended Pierce resin slurry or, alternatively, 200 μL of the Santa Cruz resin slurry per reaction was added to a 5-mL Mobicol column (approximately 0.5 mm was cut off the plastic tip of a 300-μL Rainin pipette using a sterile single-sided razor blade or scalpel to create the cut pipette tip). The column was placed into a 15-mL conical polypropylene tube. The Luer-Lock cap was attached to the Mobicol column and connected to a 5-mL air-filled disposable syringe. The plunger was gently pushed into the syringe until all liquid was removed from the column. Alternatively, the column containing resin was centrifuged for 1 minute at approximately 1,000×g at 22° C., and flow-through was discarded. The resin in the column was washed by adding 1.0 mL of coupling buffer (1×) and flow-through was discarded using the syringe technique as previously described. This wash was repeated one time.

In a separate microcentrifuge tube, coupling buffer (10×), water, and 50 μg of antibody in solution was mixed to yield a final volume of 500 μL of antibody solution at a dilution of coupling buffer (1×). This protocol was optimized for 5 μg of antibody per enzymatic reaction (one data point). Depending on the number of assays, amount of antibody, resin, cross-linker, and buffer volumes were proportionally scaled. For example, antibody received at a concentration of 1 μg/μL was mixed with 50 μL of coupling buffer (10×), 400 μL water and combined with 50 μL of the antibody in solution.

After the wash, the bottom of the column was gently tapped on a paper towel to remove any excess liquid. The bottom plug was inserted to block the column's drain. The antibody solution prepared as previously described was immediately transferred into the resin-containing column. The beads were never allowed to dry. The closing screw cap was attached to the column and the column was incubated on the rotating rotisserie at 22° C. for 1 hour. The slurry remained suspended at all times during incubation. The bottom plug and cap was removed and saved. The column was placed into a 15-mL conical collection tube and liquid was removed from the column as previously described (using pressure or centrifugation). The flow-through was saved to verify antibody coupling using the Bradford protein quantification assay (Bio Rad, USA) or the bicinchoninic acid (BCA) protein assay (Pierce, USA). The resin was washed once with 0.5 mL and then twice with 1.5 mL of coupling buffer (1×). Flow-through was removed and discarded as previously described.

Cross-Linking of the Protein A/G-Coupled Antibody.

To prepare a fresh 25-mM DSS solution, 217 µL DMSO was added into a new vial of 2 mg DSS, by inserting the pipette tip through the vial's foil covering. The solution was thoroughly mixed by pipette aspiration and dispensing multiple times until all DSS was fully dissolved. In a new microfuge tube, the 25 mM DSS solution was further diluted 1:10 with DMSO to yield 2.5 mM DSS. The bottom of the column was tapped with antibody-coated resin prepared as previously described on a paper towel to remove excess liquid. The bottom plug was inserted. Two hundred and five µL of coupling buffer (1×) was added to the antibody-coated resin and resuspended. To obtain a final concentration of 450 µM DSS, this resin solution was then combined with 45 µL of the 2.5 mM DSS solution prepared as previously described. The column was capped with a closing screw cap. The cross-linking reaction was incubated for 1 hour at 22° C. on the rotisserie. The bottom cap and plug were removed and saved. The column was placed in a collection tube and flow-through was drained as previously described. Two hundred and fifty µL of elution buffer was added to the column the liquid was drained gently, as previously described. The flow-through was saved to verify antibody cross-linking by measuring protein concentration as previously described. The column was washed twice with 0.5 mL of elution buffer to remove non-crosslinked antibody and unreacted DSS. Next, the column was washed twice with 1.0 mL of ice-cold IP/wash buffer and the liquid was drained after each wash. 0.5 mL of IP/wash buffer was added and the column with resin was transferred into a new tube. Fifty µL of this final resin suspension contained beads with approximately 5 µg antibody.

Storage Conditions.

The resin with the cross-linked antibody could be stored for up to 5 days in IP/wash buffer at 4° C. The antibody-bound resin was transferred into a new, protease-free microcentrifuge tube. For longer storage (maximum of 2 weeks at 4° C.), resin was stored in coupling buffer (1×) and the tube was wrapped with parafilm.

ALISSA for BoNT and LF

The following protocol below describes the amounts and volumes used for a single ALISSA reaction (one data point). Each reaction was conducted in a separate tube. The number of tubes can be scaled according to the number of samples to be analyzed.

Toxin Enrichment and Immobilization.

The sample to be analyzed (e.g., serum and liquid food) was combined with IP/wash buffer in a 3:1 ratio. The final volume of sample mixed with IP/wash buffer ranged from 0.5 to 5 mL. Fifteen mL conical sterile tubes were used for sample volumes larger than 1 mL and microcentrifuge tubes were used for samples less than 1 mL. Fifty µL of resin with cross-linked antibody (prepared as previously described) was added to the sample/IP/wash buffer. This solution was mixed and was incubated by gentle mixing on the rotisserie for 1-2 hours at 22° C. or 16 hours at 4° C. A syringe was used to transfer the resin-containing sample into a spin cup column (Mobicol 1 mL or Pierce 1 mL spin column) with Luer-Lock connector and placed into a collection tube (FIG. 37a). Liquid was discarded. Sample volumes larger than 1 mL were also processed using 5-mL Mobicol columns with filter inserts and liquid was removed by centrifugation. Two hundred mL of IP/wash buffer were added to the resin and centrifuged with spin column placed into collection tube (FIG. 37b). Flow-through was discarded. An alternative buffer, 20 mM HEPES, pH 7.5, with 0.1% Tween-20, was used for BoNT assays. This process was repeated five times. Next, resin was washed once with 100 µL of conditioning buffer (1×), once with 100 µL of 2.5 M NaCl, and twice with 200 µL of ultrapure protease-free water. Resin was then resuspended in 100 µL of ultrapure protease-free water, and transferred into a new microcentrifuge tube using a cut pipette tip. Finally, resin was wrapped with parafilm and stored at 4° C. until used (up to 5 days).

Reaction of the Fluorogenic Peptide Substrate.

Each sample for the ALISSA required 10 µL of a prediluted 250 µM substrate stock, and the final concentration of the fluorogenic substrate in the reaction buffer was 5 µM. Thus, the 2.5 mM peptide stock solution of the appropriate fluorogenic peptide substrate was diluted with 30% $CH_3CN$ in ultrapure protease-free water to a final concentration of 250 µM. The reaction buffer was prepared by diluting the prediluted fluorogenic peptide stock 50-fold in the appropriate toxin reaction buffer. Each sample required 450 µL of reaction buffer. In a 2.0-mL amber microcentrifuge tube, 50 µL of resin of the immobilized toxin sample was combined with 450 µL of the substrate-containing reaction buffer. A sample of 450 µL substrate-containing reaction buffer with 50 µL toxin-free resin was included as a control. This control was used to establish the baseline of the fluorescence background. Each sample was incubated 1-3 hours by gently rotating the amber reaction tube(s) on the rotisserie inside an incubator at 37° C. The o-Abz-conjugated peptides react slowly; therefore, these reactions were prolonged for up to 16 hours. Two hundred and twenty microliters of the reaction mixture (beads included) were transferred into a well of a 96-well black microplate (300 µL well volume).

Fluorescence was measured with a Wallac 1420 Multilabel Counter Victor2 spectrofluorometer or comparable plate reader. Excitation wavelengths of $\lambda_{ex}$=485 nm and $\lambda_{ex}$=535 nm were used for BoNT and LF reactions with FITC/Dabcyl-peptides, respectively, and excitation wavelengths of $\lambda_{ex}$=321 nm and $\lambda_{ex}$=418 nm were used for o-Abz/Dnp-peptide, respectively. The fluorescence intensity of the baseline (toxin-free control) was subtracted from the fluorescence intensity of each of the measured samples.

Calibration Curve.

The following protocol was adapted from the List Biological Laboratories Standard Curve protocol (Campbell, Calif., USA) and contains some additional modifications. Calibration peptides that correspond to the cleaved, fluorescent substrate product were used to generate a calibration curve that allowed conversion of relative fluorescence units (RFU) into molar units of cleaved substrate. This value was also used to calculate specific enzymatic activity, when the reaction time, volume, and protein amount were also recorded. (Bagramyan, K., et al., 2008). A 0.5-mM stock solution was prepared by dissolving 1 vial of calibration peptide (~49.4 nmol) in 98.8 µL of DMSO. The calibration peptide was further diluted to a 1.0-µM solution by adding 5 µL of the 0.5 mM calibration peptide stock solution to 2,495 µL of toxin reaction buffer. Each dilution was performed in triplicate using 220 µL/well for a 300-µL well volume (96-well black microplate) or 120 µL of total reaction buffer for a 150-µL well volume (reduced volume 96-well black microplate). The dilution series was prepared as provided in FIG. 38.

Figure 36:
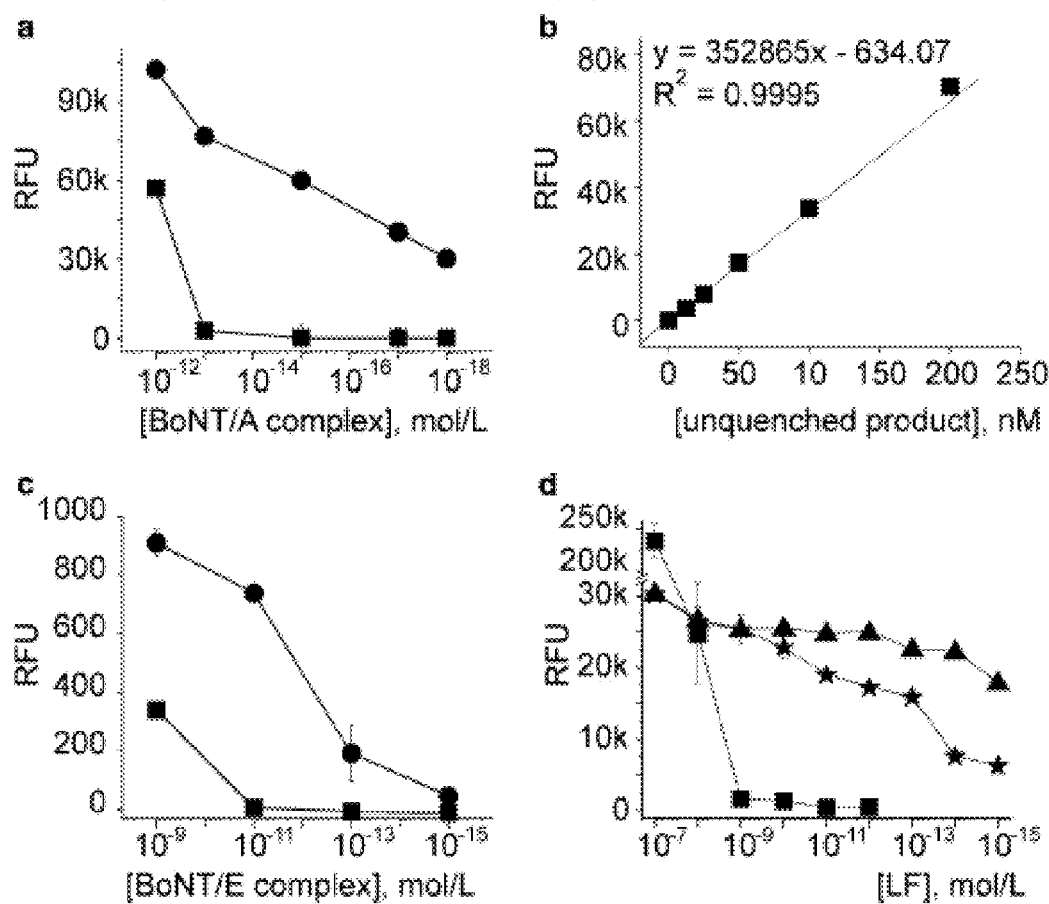

The ALISSA assay was performed using BoNT/A, E and anthrax LF using protein G and A in a bead free assay. As shown in FIG. 36D, the ALISSA technology is applicable for use with anthrax LF and (FIG. 36 d). ALISSA has now been expanded to detect anthrax LF and BoNT serotype E, but the detection of many other targets seems feasible, provided that suitable antibodies and substrates can be obtained. Thus, ALISSA has the potential to significantly improve the diagnosis of botulism, anthrax infection and potentially other serious infections, and could serve to protect humans in biomedical and biodefense scenarios.

Example 18

ALISSA Technology on Additional Targets

The ALISSA technology is also applicable for use with targets such as enzymes or toxins other than BoNT. The ALISSA technology was also extended to detection of human chitinases (e.g. CHIT1 and AMCase) (FIG. 39) and non-metalloproteases (Pep1 and Pep2 of *Aspergillus fumigatus*) (FIGS. 40A and B). As shown in FIGS. 39 and 40*a-b*, the ALISSA technology is applicable for use with a wide variety of targets including non-toxin targets and enzymes.

Example 19

ALISSA Technology Using BoNT Holoenzymes, Complexes, and Light Chains

Materials

Different antibodies that recognize epitopes on BoNT or BoNT light chains (BoNT LC) were used to prepare the bead-based immuno-affinity matrix for the ALISSA. The monoclonal antibody, 5A20.4, which specifically recognizes the BoNT/A LC, and the monoclonal antibody, 2B24, which specifically recognizes the BoNT/B light chain (BoNT/B LC), were both received from J. Marks, Department of Anesthesia and Perioperative Care, University of California, San Francisco, Calif., USA. The camelid heavy-chain-only antibodies $V_H$ (VHH) that recognize BoNT/A and BoNT/B were received from C. Shoemaker, Tufts School of Veterinary Medicine, North Grafton, Mass. Protein A/G PLUS-agarose was from Santa Cruz Biotechnology, Inc. (cat. #sc-2003), the Pierce Crosslink Immunoprecipitation Kit was from Pierce (cat. #26147), Cyanogen bromide-activated Sepharose 4B was from Sigma (CNBr-activated sepharose, cat. #C9142), and wash spin cups were from MoBiTec (Mobicols, 10 μm filter, cat. #M1002S).

Preparation of Beads Coupled with Anti-BoNT and Anti-BoNT Light Chain Antibodies Antibodies that recognize BoNT/A and BoNT/B (camelid heavy chain antibodies), BoNT/A light chains (BoNT/A LC) (5A20.4 monoclonal antibody), and BoNT/B LCs (2B24) were coupled to CNBr-activated Sepharose beads for use in the bead-based ALISSA. Briefly, 660 mg of CNBr-activated Sepharose beads were weighed and transferred into a disposable polysterene column washed with autoclaved $H_2O$. The beads were swelled for approximately 15 minutes at room temperature using ice-cold 1 mM HCl that was prepared by diluting 100 μl 10M HCl in 1 liter $H_2O$. The beads were subsequently washed with 200 ml of 1 mM HCl, drained, and capped. Two mg of each antibody was prepared by adjusting the volume of antibody with 2 mL of coupling buffer containing 0.1 M $NaHCO_3$ (sodium bicarbonate) and 0.5 M NaCl, pH 8.3-8.5 (pH was adjusted with 1 M NaOH). The antibody solution obtained in the previous step was transferred onto the column with CNBr-activated swollen beads. A portion of antibody solution was saved to verify antibody coupling. An additional 4 mL of coupling buffer was added onto the column with antibody and CNBr-activated beads. The column was rotated gently at room temperature for 2-3 hours or at 4° C. overnight ensuring that the beads remained suspended during incubation. Flow-through was saved to verify antibody coupling. The excess antibody was washed away with 10 gel volumes of coupling buffer. The remaining active groups were blocked with 0.3 M Ethanolamine, pH 8.0 (+/− 0.05) (active groups can also be blocked with 0.3 M Tris pH 8.0). The beads were gently re-suspended and placed on a rotator for 2 hours at room temperature (25° C.) or overnight at 4° C. The beads were then washed with 10 gel volumes at least three times with buffers of alternating pH. Specifically, the beads were first washed with basic coupling buffer (0.1 M $NaHCO_3$, 0.5 M NaCl, pH 8.3-8.5), followed by a wash with 0.1 M $CH_3COONa$ (sodium acetate), and lastly, a wash of 0.5 M NaCl, pH 4.0 (adjust pH with 10M HCl). Finally, the beads were washed with 10 ml 1×PBS (Dulbbelco's PBS, Mediatech cat. #21-031-CM). Antibody coupled beads that were used immediately were re-suspended in 1×PBS, placed on ice to settle, and adjusted to a final volume for a 50% suspension. Antibody coupled beads that were not used immediately were re-suspended in 100 mM ammonium bicarbonate, lyophilized, and stored at 4° C.

Immunocapturing of BoNT Holotoxin, Complex and BoNT Light Chains

An immunocapture method was utilized to capture the BoNT/A and BoNT/B holotoxins, complexes and light chains (LCs) using antibody coupled beads that were prepared as previously described. A standard curve was created by preparing serial dilutions of each enzyme including BoNT/A holotoxin, BoNT/A complex, BoNT/A LC (recombinant form), BoNT/B holotoxin, BoNT/B complex, and BoNT/B LC (recombinant form). One tube was included in each series for a toxin negative control. Two hundred μL of antibody-coupled beads were transferred into each tube of the standard curve dilution series, including the toxin-negative control. The antibody-bound beads and enzymes were gently rotated for 4-5 hours at room temperature or 1 hour at room temperature followed by overnight rotation at 4° C. on a rottiserie. Beads were pelleted by centrifugation for 1 minute (1000×g). Spin cups were washed once with 500 μL protease-free water before use. Five hundred μL aliquots of each serum/bead mixture were centrifuged through the spin cups until the entire sample was processed. The beads were then washed with a series of ice-cold buffers including two washes with Immunoprecipitation (IP) Binding Buffer/Wash Buffer (0.025M Tris, 0.15M NaCl, 1% NP-40, 5% glycerol), one optional wash with Conditioning Buffer (Pierce, cat. #26147), and three washes with protease-free water. Beads were re-suspended in $H_2O$ (2×100 μL for duplicate reactions or 3×100 μL for triplicate reactions) and transferred to an Eppendorf tube.

Enzymatic Reaction with Immuocaptured and Immobilized BoNTs

The enzymatic activity of immobilized BoNT/A and BoNT/B holotoxins, complexes, and light chains (LCs) was determined by cleavage of previously described BoNT/A cleavable fluorogenic substrates (#115 (SEQ ID NO: 21) and #116 (SEQ ID: NO 22). In order to reduce and pre-activate the enzymes, the BoNT/A and BoNT/B holotoxins and complexes were pre-incubated with DTT (the BoNT/A LC and BoNT/B LC do not require pre-incubation with DTT). For each replicate (BoNT/A holoenzyme and complex, BoNT/B holoenzyme and complex), including the toxin negative control, 100 μL of antibody-bound beads with immobilized enzymes (prepared as previously described above in Immunocapturing of BoNTs and BoNT Light Chains) was transferred into 250 μL of BoNT/A reaction buffer containing 20 mM HEPES, pH 7.4-7.5, 20 μM $ZnSO_4$, 0.1% Tween-20, 10 mM DTT. For the bead negative control, 100 μL of water was transferred into the reaction buffer. Samples were incubated for 20-30 minutes at room temperature. A solution of 250 μl of BoNT reaction buffer without DTT containing a final concentration of 12 μM of BoNT-cleavable peptides and non-cleavable peptides was prepared. Solutions were prepared for the BoNT/A 5-FAM and 4-MU cleavable (#115 (SEQ ID NO: 21) and #116 (SEQ ID NO: 22), respectively) and control peptides (#112 (SEQ ID NO: 19) and #113 (SEQ ID NO: 5)) and the 5-FAM BoNT/B cleavable peptide (SEQ ID NO: 24) for each replicate. Briefly, a 1:10 dilution of peptide was prepared from a 2.5 mM DMSO stock (stored at −20° C.) in 30% CH$_3$CN (acetonitrile) and then transferred into BoNT Reaction Buffer. Two-hundred fifty μL of peptide-containing buffer was distributed into each tube containing BoNT-bound antibody-bound beads. The final concentration of peptide was 5 μM.

For BoNT/A and BoNT/B LCs, 100 μL of antibody-bound beads with immobilized enzymes (prepared as previously described above in Immunocapturing of BoNTs and BoNT Light Chains) was transferred into 500 μL of BoNT reaction buffer containing 20 mM HEPES, pH 7.6, 20 μM ZnSO4, 0.1% Tween-20 and 1% BSA and 6 μM of BoNT/A 5-FAM and 4-MU cleavable (#115 (SEQ ID NO: 21) and #116 (SEQ ID NO: 22), respectively) and control peptides (#112 (SEQ ID NO: 19) and #113 (SEQ ID NO: 5)), respectively).

Eppendorf tubes containing the antibody-bound beads with immobilized enzymes and peptides were transferred in a carton box (protected from light), placed on a rotary shaker, and left at room temperature overnight. The following day, tubes were centrifuged for 1 minute (1000×g) to re-pellet beads. Approximately 250-275 μL of solution was transferred into each well of a black 96-well plate (Nalgene (Nunc, Fisher, cat. #12-566-09)) starting from the lowest concentration of BoNT. Each fluorescence was measured twice, once at Ex 485 nm/Em 535 nm for the 5-FAM peptides, and then at Ex 355 nm/Em 460 nm, for the 4-MU peptides.

Example 20

BoNT/A ALISSA in a Systemic Mouse Model of Botulism

The pharmacokinetics of BoNT/A intoxication in mice were studied using the ALISSA approach described herein. Serum samples from intravenous (i.v.) and intragastric (i.g.) intoxication models were provided by Dr. Luisa W. Cheng (United States Department of Agriculture, Albany, Calif.). 5A20.4 monoclonal anti-BoNT/A light chain antibody-coupled CNBr-activated sepharose beads were used in the ALISSAs to capture BoNT/A. (FIGS. 41-42). Serum samples from intoxicated mice were analyzed by ALISSA using two sets of BoNT-cleavable fluorogenic peptide substrates and BoNT non-cleavable controls, which provided a method to qualitatively distinguish between BoNT and non-BoNT related protease activities. The BoNT/A cleavable peptides and control peptides were fluorescently labelled with either 5-carboxyfluorescein (5-FAM) or 4-Methylumbelliferone (4-MU) conjugated to their α-amino group and a dark quencher, DABCYL, conjugated near their C-terminus. Each peptide substrate was combined with a BoNT/A1 non-cleavable control peptide that was conjugated with the respective other fluorophore. For example, a 5-FAM-labeled control was combined with a 4-MU-labeled substrate and vice versa (control peptide #112 (5-FAM; SEQ ID NO:19) was used in combination with BoNT/A cleavable peptide #116 (4-MU; SEQ ID NO: 22), while control peptide #113 (4-MU; SEQ ID NO: 5), was used in combination with BoNT/A cleavable peptide #115 (5-FAM; SEQ ID NO: 21)) (FIG. 42). The difference in fluorescence intensities corresponded to the real signal produced by BoNT/A only. Two different standard curves with BoNT/A cleavable and control peptides were generated in parallel with the same antibody in pooled normal (non-intoxicated) mouse serum spiked with BoNT/A1 complex. These standard curves were used to convert the relative fluorescent unit numbers into BoNT/A molar concentrations (FIGS. 43A and B). The ALISSA results from different combinations of BoNT cleavable and control substrates produced comparable results. BoNT/A concentrations in the tail blood of intoxicated mice were measured at different time points after i.v. and i.g. delivery of low quantities of BoNT/A1 complex. I.v. delivery of different concentrations of BoNT/A complex (0, 4 pg, 20 pg and 100 pg BoNT/A complex per mouse) were followed for one hour and i.v. delivery of 100 pg BoNT/A per mouse was followed over time (FIG. 44 (Group I and II, respectively), FIGS. 45 A and B). Additionally, i.g. delivery of 4 μg BoNT/A complex per mouse was followed over time (FIG. 44 (Group III)).

ALISSA detected approximately 7 to 13 aM BoNT/A in the mouse serum one hour after i.v. injection with 4 pg BoNT/A (n=4). A time course analysis with 100 pg BoNT/A/mouse (n=3) showed femtomolar toxin concentrations detected in mouse serum after only one hour post i.v. injection (FIG. 45 B). However, no toxin was detected at later time points (FIGS. 45 B and C, >3 hours), which indicates that the systemic toxin is rapidly absorbed, most likely due to neural absorption.

In contrast, in the i.g. intoxication model, BoNT was slowly released into the system as substantial time was required for the toxin to reach the blood stream. BoNT/A serum levels were not detectable one hour after i.g. intoxication with 4 μg BoNT/A complex per mouse. The BoNT/A serum concentrations rose slowly and were 165-235 aM at two hours, and 647-723 aM at seven hours after i.g. delivery of the toxin (FIGS. 46 A and B). These results indicate that systemic BoNT/A becomes detectable 5-7 hours after intoxication, manifested by the presence of 18-38 aM of toxin in mouse serum. Twenty-four hours after intoxication, most BoNT/A was likely absorbed by nerve endings, resulting in undetectable levels of toxin. Most of the animals did not survive after more than 48 hours after intoxication.

The pharmacokinetic measurements of BoNT were further tested in an additional i.g. intoxication mouse model. Mice (n=3) were orally intoxicated with 1 μg BoNT/A1 complex and BoNT/A concentrations in the tail blood of intoxicated mice were measured at different time points (2, 5, 7, 8, 24, and 48 hours after toxin delivery, FIG. 46 C). Systemic BoNT/A1 became detectable in serum between 5 to 8 hours after gavage, leading to a spike at 7 hours with a serum equivalent concentration of 18-38 aM BoNT/A1. Twenty-four hours after intoxication, most BoNT/A1 was removed from the blood (FIG. 46 C). The transition of BoNT from the gastric tract into the bloodstream was the rate limiting step in the i.g. intoxication model.

The ALISSA approach allowed real-time quantification of BoNT/A1 in serum of i.v., i.g. and orally intoxicated mice by demonstrating atto- to femtomolar blood toxin concentrations. This assay demonstrates that BoNT/A ALISSA would be a useful tool to conduct pharmacokinetic studies of BoNT in humans with botulism or in patients who receive BoNT-based medical treatments.

Example 21

Quantification of BoNT in Intoxicated Neurons

ALISSA was used for the precise quantification of BoNT in intoxicated neurons. Primary neuronal cells from 18-day old fetal rat hippocampi were cultured for 14 days after seeding into neurobasal medium supplemented with 200 mM GLUTAMAX-1 and 50×B27 (Invitrogen). Neuronal cells were exposed to 0, 2, or 20 nM BoNT/A in the presence of 55 mM KCL for 30 minutes and then thoroughly washed. Neurons were plated onto coverslips coated with poly-D-lysine (30 g/ml) and laminin (2 g/ml) at a density of 75,000 per coverslip and shipped to City of Hope, Duarte, Calif. Monoclonal anti-BoNT/A light chain antibody (5A20.4) from the University of California, San Francisco was used in the ALISSA. BoNT was extracted using a lysis buffer containing: 0.025M Tris, 0.15M NaCl, 1% NP-40, and 5% glycerol (FIG. 47).

Figure 49:
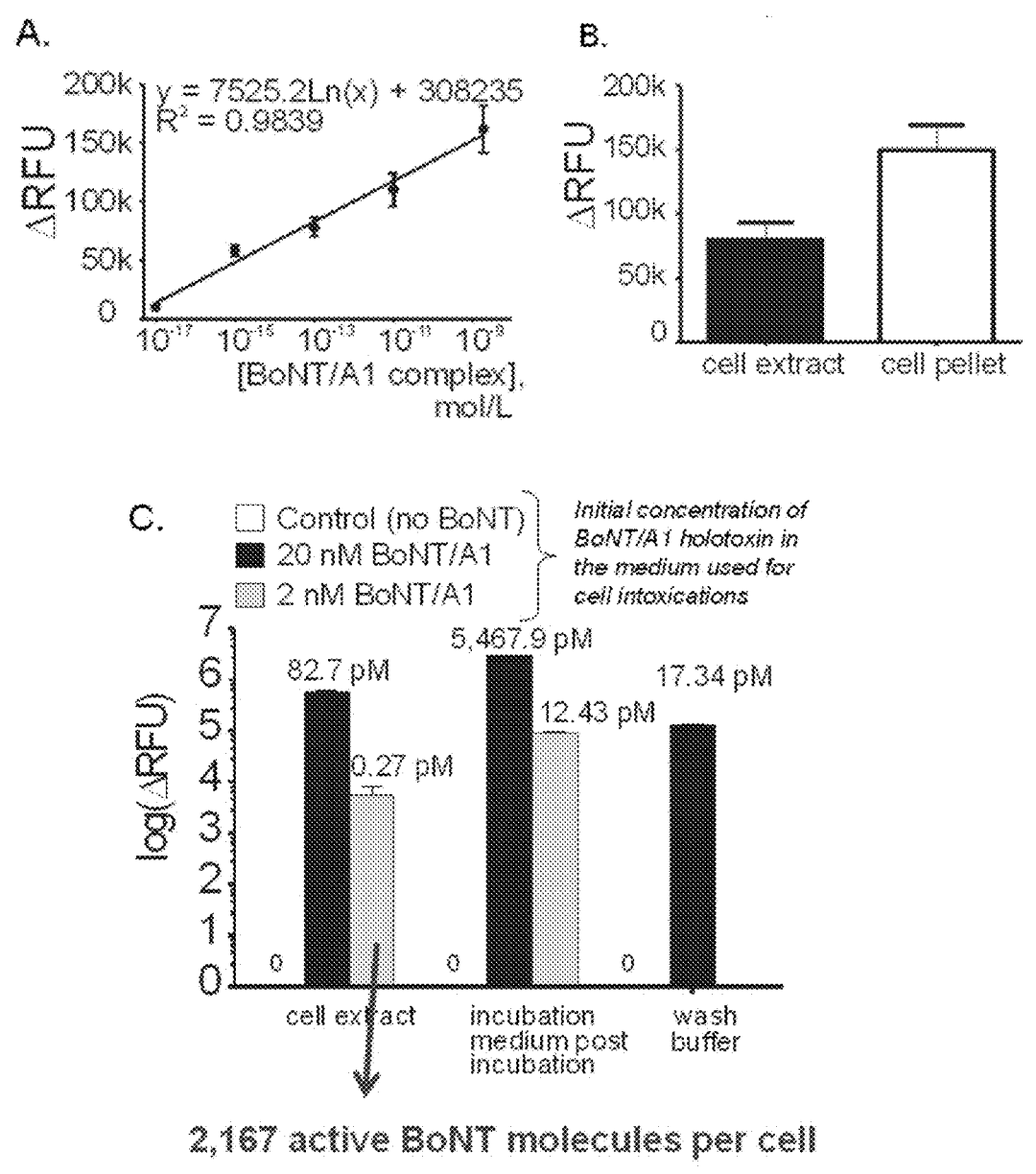

A number of different experiments with BoNT/A1-intoxicated rat hippocampal primary neuronal cells were performed using the ALISSA approach. BoNT/A1 standards with recombinant BoNT/A light chain or BoNT complex were generated using 20 nM toxin to test for the presence of toxin in high $K^+$ medium with 20 nM BoNT/A1 (FIGS. 48 A and B). The second standard, containing low (nM to aM) concentrations of BoNT/A1 complex spiked into the cell lysis buffer, was prepared to quantify the amount of BoNT/Absorbed by neuronal cells (FIG. 49 A). The ALISSA quantification of BoNT/A was performed in both cytosolic and pellet fractions, and compared to standard curves prepared with serial dilutions of BoNT/A holotoxin (FIG. 49 B). Very mild conditions were used to extract the toxin from the neurons. BoNT-treated neurons were detached and collected from coverslips/wells by application of the lysis buffer. The detached and partially lysed neurons were shock frozen in liquid nitrogen and shipped on dry ice from UCSF to City of Hope in a blinded format. ALISSA was performed on the neuronal extracts, the supernatant of the BoNT-containing medium, and the wash buffer that was used to wash the cells after co-incubation with BoNT (FIG. 49 C). When incubated with BoNT at 2 nM concentration, 75,000 cells still retained 270 attomol (270e-18 mol) BoNT, corresponding to 2,167 active molecules per cell (FIG. 49 C). The results from this assay represent the first quantitative measurements of active BoNT molecules in intoxicated cells. In certain embodiments the ALISSA is conducted with Neuro2A and M17 cells in vitro as well as with isolated neurons.

Example 22

BoNT/A ALISSA with Sera from Adult Botulism Patients

Patient serum, obtained from uninfected adults or adult patients infected with food-borne or wound botulism, was tested using BoNT/A ALISSA. A BoNT/A cleavable substrate (#115 (SEQ ID NO: 21), black bar)) was used to detect the presence of BoNT/A and a non-cleavable peptide (#112 (SEQ ID NO: 19), grey bar) was used as a control (FIG. 50). BoNT/A was detected in serum samples from well characterized clinical cases of BoNT/A food-borne botulism and wound botulism, but not in pooled human serum. This represents the first BoNT/A ALISSA using sera from adult botulism patients. These exemplary results demonstrate that ALISSA is particularly useful for detection of botulism in clinical specimens.

Example 23

BoNT/A ALISSA with Infant Botulism Patient Serum

BoNT/A ALISSA measurements were performed using a serum sample of a well characterized clinical case of BoNT/A infant botulism (IB). The sample was provided by Dr. Stephen Arnon's laboratory at the California Department of Public Health (C.D.P.H.) under CDPH-IB approval. BoNT/A activity was measured using a BoNT/A cleavable peptide substrate (#115 (SEQ ID NO: 21), green bar)) and a control peptide (#112 (SEQ ID NO: 19) (FIG. 51 A). The differential fluorescence signal was converted into molar BoNT/A concentrations using a standard curve (FIG. 51 B) and found to be approximately 0.3 pg/mL holotoxin. This corresponds to a concentration of approximately 1.8 pg/mL BoNT/A 900-kDa complex, which is 44 times lower than the detection limit of the mouse bioassay. This represents the first BoNT/A ALISSA performed using sera from infant botulism patients. These results illustrate the exemplary specificity of the ALISSA compared with the "gold standard" life mouse assay used to detect botulism, which demonstrates how the ALISSA is useful as a diagnostic tool and will improve public health by being directly applicable to naturally occurring botulism such as infant botulism. In certain embodiments a reproducible ALISSA platform may be used to test serum samples from human cases of botulism. In some embodiments, the use of the ALISSA may be used regulatory approved for clinical diagnostic use.

Example 24

Reagents for Microcolumn-Capture of BoNT Serotypes a and B (Including Subtypes)

Single Chain Antibodies (VHH) for BoNT ALISSA.

Microcolumn-enrichment of BoNT requires affinity reagents that 1) can be directed and covalently attached to the column material to avoid bleeding of the reagent; 2) bind to the light chain (LC) of BoNTs without inhibition of its enzymatic activity; 3) have a very high affinity and specificity for a desired BoNT serotype. Although the original ALISSA was based on antibodies, such substances are not necessarily required as affinity reagents for microcolumns. Fusion proteins that contain antigen-binding fragments like scFvs or the binding domains of single chain antibodies can be used instead and have the advantage that they can also be engineered to accommodate a robust on-column immobilization chemistry and multivalent epitope recognition. However, the use of scFvs can be less efficient that other types of antibodies, for example single chain antibodies from camels or camel-like animals (camelids). Therefore, recombinant alpaca single chain antibodies (VHHs) were used in the bead-based ALISSA for the detection of BoNT/A. BoNT-specific VHH antibodies were provided by Dr. Charles Shoemaker of Tufts Cummings School of Veterinary Medicine (Maass 2007; Tremblay 2010). In the ALISSA for BoNT/A-detection in spiked serum samples, the VHHs JDY-46 and JEP-2 performed similarly as did the monoclonal antibody (mAb) 5A20.4 provided by Dr. James Marks (University of California at San Francisco). However, compared to the mAb, assay linearity and sensitivity were inferior when using the VHHs (FIG. 52 A).

All VHHs tested were fusion proteins of E. coli thioredoxin (Trx) with the antigen-binding domain (VHH) of a BoNT-specific alpaca single chain antibody. With the goal to improve the ALISSA limit of detection (LOD) and to design a chemical anchor that would tightly bind the affinity reagent to a bead or column surface while directing the antigen-binding domain away from the surface, the ALISSA performance of multivalent VHH multimers with aminogroup-rich peptide appendices was determined. For example, the ALISSA performance of bivalent VHH molecules that contain two BoNT-binding VHH domains was explored (H7 and C2, FIG. 52 B). Other bi- and tri-valent VHH multimers consisted of Dr. Shoemaker's H7, D12 (JIA-44) and H7, B5, C2 (JIA-31) molecules, respectively (FIG. 53 A) (Mukherjee 2012). ALISSA with these multivalent VHHs showed improved linearity and a LOD of ~10 attomolar for JIA-44 and 1 femtomolar for JIA-31. H7 and D12 target different epitopes on the BoNT/A LC surface, while C2 has only weak LC-binding and associates strongly with the BoNT/A heavy chain (HC) (Gu 2012). This may explain the superior ALISSA results obtained with the H7/D12 VHH heterodimer. Kinetic analysis of JIA-44 revealed a binding constant of ~65 pM for BoNT/A LC (FIG. 53 B, C). VHHs with decalysine peptide extensions to provide consistent amino-rich chemical anchor points are currently being designed. As cyanogen bromide activation of sepharose is used to couple VHHs or antibodies to ALISSA beads, a similar aminogroup-reactive chemistry will be used for the microcolumns which will be developed in conjunction with the fully automated BoNT ALISSA detector.

Affinity Maturation of VHHs.

Figure 54:
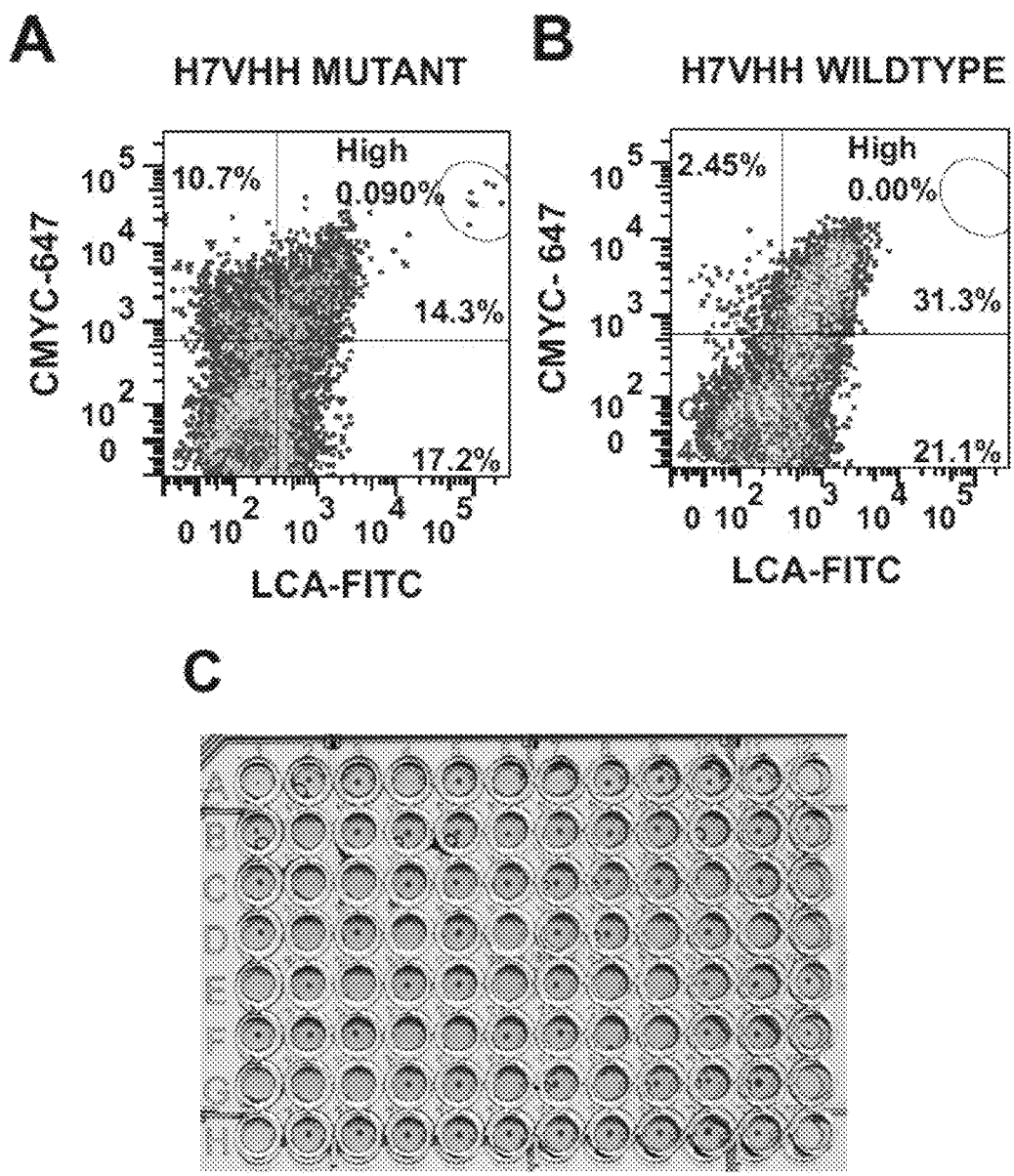

The VHHs provided by Dr. Shoemaker were derived from a cDNA library of BoNT-immunized alpacas. The VHHs had their original natural binding affinity for BoNT/A, because none of the VHHs had been affinity matured thus far. Therefore, a system for affinity maturation of BoNT/A LC-specific VHHs by modifying Wittrup's yeast surface display approach was established (Boder 1997). In the original approach, a fusion protein of Saccharomyces cerevisiae Aga2p, an HA tag, a scFv, and a c-myc tag is expressed in yeast and displayed on its surface, whereby the Aga2p portion of the construct is bound via two disulfide bonds to cell wall-embedded Aga1p (Boder 1997). In the present method, the scFv-coding DNA sequence was replaced with that of the H7 VHH provided by Dr. Shoemaker. Additionally, a labeling technique with FITC-BoNT/A LC and Alexa Fluor$^{647\ nm}$-conjugated anti-c-Myc antibody was developed that allows for detection and sorting of VHH-displaying yeast cells using a Fluorescence Activated Cell Sorter (FACS) (FIG. 54 A). Error-prone PCR was performed to introduce random mutations into the VHH, and then single cell selection was used to isolate cells that produced high levels of VHH (c-Myc$^{high}$) at high affinity (FITC-LC$^{high}$) into single wells of medium containing 96-well plates (FIGS. 54 B and C). At least seven cycles of affinity selection for mutated VHHs will be performed.

Screening for VHHs Directed to BoNT/B.

To extend the ALISSA detection to BoNT serotype B, eleven VHH proteins from Dr. Shoemaker were screened to identify further suitable affinity reagents. The VHHs JGA-3, JFZ-28 appeared to yield the best performance characteristics in terms of dynamic range and LOD. Attomolar detection limits were achieved in bead based ALISSA using pooled human serum with a dilution series of BoNT/B LC (FIG. 55).

Microcolumn-Based ALISSA.

The ALISSA technology was further optimized for use with pipette tip columns (FIG. 56 A). The pipette tip columns were affinity microcolumns that contained a bead-based immunomatrix with immobilized BoNT antibody mounted into disposable pipette tips (FIG. 56 B). The antibodies selected for the experiments were tested by Dr. Nedelkov at Intrinsic Bioprobes Inc. for antigen binding after immobilization via amine-reactive groups using a BiaCore chips and a surface plasmon resonance instrument. The chemistry used for immobilization on BiaCore chips was the same as for immobilization in the microfluidic affinity columns. Interestingly, the data suggested that some antibodies can readily be utilized for the ALISSA after direct immobilization via amine groups instead of using an immobilization matrix of protein A/G-coated beads. An ALISSA utilizing affinity pipettes with microcolumns mounted into disposable pipette tips was performed for detection of BoNT/A (FIG. 56 A). Briefly, a biological sample was added to an affinity pipette tip with a microcolumn containing the immobilized BoNT/A antibody immunomatrix. BoNT/A from the biological sample was bound and enriched on the immunomatrix while the non-specific molecules (flow-through) were washed away. Next, fluorogenic BoNT/A specific peptide was added to the affinity pipette tip containing the bound BoNT/A. Upon substrate cleavage and subsequent release of unquenched fluorophore, the fluorescence of the sample was read using a waveguide sensor. The affinity pipette tips can be used in conjunction with an electric multichannel pipettor (FIG. 56 B, left panel) and also a fully-automated robotic pipetting workstation (FIG. 56 B, right panel).

The ALISSA with affinity microcolumns was tested using increasing amounts of BoNT/A light chain in pooled human serum (FIG. 57 A). Dextran glass columns from Intrinsic Bioprobes, Inc. (acquired by Thermo Fischer Scientific) were used for the microcolumns. The affinity microcolumn immunomatrix contained the 5A20.4 (anti BoNT/A light chain) antibody. Results demonstrated that an increasing amount of BoNT/A-cleavable substrate, #201a, was cleaved upon the addition of increasing concentrations of BoNT/A (FIG. 57A). Additionally, the ALISSA with affinity microcolumns was tested using several different controls to verify the specific binding and activity of BoNT/A (FIGS. 57 B-E). The control experiments demonstrate that the cleavage of the BoNT/A specific substrate is due to BoNT/A activity as BoNT/A specifically binds the immunomatrix conjugated with BoNT/A antibodies.

Additionally, a microcolumn robotic pipetting workstation (Versette, Thermo Fischer Scientific) was obtained for the development of an automated microcolumn based BoNT ALISSA detection system. Affinity tips that hold microcolumns were designed that fit the Versette pipette workstation. The Versette workstation was used for fully automated ALISSAs (FIG. 56B, right panel). The system was programmed to conduct microcolumn-enrichment of BoNT/A LC from spiked samples of human serum. Subsequently, the pipetting station performed automated washes of the columns, followed by enzymatic reaction with fluorogenic BoNT/A cleavable substrates. The approach is still under development, but an example of a successful ALISSA run is shown in FIG. 57 F. This non-optimized version of a microcolumn-based automated ALISSA can readily detect 100 fmolar BoNT/A LC concentrations in 150 µL-sized samples of spiked human serum within 8 hours. In one embodiment the affinity microcolumns may also be optimized to contain optimized VHH proteins generated from affinity maturation of BoNT/A and BoNT/B specific VHH reagents using the yeast display technique described previously.

These results demonstrate a robust and fully automated ALISSA used for the detection of BoNT. This method is expected to improve public health and safety by offering a means to detect botulinum neurotoxins in biological samples in a sensitive, fast, and inexpensive fashion.

The examples disclosed herein are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention. It will be understood that many variations can be made in the procedures herein described while still remaining within the bounds of the present invention. It is the intention of the inventors that such variations are included within the scope of the invention. All references cited herein are incorporated by reference as if fully set forth herein.

REFERENCES

1. Arnon, S. S. et al. Botulinum toxin as a biological weapon: medical and public health management. *Jama* 285, 1059-1070 (2001).
2. Wein, L. M. & Liu, Y. Analyzing a bioterror attack on the food supply:
the case of botulinum toxin in milk. *Proc Natl Acad Sci USA* 102, 9984-9989 (2005).
3. Arnon, S. S., Schechter, R., Maslanka, S. E., Jewell, N. P. & Hatheway, C. L. Human botulism immune globulin for the treatment of infant botulism. *N Engl J Med* 354, 462-471 (2006).
4. Schantz, E. J. & Johnson, E. A. Properties and use of botulinum toxin and other microbial neurotoxins in medicine. *Microbiol. Rev* 56, 80-99 (1992).
5. Sakaguchi, G. *Clostridium botulinum* toxins. *Pharmacol Ther* 19, 165-194 (1982).
6. Chen, F., Kuziemko, G. M. & Stevens, R. C. Biophysical characterization of the stability of the 150-kilodalton botulinum toxin, the nontoxic component, and the 900-kilodalton botulinum toxin complex species. *Infect Immun* 66, 2420-2425 (1998).
7. Sharma, S. K., Ramzan, M. A. & Singh, B. R. Separation of the components of type A botulinum neurotoxin complex by electrophoresis. *Toxicon* 41, 321-331 (2003).
8. Melling, J., Hambleton, P. & Shone, C. C. *Clostridium botulinum* toxins: nature and preparation for clinical use. *Eye* 2 (Pt 1), 16-23 (1988).
9. Zhang, L., Lin, W. J., Li, S. & Aoki, K. R. Complete DNA sequences of the botulinum neurotoxin complex of *Clostridium botulinum* type A-Hall (Allergan) strain. *Gene* 315, 21-32 (2003).
10. Aoki, K. R. & Guyer, B. Botulinum toxin type A and other botulinum toxin serotypes: a comparative review of biochemical and pharmacological actions. *Eur J Neurol* 8 Suppl 5, 21-29 (2001).
11. Smith, L. D. The occurrence of *Clostridium botulinum* and *Clostridium tetani* in the soil of the United States. *Health Lab Sci* 15, 74-80 (1978).
12. Schiavo, G., Matteoli, M. & Montecucco, C. Neurotoxins affecting neuroexocytosis. *Physiol Rev* 80, 717-766 (2000).
13. Kurazono, H. et al. Minimal essential domains specifying toxicity of the light chains of tetanus toxin and botulinum neurotoxin type A. *J Biol Chem* 267, 14721-14729 (1992).
14. Lacy, D. B., Tepp, W., Cohen, A. C., DasGupta, B. R. & Stevens, R. C. Crystal structure of botulinum neurotoxin type A and implications for toxicity. *Nat Struct Biol* 5, 898-902 (1998).
15. Cai, S., Sarkar, H. K. & Singh, B. R. Enhancement of the endopeptidase activity of botulinum neurotoxin by its associated proteins and dithiothreitol. *Biochemistry* 38, 6903-6910 (1999).
16. Cai, S. & Singh, B. R. Role of the disulfide cleavage induced molten globule state of type a botulinum neurotoxin in its endopeptidase activity. *Biochemistry* 40, 15327-15333 (2001).
17. Ferreira, J. L., Maslanka, S., Johnson, E. & Goodnough, M. Detection of botulinal neurotoxins A, B, E, and F by amplified enzyme-linked immunosorbent assay: collaborative study. *J AOAC Int* 86, 314-331 (2003).
18. Kautter, D. A. & Solomon, H. M. Collaborative study of a method for the detection of *Clostridium botulinum* and its toxins in foods. *J Assoc Off Anal Chem* 60, 541-545 (1977).
19. Sharma, S. K., Ferreira, J. L., Eblen, B. S. & Whiting, R. C. Detection of type A, B, E, and F *Clostridium botulinum* neurotoxins in foods by using an amplified enzyme-linked immunosorbent assay with digoxigenin-labeled antibodies. *Appl Environ Microbiol* 72, 1231-1238 (2006).
20. Sugiyama, H. *Clostridium botulinum* neurotoxin. *Microbiol. Rev* 44, 419-448 (1980).
21. Varnum, S. M. et al. Enzyme-amplified protein microarray and a fluidic renewable surface fluorescence immunoassay for botulinum neurotoxin detection using high-affinity recombinant antibodies. *Analytica Chimica Acta* 570, 137-143 (2006).
22. Kalb, S. R. et al. The use of Endopep-MS for the detection of botulinum toxins A, B, E, and F in serum and stool samples. *Anal Biochem* 351, 84-92 (2006).
23. Barr, J. R. et al. Botulinum neurotoxin detection and differentiation by mass spectrometry. *Emerg Infect Dis* 11, 1578-1583 (2005).
24. Kalb, S. R., Goodnough, M. C., Malizio, C. J., Pirkle, J. L. & Barr, J. R. Detection of botulinum neurotoxin A in a spiked milk sample with subtype identification through toxin proteomics. *Anal Chem* 77, 6140-6146 (2005).
25. Boyer, A. E. et al. From the mouse to the mass spectrometer:
detection and differentiation of the endoproteinase activities of botulinum neurotoxins A-G by mass spectrometry. *Anal Chem* 77, 3916-3924 (2005).
26. Chao, H. Y., Wang, Y. C., Tang, S. S. & Liu, H. W. A highly sensitive immuno-polymerase chain reaction assay for *Clostridium botulinum* neurotoxin type A. *Toxicon* 43, 27-34 (2004).
27. Mason, J. T., Xu, L., Sheng, Z. M. & O'Leary, T. J. A liposome-PCR assay for the ultrasensitive detection of biological toxins. *Nat Biotechnol* 24, 555-557 (2006).
28. Mason, J. T., Xu, L., Sheng, Z. M., He, J. & O'Leary, T. J. Liposome polymerase chain reaction assay for the sub-attomolar detection of cholera toxin and botulinum neurotoxin type A. *Nature Protocols* 1, 2003-2011 (2006).
29. Ekong, T. A., McLellan, K. & Sesardic, D. Immunological detection of *Clostridium botulinum* toxin type A in therapeutic preparations. *J Immunol Methods* 180, 181-191 (1995).
30. Schmidt, J. J. & Stafford, R. G. Fluorogenic substrates for the protease activities of botulinum neurotoxins, serotypes A, B, and F. *Appl Environ Microbiol* 69, 297-303 (2003).

31. Schiavo, G. et al. Identification of the nerve terminal targets of botulinum neurotoxin serotypes A, D, and E. *J Biol Chem* 268, 23784-23787 (1993).
32. Schiavo, G. et al. Botulinum neurotoxins serotypes A and E cleave SNAP-25 at distinct COOH-terminal peptide bonds. *FEBS Lett* 335, 99-103 (1993).
33. Bagramyan, K. et al. Attomolar detection of botulinum toxin type A in complex biological matrices. *PLoS One* 3:e2041 (2008).
34. Brossier, F. et al. Toxins of *Bacillus anthracis*. *Toxicon* 39:1747-1755 (2001).
35. Hanna, P. C. et al. On the role of macrophages in anthrax. *Proc Natl Acad Sci USA* 90:10198-10201 (1993).
36. Boyer, A. E. et al. Detection and quantification of anthrax lethal factor in serum by mass spectrometry. *Anal Chem* 79:8463-8470 (2007).
37. Schantz, E. J. et al. Properties and use of botulinum toxin and other microbial neurotoxins in medicine. *Microbiol. Rev* 56:80-99 (1992).
38. Johnson, E. A. et al. Clostridial toxins as therapeutic agents:
benefits of nature's most toxic proteins. *Annu Rev Microbiol* 53:551-575 (1999).
39. Partikian, A. et al. Iatrogenic botulism in a child with spastic quadriparesis. *J Child Neurol* 22:1235-1237 (2007).
40. Crowner, B. E. et al. Iatrogenic botulism due to therapeuticbotulinum toxin A injection in a pediatric patient. *Clin Neuropharmacol* 30:310-313 (1998).
41. Henkel J S, Jacobson M, Tepp W, Pier C, Johnson E A, & Barbieri J T. Catalytic properties of botulinum neurotoxin subtypes A3 and A4. *Biochemistry* 48(11):2522-2528 (2009).
42. Bagramyan, K, Barash, J R, Arnon, S S, and Kalkum, M. 2008. Attomolar Detection of Botulinum Toxin Type A in Complex Biological Matrices. PLoS ONE 3:e2041.
43. Bagramyan, K, and Kalkum, M. 2011. Ultrasensitive Detection of Botulinum Neurotoxins and Anthrax Lethal Factor in Biological Samples by ALISSA. Methods Mol Biol 739:23-36.
44. Boder, E T, and Wittrup, K D. 1997. Yeast surface display for screening combinatorial polypeptide libraries. Nat Biotechnol 15:553-557.
45. Gu, S, Rumpel, S, Zhou, J, Strotmeier, J, Bigalke, H, Perry, K, Shoemaker, C B, Rummel, A, and Jin, R. 2012. Botulinum neurotoxin is shielded by NTNHA in an interlocked complex. Science 335:977-981.
46. Maass, D R, Sepulveda, J, Pernthaner, A, and Shoemaker, C B. 2007. Alpaca (Lama pacos) as a convenient source of recombinant camelid heavy chain antibodies (VHHs). J Immunol Methods 324:13-25.
47. Mukherjee, J, Tremblay, J M, Leysath, C E, Ofori, K, Baldwin, K, Feng, X, Bedenice, D, Webb, R P, Wright, P M, Smith, L A, Tzipori, S, and Shoemaker, C B. 2012. A novel strategy for development of recombinant antitoxin therapeutics tested in a mouse botulism model. PLoS ONE 7:e29941.
48. Tremblay, J M, Kuo, C L, Abeijon, C, Sepulveda, J, Oyler, G, Hu, X, Jin, M M, and Shoemaker, C B. 2010. Camelid single domain antibodies (VHHs) as neuronal cell intrabody binding agents and inhibitors of *Clostridium botulinum* neurotoxin (BoNT) proteases. Toxicon 56:990-998.
49. Crowner B E, Brunstrom J E, & Racette B A Iatrogenic botulism due to therapeutic botulinum toxin A injection in a pediatric patient. *Clin Neuropharmacol* 30(5):310-313 (2007).
50. Jankovic J. Botulinum toxin in clinical practice. *J Neurol Neurosurg Psychiatry* 75(7):951-957 (2004).
51. Bagramyan, K and Kalkum, M (2011) "Ultra Sensitive Detection of Botulinum Neurotoxins and Anthrax Lethal Factor in Biological Samples by ALISSA", book chapter in "Microbial Toxins", *Methods in Molecular Biology,* 739, 23-36, DOI: 10.1007/978-1-61779-102-4_3 (2011).
52. Gill D M (1982) Bacterial toxins: a table of lethal amounts. Microbiol. Rev 46:86-94.
53. Arnon S S, Schechter R, Inglesby T V, Henderson D A, Bartlett J G et al (2001) Botulinum toxin as a biological weapon: medical and public health management. JAMA 285:1059-1070.
54. Long S S (2007) Infant botulism and treatment with BIG-IV (BabyBIG). Pediatr Infect Dis J 26:261-262.
55. Koepke R, Sobel J, Arnon S S (2008) Global occurrence of infant botulism, 1976-2006. Pediatrics 122:e73-82.
56. Werner S B, Passaro D, McGee J, Schechter R, Vugia D J (2000) Wound botulism in California, 1951-1998: recent epidemic in heroin injectors. Clin Infect Dis 31:1018-1024.
57. Sobel J, Tucker N, Sulka A, McLaughlin J, Maslanka S (2004) Foodborne botulism in the United States, 1990-2000. Emerg Infect Dis 10:1606-1611.
58. Simpson L L (1981) The origin, structure, and pharmacological activity of botulinum toxin. Pharmacol Rev 33:155-188.
59. Sakaguchi G (1982) *Clostridium botulinum* toxins. Pharmacol Ther 19:165-194.
60. Volknandt W (1995) The synaptic vesicle and its targets. Neuroscience 64:277-300.
61. Lalli G, Bohnert S, Deinhardt K, Verastegui C., Schiavo G (2003) The journey of tetanus and botulinum neurotoxins in neurons. Trends Microbiol 11:431-437.
62. Schiavo G, Santucci A, Dasgupta B R, Mehta P P, Jontes J et al (1993) Botulinum neurotoxins serotypes A and E cleave SNAP-25 at distinct COON-terminal peptide bonds. FEBS Lett 335:99-103.
63. Schiavo G, Rossetto O, Catsicas S, Polyerino de Laureto P, DasGupta B R et al (1993) Identification of the nerve terminal targets of botulinum neurotoxin serotypes A, D, and E. J Biol Chem 268:23784-23787.
64. Schiavo G, Matteoli M, Montecucco C (2000) Neurotoxins affecting neuroexocytosis. Physiol Rev 80:717-766.
65. Schiavo G, Benfenati F, Poulain B, Rossetto 0, Polyerino de Laureto P et al (1992) Tetanus and botulinum-B neurotoxins block neurotransmitter release by proteolytic cleavage of synaptobrevin. Nature 359:832-835.
66. Schantz E J, Johnson E A (1992) Properties and use of botulinum toxin and other microbial neurotoxins in medicine. Microbiol. Rev 56:80-99.
67. Johnson E A (1999) Clostridial toxins as therapeutic agents: benefits of nature's most toxic proteins. Annu Rev Microbiol 53:551-575.
68. Partikian A, Mitchell W G (2007) Iatrogenic botulism in a child with spastic quadriparesis. J Child Neurol 22:1235-1237.
69. Crowner B E, Brunstrom J E, Racette B (2007) Iatrogenic botulism due to therapeuticbotulinum toxin A injection in a pediatric patient. Clin Neuropharmacol 30:310-313.
70. Centers for Disease Control and Prevention: Botulism in the United States, 1899-1996 (1998). Handbook for Epidemiologists, Clinicians, and Laboratory Workers. Atlanta, Ga.: U. S. Department of Health and Human Services, Public Health Service, CDC and Prevention. pp. 1-42.
71. Schantz E, Kautter D A (1978) Standardized assay for *Clostridium botulinum* toxins. J AOAC Int 61:96-99.

What is claimed is:

1. A method for detecting the presence of a botulinum (BoNT) toxin in a sample comprising:
   (a) exposing the sample putatively containing a BoNT toxin to:
      (i) an enrichment matrix comprising a BoNT-specific antibody that binds BoNT and a toxin substrate-specific antibody that binds toxin substrate in the sample, and
      (ii) a substrate composition comprising the toxin substrate that is capable of eliciting a detectable fluorogenic or luminogenic signal when modified by the BoNT toxin, the exposure occurring under conditions permitting binding of the BoNT toxin to the antibody and a modification of the toxin substrate by the BoNT toxin, the toxin substrate comprising one or more BoNT cleavage sites wherein:
      (1) if the BoNT toxin is BoNT/A, the toxin substrate comprises a fragment of the synaptosome-associated protein of 25 kDa (SNAP25) containing the BoNT/A cleavage site;
      (2) if the BoNT toxin is BoNT/B, the toxin substrate comprises a fragment of vesicle-associated membrane protein (VAMP) containing the BoNT/B cleavage site;
      (3) if the BoNT toxin is BoNT/C, the toxin substrate comprises a fragment of VAMP containing the BoNT/C cleavage site or a fragment of SNAP25 containing the BoNT/C cleavage site;
      (4) if the BoNT toxin is BoNT/D, the toxin substrate comprises a fragment of VAMP containing the BoNT/D cleavage site;
      (5) if the BoNT toxin is BoNT/E, the toxin substrate comprises a fragment of SNAP25 containing the BoNT/E cleavage site;

(6) if the BoNT toxin is BoNT/F, the toxin substrate comprises a fragment of VAMP containing the BoNT/F cleavage site; and (7) if the BoNT toxin is BoNT/G, the toxin substrate comprises a fragment of VAMP containing the BoNT/G cleavage site; and (b) detecting the presence of the botulinum toxin by measuring a change in detectable fluorogenic or luminogenic signal in the sample.

2. The method of claim 1 wherein said toxin is BoNT/A and the toxin substrate is one or more peptides selected from the group consisting of:
- (5-Fam)-ThrArgIleAspGluAlaAsnGlnArgAlaThrLys[DABCYL]-Nle (SEQ ID NO: 21);
- (4-Mu)-ThrArgIleAspGluAlaAsnGlnArgAlaThrLys[DABCYL]-Nle (SEQ ID NO: 22);
- Lys-(4MU)-IleAspGluAlaAsnGlnArgAlaThrLys[DABCYL]-Nle-CONH2 (SEQ ID NO: 27); and optionally, wherein the substrate composition further comprises one or more control peptides selected from the group consisting of:
- (4-Mu)-ThrArgIleAspGluAlaAsnGlnArgAlaThrLys[DABCYL]Hex (SEQ ID NO: 5);
- (5-Fam)-ThrArgIleAspGluAlaAsnGlnArgAlaThrLys[DABCYL]Hex (SEQ ID NO: 19);
- Lys(5FAM)-IleAspGluAlaAsnGlnArgAlaThrLys[DABCYL]-Hex-CONH2 (SEQ ID NO: 28),
- Lys(4MU)-IleAspGluAlaAsnGlnArgAlaThrLys[DABCYL]-Hex-CONH2 (SEQ ID NO: 29),
- 5-FAM-ThrArgIleAspGluAlaAsnGlnArgAlaThrLys[DABCYL] (SEQ ID NO: 20);
- 4-MU-ThrArgIleAspGluAlaAsnGlnArgAlaThrLys[DABCYL] (SEQ ID NO: 23);
- (5-Fam)-LysIleAspGluAlaAsnGlnGluLeuThrLys[DABCYL]Nle-CONH2 (SEQ ID NO: 17); and
- Lys(5-Fam)IleAspGluAlaAsnGlnGluLeuThrLys[DABCYL]Nle-CONH2 (SEQ ID NO: 18).

3. The method of claim 1 wherein said toxin is BoNT/B and the toxin substrate is:
- Lys(5-Fam)LeuSerGluLeuAspAspArgAlaAspAlaLeuGlnAlaGlyAlaSerGlnPheGlu ThrSerAlaAlaLysLeuLysArgLys[DABCYL]-amide (SEQ ID NO: 24).

4. The method of claim 1 wherein the toxin substrate contains at least one fluorogenic label conjugated via a peptide bond at or near the N-terminus, at least one dark quencher conjugated at or near the C-terminus, and a norleucine at the C-terminus, and optionally, wherein the substrate composition further comprises a control peptide that contains a fluorogenic label conjugated via a peptide bond at or near the N-terminus, a dark quencher conjugated at or near the C-terminus, and a 6-aminohexanoic acid at the C-terminus.

5. The method of claim 1 wherein the toxin substrate-specific antibody binds a region of the substrate wherein,
if the region of the substrate is the fluorophore conjugated to the substrate, the antibody is an anti-fluorescein antibody;
if the region of the substrate is the quencher conjugated to the substrate, the antibody is an anti-DABYCL antibody; and
if the region of the substrate is the peptide structure, the antibody is a SNAP-25 sequence-specific antibody.

6. The method of claim 1 wherein said BoNT toxin consists of one or more BoNT light chains.

7. The method of claim 1 wherein the enrichment matrix is provided in a column and the sample is exposed to the enrichment matrix prior to being exposed to the substrate composition.

8. The method of claim 7 wherein the column comprises one or more columns selected from the group comprising:
affinity microcolumns, and
pipette tip columns containing mounted affinity microcolumns.

9. The method of claim 8 wherein multiple columns are used in conjunction with a high throughput system.

10. The method of claim 9 wherein the high throughput system is an automated robotic pipetting system.

11. The method of claim 1 wherein said BoNT-specific antibody is bound to one or more beads selected from the group comprising:
Sepharose, agarose, or magnetic beads coated with any of protein A, G, or NG molecules; or
CNBr-activated Sepharose beads.

12. The method of claim 1 wherein the enrichment matrix comprises CNBr-activated Sepharose beads or Ni-NTA beads.

13. The method of claim 1 wherein the toxin substrate comprises one or more protein constructs selected from the group consisting of:
(i) a fusion protein comprising a luciferase protein and a BoNT cleavage site;
(ii) a first fusion protein comprising an N-terminal luciferase fragment fused to a first binding domain, and a second fusion protein, capable of binding to the first fusion protein, comprising a second binding domain fused to a C-terminal luciferase fragment further fused to a BoNT cleavable SNAP25 sequence or a BoNT cleavable VAMP sequence; and
(iii) a fusion protein comprising SEQ ID: NO 25.

14. The method of claim 13 wherein the fusion protein of (i) comprises overlapping luciferase fragments interrupted by a BoNT cleavage site.

15. The method of claim 14 wherein the BoNT toxin is BoNT/A and the fusion protein comprises:
a first firefly luciferase fragment of amino acid residues 1-475 or amino acid residues 1-478 of SEQ ID NO: 26 fused to a SNAP protein having a BoNT cleavage site, and a second firefly luciferase fragment of amino acid residues 265-550 of SEQ ID NO: 26.

16. The method of claim 13 wherein the two protein constructs of (ii) comprise the first fusion protein comprising an N-terminal firefly luciferase fragment of amino acid residues 1-475 of SEQ ID NO: 26 and the second fusion protein comprising a C-terminal firefly luciferase fragment of amino acid residues 476-550 of SEQ ID NO: 26.

17. The method of claim 13 wherein the first fusion protein of (ii) is immobilized to beads via the first binding domain.

18. The method of claim 13 wherein the second fusion protein of (ii) is immobilized to beads via an affinity tag fused to the BoNT cleavable SNAP25 sequence or the BoNT cleavable VAMP sequence.

19. The method of claim 13 wherein the luciferase protein of (i) is firefly luciferase or *Renilla reniformis* luciferase.

20. The method of claim 13 wherein the luciferase fragments of (ii) are firefly luciferase or *Renilla reniformis* luciferase.

21. The method of claim 13, wherein the BoNT toxin is BoNT/A and the fusion protein comprises SEQ ID NO: 4.

* * * * *

UNITED STATES PATENT AND TRADEMARK OFFICE
CERTIFICATE OF CORRECTION

PATENT NO. : 8,753,831 B2  
APPLICATION NO. : 13/600186  
DATED : June 17, 2014  
INVENTOR(S) : Kalkum et al.

Page 1 of 1

It is certified that error appears in the above-identified patent and that said Letters Patent is hereby corrected as shown below:

In the Claims

Claim 11, column 114, line 18, replace "NG" with --A/G--.

Signed and Sealed this  
Eleventh Day of November, 2014

Michelle K. Lee  
*Deputy Director of the United States Patent and Trademark Office*

UNITED STATES PATENT AND TRADEMARK OFFICE
CERTIFICATE OF CORRECTION

PATENT NO. : 8,753,831 B2  
APPLICATION NO. : 13/600186  
DATED : June 17, 2014  
INVENTOR(S) : Kalkum et al.

Page 1 of 1

It is certified that error appears in the above-identified patent and that said Letters Patent is hereby corrected as shown below:

In the Specification

In the Government Interest section, Column 1, Lines 16-18, please delete:
"The present invention was supported by National Institutes of Health grant AI-65359. The government may have certain rights in the present invention."
And replace with:
--This invention was made with government support under AI065359 awarded by the National Institutes of Health. The government has certain rights in the invention.--

Signed and Sealed this  
Twenty-second Day of November, 2022

Katherine Kelly Vidal  
*Director of the United States Patent and Trademark Office*

SEQUENCE LISTING

<160> NUMBER OF SEQ ID NOS: 29

<210> SEQ ID NO 1
<211> LENGTH: 17
<212> TYPE: PRT
<213> ORGANISM: Artificial Sequence
<220> FEATURE:
<223> OTHER INFORMATION: SNAP25 insert

<400> SEQUENCE: 1

Ser Asn Lys Thr Arg Ile Asp Glu Ala Asn Gln Arg Ala Thr Lys Met
1               5                   10                  15

Leu

<210> SEQ ID NO 2
<211> LENGTH: 10
<212> TYPE: PRT
<213> ORGANISM: Artificial Sequence
<220> FEATURE:
<223> OTHER INFORMATION: botulinum neurotoxin serotype A (BoNT/A)
      cleavage and recognition site

<400> SEQUENCE: 2

Ile Asp Glu Ala Asn Gln Arg Ala Thr Lys
1               5                   10

<210> SEQ ID NO 3
<211> LENGTH: 2370
<212> TYPE: DNA
<213> ORGANISM: Artificial Sequence
<220> FEATURE:
<223> OTHER INFORMATION: nucleic acid sequence for FFL fusion protein
      FFL1-478SNAP25FFL265-550

<400> SEQUENCE: 3

| | | | | | |
|---|---|---|---|---|---|
| atggaagacg | ccaaaaacat | aaagaaaggc | ccggcgccat | tctatcctct | agaggatgga | 60 |
| accgctggag | agcaactgca | taaggctatg | aagagatacg | ccctggttcc | tggaacaatt | 120 |
| gcttttacag | atgcacatat | cgaggtgaac | atcacgtacg | cggaatactt | cgaaatgtcc | 180 |
| gttcggttgg | cagaagctat | gaaacgatat | gggctgaata | caaatcacag | aatcgtcgta | 240 |
| tgcagtgaaa | actctcttca | attctttatg | ccggtgttgg | gcgcgttatt | tatcggagtt | 300 |
| gcagttgcgc | ccgcgaacga | catttataat | gaacgtgaat | tgctcaacag | tatgaacatt | 360 |
| tcgcagccta | ccgtagtgtt | tgtttccaaa | aaggggttgc | aaaaaatttt | gaacgtgcaa | 420 |
| aaaaaattac | caataatcca | gaaaattatt | atcatggatt | ctaaaacgga | ttaccaggga | 480 |
| tttcagtcga | tgtacacgtt | cgtcacatct | catctacctc | ccggttttaa | tgaatacgat | 540 |
| tttgtaccag | agtcctttga | tcgtgacaaa | acaattgcac | tgataatgaa | ttcctctgga | 600 |
| tctactgggt | tacctaaggg | tgtggcccct | ccgcatagaa | ctgcctgcgt | cagattctcg | 660 |
| catgccagag | atcctatttt | tggcaatcaa | atcattccgg | atactgcgat | tttaagtgtt | 720 |
| gttccattcc | atcacggttt | tggaatgttt | actacactcg | gatatttgat | atgtggattt | 780 |
| cgagtcgtct | taatgtatag | atttgaagaa | gagctgtttt | tacgatccct | tcaggattac | 840 |
| aaaattcaaa | gtgcgttgct | agtaccaacc | ctattttcat | tcttcgccaa | aagcactctg | 900 |
| attgacaaat | acgatttatc | taatttacac | gaaattgctt | ctgggggcgc | acctctttcg | 960 |
| aaagaagtcg | ggaagcggt | tgcaaaacgc | ttccatcttc | cagggatacg | acaaggatat | 1020 |
| gggctcactg | agactacatc | agctattctg | attacacccg | aggggatga | taaaccgggc | 1080 |

-continued

```
gcggtcggta aagttgttcc attttttgaa gcgaaggttg tggatctgga taccgggaaa    1140
acgctgggcg ttaatcagag aggcgaatta tgtgtcagag gacctatgat tatgtccggt    1200
tatgtaaaca atccggaagc gaccaacgcc ttgattgaca aggatggatg gctacattct    1260
ggagacatag cttactggga cgaagacgaa cacttcttca tagttgaccg cttgaagtct    1320
ttaattaaat acaaaggata tcaggtggcc cccgctgaat tggaatcgat attgttacaa    1380
cacccccaaca tcttcgacgc gggcgtggca ggtcttcccg acgatgacgc cgggagcaac    1440
aaaacccgta ttgatgaagc gaaccagcgt gcgaccaaaa tgctgatgta tagatttgaa    1500
gaagagctgt ttttacgatc ccttcaggat tacaaaattc aaagtgcgtt gctagtacca    1560
accctatttt cattcttcgc caaaagcact ctgattgaca aatacgattt atctaattta    1620
cacgaaattg cttctggggg cgcacctctt tcgaaagaag tcggggaagc ggttgcaaaa    1680
cgcttccatc ttccagggat acgacaagga tatgggctca ctgagactac atcagctatt    1740
ctgattacac ccgaggggga tgataaaccg ggcgcggtcg gtaaagttgt tccattttt    1800
gaagcgaagg ttgtggatct ggataccggg aaaacgctgg gcgttaatca gagaggcgaa    1860
ttatgtgtca gaggacctat gattatgtcc ggttatgtaa acaatccgga agcgaccaac    1920
gccttgattg acaaggatgg atggctacat tctggagaca tagcttactg ggacgaagac    1980
gaacacttct tcatagttga ccgcttgaag tctttaatta atacaaagg atatcaggtg    2040
gcccccgctg aattggaatc gatattgtta caacacccca acatcttcga cgcgggcgtg    2100
gcaggtcttc ccgacgatga cgccggtgaa cttcccgccg ccgttgttgt tttggagcac    2160
ggaaagacga tgacggaaaa agagatcgtg gattacgtcg ccagtcaagt aacaaccgcg    2220
aaaaagttgc gcggaggagt tgtgtttgtg gacgaagtac cgaaaggtct taccggaaaa    2280
ctcgacgcaa gaaaaatcag agagatcctc ataaaggcca gaagggcgg aaagtccgag    2340
ttgctcgagc accaccacca ccaccactga                                     2370
```

<210> SEQ ID NO 4
<211> LENGTH: 789
<212> TYPE: PRT
<213> ORGANISM: Artificial Sequence
<220> FEATURE:
<223> OTHER INFORMATION: amino acid sequence for FFL fusion protein FFL1-478SNAP25FFL265-550

<400> SEQUENCE: 4

```
Met Glu Asp Ala Lys Asn Ile Lys Lys Gly Pro Ala Pro Phe Tyr Pro
1               5                   10                  15
Leu Glu Asp Gly Thr Ala Gly Glu Gln Leu His Lys Ala Met Lys Arg
            20                  25                  30
Tyr Ala Leu Val Pro Gly Thr Ile Ala Phe Thr Asp Ala His Ile Glu
        35                  40                  45
Val Asn Ile Thr Tyr Ala Glu Tyr Phe Glu Met Ser Val Arg Leu Ala
    50                  55                  60
Glu Ala Met Lys Arg Tyr Gly Leu Asn Thr Asn His Arg Ile Val Val
65                  70                  75                  80
Cys Ser Glu Asn Ser Leu Gln Phe Phe Met Pro Val Leu Gly Ala Leu
                85                  90                  95
Phe Ile Gly Val Ala Val Ala Pro Ala Asn Asp Ile Tyr Asn Glu Arg
            100                 105                 110
Glu Leu Leu Asn Ser Met Asn Ile Ser Gln Pro Thr Val Val Phe Val
        115                 120                 125
Ser Lys Lys Gly Leu Gln Lys Ile Leu Asn Val Gln Lys Lys Leu Pro
```

-continued

```
            130                 135                 140
Ile Ile Gln Lys Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
                180                 185                 190

Ala Leu Ile Met Asn Ser Ser Gly Ser Thr Gly Leu Pro Lys Gly Val
                195                 200                 205

Ala Leu Pro His Arg Thr Ala Cys Val Arg Phe Ser His Ala Arg Asp
210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
                260                 265                 270

Phe Leu Arg Ser Leu Gln Asp Tyr Lys Ile Gln Ser Ala Leu Leu Val
                275                 280                 285

Pro Thr Leu Phe Ser Phe Phe Ala Lys Ser Thr Leu Ile Asp Lys Tyr
                290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
                340                 345                 350

Pro Glu Gly Asp Asp Lys Pro Gly Ala Val Gly Lys Val Val Pro Phe
                355                 360                 365

Phe Glu Ala Lys Val Val Asp Leu Asp Thr Gly Lys Thr Leu Gly Val
                370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
                420                 425                 430

Phe Ile Val Asp Arg Leu Lys Ser Leu Ile Lys Tyr Lys Gly Tyr Gln
                435                 440                 445

Val Ala Pro Ala Glu Leu Glu Ser Ile Leu Leu Gln His Pro Asn Ile
450                 455                 460

Phe Asp Ala Gly Val Ala Gly Leu Pro Asp Asp Asp Ala Gly Ser Asn
465                 470                 475                 480

Lys Thr Arg Ile Asp Glu Ala Asn Gln Arg Ala Thr Lys Met Leu Met
                485                 490                 495

Tyr Arg Phe Glu Glu Glu Leu Phe Leu Arg Ser Leu Gln Asp Tyr Lys
                500                 505                 510

Ile Gln Ser Ala Leu Leu Val Pro Thr Leu Phe Ser Phe Phe Ala Lys
                515                 520                 525

Ser Thr Leu Ile Asp Lys Tyr Asp Leu Ser Asn Leu His Glu Ile Ala
                530                 535                 540

Ser Gly Gly Ala Pro Leu Ser Lys Glu Val Gly Glu Ala Val Ala Lys
545                 550                 555                 560
```

```
Arg Phe His Leu Pro Gly Ile Arg Gln Gly Tyr Gly Leu Thr Glu Thr
                565                 570                 575

Thr Ser Ala Ile Leu Ile Thr Pro Glu Gly Asp Asp Lys Pro Gly Ala
            580                 585                 590

Val Gly Lys Val Val Pro Phe Phe Glu Ala Lys Val Val Asp Leu Asp
        595                 600                 605

Thr Gly Lys Thr Leu Gly Val Asn Gln Arg Gly Glu Leu Cys Val Arg
    610                 615                 620

Gly Pro Met Ile Met Ser Gly Tyr Val Asn Asn Pro Glu Ala Thr Asn
625                 630                 635                 640

Ala Leu Ile Asp Lys Asp Gly Trp Leu His Ser Gly Asp Ile Ala Tyr
                645                 650                 655

Trp Asp Glu Asp Glu His Phe Phe Ile Val Asp Arg Leu Lys Ser Leu
            660                 665                 670

Ile Lys Tyr Lys Gly Tyr Gln Val Ala Pro Ala Glu Leu Glu Ser Ile
        675                 680                 685

Leu Leu Gln His Pro Asn Ile Phe Asp Ala Gly Val Ala Gly Leu Pro
    690                 695                 700

Asp Asp Asp Ala Gly Glu Leu Pro Ala Ala Val Val Val Leu Glu His
705                 710                 715                 720

Gly Lys Thr Met Thr Glu Lys Glu Ile Val Asp Tyr Val Ala Ser Gln
                725                 730                 735

Val Thr Thr Ala Lys Lys Leu Arg Gly Gly Val Val Phe Val Asp Glu
            740                 745                 750

Val Pro Lys Gly Leu Thr Gly Lys Leu Asp Ala Arg Lys Ile Arg Glu
        755                 760                 765

Ile Leu Ile Lys Ala Lys Lys Gly Gly Lys Ser Glu Leu Leu Glu His
    770                 775                 780

His His His His His
785

<210> SEQ ID NO 5
<211> LENGTH: 13
<212> TYPE: PRT
<213> ORGANISM: Artificial Sequence
<220> FEATURE:
<223> OTHER INFORMATION: substrate for the detection of botulinum
      neurotoxin activity
<220> FEATURE:
<221> NAME/KEY: MISC_FEATURE
<222> LOCATION: (1)..(1)
<223> OTHER INFORMATION: Thr at position 1 is a Threonine with 4-
      Methylumbelliferone conjugated to its alpha-amino group
      ("[4-Mu]Thr")
<220> FEATURE:
<221> NAME/KEY: MISC_FEATURE
<222> LOCATION: (12)..(12)
<223> OTHER INFORMATION: Lys at position 12 is a Lysine with 4-
      (dimethylaminoazo) benzene-4-carboxy] (DABCYL) conjugated to its
      epsilon-amino group ("Lys[DABCYL]")
<220> FEATURE:
<221> NAME/KEY: MISC_FEATURE
<222> LOCATION: (13)..(13)
<223> OTHER INFORMATION: Xaa at position 13 is 6-aminohexanoic acid

<400> SEQUENCE: 5

Thr Arg Ile Asp Glu Ala Asn Gln Arg Ala Thr Lys Xaa
1               5                   10

<210> SEQ ID NO 6
<211> LENGTH: 51
<212> TYPE: DNA
<213> ORGANISM: Artificial Sequence
```

```
<220> FEATURE:
<223> OTHER INFORMATION: botulinum neurotoxin serotype A (BONT/A)
      cleavage site for SNAP25

<400> SEQUENCE: 6
agcaacaaaa cccgtattga tgaagcgaac cagcgtgcga ccaaaatgct g              51

<210> SEQ ID NO 7
<211> LENGTH: 80
<212> TYPE: DNA
<213> ORGANISM: Artificial Sequence
<220> FEATURE:
<223> OTHER INFORMATION: primer

<400> SEQUENCE: 7
atcgatggta cccagcattt tggtcgcacg ctggttcgct tcatcaatac gggttttgtt    60
gctatcgtcg ggaagacctg                                                80

<210> SEQ ID NO 8
<211> LENGTH: 35
<212> TYPE: DNA
<213> ORGANISM: Artificial Sequence
<220> FEATURE:
<223> OTHER INFORMATION: primer

<400> SEQUENCE: 8
tcttaatgta tagatttgaa gaagagctgt tttta                                35

<210> SEQ ID NO 9
<211> LENGTH: 5015
<212> TYPE: DNA
<213> ORGANISM: Artificial Sequence
<220> FEATURE:
<223> OTHER INFORMATION: plasmid "1"

<400> SEQUENCE: 9
taatacgact cactataggg gaattgtgag cggataacaa ttcccctcta gacttacaat    60
ttccattcgc cattcaggct gcgcaactgt tgggaagggc gatcggtacg ggcctcttcg   120
ctattacgcc agcttgcgaa cggtgggtgc gctgcaaggc gattaagttg ggtaacgcca   180
ggattctccc agtcacgacg ttgtaaaacg acggccagcg agagatcttg attggctagc   240
agaataattt tgtttaactt taagaaggag atataccatg gaagacgcca aaaacataaa   300
gaaaggcccg gcgccattct atcctctaga ggatggaacc gctggagagc aactgcataa   360
ggctatgaag agatacgccc tggttcctgg aacaattgct tttacagatg cacatatcga   420
ggtgaacatc acgtacgcgg aatacttcga aatgtccgtt cggttggcag aagctatgaa   480
acgatatggg ctgaatacaa atcacagaat cgtcgtatgc agtgaaaact ctcttcaatt   540
ctttatgccg gtgttgggcg cgttatttat cggagttgca gttgcgcccg cgaacgacat   600
ttataatgaa cgtgaattgc tcaacagtat gaacatttcg cagcctaccg tagtgtttgt   660
ttccaaaaag gggttgcaaa aattttgaa cgtgcaaaaa aaattaccaa taatccagaa   720
aattattatc atggattcta aaacggatta ccagggattt cagtcgatgt acacgttcgt   780
cacatctcat ctacctcccg gttttaatga atacgatttt gtaccagagt cctttgatcg   840
tgacaaaaca attgcactga taatgaattc ctctggatct actgggttac ctaagggtgt   900
ggcccttccg catagaactg cctgcgtcag attctcgcat gccagagatc ctattttgg   960 caatcaaatc attccggata ctgcgatttt aagtgttgtt ccattccatc acggttttgg  1020
aatgtttact acactcggat atttgatatg tggatttcga gtcgtcttaa tgtatagatt  1080
```

```
tgaagaagag ctgtttttac gatcccttca ggattacaaa attcaaagtg cgttgctagt    1140 accaaccta ttttcattct tcgccaaaag cactctgatt gacaaatacg atttatctaa    1200
tttacacgaa attgcttctg ggggcgcacc tctttcgaaa gaagtcgggg aagcggttgc    1260
aaaacgcttc catcttccag ggatacgaca aggatatggg ctcactgaga ctacatcagc    1320
tattctgatt acacccgagg gggatgataa accgggcgcg tcggtaaag ttgttccatt     1380 ttttgaagcg aaggttgtgg atctggatac cgggaaaacg ctgggcgtta atcagagagg    1440
cgaattatgt gtcagaggac ctatgattat gtccggttat gtaaacaatc cggaagcgac    1500
caacgccttg attgacaagg atggatggct acattctgga gacatagctt actgggacga    1560
agacgaacac ttcttcatag ttgaccgctt gaagtcttta attaaataca aaggatatca    1620 ggtgccccc gctgaattgg aatcgatatt gttacaacac cccaacatct tcgacgcggg    1680
cgtggcaggt cttcccgacg atggtaccat cgatacgcgt tcgaagcttg cggccgcaca    1740
gctgtataca cgtgcaagcc agccagaact cgctcctgaa gacccagagg atctcgagca    1800
ccaccaccac caccactaat gttaattaag ttgggcgttg taatcatagt cataatcaat    1860
actcctgact gcgttagcaa tttaactgtg ataaactacc gcattaaagc tattcgatga    1920
taagctgtca acatgataa ttcttgaaga cgaaagggcc taggctgata aaacagaatt     1980
tgcctggcgg cagtagcgcg gtggtccac ctgaccccat gccgaactca gaagtgaaac     2040
gccgtagcgc cgatggtagt gtgggtctc cccatgcgag agtagggaac tgccaggcat     2100
caaataaaac gaaaggctca gtcgaaagac tgggcctttc gttttatctg ttgtttgtcg    2160
gtgaacgctc tcctgagtag gacaaatccg ccgggagcgg atttgaacgt tgcgaagcaa    2220
cggcccggag ggtggcgggc aggacgcccg ccataaactg ccaggcatca aattaagcag    2280
aaggccatcc tgacggatgg ccttttttgcg tttctacaaa ctcttttgtt tattttttcta  2340 aatacattca aatatgtatc cgctgagcaa taactagcat aaccccttgg ggcctctaaa    2400
cgggtcttga ggggttttt gctgaaagga ggaactatat ccggattggc gaatgggacg     2460
cgccctgtag cggcgcatta agcgcggcgg gtgtggtggt tacgcgcagc gtgaccgcta    2520
cacttgccag cgccctagcg cccgctcctt tcgctttctt cccttccttt ctcgccacgt    2580
tcgccggctt tccccgtcaa gctctaaatc ggggctccc tttagggttc gatttagtg      2640 ctttacggca cctcgacccc aaaaaacttg attagggtga tggttcacgt agtgggccat    2700
cgccctgata cggttttt cgcccttga cgttggagtc cacgttcttt aatagtggac        2760
tcttgttcca aactgaaca acactcaacc ctatctcggt ctattctttt gatttataag     2820 ggatttttgcc gatttcggcc tattggttaa aaaatgagct gatttaacaa aaatttaacg   2880
cgaattttaa caaaatatta acgtttacaa tttctggcgg cacgatggca tgagattatc    2940
aaaaaggatc ttcacctaga tccttttaaa ttaaaaatga gttttaaat caatctaaag     3000 tatatatgag taaacttggt ctgacagtta ccaatgctta atcagtgagg cacctatctc    3060
agcgatctgt ctatttcgtt catccatagt tgcctgactc cccgtcgtgt agataactac    3120
gatacgggag gcttaccat ctggcccag tgctgcaatg ataccgcgag acccacgctc      3180
accggctcca gatttatcag caataaacca gccagccgga agggccgagc gcagaagtgg    3240
tcctgcaact ttatccgcct ccatccagtc tattaattgt tgccgggaag ctagagtaag    3300
tagttcgcca gttaatagtt tgcgcaacgt tgttgccatt gctacaggca tcgtggtgtc    3360
acgctcgtcg tttggtatgg cttcattcag ctccggttcc caacgatcaa ggcgagttac    3420
atgatccccc atgttgtgca aaaaagcggt tagctccttc ggtcctccga tcgttgtcag    3480
```

```
aagtaagttg gccgcagtgt tatcactcat ggttatggca gcactgcata attctcttac   3540
tgtcatgcca tccgtaagat gcttttctgt gactggtgag tactcaacca agtcattctg   3600
agaatagtgt atgcggcgac cgagttgctc ttgcccggcg tcaatacggg ataataccgc   3660
gccacatagc agaactttaa aagtgctcat cattggaaaa cgttcttcgg ggcgaaaact   3720
ctcaaggatc ttaccgctgt tgagatccag ttcgatgtaa cccactcgtg cacccaactg   3780
atcttcagca tcttttactt tcaccagcgt ttctgggtga gcaaaaacag gaaggcaaaa   3840
tgccgcaaaa aagggaataa gggcgacacg gaaatgttga atactcatac tcttcctttt   3900
tcaatcatga ccaaaatccc ttaacgtgag ttttcgttcc actgagcgtc agacccgta    3960 gaaaagatca aggatcttc ttgagatcct ttttttctgc gcgtaatctg ctgcttgcaa    4020
acaaaaaaac caccgctacc agcggtggtt tgtttgccgg atcaagagct accaactctt   4080
tttccgaagg taactggctt cagcagagcg cagataccaa atactgtcct tctagtgtag   4140
ccgtagttag gccaccactt caagaactct gtagcaccgc ctacatacct cgctctgcta   4200
atcctgttac cagtggctgc tgccagtggc gataagtcgt gtcttaccgg gttggactca   4260
agacgatagt taccggataa ggcgcagcgg tcgggctgaa cggggggttc gtgcacacag   4320
cccagcttgg agcgaacgac ctacaccgaa ctgagatacc tacagcgtga gctatgagaa   4380
agcgccacgc ttcccgaagg gagaaaggcg gacaggtatc cggtaagcgg cagggtcgga   4440
acaggagagc gcacgaggga gcttccaggg ggaaacgcct ggtatcttta tagtcctgtc   4500
gggtttcgcc acctctgact tgagcgtcga ttttgtgat gctcgtcagg ggggcggagc    4560
ctatggaaaa acgccagcaa cgcggccttt ttacggttcc tggcctttg ctggcctttt    4620 gctcacatgt tctttcctgc gttatcccct gattctgtgg ataaccgtat taccgccttt   4680
gagtgagctg ataccgctcg ccgcagccga acgaccgagc gcagcgagtc agtgagcgag   4740 gaagcggcg ataatggcct gcttctcgcc gaaacgtttg gtggcgggac cagtgacgaa    4800
ggcttgagcg agggcgtgca agattccgaa taccgcaagc gacaggccga tcatcgtcgc   4860
gctccagcga aagcggtcct cgccgaaaat gacccagagc gctgccggca cctgtcctac   4920
gagttgcatg ataaagaaga cagtcataag tgcggcgacg accggtgaat tgtgagcgct   4980
cacaattctc gtgacatcat aacgtcccgc gaaat                               5015
```

<210> SEQ ID NO 10
<211> LENGTH: 5897
<212> TYPE: DNA
<213> ORGANISM: Artificial Sequence
<220> FEATURE:
<223> OTHER INFORMATION: plasmid "2"

<400> SEQUENCE: 10

```
taatacgact cactataggg gaattgtgag cggataacaa ttcccctcta gacttacaat     60
ttccattcgc cattcaggct gcgcaactgt tgggaagggc gatcggtacg ggcctcttcg    120
ctattacgcc agcttgcgaa cggtgggtgc gctgcaaggc gattaagttg ggtaacgcca    180
ggattctccc agtcacgacg ttgtaaaacg acggccagcg agatcttg attggctagc      240 agaataattt tgtttaactt taagaaggag atataccatg gaagacgcca aaaacataaa    300
gaaaggcccg gcgccattct atcctctaga ggatggaacc gctggagagc aactgcataa    360
ggctatgaag agatacgccc tggttcctgg aacaattgct tttacagatg cacatatcga    420
ggtgaacatc acgtacgcgg aatacttcga aatgtccgtt cggttggcag aagctatgaa    480
acgatatggg ctgaatacaa atcacagaat cgtcgtatgc agtgaaaact ctcttcaatt    540
```

```
ctttatgccg gtgttgggcg cgttatttat cggagttgca gttgcgcccg cgaacgacat    600
ttataatgaa cgtgaattgc tcaacagtat gaacatttcg cagcctaccg tagtgtttgt    660
ttccaaaaag gggttgcaaa aaattttgaa cgtgcaaaaa aaattaccaa taatccagaa    720
aattattatc atggattcta aaacggatta ccagggattt cagtcgatgt acacgttcgt    780
cacatctcat ctacctcccg gttttaatga atacgatttt gtaccagagt cctttgatcg    840
tgacaaaaca attgcactga taatgaattc ctctggatct actgggttac ctaagggtgt    900
ggcccttccg catagaactg cctgcgtcag attctcgcat gccagagatc ctattttggg    960
caatcaaatc attccggata ctgcgatttt aagtgttgtt ccattccatc acggttttgg   1020
aatgtttact acactcggat atttgatatg tggatttcga gtcgtcttaa tgtatagatt   1080
tgaagaagag ctgttttttac gatcccttca ggattacaaa attcaaagtg cgttgctagt   1140
accaacccta ttttcattct cgccaaaaag cactctgatt gacaaatacg atttatctaa   1200
tttacacgaa attgcttctg ggcgcacc tctttcgaaa gaagtcgggg aagcggttgc   1260
aaaacgcttc catcttccag ggatacgaca aggatatggg ctcactgaga ctacatcagc   1320
tattctgatt acacccgagg gggatgataa accgggcgcg gtcggtaaag ttgttccatt   1380
ttttgaagcg aaggttgtgg atctggatac cgggaaaacg ctgggcgtta atcagagagg   1440
cgaattatgt gtcagaggac ctatgattat gtccggttat gtaaacaatc cggaagcgac   1500
caacgccttg attgacaagg atggatggct acattctgga gacatagctt actgggacga   1560
agacgaacac ttcttcatag ttgaccgctt gaagtcttta attaaataca aaggatatca   1620
ggtggccccc gctgaattgg aatcgatatt gttacaacac cccaacatct cgacgcggg   1680 cgtggcaggt cttcccgacg atagcaacaa aacccgtatt gatgaagcga accagcgtgc   1740
gaccaaaatg ctgggtacca tgtatagatt tgaagaagag ctgttttttac gatcccttca   1800 ggattacaaa attcaaagtg cgttgctagt accaacccta ttttcattct cgccaaaaag   1860
cactctgatt gacaaatacg atttatctaa tttacacgaa attgcttctg ggcgcacc   1920 tctttcgaaa gaagtcgggg aagcggttgc aaaacgcttc catcttccag ggatacgaca   1980
aggatatggg ctcactgaga ctacatcagc tattctgatt acacccgagg gggatgataa   2040
accgggcgcg gtcggtaaag ttgttccatt ttttgaagcg aaggttgtgg atctggatac   2100
cgggaaaacg ctgggcgtta atcagagagg cgaattatgt gtcagaggac ctatgattat   2160
gtccggttat gtaaacaatc cggaagcgac caacgccttg attgacaagg atggatggct   2220
acattctgga gacatagctt actgggacga agacgaacac ttcttcatag ttgaccgctt   2280
gaagtcttta attaaataca aaggatatca ggtggccccc gctgaattgg aatcgatatt   2340
gttacaacac cccaacatct cgacgcggg cgtggcaggt cttcccgacg atgacgccgg   2400
tgaacttccc gccgccgttg ttgttttgga gcacggaaag acgatgacgg aaaaagagat   2460
cgtggattac gtcgccagtc aagtaacaac cgcgaaaaag ttgcgcggag gagttgtgtt   2520
tgtggacgaa gtaccgaaag gtcttaccgg aaaactcgac gcaagaaaaa tcagagagat   2580
cctcataaag gccaagaagg gcggaaagtc cgagttgtaa cagctgtata cacgtgcaag   2640
ccagccagaa ctcgctcctg aagacccaga ggatctcgag caccaccacc accaccacta   2700
atgttaatta agttgggcgt tgtaatcata gtcataatca atactcctga ctgcgttagc   2760
aatttaactg tgataaacta ccgcattaaa gctattcgat gataagctgt caaacatgat   2820
aattcttgaa gacgaaaggg cctaggctga taaaacagaa tttgcctggc ggcagtagcg   2880
cggtggtccc acctgacccc atgccgaact cagaagtgaa acgccgtagc gccgatggta   2940
```

```
gtgtggggtc tccccatgcg agagtaggga actgccaggc atcaaataaa acgaaaggct    3000
cagtcgaaag actgggcctt tcgttttatc tgttgtttgt cggtgaacgc tctcctgagt    3060
aggacaaatc cgccgggagc ggatttgaac gttgcgaagc aacggcccgg agggtggcgg    3120
gcaggacgcc cgccataaac tgccaggcat caaattaagc agaaggccat cctgacggat    3180 ggccttttg cgtttctaca aactcttttg tttattttc taaatacatt caaatatgta     3240
tccgctgagc aataactagc ataacccctt ggggcctcta aacgggtctt gaggggtttt    3300
ttgctgaaag gaggaactat atccggattg cgaatggga cgcgccctgt agcggcgcat     3360
taagcgcggc gggtgtggtg gttacgcgca gcgtgaccgc tacacttgcc agcgccctag    3420
cgcccgctcc tttcgctttc ttcccttcct ttctcgccac gttcgccggc tttccccgtc    3480
aagctctaaa tcggggctc cctttagggt tccgatttag tgctttacgg cacctcgacc     3540
ccaaaaaact tgattagggt gatggttcac gtagtgggcc atcgccctga tagacggttt    3600
ttcgcccttt gacgttggag tccacgttct ttaatagtgg actcttgttc caaactggaa    3660
caacactcaa ccctatctcg gtctattctt ttgatttata agggattttg ccgatttcgg    3720
cctattggtt aaaaatgag ctgatttaac aaaaatttaa cgcgaatttt aacaaaatat     3780
taacgtttac aatttctggc ggcacgatgg catgagatta tcaaaaagga tcttcaccta    3840 gatccttta aattaaaaat gaagttttaa atcaatctaa agtatatatg agtaaacttg     3900
gtctgacagt taccaatgct taatcagtga ggcacctatc tcagcgatct gtctatttcg    3960
ttcatccata gttgcctgac tccccgtcgt gtagataact acgatacggg agggcttacc    4020
atctggcccc agtgctgcaa tgataccgcg agacccacgc tcaccggctc cagatttatc    4080
agcaataaac cagccagccg gaagggccga gcgcagaagt ggtcctgcaa ctttatccgc    4140
ctccatccag tctattaatt gttgccggga agctagagta agtagttcgc cagttaatag    4200
tttgcgcaac gttgttgcca ttgctacagg catcgtggtg tcacgctcgt cgtttggtat    4260
ggcttcattc agctccggtt cccaacgatc aaggcgagtt acatgatccc ccatgttgtg    4320
caaaaaagcg gttagctcct tcggtcctcc gatcgttgtc agaagtaagt tggccgcagt    4380
gttatcactc atggttatgg cagcactgca taattctctt actgtcatgc catccgtaag    4440 atgctttct gtgactggtg agtactcaac caagtcattc tgagaatagt gtatgcggcg     4500
accgagttgc tcttgcccgg cgtcaatacg ggataatacc gcgccacata gcagaacttt    4560
aaaagtgctc atcattggaa aacgttcttc ggggcgaaaa ctctcaagga tcttaccgct    4620
gttgagatcc agttcgatgt aacccactcg tgcacccaac tgatcttcag catcttttac    4680
tttcaccagc gtttctgggt gagcaaaaac aggaaggcaa aatgccgcaa aaaagggaat    4740
aagggcgaca cggaaatgtt gaatactcat actcttcctt tttcaatcat gaccaaaatc    4800
ccttaacgtg agttttcgtt ccactgagcg tcagaccccg tagaaaagat caaaggatct    4860
tcttgagatc ctttttttct gcgcgtaatc tgctgcttgc aaacaaaaaa accaccgcta    4920
ccagcggtgg tttgtttgcc ggatcaagag ctaccaactc ttttccgaa ggtaactggc     4980 ttcagcagag cgcagatacc aaatactgtc cttctagtgt agccgtagtt aggccaccac    5040
ttcaagaact ctgtagcacc gcctacatac ctcgctctgc taatcctgtt accagtggct    5100
gctgccagtg gcgataagtc gtgtcttacc gggttggact caagacgata gttaccggat    5160
aaggcgcagc ggtcgggctg aacggggggt tcgtgcacac agcccagctt ggagcgaacg    5220
acctacaccg aactgagata cctacagcgt gagctatgag aaagcgccac gcttcccgaa    5280
gggagaaagg cggacaggta tccggtaagc ggcagggtcg aacaggaga gcgcacgagg     5340
```

```
gagcttccag ggggaaacgc ctggtatctt tatagtcctg tcgggtttcg ccacctctga    5400
cttgagcgtc gattttgtg atgctcgtca gggggggcgga gcctatggaa aaacgccagc    5460
aacgcggcct ttttacggtt cctggccttt tgctggcctt ttgctcacat gttctttcct    5520
gcgttatccc ctgattctgt ggataaccgt attaccgcct ttgagtgagc tgataccgct    5580
cgccgcagcc gaacgaccga gcgcagcgag tcagtgagcg aggaagccgg cgataatggc    5640
ctgcttctcg ccgaaacgtt tggtggcggg accagtgacg aaggcttgag cgagggcgtg    5700
caagattccg aataccgcaa gcgacaggcc gatcatcgtc gcgctccagc gaaagcggtc    5760
ctcgccgaaa atgacccaga gcgctgccgg cacctgtcct acgagttgca tgataaagaa    5820
gacagtcata agtgcggcga cgaccggtga attgtgagcg ctcacaattc tcgtgacatc    5880
ataacgtccc gcgaaat                                                   5897
```

<210> SEQ ID NO 11
<211> LENGTH: 206
<212> TYPE: PRT
<213> ORGANISM: Homo sapiens

<400> SEQUENCE: 11

```
Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205
```

<210> SEQ ID NO 12
<211> LENGTH: 12
<212> TYPE: PRT
<213> ORGANISM: Artificial Sequence
<220> FEATURE:
<223> OTHER INFORMATION: substrate for the detection of boulinum neurotoxin activity
<220> FEATURE:
<221> NAME/KEY: MISC_FEATURE
<222> LOCATION: (1)..(1)
<223> OTHER INFORMATION: Lys at position 1 is Lysine with 5-carboxyfluorescein conjugated it its epsilon-amino group

```
              ("Lys[5-Fam]")
<220> FEATURE:
<221> NAME/KEY: MISC_FEATURE
<222> LOCATION: (11)..(11)
<223> OTHER INFORMATION: Lys at position 11 is a Lysine with 4-
      (dimethylaminoazo) benzene-4-carboxyl (DABCYL) conjugated to its
      epsilon-amino group ("Lys[DABCYL]")
<220> FEATURE:
<221> NAME/KEY: MISC_FEATURE
<222> LOCATION: (12)..(12)
<223> OTHER INFORMATION: Xaa at position 12 is Norleucine with an aminde
      C-terminus

<400> SEQUENCE: 12

Lys Ile Asp Glu Ala Asn Gln Arg Ala Thr Lys Xaa
1               5                   10

<210> SEQ ID NO 13
<211> LENGTH: 12
<212> TYPE: PRT
<213> ORGANISM: Artificial Sequence
<220> FEATURE:
<223> OTHER INFORMATION: substrate for the detection of botulinum
      neurotoxin activity
<220> FEATURE:
<221> NAME/KEY: MISC_FEATURE
<222> LOCATION: (1)..(1)
<223> OTHER INFORMATION: Lys at position 1 is a Lysine with 5-
      carboxyfluorescein conjugated to its alpha- and epsilon-amino
      groups (("5-Fam-Lys[5-Fam]")
<220> FEATURE:
<221> NAME/KEY: MISC_FEATURE
<222> LOCATION: (11)..(11)
<223> OTHER INFORMATION: Lys at position 11 is a Lysine with 4-
      (dimethylaminoazo) benzene-4-carboxyl (DABCYL) conjugated to its
      epsilon-amino group ("Lys[DABCY]")
<220> FEATURE:
<221> NAME/KEY: MISC_FEATURE
<222> LOCATION: (12)..(12)
<223> OTHER INFORMATION: Xaa is Norleucine with an amide C-terminus

<400> SEQUENCE: 13

Lys Ile Asp Glu Ala Asn Gln Arg Ala Thr Lys Xaa
1               5                   10

<210> SEQ ID NO 14
<211> LENGTH: 12
<212> TYPE: PRT
<213> ORGANISM: Artificial Sequence
<220> FEATURE:
<223> OTHER INFORMATION: substrate for the detection of botulinum
      neurotoxin activity
<220> FEATURE:
<221> NAME/KEY: MISC_FEATURE
<222> LOCATION: (1)..(1)
<223> OTHER INFORMATION: Lys at position 1 is a Lysine with 5-
      carboxyfluorescein conjugated to its alpha-amino group
      ("5-Fam-Lys")
<220> FEATURE:
<221> NAME/KEY: MISC_FEATURE
<222> LOCATION: (11)..(11)
<223> OTHER INFORMATION: Lys at position 11 is a Lysine with 4-
      (dimethylaminoazo) benzene-4-carboxyl (DABCYL) conjugated to its
      epsilon-amino group ("Lys[DABCYL]")
<220> FEATURE:
<221> NAME/KEY: MISC_FEATURE
<222> LOCATION: (12)..(12)
<223> OTHER INFORMATION: Xaa at position 12 is Norleucine with an amide
      C-terminus

<400> SEQUENCE: 14

Lys Ile Asp Glu Ala Asn Gln Arg Ala Thr Lys Xaa
1               5                   10
```

```
<210> SEQ ID NO 15
<211> LENGTH: 12
<212> TYPE: PRT
<213> ORGANISM: Artificial Sequence
<220> FEATURE:
<223> OTHER INFORMATION: substrate for the detection of botulinum
      neurotoxin activity
<220> FEATURE:
<221> NAME/KEY: MISC_FEATURE
<222> LOCATION: (1)..(1)
<223> OTHER INFORMATION: Lys at position 1 is a Lysine with 5-
      carboxyfluorescein conjugated to both its alpha- and epsilon-amino
      group ("5-Fam-Lys[5-Fam]")
<220> FEATURE:
<221> NAME/KEY: MISC_FEATURE
<222> LOCATION: (11)..(11)
<223> OTHER INFORMATION: Lys at position 11 is Lysine with 4-
      (dimethylaminoazo) benzene-4-carboxyl (DABCYL) conjugated to its
      epsilon-amino group ("Lys[DABCYL]")
<220> FEATURE:
<221> NAME/KEY: MISC_FEATURE
<222> LOCATION: (12)..(12)
<223> OTHER INFORMATION: Xaa at position 12 is Norleucine with an amide
      C-terminus

<400> SEQUENCE: 15

Lys Ile Asp Glu Ala Asn Gln Glu Leu Thr Lys Xaa
1               5                   10

<210> SEQ ID NO 16
<211> LENGTH: 12
<212> TYPE: PRT
<213> ORGANISM: Artificial Sequence
<220> FEATURE:
<223> OTHER INFORMATION: substrate for the detection of botulinum
      neurotoxin activity
<220> FEATURE:
<221> NAME/KEY: MISC_FEATURE
<222> LOCATION: (12)..(12)
<223> OTHER INFORMATION: Xaa at position 12 is Norleucine

<400> SEQUENCE: 16

Lys Ile Asp Glu Ala Asn Gln Arg Ala Thr Lys Xaa
1               5                   10

<210> SEQ ID NO 17
<211> LENGTH: 12
<212> TYPE: PRT
<213> ORGANISM: Artificial Sequence
<220> FEATURE:
<223> OTHER INFORMATION: substrate for the detection of botulinum
      neurotoxin activity
<220> FEATURE:
<221> NAME/KEY: MISC_FEATURE
<222> LOCATION: (1)..(1)
<223> OTHER INFORMATION: Lys at position 1 is Lysine with 5-
      carboxyfluorescein conjugated to its alpha-amino group
      ("5-Fam-Lys")
<220> FEATURE:
<221> NAME/KEY: MISC_FEATURE
<222> LOCATION: (11)..(11)
<223> OTHER INFORMATION: Lys at position 11 is Lysine with 4-
      (dimethylaminoazo) benzene-4-carboxyl (DABCYL) conjugated to its
      epsilon-amino group ("Lys[DABCYL]")
<220> FEATURE:
<221> NAME/KEY: MISC_FEATURE
<222> LOCATION: (12)..(12)
<223> OTHER INFORMATION: Xaa at position 12 is Norleucine with an amide
      C-terminus

<400> SEQUENCE: 17

Lys Ile Asp Glu Ala Asn Gln Glu Leu Thr Lys Xaa
1               5                   10
```

```
<210> SEQ ID NO 18
<211> LENGTH: 12
<212> TYPE: PRT
<213> ORGANISM: Artificial Sequence
<220> FEATURE:
<223> OTHER INFORMATION: substrate for the detection of botulinum
      neurotoxin activity
<220> FEATURE:
<221> NAME/KEY: MISC_FEATURE
<222> LOCATION: (1)..(1)
<223> OTHER INFORMATION: Lys at position 1 is Lysine with 5-
      carboxyfluorescein conjugated to its epsilon-amino group
      ("Lys[5-Fam]")
<220> FEATURE:
<221> NAME/KEY: MISC_FEATURE
<222> LOCATION: (11)..(11)
<223> OTHER INFORMATION: Lys at position 11 is Lysine with 4-
      (dimethylaminoazo) benzene-4-carboxyl (DABCYL) conjugated to its
      epsilon-amino group ("Lys[DABCYL]")
<220> FEATURE:
<221> NAME/KEY: MISC_FEATURE
<222> LOCATION: (12)..(12)
<223> OTHER INFORMATION: Xaa is Norleucine with an aminde C-terminus

<400> SEQUENCE: 18

Lys Ile Asp Glu Ala Asn Gln Glu Leu Thr Lys Xaa
1               5                   10

<210> SEQ ID NO 19
<211> LENGTH: 13
<212> TYPE: PRT
<213> ORGANISM: Artificial Sequence
<220> FEATURE:
<223> OTHER INFORMATION: substrate for the detection of botulinum
      neurotoxin activity
<220> FEATURE:
<221> NAME/KEY: MISC_FEATURE
<222> LOCATION: (1)..(1)
<223> OTHER INFORMATION: Thr at position 1 is Threonine with 5-
      carboxyfluorescein conjugated to its alpha-amino group
      ("[5-Fam]Thr")
<220> FEATURE:
<221> NAME/KEY: MISC_FEATURE
<222> LOCATION: (12)..(12)
<223> OTHER INFORMATION: Lys at position 12 is Lysine with 4-
      (dimethylaminoazo) benzene-4-carboxyl (DABCYL) conjugated to its
      epsilon-amino group ("Lys[DABCYL]")
<220> FEATURE:
<221> NAME/KEY: MISC_FEATURE
<222> LOCATION: (13)..(13)
<223> OTHER INFORMATION: Xaa at position 13 is 6-amino hexanoic acid

<400> SEQUENCE: 19

Thr Arg Ile Asp Glu Ala Asn Gln Arg Ala Thr Lys Xaa
1               5                   10

<210> SEQ ID NO 20
<211> LENGTH: 12
<212> TYPE: PRT
<213> ORGANISM: Artificial Sequence
<220> FEATURE:
<223> OTHER INFORMATION: substrate for the detection of botulinum
      neurotoxin activity
<220> FEATURE:
<221> NAME/KEY: MISC_FEATURE
<222> LOCATION: (1)..(1)
<223> OTHER INFORMATION: Thr at position 1 is Threonine with 5-
      carboxyfluorescein conjugated to its alpha-amino group
      ("[5-Fam]Thr")
<220> FEATURE:
<221> NAME/KEY: MISC_FEATURE
<222> LOCATION: (12)..(12)
<223> OTHER INFORMATION: Lys at position 12 is Lysine with 4-
      (dimethylaminoazo) benzene-4-carboxyl (DABCYL) conjugated to its
      epsilon-amino group ("Lys[DABCYL]")
```

-continued

```
<400> SEQUENCE: 20

Thr Arg Ile Asp Glu Ala Asn Gln Arg Ala Thr Lys
1               5                   10

<210> SEQ ID NO 21
<211> LENGTH: 13
<212> TYPE: PRT
<213> ORGANISM: Artificial Sequence
<220> FEATURE:
<223> OTHER INFORMATION: substrate for the detection of botulinum
      neurotoxin activity
<220> FEATURE:
<221> NAME/KEY: MISC_FEATURE
<222> LOCATION: (1)..(1)
<223> OTHER INFORMATION: Thr at position 1 is Threonine with 5-
      carboxyfluorescein conjugated to its alpha-amino group
      ("[5-Fam]Thr")
<220> FEATURE:
<221> NAME/KEY: MISC_FEATURE
<222> LOCATION: (12)..(12)
<223> OTHER INFORMATION: Lys at position 12 is Lysine with 4-
      (dimethylaminoazo) benzene-4-carboxyl (DABCYL) conjugated to its
      epsilon-amino group ("Lys[DABCYL]")
<220> FEATURE:
<221> NAME/KEY: MISC_FEATURE
<222> LOCATION: (13)..(13)
<223> OTHER INFORMATION: Xaa at position 13 is Norleucine with an amide
      C-terminus

<400> SEQUENCE: 21

Thr Arg Ile Asp Glu Ala Asn Gln Arg Ala Thr Lys Xaa
1               5                   10

<210> SEQ ID NO 22
<211> LENGTH: 13
<212> TYPE: PRT
<213> ORGANISM: Artificial Sequence
<220> FEATURE:
<223> OTHER INFORMATION: substrate for the detection of botulinum
      neurotoxin activity
<220> FEATURE:
<221> NAME/KEY: MISC_FEATURE
<222> LOCATION: (1)..(1)
<223> OTHER INFORMATION: Thr at position 1 is Threonine with 4-
      Methylumbelliferone conjugated to its alpha-amino group
      ("[4-Mu]Thr")
<220> FEATURE:
<221> NAME/KEY: MISC_FEATURE
<222> LOCATION: (12)..(12)
<223> OTHER INFORMATION: Lys at position 12 is Lysine with 4-
      (dimethylaminoazo) benzene-4-carboxyl (DABCYL) conjugated to its
      epsilon-amino group ("Lys[DABCYL]")
<220> FEATURE:
<221> NAME/KEY: MISC_FEATURE
<222> LOCATION: (13)..(13)
<223> OTHER INFORMATION: Xaa at position 13 is Norleucine with an amide
      C-terminus

<400> SEQUENCE: 22

Thr Arg Ile Asp Glu Ala Asn Gln Arg Ala Thr Lys Xaa
1               5                   10

<210> SEQ ID NO 23
<211> LENGTH: 12
<212> TYPE: PRT
<213> ORGANISM: Artificial Sequence
<220> FEATURE:
<223> OTHER INFORMATION: substrate for the detection of botulinum
      neurotoxin activity
<220> FEATURE:
<221> NAME/KEY: MISC_FEATURE
<222> LOCATION: (1)..(1)
<223> OTHER INFORMATION: Thr at position 1 is Threonine with 4-
      Methylumbelliferone conjugated to its alpha-amino group
```

```
           ("[4-Mu]Thr")
<220> FEATURE:
<221> NAME/KEY: MISC_FEATURE
<222> LOCATION: (12)..(12)
<223> OTHER INFORMATION: Lys at position 12 is Lysine with 4-
      (dimethylaminoazo) benzene-4-carboxyl (DABCYL) conjugated to its
      epsilon-amino group

<400> SEQUENCE: 23

Thr Arg Ile Asp Glu Ala Asn Gln Arg Ala Thr Lys
1               5                   10

<210> SEQ ID NO 24
<211> LENGTH: 29
<212> TYPE: PRT
<213> ORGANISM: Artificial Sequence
<220> FEATURE:
<223> OTHER INFORMATION: substrate for the detection of botulinum
      neurotoxin activity
<220> FEATURE:
<221> NAME/KEY: MISC_FEATURE
<222> LOCATION: (1)..(1)
<223> OTHER INFORMATION: Lys at position 1 is Lysine with 4-
      Methylumbelliferone conjugated to its epsilon-amino group
      ("Lys[5-Fam]")
<220> FEATURE:
<221> NAME/KEY: MISC_FEATURE
<222> LOCATION: (29)..(29)
<223> OTHER INFORMATION: Lys at position 29 is Lysine with 4-
      (dimethylaminoazo) benzene-4-carboxyl (DABCYL) conjugated to its
      epsilon-amino group ("Lys[DABCYL]")

<400> SEQUENCE: 24

Lys Leu Ser Glu Leu Asp Asp Arg Ala Asp Ala Leu Gln Ala Gly Ala
1               5                   10                  15

Ser Gln Phe Glu Thr Ser Ala Ala Lys Leu Lys Arg Lys
            20                  25

<210> SEQ ID NO 25
<211> LENGTH: 626
<212> TYPE: PRT
<213> ORGANISM: Artificial Sequence
<220> FEATURE:
<223> OTHER INFORMATION: "FFL-L1SL2TAH": FFL[1-550] L1[G4SG4]
      SNAP25[171-206] L2[G6] T[ENLYFQG] A[K8-10+GLE]-histag

<400> SEQUENCE: 25

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140
```

```
-continued

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
            165                 170                 175

Asn Glu Tyr Asp Phe Val Pro Glu Ser Phe Asp Arg Asp Lys Thr Ile
        180                 185                 190

Ala Leu Ile Met Asn Ser Ser Gly Ser Thr Gly Leu Pro Lys Gly Val
    195                 200                 205

Ala Leu Pro His Arg Thr Ala Cys Val Arg Phe Ser His Ala Arg Asp
210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
            245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
            325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
            355                 360                 365

Phe Glu Ala Lys Val Val Asp Leu Asp Thr Gly Lys Thr Leu Gly Val
370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp His Phe
            420                 425                 430

Phe Ile Val Asp Arg Leu Lys Ser Leu Ile Lys Tyr Lys Gly Tyr Gln
            435                 440                 445

Val Ala Pro Ala Glu Leu Glu Ser Ile Leu Leu Gln His Pro Asn Ile
450                 455                 460

Phe Asp Ala Gly Val Ala Gly Leu Pro Asp Asp Ala Gly Glu Leu
465                 470                 475                 480

Pro Ala Ala Val Val Val Leu Glu His Gly Lys Thr Met Thr Glu Lys
            485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
            515                 520                 525

Lys Leu Asp Ala Arg Lys Ile Arg Glu Ile Leu Ile Lys Ala Lys Lys
530                 535                 540

Gly Gly Lys Ser Lys Leu Gly Gly Gly Ser Gly Gly Gly Ile
545                 550                 555                 560

Asp Thr Gln Asn Arg Gln Ile Asp Arg Ile Met Glu Lys Ala Asp Ser
                565                 570                 575
```

```
Asn Lys Thr Arg Ile Asp Glu Ala Asn Gln Arg Ala Thr Lys Met Leu
            580                 585                 590
Gly Ser Gly Gly Gly Gly Gly Gly Glu Asn Leu Tyr Phe Gln Gly
        595                 600                 605
Lys Lys Lys Lys Lys Lys Lys Lys Gly Leu Glu His His His His
    610                 615                 620
His His
625

<210> SEQ ID NO 26
<211> LENGTH: 550
<212> TYPE: PRT
<213> ORGANISM: Artificial Sequence
<220> FEATURE:
<223> OTHER INFORMATION: full length firefly luciferase "FFL"

<400> SEQUENCE: 26

Met Glu Asp Ala Lys Asn Ile Lys Lys Gly Pro Ala Pro Phe Tyr Pro
1               5                   10                  15
Leu Glu Asp Gly Thr Ala Gly Glu Gln Leu His Lys Ala Met Lys Arg
            20                  25                  30
Tyr Ala Leu Val Pro Gly Thr Ile Ala Phe Thr Asp Ala His Ile Glu
        35                  40                  45
Val Asn Ile Thr Tyr Ala Glu Tyr Phe Glu Met Ser Val Arg Leu Ala
    50                  55                  60
Glu Ala Met Lys Arg Tyr Gly Leu Asn Thr Asn His Arg Ile Val Val
65                  70                  75                  80
Cys Ser Glu Asn Ser Leu Gln Phe Phe Met Pro Val Leu Gly Ala Leu
                85                  90                  95
Phe Ile Gly Val Ala Val Ala Pro Ala Asn Asp Ile Tyr Asn Glu Arg
            100                 105                 110
Glu Leu Leu Asn Ser Met Asn Ile Ser Gln Pro Thr Val Val Phe Val
        115                 120                 125
Ser Lys Lys Gly Leu Gln Lys Ile Leu Asn Val Gln Lys Lys Leu Pro
    130                 135                 140
Ile Ile Gln Lys Ile Ile Ile Met Asp Ser Lys Thr Asp Tyr Gln Gly
145                 150                 155                 160
Phe Gln Ser Met Tyr Thr Phe Val Thr Ser His Leu Pro Pro Gly Phe
                165                 170                 175
Asn Glu Tyr Asp Phe Val Pro Glu Ser Phe Asp Arg Asp Lys Thr Ile
            180                 185                 190
Ala Leu Ile Met Asn Ser Ser Gly Ser Thr Gly Leu Pro Lys Gly Val
        195                 200                 205
Ala Leu Pro His Arg Thr Ala Cys Val Arg Phe Ser His Ala Arg Asp
    210                 215                 220
Pro Ile Phe Gly Asn Gln Ile Ile Pro Asp Thr Ala Ile Leu Ser Val
225                 230                 235                 240
Val Pro Phe His His Gly Phe Gly Met Phe Thr Thr Leu Gly Tyr Leu
                245                 250                 255
Ile Cys Gly Phe Arg Val Val Leu Met Tyr Arg Phe Glu Glu Glu Leu
            260                 265                 270
Phe Leu Arg Ser Leu Gln Asp Tyr Lys Ile Gln Ser Ala Leu Leu Val
        275                 280                 285
Pro Thr Leu Phe Ser Phe Ala Lys Ser Thr Leu Ile Asp Lys Tyr
    290                 295                 300
```

```
Asp Leu Ser Asn Leu His Glu Ile Ala Ser Gly Gly Ala Pro Leu Ser
305                 310                 315                 320
Lys Glu Val Gly Glu Ala Val Ala Lys Arg Phe His Leu Pro Gly Ile
                325                 330                 335
Arg Gln Gly Tyr Gly Leu Thr Glu Thr Thr Ser Ala Ile Leu Ile Thr
            340                 345                 350
Pro Glu Gly Asp Asp Lys Pro Gly Ala Val Gly Lys Val Val Pro Phe
        355                 360                 365
Phe Glu Ala Lys Val Val Asp Leu Asp Thr Gly Lys Thr Leu Gly Val
    370                 375                 380
Asn Gln Arg Gly Glu Leu Cys Val Arg Gly Pro Met Ile Met Ser Gly
385                 390                 395                 400
Tyr Val Asn Asn Pro Glu Ala Thr Asn Ala Leu Ile Asp Lys Asp Gly
                405                 410                 415
Trp Leu His Ser Gly Asp Ile Ala Tyr Trp Asp Glu Asp Glu His Phe
            420                 425                 430
Phe Ile Val Asp Arg Leu Lys Ser Leu Ile Lys Tyr Lys Gly Tyr Gln
        435                 440                 445
Val Ala Pro Ala Glu Leu Glu Ser Ile Leu Leu Gln His Pro Asn Ile
    450                 455                 460
Phe Asp Ala Gly Val Ala Gly Leu Pro Asp Asp Asp Ala Gly Glu Leu
465                 470                 475                 480
Pro Ala Ala Val Val Val Leu Glu His Gly Lys Thr Met Thr Glu Lys
                485                 490                 495
Glu Ile Val Asp Tyr Val Ala Ser Gln Val Thr Thr Ala Lys Lys Leu
            500                 505                 510
Arg Gly Gly Val Val Phe Val Asp Glu Val Pro Lys Gly Leu Thr Gly
        515                 520                 525
Lys Leu Asp Ala Arg Lys Ile Arg Glu Ile Leu Ile Lys Ala Lys Lys
    530                 535                 540
Gly Gly Lys Ser Lys Leu
545                 550

<210> SEQ ID NO 27
<211> LENGTH: 12
<212> TYPE: PRT
<213> ORGANISM: Artificial Sequence
<220> FEATURE:
<223> OTHER INFORMATION: substrate for the detection of botulinum
      neurotoxin activity
<220> FEATURE:
<221> NAME/KEY: MISC_FEATURE
<222> LOCATION: (1)..(1)
<223> OTHER INFORMATION: Lys at position 1 is Lysine with 4-
      methyllumbelliferone conjugated to its alpha-amino group
      ("Lys-(4-Mu)")
<220> FEATURE:
<221> NAME/KEY: MISC_FEATURE
<222> LOCATION: (11)..(11)
<223> OTHER INFORMATION: Lys at position 11 is Lysine with 4-
      (dimethylaminoazo) benzene-4-carboxyl (DABCYL) conjugated to its
      epsilon-amino group ("Lys[DABCYL]")
<220> FEATURE:
<221> NAME/KEY: MISC_FEATURE
<222> LOCATION: (12)..(12)
<223> OTHER INFORMATION: Xaa at position 12 is Norleucine with an amide
      C-terminus

<400> SEQUENCE: 27

Lys Ile Asp Glu Ala Asn Gln Arg Ala Thr Lys Xaa
1               5                   10
```

```
<210> SEQ ID NO 28
<211> LENGTH: 12
<212> TYPE: PRT
<213> ORGANISM: Artificial Sequence
<220> FEATURE:
<223> OTHER INFORMATION: substrate for the detection of botulinum
      neurotoxin activity
<220> FEATURE:
<221> NAME/KEY: MISC_FEATURE
<222> LOCATION: (1)..(1)
<223> OTHER INFORMATION: Lys at position 1 is Lysine with 5-
      carboxyfluorescein conjugated to its epsilon-amino group
      ("Lys[5-Fam]")
<220> FEATURE:
<221> NAME/KEY: MISC_FEATURE
<222> LOCATION: (11)..(11)
<223> OTHER INFORMATION: Lys at position 11 is Lysine with 4-
      (dimethylaminoazo) benzene-4-carboxyl (DABCYL) conjugated to its
      epsilon-amino group ("Lys[DABCYL]")
<220> FEATURE:
<221> NAME/KEY: MISC_FEATURE
<222> LOCATION: (12)..(12)
<223> OTHER INFORMATION: Xaa is a 6-Amino hexanoic acid

<400> SEQUENCE: 28

Lys Ile Asp Glu Ala Asn Gln Arg Ala Thr Lys Xaa
1               5                   10

<210> SEQ ID NO 29
<211> LENGTH: 12
<212> TYPE: PRT
<213> ORGANISM: Artificial Sequence
<220> FEATURE:
<223> OTHER INFORMATION: substrate for the detection of botulinum
      neurotoxin activity
<220> FEATURE:
<221> NAME/KEY: MISC_FEATURE
<222> LOCATION: (1)..(1)
<223> OTHER INFORMATION: Lys at position 1 is Lysine with 4-
      methylumbelliferone conjugated to its epsilon-amino group
      ("Lys-(4-Mu)")
<220> FEATURE:
<221> NAME/KEY: MISC_FEATURE
<222> LOCATION: (11)..(11)
<223> OTHER INFORMATION: Lys at position 11 is Lysine with 4-
      (dimethylaminoazo) benzene-4-carboxyl (DABCYL) conjugated to its
      epsilon-amino group ("Lys[DABCYL]")
<220> FEATURE:
<221> NAME/KEY: MISC_FEATURE
<222> LOCATION: (12)..(12)
<223> OTHER INFORMATION: Xaa at position 12 is 6-Amino hexanoic acid

<400> SEQUENCE: 29

Lys Ile Asp Glu Ala Asn Gln Arg Ala Thr Lys Xaa
1               5                   10
```